US010300118B2

(12) United States Patent
Lee et al.

(10) Patent No.: US 10,300,118 B2
(45) Date of Patent: May 28, 2019

(54) CELL PENETRATING PEPTIDE, CONJUGATE THEREOF WITH BOTULINUM TOXIN, AND USE THEREOF

(71) Applicants: Procell Therapeutics Inc., Seoul (KR); ATGC CO., LTD., Gyeonggi-do (KR)

(72) Inventors: Byung Kyu Lee, Gyeonggi-do (KR); Kang Jin Lee, Gangnam-go (KR); MinJoong Kim, Gyeonggi-do (KR); HongGyu Park, Seoul (KR)

(73) Assignee: PROCELL THEREPAUTICS INC. (KR)

( * ) Notice: Subject to any disclaimer, the term of this patent is extended or adjusted under 35 U.S.C. 154(b) by 0 days.

(21) Appl. No.: 15/313,259

(22) PCT Filed: May 29, 2015

(86) PCT No.: PCT/KR2015/005434
§ 371 (c)(1),
(2) Date: Nov. 22, 2016

(87) PCT Pub. No.: WO2015/183044
PCT Pub. Date: Dec. 3, 2015

(65) Prior Publication Data

US 2017/0246266 A1 Aug. 31, 2017

Related U.S. Application Data

(60) Provisional application No. 62/004,426, filed on May 29, 2014.

(51) Int. Cl.

| | |
|---|---|
| ***A61K 38/48*** | (2006.01) |
| ***A61K 38/10*** | (2006.01) |
| ***C12N 15/70*** | (2006.01) |
| ***A61K 39/08*** | (2006.01) |
| ***C07K 7/08*** | (2006.01) |
| ***C07K 19/00*** | (2006.01) |
| ***A61K 9/00*** | (2006.01) |
| ***C12N 9/52*** | (2006.01) |
| ***A61K 47/50*** | (2017.01) |

(52) U.S. Cl.
CPC ........ *A61K 38/4893* (2013.01); *A61K 9/0014* (2013.01); *A61K 38/10* (2013.01); *A61K 39/08* (2013.01); *A61K 47/50* (2017.08); *C07K 7/08* (2013.01); *C07K 19/00* (2013.01); *C12N 9/52* (2013.01); *C12N 15/70* (2013.01); *C12Y 304/24069* (2013.01); *C07K 2319/55* (2013.01)

(58) Field of Classification Search
None
See application file for complete search history.

(56) References Cited

U.S. PATENT DOCUMENTS

| | | | | |
|---|---|---|---|---|
| 7,192,596 | B2 | 3/2007 | Shone et al. | |
| 8,273,865 | B2 * | 9/2012 | Steward | A61K 38/4886 424/184.1 |
| 8,491,917 | B1 * | 7/2013 | Bender | A61K 38/48 424/239.1 |
| 8,629,097 | B2 | 1/2014 | Jo et al. | |
| 8,936,790 | B2 * | 1/2015 | Turkel | A61K 38/4893 424/239.1 |
| 8,968,747 | B2 * | 3/2015 | Turkel | A61K 38/4893 424/239.1 |
| 9,259,481 | B2 * | 2/2016 | Shin | C07K 7/06 |
| 9,279,001 | B2 * | 3/2016 | Turkel | A61K 38/4893 |
| 9,694,087 | B2 * | 7/2017 | Shin | C07K 7/06 |
| 9,764,011 | B2 * | 9/2017 | Turkel | A61K 38/4893 |
| 2004/0209797 | A1 | 10/2004 | Karas | |
| 2015/0231068 | A1 * | 8/2015 | Binder | A61K 9/0085 424/94.63 |
| 2017/0246266 | A1 * | 8/2017 | Lee | A61K 38/4893 |
| 2018/0028624 | A1 * | 2/2018 | Turkel | A61K 38/4893 |

FOREIGN PATENT DOCUMENTS

| | | | | |
|---|---|---|---|---|
| KR | 2009-0103957 A | | 10/2009 | |
| KR | 10-1258279 B1 | | 4/2013 | |
| WO | WO-2013137969 A1 | * | 9/2013 | A61K 38/4893 |
| WO | WO-2014080206 A1 | * | 5/2014 | C12Q 1/37 |
| WO | WO-2015183044 A1 | * | 12/2015 | A61K 39/08 |

OTHER PUBLICATIONS

Salzano et al, Cell-Penetrating Peptides: Methods and Protocols, Methods in Molecular Biology, vol. 1324:357-368, 2015 (Year: 2015).*
Lee et al, Cell-Penetrating Peptides: Methods and Protocols, Methods in Molecular Biology, vol. 1324:397-415, 2015 (Year: 2015).*
Nakase et al, Cell-Penetrating Peptides: Methods and Protocols, Methods in Molecular Biology, vol. 1324:387-396, 2015 (Year: 2015).*
Cha et al, Journal of Voice, vol. 31, No. 3, pp. 378.e19-378.e24, 2017 (Year: 2017).*
Bradley et al, Journal of Voice, vol. 31, No. 3, pp. 363-365, 2017 (Year: 2017).*
Amand et al, BBA 1808 (2011) 1860-1867. available online Apr. 5, 2011 (Year: 2011).*

(Continued)

*Primary Examiner* — Nita M. Minnifield
(74) *Attorney, Agent, or Firm* — Riverside Law LLP

(57) ABSTRACT

The present invention relates to: a novel cell penetrating peptide; a cell penetrating botulinum toxin recombinant protein composition in which the cell penetrating peptide and the light chain of a botulinum toxin are fused; and a use thereof and, more specifically, to a composition enabling the transdermal delivery of a cell penetrating botulinum toxin recombinant protein and capable of being locally used for various treatments of the skin and cosmetic purposes. The cell penetrating peptide-botulinum toxin recombinant protein of the present invention can be transdermally delivered, thereby having the intrinsic effect of a botulinum toxin and simultaneously having greater convenience of use, and thus can be effectively applied as a local agonist for the treatment of various diseases and aesthetic and/or cosmetic purposes.

8 Claims, 28 Drawing Sheets

Specification includes a Sequence Listing.

(56) References Cited

OTHER PUBLICATIONS

Milletti, Drug Discovery Today, Aug. 2012, vol. 17, Nos. 15/16, pp. 850-860 (Year: 2012).*
Burgess et al, Journal of Cell Biology, 1990, 111:2129-2138 (Year: 1990).*
Greenspan et al, Nature Biotechnology 7: 936-937, 1999 (Year: 1999).*
Lazar et al., Molecular and CellularBiology, 1988, 8:1247-1252 (Year: 1988).*
Thomas E. Creighton, "Proteins: Structures and Molecular Properties, 1984", (pp. 314-315) (Year: 1984).*
Mae et al, Current Opinion in Pharmacology, 2006, 6:509-514. available online:Jul. 24, 2006 (Year: 2006).*
Brunger et al. (2007) "Botulinum Neurotoxin Heavy Chain Belt as an Intramolecular Chaperone for the Light Chain" Plos Pathogens, vol. 3, Issue 9, Article No. e113, pp. 1191-1194.

* cited by examiner

FIG. 1

| Name (A/a) | Structure | Peptide properties | | | | | | | | |
|---|---|---|---|---|---|---|---|---|---|---|
| | α-helicity (HNN) | Amphipathicity | Aliphatic index | Instability index | Hydrophilicity | SVM Score | Hydrophobicity at pH6.8 | Hydropathicity ~ GRAVY | Net charge (pH 7.4) | Pi |
| TD1 (13) | ceeeeeeecccccc | 0.68 | 97.69 | 49.85 | -0.30 | -0.19 | 29.2 | 0.000 | 2 | 9.31 |

FIG. 2
| Peptide | Wheel plot | 3D structure |
|---|---|---|
| TD1 | 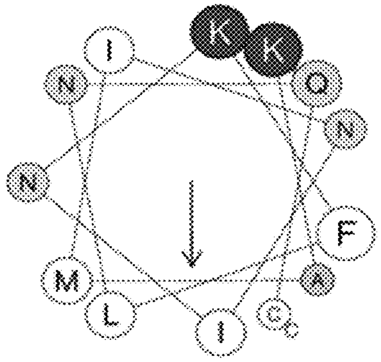 | 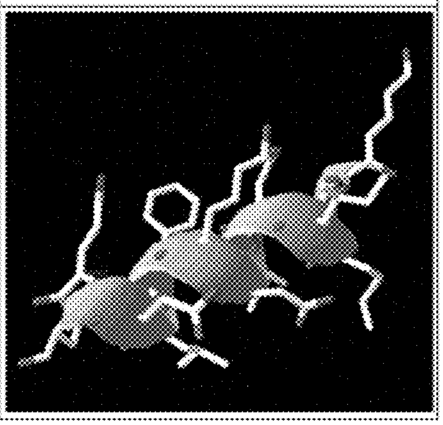 |

Treatment condition: 5 μM, 6 hrs

Treatment condition: 5 μM

FIG. 13

| IRRITATION INDEX | TYPE OF DERMAL SYMPTOM OR SIGN |
|---|---|
| ?0.5 | DOUBTFUL VISIBLE ERYTHEMA |
| +1 | SLIGHT ERYTHEMA, EITHER SPOTTY OR DIFFUSE |
| ++2 | MODERATE UNIFORM ERYTHEMA |
| +++3 | INTENSE ERYTHEMA WITH EDEMA |
| ++++4 | INTENSE ERYTHEMA WITH EDEMA & VESICLES |
| - (NEGATIVE) | NEGATIVE REACTIONS |
| IR (IRRITANT REACTION) | VARIOUS TYPES OF IRRITANT REACTIONS (INCLUDING ADHESIVE IRRITATION) |
| NT (NOT TESTED) | INTERRUPTION OF TEST DUE TO OCCURRENCE OF IRRITANT REACTION OR OTHER REASONS |

| SAMPLE NO. | NO* | NUMBER OF PERSONS SHOWING REACTION | MEAN SCORE | | | |
|---|---|---|---|---|---|---|
| | | | FIRST | SECOND | DERMAL MEAN REACTIVITY | |
| 1 | A4230 | 0 | 0.000 | 0.000 | 0.000 | NO REACTION |
| * SAMPLE REGISTRATION NUMBER OF I.E.C. KOREA | | | | | | |

FIG. 14a

* SKIN WRINKLE ANALYSIS RESULT

| N=22 | BEFORE USE (D0) | 4-WEEK AFTER USE(D28) | *Change rate(%)* | *p-value*[†] |
| --- | --- | --- | --- | --- |
| Ra (μm) | 20.530±5.349 | 17.512±3.715 | -14.70% | **0.003** |
| Rmax (μm) | 155.145±49.093 | 134.993±37.498 | -12.99% | **0.007^** |
| R3z (μm) | 64.338±15.296 | 55.189±10.247 | -14.22% | **0.007** |
| Rz (μm) | 108.148±28.245 | 93.075±18.683 | -13.94% | **0.003** |
| Rt (um) | 162.728±52.147 | 141.060±38.185 | -13.32% | **0.006^** |

FIG. 14b

* ANALYSIS RESULT FOR SKIN ELASTICITY

| N=22 | BEFORE USE (D0) | 4-WEEK AFTER USE (D28) | *Change rate(%)* | *p-value[†]* |
|---|---|---|---|---|
| R5 | 0.654±0.067 | 0.751±0.057 | 14.82% | **<0.001** |
| R7 | 0.413±0.038 | 0.452±0.052 | 9.26% | **0.004** |

*Mean±Standard deviation (Std)*

FIG. 14c

■ VISUAL EVALUATION RESULT FOR NASOLABIAL FOLD

| N=22 | BEFORE USE(D0) | 4-WEEK AFTER USE(D28) | *Change rate(%)* | *p-value*[†] |
|---|---|---|---|---|
| Assessor | 2.32±0.75 | 1.91±0.72 | -17.65% | **<0.001** |

* VISUAL EVALUATION FOR NASOLABIAL FOLD

Day 0 Day 28

SEQUENCE LISTING

```
<160> NUMBER OF SEQ ID NOS: 90

<210> SEQ ID NO 1
<211> LENGTH: 13
<212> TYPE: PRT
<213> ORGANISM: Artificial Sequence
<220> FEATURE:
<223> OTHER INFORMATION: TD1 Amino Acid Sequence

<400> SEQUENCE: 1

Lys Ala Met Ile Asn Ile Asn Lys Phe Leu Asn Gln Cys
1               5                   10
```

<210> SEQ ID NO 2
<211> LENGTH: 39
<212> TYPE: DNA
<213> ORGANISM: Artificial Sequence
<220> FEATURE:
<223> OTHER INFORMATION: TD1 cDNA Sequence

<400> SEQUENCE: 2
aaggcgatga taaacataaa caagttcctg aaccagtgc 39

<210> SEQ ID NO 3
<211> LENGTH: 448
<212> TYPE: PRT
<213> ORGANISM: Artificial Sequence
<220> FEATURE:
<223> OTHER INFORMATION: BoNT/A Light chain Amino Acid Sequence

<400> SEQUENCE: 3

```
Met Pro Phe Val Asn Lys Gln Phe Asn Tyr Lys Asp Pro Val Asn Gly
1               5                   10                  15

Val Asp Ile Ala Tyr Ile Lys Ile Pro Asn Ala Gly Gln Met Gln Pro
            20                  25                  30

Val Lys Ala Phe Lys Ile His Asn Lys Ile Trp Val Ile Pro Glu Arg
        35                  40                  45

Asp Thr Phe Thr Asn Pro Glu Glu Gly Asp Leu Asn Pro Pro Pro Glu
    50                  55                  60

Ala Lys Gln Val Pro Val Ser Tyr Tyr Asp Ser Thr Tyr Leu Ser Thr
65                  70                  75                  80

Asp Asn Glu Lys Asp Asn Tyr Leu Lys Gly Val Thr Lys Leu Phe Glu
                85                  90                  95

Arg Ile Tyr Ser Thr Asp Leu Gly Arg Met Leu Leu Thr Ser Ile Val
            100                 105                 110

Arg Gly Ile Pro Phe Trp Gly Gly Ser Thr Ile Asp Thr Glu Leu Lys
        115                 120                 125

Val Ile Asp Thr Asn Cys Ile Asn Val Ile Gln Pro Asp Gly Ser Tyr
    130                 135                 140

Arg Ser Glu Glu Leu Asn Leu Val Ile Ile Gly Pro Ser Ala Asp Ile
145                 150                 155                 160

Ile Gln Phe Glu Cys Lys Ser Phe Gly His Glu Val Leu Asn Leu Thr
                165                 170                 175

Arg Asn Gly Tyr Gly Ser Thr Gln Tyr Ile Arg Phe Ser Pro Asp Phe
            180                 185                 190

Thr Phe Gly Phe Glu Glu Ser Leu Glu Val Asp Thr Asn Pro Leu Leu
        195                 200                 205

Gly Ala Gly Lys Phe Ala Thr Asp Pro Ala Val Thr Leu Ala His Glu
    210                 215                 220

Leu Ile His Ala Gly His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
                245                 250                 255

Glu Val Ser Phe Glu Glu Leu Arg Thr Phe Gly Gly His Asp Ala Lys
            260                 265                 270

Phe Ile Asp Ser Leu Gln Glu Asn Glu Phe Arg Leu Tyr Tyr Tyr Asn
        275                 280                 285

Lys Phe Lys Asp Ile Ala Ser Thr Leu Asn Lys Ala Lys Ser Ile Val
    290                 295                 300
```

Gly Thr Thr Ala Ser Leu Gln Tyr Met Lys Asn Val Phe Lys Glu Lys
305 310 315 320

Tyr Leu Leu Ser Glu Asp Thr Ser Gly Lys Phe Ser Val Asp Lys Leu
325 330 335

Lys Phe Asp Lys Leu Tyr Lys Met Leu Thr Glu Ile Tyr Thr Glu Asp
340 345 350

Asn Phe Val Lys Phe Phe Lys Val Leu Asn Arg Lys Thr Tyr Leu Asn
355 360 365

Phe Asp Lys Ala Val Phe Lys Ile Asn Ile Val Pro Lys Val Asn Tyr
370 375 380

Thr Ile Tyr Asp Gly Phe Asn Leu Arg Asn Thr Asn Leu Ala Ala Asn
385 390 395 400

Phe Asn Gly Gln Asn Thr Glu Ile Asn Asn Met Asn Phe Thr Lys Leu
405 410 415

Lys Asn Phe Thr Gly Leu Phe Glu Phe Tyr Lys Leu Leu Cys Val Arg
420 425 430

Gly Ile Ile Thr Ser Lys Thr Lys Ser Leu Asp Lys Gly Tyr Asn Lys
435 440 445

<210> SEQ ID NO 4
<211> LENGTH: 441
<212> TYPE: PRT
<213> ORGANISM: Artificial Sequence
<220> FEATURE:
<223> OTHER INFORMATION: BoNT/B Light chain Amino Acid Sequence

<400> SEQUENCE: 4

Met Pro Val Thr Ile Asn Asn Phe Asn Tyr Asn Asp Pro Ile Asp Asn
1 5 10 15

Asn Asn Ile Ile Met Met Glu Pro Pro Phe Ala Arg Gly Thr Gly Arg
20 25 30

Tyr Tyr Lys Ala Phe Lys Ile Thr Asp Arg Ile Trp Ile Ile Pro Glu
35 40 45

Arg Tyr Thr Phe Gly Tyr Lys Pro Glu Asp Phe Asn Lys Ser Ser Gly
50 55 60

Ile Phe Asn Arg Asp Val Cys Glu Tyr Tyr Asp Pro Asp Tyr Leu Asn
65 70 75 80

Thr Asn Asp Lys Lys Asn Ile Phe Leu Gln Thr Met Ile Lys Leu Phe
85 90 95

Asn Arg Ile Lys Ser Lys Pro Leu Gly Glu Lys Leu Leu Glu Met Ile
100 105 110

Ile Asn Gly Ile Pro Tyr Leu Gly Asp Arg Arg Val Pro Leu Glu Glu
115 120 125

Phe Asn Thr Asn Ile Ala Ser Val Thr Val Asn Lys Leu Ile Ser Asn
130 135 140

Pro Gly Glu Val Glu Arg Lys Lys Gly Ile Phe Ala Asn Leu Ile Ile
145 150 155 160

Phe Gly Pro Gly Pro Val Leu Asn Glu Asn Glu Thr Ile Asp Ile Gly
165 170 175

Ile Gln Asn His Phe Ala Ser Arg Glu Gly Phe Gly Gly Ile Met Gln
180 185 190

Met Lys Phe Cys Pro Glu Tyr Val Ser Val Phe Asn Asn Val Gln Glu
195 200 205

Asn Lys Gly Ala Ser Ile Phe Asn Arg Arg Gly Tyr Phe Ser Asp Pro
210 215 220

Ala Leu Ile Leu Met His Glu Leu Ile His Val Leu His Gly Leu Tyr
225 230 235 240

Gly Ile Lys Val Asp Asp Leu Pro Ile Val Pro Asn Glu Lys Lys Phe
245 250 255

Phe Met Gln Ser Thr Asp Ala Ile Gln Ala Glu Glu Leu Tyr Thr Phe
260 265 270

Gly Gly Gln Asp Pro Ser Ile Ile Thr Pro Ser Thr Asp Lys Ser Ile
275 280 285

Tyr Asp Lys Val Leu Gln Asn Phe Arg Gly Ile Val Asp Arg Leu Asn
290 295 300

Lys Val Leu Val Cys Ile Ser Asp Pro Asn Ile Asn Ile Asn Ile Tyr
305 310 315 320

Lys Asn Lys Phe Lys Asp Lys Tyr Lys Phe Val Glu Asp Ser Glu Gly
325 330 335

Lys Tyr Ser Ile Asp Val Glu Ser Phe Asp Lys Leu Tyr Lys Ser Leu
340 345 350

Met Phe Gly Phe Thr Glu Thr Asn Ile Ala Glu Asn Tyr Lys Ile Lys
355 360 365

Thr Arg Ala Ser Tyr Phe Ser Asp Ser Leu Pro Pro Val Lys Ile Lys
370 375 380

Asn Leu Leu Asp Asn Glu Ile Tyr Thr Ile Glu Glu Gly Phe Asn Ile
385 390 395 400

Ser Asp Lys Asp Met Glu Lys Glu Tyr Arg Gly Gln Asn Lys Ala Ile
405 410 415

Asn Lys Gln Ala Tyr Glu Glu Ile Ser Lys Glu His Leu Ala Val Tyr
420 425 430

Lys Ile Gln Met Cys Lys Ser Val Lys
435 440

<210> SEQ ID NO 5
<211> LENGTH: 449
<212> TYPE: PRT
<213> ORGANISM: Artificial Sequence
<220> FEATURE:
<223> OTHER INFORMATION: BoNT/C Light chain Amino Acid Sequence

<400> SEQUENCE: 5

Met Pro Ile Thr Ile Asn Asn Phe Asn Tyr Ser Asp Pro Val Asp Asn
1 5 10 15

Lys Asn Ile Leu Tyr Leu Asp Thr His Leu Asn Thr Leu Ala Asn Glu
20 25 30

Pro Glu Lys Ala Phe Arg Ile Thr Gly Asn Ile Trp Val Ile Pro Asp
35 40 45

Arg Phe Ser Arg Asn Ser Asn Pro Asn Leu Asn Lys Pro Pro Arg Val
50 55 60

Thr Ser Pro Lys Ser Gly Tyr Tyr Asp Pro Asn Tyr Leu Ser Thr Asp
65 70 75 80

Ser Asp Lys Asp Pro Phe Leu Lys Glu Ile Ile Lys Leu Phe Lys Arg
85 90 95

Ile Asn Ser Arg Glu Ile Gly Glu Glu Leu Ile Tyr Arg Leu Ser Thr
100 105 110

Asp Ile Pro Phe Pro Gly Asn Asn Asn Thr Pro Ile Asn Thr Phe Asp
115 120 125

Phe Asp Val Asp Phe Asn Ser Val Asp Val Lys Thr Arg Gln Gly Asn
130 135 140

-continued

```
Asn Trp Val Lys Thr Gly Ser Ile Asn Pro Ser Val Ile Ile Thr Gly
145                 150                 155                 160

Pro Arg Glu Asn Ile Ile Asp Pro Glu Thr Ser Thr Phe Lys Leu Thr
                165                 170                 175

Asn Asn Thr Phe Ala Ala Gln Glu Gly Phe Gly Ala Leu Ser Ile Ile
            180                 185                 190

Ser Ile Ser Pro Arg Phe Met Leu Thr Tyr Ser Asn Ala Thr Asn Asp
        195                 200                 205

Val Gly Glu Gly Arg Phe Ser Lys Ser Glu Phe Cys Met Asp Pro Ile
    210                 215                 220

Leu Ile Leu Met His Glu Leu Asn His Ala Met His Asn Leu Tyr Gly
225                 230                 235                 240

Ile Ala Ile Pro Asn Asp Gln Thr Ile Ser Ser Val Thr Ser Asn Ile
                245                 250                 255

Phe Tyr Ser Gln Tyr Asn Val Lys Leu Glu Tyr Ala Glu Ile Tyr Ala
            260                 265                 270

Phe Gly Gly Pro Thr Ile Asp Leu Ile Pro Lys Ser Ala Arg Lys Tyr
        275                 280                 285

Phe Glu Glu Lys Ala Leu Asp Tyr Tyr Arg Ser Ile Ala Lys Arg Leu
    290                 295                 300

Asn Ser Ile Thr Thr Ala Asn Pro Ser Ser Phe Asn Lys Tyr Ile Gly
305                 310                 315                 320

Glu Tyr Lys Gln Lys Leu Ile Arg Lys Tyr Arg Phe Val Val Glu Ser
                325                 330                 335

Ser Gly Glu Val Thr Val Asn Arg Asn Lys Phe Val Glu Leu Tyr Asn
            340                 345                 350

Glu Leu Thr Gln Ile Phe Thr Glu Phe Asn Tyr Ala Lys Ile Tyr Asn
        355                 360                 365

Val Gln Asn Arg Lys Ile Tyr Leu Ser Asn Val Tyr Thr Pro Val Thr
    370                 375                 380

Ala Asn Ile Leu Asp Asp Asn Val Tyr Asp Ile Gln Asn Gly Phe Asn
385                 390                 395                 400

Ile Pro Lys Ser Asn Leu Asn Val Leu Phe Met Gly Gln Asn Leu Ser
                405                 410                 415

Arg Asn Pro Ala Leu Arg Lys Val Asn Pro Glu Asn Met Leu Tyr Leu
            420                 425                 430

Phe Thr Lys Phe Cys His Lys Ala Ile Asp Gly Arg Ser Leu Tyr Asn
        435                 440                 445

Lys
```

<210> SEQ ID NO 6
<211> LENGTH: 442
<212> TYPE: PRT
<213> ORGANISM: Artificial Sequence
<220> FEATURE:
<223> OTHER INFORMATION: BoNT/D Light chain Amino Acid Sequence

<400> SEQUENCE: 6

```
Met Thr Trp Pro Val Lys Asp Phe Asn Tyr Ser Asp Pro Val Asn Asp
1               5                   10                  15

Asn Asp Ile Leu Tyr Leu Arg Ile Pro Gln Asn Lys Leu Ile Thr Thr
            20                  25                  30

Pro Val Lys Ala Phe Met Ile Thr Gln Asn Ile Trp Val Ile Pro Glu
        35                  40                  45
```

-continued

```
Arg Phe Ser Ser Asp Thr Asn Pro Ser Leu Ser Lys Pro Pro Arg Pro
    50                  55                  60

Thr Ser Lys Tyr Gln Ser Tyr Tyr Asp Pro Ser Tyr Leu Ser Thr Asp
65                  70                  75                  80

Glu Gln Lys Asp Thr Phe Leu Lys Gly Ile Ile Lys Leu Phe Lys Arg
                85                  90                  95

Ile Asn Glu Arg Asp Ile Gly Lys Lys Leu Ile Asn Tyr Leu Val Val
            100                 105                 110

Gly Ser Pro Phe Met Gly Asp Ser Ser Thr Pro Glu Asp Thr Phe Asp
        115                 120                 125

Phe Thr Arg His Thr Thr Asn Ile Ala Val Glu Lys Phe Glu Asn Gly
    130                 135                 140

Ser Trp Lys Val Thr Asn Ile Ile Thr Pro Ser Val Leu Ile Phe Gly
145                 150                 155                 160

Pro Leu Pro Asn Ile Leu Asp Tyr Thr Ala Ser Leu Thr Leu Gln Gly
                165                 170                 175

Gln Gln Ser Asn Pro Ser Phe Glu Gly Phe Gly Thr Leu Ser Ile Leu
            180                 185                 190

Lys Val Ala Pro Glu Phe Leu Leu Thr Phe Ser Asp Val Thr Ser Asn
        195                 200                 205

Gln Ser Ser Ala Val Leu Gly Lys Ser Ile Phe Cys Met Asp Pro Val
    210                 215                 220

Ile Ala Leu Met His Glu Leu Thr His Ser Leu His Gln Leu Tyr Gly
225                 230                 235                 240

Ile Asn Ile Pro Ser Asp Lys Arg Ile Arg Pro Gln Val Ser Glu Gly
                245                 250                 255

Phe Phe Ser Gln Asp Gly Pro Asn Val Gln Phe Glu Glu Leu Tyr Thr
            260                 265                 270

Phe Gly Gly Leu Asp Val Glu Ile Ile Pro Gln Ile Glu Arg Ser Gln
        275                 280                 285

Leu Arg Glu Lys Ala Leu Gly His Tyr Lys Asp Ile Ala Lys Arg Leu
    290                 295                 300

Asn Asn Ile Asn Lys Thr Ile Pro Ser Ser Trp Ile Ser Asn Ile Asp
305                 310                 315                 320

Lys Tyr Lys Lys Ile Phe Ser Glu Lys Tyr Asn Phe Asp Lys Asp Asn
                325                 330                 335

Thr Gly Asn Phe Val Val Asn Ile Asp Lys Phe Asn Ser Leu Tyr Ser
            340                 345                 350

Asp Leu Thr Asn Val Met Ser Glu Val Val Tyr Ser Ser Gln Tyr Asn
        355                 360                 365

Val Lys Asn Arg Thr His Tyr Phe Ser Arg His Tyr Leu Pro Val Phe
    370                 375                 380

Ala Asn Ile Leu Asp Asp Asn Ile Tyr Thr Ile Arg Asp Gly Phe Asn
385                 390                 395                 400

Leu Thr Asn Lys Gly Phe Asn Ile Glu Asn Ser Gly Gln Asn Ile Glu
                405                 410                 415

Arg Asn Pro Ala Leu Gln Lys Leu Ser Ser Glu Ser Val Val Asp Leu
            420                 425                 430

Phe Thr Lys Val Cys Leu Arg Leu Thr Lys
        435                 440
```

<210> SEQ ID NO 7
<211> LENGTH: 422
<212> TYPE: PRT

-continued

<213> ORGANISM: Artificial Sequence
<220> FEATURE:
<223> OTHER INFORMATION: BoNT/E Light chain Amino Acid Sequence

<400> SEQUENCE: 7

```
Met Pro Thr Ile Asn Ser Phe Asn Tyr Asn Asp Pro Val Asn Asn Arg
1               5                   10                  15

Thr Ile Leu Tyr Ile Lys Pro Gly Gly Cys Gln Gln Phe Tyr Lys Ser
            20                  25                  30

Phe Asn Ile Met Lys Asn Ile Trp Ile Ile Pro Glu Arg Asn Val Ile
        35                  40                  45

Gly Thr Ile Pro Gln Asp Phe Leu Pro Pro Thr Ser Leu Lys Asn Gly
    50                  55                  60

Asp Ser Ser Tyr Tyr Asp Pro Asn Tyr Leu Gln Ser Asp Gln Glu Lys
65                  70                  75                  80

Asp Lys Phe Leu Lys Ile Val Thr Lys Ile Phe Asn Arg Ile Asn Asp
                85                  90                  95

Asn Leu Ser Gly Arg Ile Leu Leu Glu Glu Leu Ser Lys Ala Asn Pro
            100                 105                 110

Tyr Leu Gly Asn Asp Asn Thr Pro Asp Gly Asp Phe Ile Ile Asn Asp
        115                 120                 125

Ala Ser Ala Val Pro Ile Gln Phe Ser Asn Gly Ser Gln Ser Ile Leu
    130                 135                 140

Leu Pro Asn Val Ile Ile Met Gly Ala Glu Pro Asp Leu Phe Glu Thr
145                 150                 155                 160

Asn Ser Ser Asn Ile Ser Leu Arg Asn Asn Tyr Met Pro Ser Asn His
                165                 170                 175

Gly Phe Gly Ser Ile Ala Ile Val Thr Phe Ser Pro Glu Tyr Ser Phe
            180                 185                 190

Arg Phe Lys Asp Asn Ser Met Asn Glu Phe Ile Gln Asp Pro Ala Leu
        195                 200                 205

Thr Leu Met His Glu Leu Ile His Ser Leu His Gly Leu Tyr Gly Ala
    210                 215                 220

Lys Gly Ile Thr Thr Lys Tyr Thr Ile Thr Gln Lys Gln Asn Pro Leu
225                 230                 235                 240

Ile Thr Asn Ile Arg Gly Thr Asn Ile Glu Glu Phe Leu Thr Phe Gly
                245                 250                 255

Gly Thr Asp Leu Asn Ile Ile Thr Ser Ala Gln Ser Asn Asp Ile Tyr
            260                 265                 270

Thr Asn Leu Leu Ala Asp Tyr Lys Lys Ile Ala Ser Lys Leu Ser Lys
        275                 280                 285

Val Gln Val Ser Asn Pro Leu Leu Asn Pro Tyr Lys Asp Val Phe Glu
    290                 295                 300

Ala Lys Tyr Gly Leu Asp Lys Asp Ala Ser Gly Ile Tyr Ser Val Asn
305                 310                 315                 320

Ile Asn Lys Phe Asn Asp Ile Phe Lys Lys Leu Tyr Ser Phe Thr Glu
                325                 330                 335

Phe Asp Leu Ala Thr Lys Phe Gln Val Lys Cys Arg Gln Thr Tyr Ile
            340                 345                 350

Gly Gln Tyr Lys Tyr Phe Lys Leu Ser Asn Leu Leu Asn Asp Ser Ile
        355                 360                 365

Tyr Asn Ile Ser Glu Gly Tyr Asn Ile Asn Asn Leu Lys Val Asn Phe
    370                 375                 380

Arg Gly Gln Asn Ala Asn Leu Asn Pro Arg Ile Ile Thr Pro Ile Thr
```

-continued

```
385                 390                 395                 400

Gly Arg Gly Leu Val Lys Lys Ile Ile Arg Phe Cys Lys Asn Ile Val
                405                 410                 415

Ser Val Lys Gly Ile Arg
            420


<210> SEQ ID NO 8
<211> LENGTH: 436
<212> TYPE: PRT
<213> ORGANISM: Artificial Sequence
<220> FEATURE:
<223> OTHER INFORMATION: BoNT/F Light chain Amino Acid Sequence

<400> SEQUENCE: 8

Met Pro Val Ala Ile Asn Ser Phe Asn Tyr Asn Asp Pro Val Asn Asp
1               5                   10                  15

Asp Thr Ile Leu Tyr Met Gln Ile Pro Tyr Glu Glu Lys Ser Lys Lys
            20                  25                  30

Tyr Tyr Lys Ala Phe Glu Ile Met Arg Asn Val Trp Ile Ile Pro Glu
        35                  40                  45

Arg Asn Thr Ile Gly Thr Asn Pro Ser Asp Phe Asp Pro Pro Ala Ser
    50                  55                  60

Leu Lys Asn Gly Ser Ser Ala Tyr Tyr Asp Pro Asn Tyr Leu Thr Thr
65                  70                  75                  80

Asp Ala Glu Lys Asp Arg Tyr Leu Lys Thr Thr Ile Lys Leu Phe Lys
                85                  90                  95

Arg Ile Asn Ser Asn Pro Ala Gly Lys Val Leu Leu Gln Glu Ile Ser
            100                 105                 110

Tyr Ala Lys Pro Tyr Leu Gly Asn Asp His Thr Pro Ile Asp Glu Phe
        115                 120                 125

Ser Pro Val Thr Arg Thr Thr Ser Val Asn Ile Lys Leu Ser Thr Asn
    130                 135                 140

Val Glu Ser Ser Met Leu Leu Asn Leu Leu Val Leu Gly Ala Gly Pro
145                 150                 155                 160

Asp Ile Phe Glu Ser Cys Cys Tyr Pro Val Arg Lys Leu Ile Asp Pro
                165                 170                 175

Asp Val Val Tyr Asp Pro Ser Asn Tyr Gly Phe Gly Ser Ile Asn Ile
            180                 185                 190

Val Thr Phe Ser Pro Glu Tyr Glu Tyr Thr Phe Asn Asp Ile Ser Gly
        195                 200                 205

Gly His Asn Ser Ser Thr Glu Ser Phe Ile Ala Asp Pro Ala Ile Ser
    210                 215                 220

Leu Ala His Glu Leu Ile His Ala Leu His Gly Leu Tyr Gly Ala Arg
225                 230                 235                 240

Gly Val Thr Tyr Glu Glu Thr Ile Glu Val Lys Gln Ala Pro Leu Met
                245                 250                 255

Ile Ala Glu Lys Pro Ile Arg Leu Glu Glu Phe Leu Thr Phe Gly Gly
            260                 265                 270

Gln Asp Leu Asn Ile Ile Thr Ser Ala Met Lys Glu Lys Ile Tyr Asn
        275                 280                 285

Asn Leu Leu Ala Asn Tyr Glu Lys Ile Ala Thr Arg Leu Ser Glu Val
    290                 295                 300

Asn Ser Ala Pro Pro Glu Tyr Asp Ile Asn Glu Tyr Lys Asp Tyr Phe
305                 310                 315                 320

Gln Trp Lys Tyr Gly Leu Asp Lys Asn Ala Asp Gly Ser Tyr Thr Val
```

```
                325                 330                 335

Asn Glu Asn Lys Phe Asn Glu Ile Tyr Lys Lys Leu Tyr Ser Phe Thr
            340                 345                 350

Glu Ser Asp Leu Ala Asn Lys Phe Lys Val Lys Cys Arg Asn Thr Tyr
        355                 360                 365

Phe Ile Lys Tyr Glu Phe Leu Lys Val Pro Asn Leu Leu Asp Asp Asp
    370                 375                 380

Ile Tyr Thr Val Ser Glu Gly Phe Asn Ile Gly Asn Leu Ala Val Asn
385                 390                 395                 400

Asn Arg Gly Gln Ser Ile Lys Leu Asn Pro Lys Ile Ile Asp Ser Ile
                405                 410                 415

Pro Asp Lys Gly Leu Val Glu Lys Ile Val Lys Phe Cys Lys Ser Val
            420                 425                 430

Ile Pro Arg Lys
        435


<210> SEQ ID NO 9
<211> LENGTH: 441
<212> TYPE: PRT
<213> ORGANISM: Artificial Sequence
<220> FEATURE:
<223> OTHER INFORMATION: BoNT/G Light chain Amino Acid Sequence

<400> SEQUENCE: 9

Met Pro Val Asn Ile Lys Phe Asn Tyr Asn Asp Pro Ile Asn Asn Asp
1               5                   10                  15

Asp Ile Ile Met Met Glu Pro Phe Asn Asp Pro Gly Pro Gly Thr Tyr
            20                  25                  30

Tyr Lys Ala Phe Arg Ile Ile Asp Arg Ile Trp Ile Val Pro Glu Arg
        35                  40                  45

Phe Thr Tyr Gly Phe Gln Pro Asp Gln Phe Asn Ala Ser Thr Gly Val
    50                  55                  60

Phe Ser Lys Asp Val Tyr Glu Tyr Tyr Asp Pro Thr Tyr Leu Lys Thr
65                  70                  75                  80

Asp Ala Glu Lys Asp Lys Phe Leu Lys Thr Met Ile Lys Leu Phe Asn
                85                  90                  95

Arg Ile Asn Ser Lys Pro Ser Gly Gln Arg Leu Leu Asp Met Ile Val
            100                 105                 110

Asp Ala Ile Pro Tyr Leu Gly Asn Ala Ser Thr Pro Pro Asp Lys Phe
        115                 120                 125

Ala Ala Asn Val Ala Asn Val Ser Ile Asn Lys Lys Ile Ile Gln Pro
    130                 135                 140

Gly Ala Glu Asp Gln Ile Lys Gly Leu Met Thr Asn Leu Ile Ile Phe
145                 150                 155                 160

Gly Pro Gly Pro Val Leu Ser Asp Asn Phe Thr Asp Ser Met Ile Met
                165                 170                 175

Asn Gly His Ser Pro Ile Ser Glu Gly Phe Gly Ala Arg Met Met Ile
            180                 185                 190

Arg Phe Cys Pro Ser Cys Leu Asn Val Phe Asn Asn Val Gln Glu Asn
        195                 200                 205

Lys Asp Thr Ser Ile Phe Ser Arg Arg Ala Tyr Phe Ala Asp Pro Ala
    210                 215                 220

Leu Thr Leu Met His Glu Leu Ile His Val Leu His Gly Leu Tyr Gly
225                 230                 235                 240

Ile Lys Ile Ser Asn Leu Pro Ile Thr Pro Asn Thr Lys Glu Phe Phe
```

-continued

```
                245                 250                 255

Met Gln His Ser Asp Pro Val Gln Ala Glu Glu Leu Tyr Thr Phe Gly
            260                 265                 270

Gly His Asp Pro Ser Val Ile Ser Pro Ser Thr Asp Met Asn Ile Tyr
        275                 280                 285

Asn Lys Ala Leu Gln Asn Phe Gln Asp Ile Ala Asn Arg Leu Asn Ile
    290                 295                 300

Val Ser Ser Ala Gln Gly Ser Gly Ile Asp Ile Ser Leu Tyr Lys Gln
305                 310                 315                 320

Ile Tyr Lys Asn Lys Tyr Asp Phe Val Glu Asp Pro Asn Gly Lys Tyr
                325                 330                 335

Ser Val Asp Lys Asp Lys Phe Asp Lys Leu Tyr Lys Ala Leu Met Phe
            340                 345                 350

Gly Phe Thr Glu Thr Asn Leu Ala Gly Glu Tyr Gly Ile Lys Thr Arg
        355                 360                 365

Tyr Ser Tyr Phe Ser Glu Tyr Leu Pro Pro Ile Lys Thr Glu Lys Leu
    370                 375                 380

Leu Asp Asn Thr Ile Tyr Thr Gln Asn Glu Gly Phe Asn Ile Ala Ser
385                 390                 395                 400

Lys Asn Leu Lys Thr Glu Phe Asn Gly Gln Asn Lys Ala Val Asn Lys
                405                 410                 415

Glu Ala Tyr Glu Glu Ile Ser Leu Glu His Leu Val Ile Tyr Arg Ile
            420                 425                 430

Ala Met Cys Lys Pro Val Met Tyr Lys
        435                 440


<210> SEQ ID NO 10
<211> LENGTH: 1347
<212> TYPE: DNA
<213> ORGANISM: Artificial Sequence
<220> FEATURE:
<223> OTHER INFORMATION: BoNT/A Light chain cDNA Sequence

<400> SEQUENCE: 10

atgccctttg tcaacaaaca gttcaactac aaggacccag ttaatggagt agacatcgca     60

tatatcaaga ttcccaacgc tggccagatg caacccgtta aggcatttaa aatccataac    120

aaaatctggg ttatcccaga gcgggatacc ttcaccaacc ccgaggaggg cgatctgaac    180

cccccgccgg aggcgaagca ggtcccagtg agctactacg atagcaccta cctcagcacc    240

gacaacgaga aggacaacta cctcaaagga gtcacgaagt tgttcgagag aatctactcc    300

acagacctcg gccgcatgct tctaaccagc attgtgcgtg gcattccctt ttggggcggc    360

tctaccatcg acacagagct gaaggtgata gacaccaact gcatcaacgt aatccagcct    420

gacggcagct accgaagcga ggagcttaac ctggtgatca tcggcccttc cgccgatatc    480

atccaattcg agtgcaagag cttcggccac gaggtcctga acctcacccg gaacggctat    540

ggaagcaccc agtacataag attcagccct gacttcacct tcgggtttga ggagagcttg    600

gaggtcgaca caaacccccct gctgggagcc gggaagttcg ccactgaccc agccgtgact    660

ctggcacacg agctgatcca cgccggtcac cgcctgtacg gcatagctat aaacccaaac    720

agggtgttca aagtgaacac caacgcttac tatgaaatga gcggcctgga ggtgagcttc    780

gaggagctga gaacgttcgg gggacatgat gctaaattta tcgacagcct gcaggagaac    840

gagttcaggc tgtactacta caataagttc aaggatatag cgagcactct gaacaaggcc    900

aagtccatcg taggcactac tgcatccctc cagtatatga agaatgtgtt caaagagaaa    960
```

-continued

```
tacctgctga gcgaggatac cagcggtaag ttcagcgtgg ataagcttaa gttcgacaag   1020

ctgtataaga tgctcaccga aatctacacc gaggataatt tcgttaagtt cttcaaggtc   1080

ctgaaccgga agacctacct gaacttcgac aaggccgtgt tcaagatcaa catcgtgcct   1140

aaagtgaact acaccatcta cgacgggttt aacctgagga acaccaacct ggccgctaac   1200

ttcaacgggc agaacacaga gatcaacaac atgaatttca cgaagttgaa gaacttcacc   1260

ggactgtttg agttctacaa attgctgtgt gtgcgcggga tcatcactag caagaccaag   1320

agccttgaca aaggctacaa caagtga                                       1347
```

<210> SEQ ID NO 11
<211> LENGTH: 1323
<212> TYPE: DNA
<213> ORGANISM: Artificial Sequence
<220> FEATURE:
<223> OTHER INFORMATION: BoNT/B Light chain cDNA Sequence

<400> SEQUENCE: 11

```
atgccagtta caataaataa ttttaattat aatgatccta ttgataataa taatattatt     60

atgatggagc ctccatttgc gagaggtacg gggagatatt ataaagcttt taaaatcaca    120

gatcgtattt ggataatacc ggaaagatat acttttggat ataaacctga ggattttaat    180

aaaagttccg gtatttttaa tagagatgtt tgtgaatatt atgatccaga ttacttaaat    240

actaatgata aaaagaatat atttttacaa acaatgatca agttatttaa tagaatcaaa    300

tcaaaaccat tgggtgaaaa gttattagag atgattataa atggtatacc ttatcttgga    360

gatagacgtg ttccactcga agagtttaac acaaacattg ctagtgtaac tgttaataaa    420

ttaatcagta atccaggaga agtggagcga aaaaaaggta ttttcgcaaa tttaataata    480

tttggacctg ggccagtttt aaatgaaaat gagactatag atataggtat acaaaatcat    540

tttgcatcaa gggaaggctt cgggggtata atgcaaatga agttttgccc agaatatgta    600

agcgtattta ataatgttca agaaaacaaa ggcgcaagta tatttaatag acgtggatat    660

ttttcagatc cagccttgat attaatgcat gaacttatac atgttttaca tggattatat    720

ggcattaaag tagatgattt accaattgta ccaaatgaaa aaaaattttt tatgcaatct    780

acagatgcta tacaggcaga agaactatat acatttggag gacaagatcc cagcatcata    840

actccttcta cggataaaag tatctatgat aaagttttgc aaaattttag agggatagtt    900

gatagactta acaaggtttt agtttgcata tcagatccta acattaatat taatatatat    960

aaaaataaat ttaaagataa atataaattc gttgaagatt ctgagggaaa atatagtata   1020

gatgtagaaa gttttgataa attatataaa agcttaatgt ttggttttac agaaactaat   1080

atagcagaaa attataaaat aaaaactaga gcttcttatt ttagtgattc cttaccacca   1140

gtaaaaataa aaaatttatt agataatgaa atctatacta tagaggaagg gtttaatata   1200

tctgataaag atatggaaaa agaatataga ggtcagaata aagctataaa taaacaagct   1260

tatgaagaaa ttagcaagga gcatttggct gtatataaga tacaaatgtg taaaagtgtt   1320

aaa                                                                 1323
```

<210> SEQ ID NO 12
<211> LENGTH: 1347
<212> TYPE: DNA
<213> ORGANISM: Artificial Sequence
<220> FEATURE:
<223> OTHER INFORMATION: BoNT/C Light chain cDNA Sequence

<400> SEQUENCE: 12

```
atgccaataa caattaacaa ctttaattat tcagatcctg ttgataataa aaatatttta     60
tatttagata ctcatttaaa tacactagct aatgagcctg aaaaagcctt tcgcattaca    120
ggaaatatat gggtaatacc tgatagattt tcaagaaatt ctaatccaaa tttaaataaa    180
cctcctcgag ttacaagccc taaaagtggt tattatgatc ctaattattt gagtactgat    240
tctgacaaag atacattttt aaaagaaatt ataaagttat ttaaaagaat taattctaga    300
gaaataggag aagaattaat atatagactt tcgacagata taccctttcc tgggaataac    360
aatactccaa ttaatacttt tgattttgat gtagatttta acagtgttga tgttaaaact    420
agacaaggta acaactgggt taaaactggt agcataaatc ctagtgttat aataactgga    480
cctagagaaa acattataga tccagaaact tctacgttta aattaactaa caatactttt    540
gcggcacaag aaggatttgg tgctttatca ataatttcaa tatcacctag atttatgcta    600
acatatagta atgcaactaa tgatgtagga gagggtagat ttctaagtc tgaattttgc    660
atggatccaa tactaatttt aatgcatgaa cttaatcatg caatgcataa tttatatgga    720
atagctatac caaatgatca aacaatttca tctgtaacta gtaatatttt ttattctcaa    780
tataatgtga aattagagta tgcagaaata tatgcatttg gaggtccaac tatagacctt    840
attcctaaaa gtgcaaggaa atattttgag gaaaaggcat tggattatta tagatctata    900
gctaaaagac ttaatagtat aactactgca aatccttcaa gctttaataa atatataggg    960
gaatataaac agaaacttat tagaaagtat agattcgtag tagaatcttc aggtgaagtt   1020
acagtaaatc gtaataagtt tgttgagtta tataatgaac ttacacaaat atttacagaa   1080
tttaactacg ctaaaatata taatgtacaa aataggaaaa tatatctttc aaatgtatat   1140
actccggtta cggcgaatat attagacgat aatgtttatg atatacaaaa tggatttaat   1200
atacctaaaa gtaatttaaa tgtactattt atgggtcaaa atttatctcg aaatccagca   1260
ttaagaaaag tcaatcctga aaatatgctt tatttattta caaaattttg tcataaagca   1320
atagatggta gatcattata taataaa                                       1347
```

<210> SEQ ID NO 13
<211> LENGTH: 1326
<212> TYPE: DNA
<213> ORGANISM: Artificial Sequence
<220> FEATURE:
<223> OTHER INFORMATION: BoNT/D Light chain cDNA Sequence

<400> SEQUENCE: 13

```
atgacatggc cagtaaaaga ttttaattat agtgatcctg ttaatgacaa tgatatatta     60
tatttaagaa taccacaaaa taagttaatt actacacctg taaaagcttt tatgattact    120
caaaatattt gggtaatacc agaaagattt tcatcagata ctaatccaag tttaagtaaa    180
ccgcccagac ctacttcaaa gtatcaaagt tattatgatc ctagttattt atctactgat    240
gaacaaaaag atacattttt aaaagggatt ataaaattat ttaaaagaat taatgaaaga    300
gatataggaa aaaaattaat aaattattta gtagttggtt caccttttat gggagattca    360
agtacgcctg aagatacatt tgattttaca cgtcatacta ctaatattgc agttgaaaag    420
tttgaaaatg gtagttggaa agtaacaaat attataacac caagtgtatt gatatttgga    480
ccacttccta atatattaga ctatacagca tcccttacat tgcaaggaca acaatcaaat    540
ccatcatttg aagggtttgg aacattatct atactaaaag tagcacctga atttttgtta    600
acatttagtg atgtaacatc taatcaaagt tcagctgtat taggcaaatc tatattttgt    660
```

```
atggatccag taatagcttt aatgcatgag ttaacacatt ctttgcatca attatatgga    720

ataaatatac catctgataa aaggattcgt ccacaagtta gcgagggatt tttctctcaa    780

gatggaccca acgtacaatt tgaggaatta tatacatttg gaggattaga tgttgaaata    840

atacctcaaa ttgaaagatc acaattaaga gaaaaagcat taggtcacta taaagatata    900

gcgaaaagac ttaataatat taataaaact attccttcta gttggattag taatatagat    960

aaatataaaa aaatatttc tgaaaagtat aattttgata aagataatac aggaaatttt   1020

gttgtaaata ttgataaatt caatagctta tattcagact tgactaatgt tatgtcagaa   1080

gttgtttatt cttcgcaata taatgttaaa aacaggactc attattttc aaggcattat   1140

ctacctgtat ttgcaaatat attagatgat aatatttata ctataagaga tggttttaat   1200

ttaacaaata aaggttttaa tatagaaaat tcgggtcaga atatagaaag gaatcctgca   1260

ctacaaaagc ttagttcaga aagtgtagta gatttattta caaaagtatg tttaagatta   1320

acaaaa                                                              1326
```

<210> SEQ ID NO 14
<211> LENGTH: 1266
<212> TYPE: DNA
<213> ORGANISM: Artificial Sequence
<220> FEATURE:
<223> OTHER INFORMATION: BoNT/E Light chain cDNA Sequence

<400> SEQUENCE: 14

```
atgccaacaa ttaatagttt taattataat gatcctgtta ataatagaac aattttatat     60

attaaaccag gcggttgtca acaattttat aaatcattta atattatgaa aaatatttgg    120

ataattccag agagaaatgt aattggtaca attccccaag attttcttcc gcctacttca    180

ttgaaaaatg gagatagtag ttattatgac cctaattatt tacaaagtga tcaagaaaag    240

gataaatttt taaaaatagt cacaaaaata tttaatagaa taaatgataa tctttcagga    300

aggattttat tagaagaact gtcaaaagct aatccatatt taggaaatga taatactcca    360

gatggtgact tcattattaa tgatgcatca gcagttccaa ttcaattctc aaatggtagc    420

caaagcatac tattacctaa tgttattata atgggagcag agcctgattt atttgaaact    480

aacagttcca atatttctct aagaaataat tatatgccaa gcaatcacgg ttttggatca    540

atagctatag taacattctc acctgaatat tcttttagat ttaaagataa tagtatgaat    600

gaatttattc aagatcctgc tcttacatta atgcatgaat taatacattc attacatgga    660

ctatatgggg ctaaagggat tactacaaag tatactataa cacaaaaaca aaatccccta    720

ataacaaata taagaggtac aaatattgaa gaattcttaa cttttggagg tactgattta    780

aacattatta ctagtgctca gtccaatgat atctatacta atcttctagc tgattataaa    840

aaaatagcgt ctaaacttag caaagtacaa gtatctaatc cactacttaa tccttataaa    900

gatgtttttg aagcaaagta tggattagat aaagatgcta gcggaattta ttcggtaaat    960

ataaacaaat ttaatgatat ttttaaaaaa ttatacagct ttacggaatt tgatttagca   1020

actaaatttc aagttaaatg taggcaaact tatattggac agtataaata cttcaaactt   1080

tcaaacttgt taaatgattc tatttataat atatcagaag gctataatat aaataattta   1140

aaggtaaatt ttagaggaca gaatgcaaat ttaaatccta gaattattac accaattaca   1200

ggtagaggac tagtaaaaaa aatcattaga ttttgtaaaa atattgtttc tgtaaaaggc   1260

ataagg                                                              1266
```

<210> SEQ ID NO 15
<211> LENGTH: 1308
<212> TYPE: DNA
<213> ORGANISM: Artificial Sequence
<220> FEATURE:
<223> OTHER INFORMATION: BoNT/F Light chain cDNA Sequence

<400> SEQUENCE: 15
atgccagttg caataaatag ttttaattat aatgaccctg ttaatgatga tacaatttta 60
tacatgcaga taccatatga agaaaaaagt aaaaaatatt ataaagcttt tgagattatg 120
cgtaatgttt ggataattcc tgagagaaat acaataggaa cgaatcctag tgattttgat 180
ccaccggctt cattaaagaa cggaagcagt gcttattatg atcctaatta tttaaccact 240
gatgctgaaa aagatagata tttaaaaaca acgataaaat tatttaagag aattaatagt 300
aatcctgcag ggaaagtttt gttacaagaa atatcatatg ctaaaccata tttaggaaat 360
gaccacacgc caattgatga attctctcca gttactagaa ctacaagtgt taatataaaa 420
ttatcaacta atgttgaaag ttcaatgtta ttgaatcttc ttgtattggg agcaggacct 480
gatatatttg aaagttgttg ttaccccgtt agaaaactaa tagatccaga tgtagtttat 540
gatccaagta attatggttt tggatcaatt aatatcgtga cattttcacc tgagtatgaa 600
tatactttta atgatattag tggagggcat aatagtagta cagaatcatt tattgcagat 660
cctgcaattt cactagctca tgaattgata catgcactgc atggattata cggggctagg 720
ggagttactt atgaagagac tatagaagta aagcaagcac ctcttatgat agccgaaaaa 780
cccataaggc tagaagaatt tttaaccttt ggaggtcagg atttaaatat tattactagt 840
gctatgaagg aaaaaatata taacaatctt ttagctaact atgaaaaaat agctactaga 900
cttagtgaag ttaatagtgc tcctcctgaa tatgatatta atgaatataa agattatttt 960
caatggaagt atgggctaga taaaaatgct gatggaagtt atactgtaaa tgaaaataaa 1020
tttaatgaaa tttataaaaa attatatagt tttacagaga gtgacttagc aaataaattt 1080
aaagtaaaat gtagaaatac ttattttatt aaatatgaat ttttaaaagt tccaaatttg 1140
ttagatgatg atatttatac tgtatcagag ggttttaata taggtaattt agcagtaaac 1200
aatcgcggac aaagtataaa gttaaatcct aaaattattg attccattcc agataaaggt 1260
ctagtagaaa agatcgttaa attttgtaag agcgttattc ctagaaaa 1308

<210> SEQ ID NO 16
<211> LENGTH: 1326
<212> TYPE: DNA
<213> ORGANISM: Artificial Sequence
<220> FEATURE:
<223> OTHER INFORMATION: BoNT/G Light chain cDNA Sequence
<220> FEATURE:
<221> NAME/KEY: misc_feature
<222> LOCATION: (20)..(20)
<223> OTHER INFORMATION: n is a, c, g, or t

<400> SEQUENCE: 16
atgccagtta atataaaaan ctttaattat aatgacccta ttaataatga tgacattatt 60
atgatggaac cattcaatga cccagggcca ggaacatatt ataaagcttt taggattata 120
gatcgtattt ggatagtacc agaaaggttt acttatggat ttcaacctga ccaatttaat 180
gccagtacag gagtttttag taaagatgtc tacgaatatt acgatccaac ttatttaaaa 240
accgatgctg aaaaagataa atttttaaaa acaatgatta aattatttaa tagaattaat 300
tcaaaaccat caggacagag attactggat atgatagtag atgctatacc ttatcttgga 360

```
aatgcatcta caccgcccga caaatttgca gcaaatgttg caaatgtatc tattaataaa    420

aaaattatcc aacctggagc tgaagatcaa ataaaaggtt taatgacaaa tttaataata    480

tttggaccag gaccagttct aagtgataat tttactgata gtatgattat gaatggccat    540

tccccaatat cagaaggatt tggtgcaaga atgatgataa gattttgtcc tagttgttta    600

aatgtattta ataatgttca ggaaaataaa gatacatcta tatttagtag acgcgcgtat    660

tttgcagatc cagctctaac gttaatgcat gaacttatac atgtgttaca tggattatat    720

ggaattaaga taagtaattt accaattact ccaaatacaa aagaattttt catgcaacat    780

agcgatcctg tacaagcaga agaactatat acattcggag gacatgatcc tagtgttata    840

agtccttcta cggatatgaa tatttataat aaagcgttac aaaattttca agatatagct    900

aataggctta atattgtttc aagtgcccaa gggagtggaa ttgatatttc cttatataaa    960

caaatatata aaaataaata tgattttgtt gaagatccta atggaaaata tagtgtagat   1020

aaggataagt ttgataaatt atataaggcc ttaatgtttg gctttactga aactaatcta   1080

gctggtgaat atggaataaa aactaggtat tcttatttta gtgaatattt gccaccgata   1140

aaaactgaaa aattgttaga caatacaatt tatactcaaa atgaaggctt taacatagct   1200

agtaaaaatc tcaaaacgga atttaatggt cagaataagg cggtaaataa agaggcttat   1260

gaagaaatca gcctagaaca tctcgttata tatagaatag caatgtgcaa gcctgtaatg   1320

tacaaa                                                               1326
```

```
<210> SEQ ID NO 17
<211> LENGTH: 468
<212> TYPE: PRT
<213> ORGANISM: Artificial Sequence
<220> FEATURE:
<223> OTHER INFORMATION: BoNT/A Light chain Amino Acid Sequence with
      hexahistidine

<400> SEQUENCE: 17

Met Gly Ser Ser His His His His His His Ser Ser Gly Leu Val Pro
1               5                   10                  15

Arg Gly Ser His Met Pro Phe Val Asn Lys Gln Phe Asn Tyr Lys Asp
            20                  25                  30

Pro Val Asn Gly Val Asp Ile Ala Tyr Ile Lys Ile Pro Asn Ala Gly
        35                  40                  45

Gln Met Gln Pro Val Lys Ala Phe Lys Ile His Asn Lys Ile Trp Val
    50                  55                  60

Ile Pro Glu Arg Asp Thr Phe Thr Asn Pro Glu Glu Gly Asp Leu Asn
65                  70                  75                  80

Pro Pro Pro Glu Ala Lys Gln Val Pro Val Ser Tyr Tyr Asp Ser Thr
                85                  90                  95

Tyr Leu Ser Thr Asp Asn Glu Lys Asp Asn Tyr Leu Lys Gly Val Thr
            100                 105                 110

Lys Leu Phe Glu Arg Ile Tyr Ser Thr Asp Leu Gly Arg Met Leu Leu
        115                 120                 125

Thr Ser Ile Val Arg Gly Ile Pro Phe Trp Gly Gly Ser Thr Ile Asp
    130                 135                 140

Thr Glu Leu Lys Val Ile Asp Thr Asn Cys Ile Asn Val Ile Gln Pro
145                 150                 155                 160

Asp Gly Ser Tyr Arg Ser Glu Glu Leu Asn Leu Val Ile Ile Gly Pro
                165                 170                 175
```

-continued

```
Ser Ala Asp Ile Ile Gln Phe Glu Cys Lys Ser Phe Gly His Glu Val
            180                 185                 190

Leu Asn Leu Thr Arg Asn Gly Tyr Gly Ser Thr Gln Tyr Ile Arg Phe
        195                 200                 205

Ser Pro Asp Phe Thr Phe Gly Phe Glu Glu Ser Leu Glu Val Asp Thr
    210                 215                 220

Asn Pro Leu Leu Gly Ala Gly Lys Phe Ala Thr Asp Pro Ala Val Thr
225                 230                 235                 240

Leu Ala His Glu Leu Ile His Ala Gly His Arg Leu Tyr Gly Ile Ala
                245                 250                 255

Ile Asn Pro Asn Arg Val Phe Lys Val Asn Thr Asn Ala Tyr Tyr Glu
            260                 265                 270

Met Ser Gly Leu Glu Val Ser Phe Glu Glu Leu Arg Thr Phe Gly Gly
        275                 280                 285

His Asp Ala Lys Phe Ile Asp Ser Leu Gln Glu Asn Glu Phe Arg Leu
    290                 295                 300

Tyr Tyr Tyr Asn Lys Phe Lys Asp Ile Ala Ser Thr Leu Asn Lys Ala
305                 310                 315                 320

Lys Ser Ile Val Gly Thr Thr Ala Ser Leu Gln Tyr Met Lys Asn Val
                325                 330                 335

Phe Lys Glu Lys Tyr Leu Leu Ser Glu Asp Thr Ser Gly Lys Phe Ser
            340                 345                 350

Val Asp Lys Leu Lys Phe Asp Lys Leu Tyr Lys Met Leu Thr Glu Ile
        355                 360                 365

Tyr Thr Glu Asp Asn Phe Val Lys Phe Phe Lys Val Leu Asn Arg Lys
    370                 375                 380

Thr Tyr Leu Asn Phe Asp Lys Ala Val Phe Lys Ile Asn Ile Val Pro
385                 390                 395                 400

Lys Val Asn Tyr Thr Ile Tyr Asp Gly Phe Asn Leu Arg Asn Thr Asn
                405                 410                 415

Leu Ala Ala Asn Phe Asn Gly Gln Asn Thr Glu Ile Asn Asn Met Asn
            420                 425                 430

Phe Thr Lys Leu Lys Asn Phe Thr Gly Leu Phe Glu Phe Tyr Lys Leu
        435                 440                 445

Leu Cys Val Arg Gly Ile Ile Thr Ser Lys Thr Lys Ser Leu Asp Lys
    450                 455                 460

Gly Tyr Asn Lys
465


<210> SEQ ID NO 18
<211> LENGTH: 461
<212> TYPE: PRT
<213> ORGANISM: Artificial Sequence
<220> FEATURE:
<223> OTHER INFORMATION: BoNT/B Light chain Amino Acid Sequence with
      hexahistidine

<400> SEQUENCE: 18

Met Gly Ser Ser His His His His His His Ser Ser Gly Leu Val Pro
1               5                   10                  15

Arg Gly Ser His Met Pro Val Thr Ile Asn Asn Phe Asn Tyr Asn Asp
            20                  25                  30

Pro Ile Asp Asn Asn Asn Ile Ile Met Met Glu Pro Pro Phe Ala Arg
        35                  40                  45

Gly Thr Gly Arg Tyr Tyr Lys Ala Phe Lys Ile Thr Asp Arg Ile Trp
    50                  55                  60
```

```
Ile Ile Pro Glu Arg Tyr Thr Phe Gly Tyr Lys Pro Glu Asp Phe Asn
65                  70                  75                  80

Lys Ser Ser Gly Ile Phe Asn Arg Asp Val Cys Glu Tyr Tyr Asp Pro
                85                  90                  95

Asp Tyr Leu Asn Thr Asn Asp Lys Lys Asn Ile Phe Leu Gln Thr Met
            100                 105                 110

Ile Lys Leu Phe Asn Arg Ile Lys Ser Lys Pro Leu Gly Glu Lys Leu
        115                 120                 125

Leu Glu Met Ile Ile Asn Gly Ile Pro Tyr Leu Gly Asp Arg Arg Val
    130                 135                 140

Pro Leu Glu Glu Phe Asn Thr Asn Ile Ala Ser Val Thr Val Asn Lys
145                 150                 155                 160

Leu Ile Ser Asn Pro Gly Glu Val Glu Arg Lys Lys Gly Ile Phe Ala
                165                 170                 175

Asn Leu Ile Ile Phe Gly Pro Gly Pro Val Leu Asn Glu Asn Glu Thr
            180                 185                 190

Ile Asp Ile Gly Ile Gln Asn His Phe Ala Ser Arg Glu Gly Phe Gly
        195                 200                 205

Gly Ile Met Gln Met Lys Phe Cys Pro Glu Tyr Val Ser Val Phe Asn
    210                 215                 220

Asn Val Gln Glu Asn Lys Gly Ala Ser Ile Phe Asn Arg Arg Gly Tyr
225                 230                 235                 240

Phe Ser Asp Pro Ala Leu Ile Leu Met His Glu Leu Ile His Val Leu
                245                 250                 255

His Gly Leu Tyr Gly Ile Lys Val Asp Asp Leu Pro Ile Val Pro Asn
            260                 265                 270

Glu Lys Lys Phe Phe Met Gln Ser Thr Asp Ala Ile Gln Ala Glu Glu
        275                 280                 285

Leu Tyr Thr Phe Gly Gly Gln Asp Pro Ser Ile Ile Thr Pro Ser Thr
    290                 295                 300

Asp Lys Ser Ile Tyr Asp Lys Val Leu Gln Asn Phe Arg Gly Ile Val
305                 310                 315                 320

Asp Arg Leu Asn Lys Val Leu Val Cys Ile Ser Asp Pro Asn Ile Asn
                325                 330                 335

Ile Asn Ile Tyr Lys Asn Lys Phe Lys Asp Lys Tyr Lys Phe Val Glu
            340                 345                 350

Asp Ser Glu Gly Lys Tyr Ser Ile Asp Val Glu Ser Phe Asp Lys Leu
        355                 360                 365

Tyr Lys Ser Leu Met Phe Gly Phe Thr Glu Thr Asn Ile Ala Glu Asn
    370                 375                 380

Tyr Lys Ile Lys Thr Arg Ala Ser Tyr Phe Ser Asp Ser Leu Pro Pro
385                 390                 395                 400

Val Lys Ile Lys Asn Leu Leu Asp Asn Glu Ile Tyr Thr Ile Glu Glu
                405                 410                 415

Gly Phe Asn Ile Ser Asp Lys Asp Met Glu Lys Glu Tyr Arg Gly Gln
            420                 425                 430

Asn Lys Ala Ile Asn Lys Gln Ala Tyr Glu Glu Ile Ser Lys Glu His
        435                 440                 445

Leu Ala Val Tyr Lys Ile Gln Met Cys Lys Ser Val Lys
    450                 455                 460
```

<210> SEQ ID NO 19
<211> LENGTH: 469

<212> TYPE: PRT
<213> ORGANISM: Artificial Sequence
<220> FEATURE:
<223> OTHER INFORMATION: BoNT/C Light chain Amino Acid Sequence with hexahistidine

<400> SEQUENCE: 19

```
Met Gly Ser Ser His His His His His His Ser Ser Gly Leu Val Pro
1               5                   10                  15

Arg Gly Ser His Met Pro Ile Thr Ile Asn Asn Phe Asn Tyr Ser Asp
            20                  25                  30

Pro Val Asp Asn Lys Asn Ile Leu Tyr Leu Asp Thr His Leu Asn Thr
        35                  40                  45

Leu Ala Asn Glu Pro Glu Lys Ala Phe Arg Ile Thr Gly Asn Ile Trp
    50                  55                  60

Val Ile Pro Asp Arg Phe Ser Arg Asn Ser Asn Pro Asn Leu Asn Lys
65                  70                  75                  80

Pro Pro Arg Val Thr Ser Pro Lys Ser Gly Tyr Tyr Asp Pro Asn Tyr
                85                  90                  95

Leu Ser Thr Asp Ser Asp Lys Asp Pro Phe Leu Lys Glu Ile Ile Lys
            100                 105                 110

Leu Phe Lys Arg Ile Asn Ser Arg Glu Ile Gly Glu Glu Leu Ile Tyr
        115                 120                 125

Arg Leu Ser Thr Asp Ile Pro Phe Pro Gly Asn Asn Asn Thr Pro Ile
    130                 135                 140

Asn Thr Phe Asp Phe Asp Val Asp Phe Asn Ser Val Asp Val Lys Thr
145                 150                 155                 160

Arg Gln Gly Asn Asn Trp Val Lys Thr Gly Ser Ile Asn Pro Ser Val
                165                 170                 175

Ile Ile Thr Gly Pro Arg Glu Asn Ile Ile Asp Pro Glu Thr Ser Thr
            180                 185                 190

Phe Lys Leu Thr Asn Asn Thr Phe Ala Ala Gln Glu Gly Phe Gly Ala
        195                 200                 205

Leu Ser Ile Ile Ser Ile Ser Pro Arg Phe Met Leu Thr Tyr Ser Asn
    210                 215                 220

Ala Thr Asn Asp Val Gly Glu Gly Arg Phe Ser Lys Ser Glu Phe Cys
225                 230                 235                 240

Met Asp Pro Ile Leu Ile Leu Met His Glu Leu Asn His Ala Met His
                245                 250                 255

Asn Leu Tyr Gly Ile Ala Ile Pro Asn Asp Gln Thr Ile Ser Ser Val
            260                 265                 270

Thr Ser Asn Ile Phe Tyr Ser Gln Tyr Asn Val Lys Leu Glu Tyr Ala
        275                 280                 285

Glu Ile Tyr Ala Phe Gly Gly Pro Thr Ile Asp Leu Ile Pro Lys Ser
    290                 295                 300

Ala Arg Lys Tyr Phe Glu Glu Lys Ala Leu Asp Tyr Tyr Arg Ser Ile
305                 310                 315                 320

Ala Lys Arg Leu Asn Ser Ile Thr Thr Ala Asn Pro Ser Ser Phe Asn
                325                 330                 335

Lys Tyr Ile Gly Glu Tyr Lys Gln Lys Leu Ile Arg Lys Tyr Arg Phe
            340                 345                 350

Val Val Glu Ser Ser Gly Glu Val Thr Val Asn Arg Asn Lys Phe Val
        355                 360                 365

Glu Leu Tyr Asn Glu Leu Thr Gln Ile Phe Thr Glu Phe Asn Tyr Ala
    370                 375                 380
```

```
Lys Ile Tyr Asn Val Gln Asn Arg Lys Ile Tyr Leu Ser Asn Val Tyr
385                 390                 395                 400

Thr Pro Val Thr Ala Asn Ile Leu Asp Asp Asn Val Tyr Asp Ile Gln
                405                 410                 415

Asn Gly Phe Asn Ile Pro Lys Ser Asn Leu Asn Val Leu Phe Met Gly
            420                 425                 430

Gln Asn Leu Ser Arg Asn Pro Ala Leu Arg Lys Val Asn Pro Glu Asn
        435                 440                 445

Met Leu Tyr Leu Phe Thr Lys Phe Cys His Lys Ala Ile Asp Gly Arg
    450                 455                 460

Ser Leu Tyr Asn Lys
465


<210> SEQ ID NO 20
<211> LENGTH: 462
<212> TYPE: PRT
<213> ORGANISM: Artificial Sequence
<220> FEATURE:
<223> OTHER INFORMATION: BoNT/D Light chain Amino Acid Sequence with
      hexahistidine

<400> SEQUENCE: 20

Met Gly Ser Ser His His His His His His Ser Ser Gly Leu Val Pro
1               5                   10                  15

Arg Gly Ser His Met Thr Trp Pro Val Lys Asp Phe Asn Tyr Ser Asp
            20                  25                  30

Pro Val Asn Asp Asn Asp Ile Leu Tyr Leu Arg Ile Pro Gln Asn Lys
        35                  40                  45

Leu Ile Thr Thr Pro Val Lys Ala Phe Met Ile Thr Gln Asn Ile Trp
    50                  55                  60

Val Ile Pro Glu Arg Phe Ser Ser Asp Thr Asn Pro Ser Leu Ser Lys
65                  70                  75                  80

Pro Pro Arg Pro Thr Ser Lys Tyr Gln Ser Tyr Tyr Asp Pro Ser Tyr
                85                  90                  95

Leu Ser Thr Asp Glu Gln Lys Asp Thr Phe Leu Lys Gly Ile Ile Lys
            100                 105                 110

Leu Phe Lys Arg Ile Asn Glu Arg Asp Ile Gly Lys Lys Leu Ile Asn
        115                 120                 125

Tyr Leu Val Val Gly Ser Pro Phe Met Gly Asp Ser Ser Thr Pro Glu
    130                 135                 140

Asp Thr Phe Asp Phe Thr Arg His Thr Thr Asn Ile Ala Val Glu Lys
145                 150                 155                 160

Phe Glu Asn Gly Ser Trp Lys Val Thr Asn Ile Ile Thr Pro Ser Val
                165                 170                 175

Leu Ile Phe Gly Pro Leu Pro Asn Ile Leu Asp Tyr Thr Ala Ser Leu
            180                 185                 190

Thr Leu Gln Gly Gln Gln Ser Asn Pro Ser Phe Glu Gly Phe Gly Thr
        195                 200                 205

Leu Ser Ile Leu Lys Val Ala Pro Glu Phe Leu Leu Thr Phe Ser Asp
    210                 215                 220

Val Thr Ser Asn Gln Ser Ser Ala Val Leu Gly Lys Ser Ile Phe Cys
225                 230                 235                 240

Met Asp Pro Val Ile Ala Leu Met His Glu Leu Thr His Ser Leu His
                245                 250                 255

Gln Leu Tyr Gly Ile Asn Ile Pro Ser Asp Lys Arg Ile Arg Pro Gln
```

-continued

```
            260                 265                 270

Val Ser Glu Gly Phe Phe Ser Gln Asp Gly Pro Asn Val Gln Phe Glu
        275                 280                 285

Glu Leu Tyr Thr Phe Gly Gly Leu Asp Val Glu Ile Ile Pro Gln Ile
    290                 295                 300

Glu Arg Ser Gln Leu Arg Glu Lys Ala Leu Gly His Tyr Lys Asp Ile
305                 310                 315                 320

Ala Lys Arg Leu Asn Asn Ile Asn Lys Thr Ile Pro Ser Ser Trp Ile
                325                 330                 335

Ser Asn Ile Asp Lys Tyr Lys Lys Ile Phe Ser Glu Lys Tyr Asn Phe
            340                 345                 350

Asp Lys Asp Asn Thr Gly Asn Phe Val Val Asn Ile Asp Lys Phe Asn
        355                 360                 365

Ser Leu Tyr Ser Asp Leu Thr Asn Val Met Ser Glu Val Val Tyr Ser
    370                 375                 380

Ser Gln Tyr Asn Val Lys Asn Arg Thr His Tyr Phe Ser Arg His Tyr
385                 390                 395                 400

Leu Pro Val Phe Ala Asn Ile Leu Asp Asp Asn Ile Tyr Thr Ile Arg
                405                 410                 415

Asp Gly Phe Asn Leu Thr Asn Lys Gly Phe Asn Ile Glu Asn Ser Gly
            420                 425                 430

Gln Asn Ile Glu Arg Asn Pro Ala Leu Gln Lys Leu Ser Ser Glu Ser
        435                 440                 445

Val Val Asp Leu Phe Thr Lys Val Cys Leu Arg Leu Thr Lys
    450                 455                 460


<210> SEQ ID NO 21
<211> LENGTH: 442
<212> TYPE: PRT
<213> ORGANISM: Artificial Sequence
<220> FEATURE:
<223> OTHER INFORMATION: BoNT/E Light chain Amino Acid Sequence with
      hexahistidine

<400> SEQUENCE: 21

Met Gly Ser Ser His His His His His His Ser Ser Gly Leu Val Pro
1               5                   10                  15

Arg Gly Ser His Met Pro Thr Ile Asn Ser Phe Asn Tyr Asn Asp Pro
            20                  25                  30

Val Asn Asn Arg Thr Ile Leu Tyr Ile Lys Pro Gly Gly Cys Gln Gln
        35                  40                  45

Phe Tyr Lys Ser Phe Asn Ile Met Lys Asn Ile Trp Ile Ile Pro Glu
    50                  55                  60

Arg Asn Val Ile Gly Thr Ile Pro Gln Asp Phe Leu Pro Pro Thr Ser
65                  70                  75                  80

Leu Lys Asn Gly Asp Ser Ser Tyr Tyr Asp Pro Asn Tyr Leu Gln Ser
                85                  90                  95

Asp Gln Glu Lys Asp Lys Phe Leu Lys Ile Val Thr Lys Ile Phe Asn
            100                 105                 110

Arg Ile Asn Asp Asn Leu Ser Gly Arg Ile Leu Leu Glu Glu Leu Ser
        115                 120                 125

Lys Ala Asn Pro Tyr Leu Gly Asn Asp Asn Thr Pro Asp Gly Asp Phe
    130                 135                 140

Ile Ile Asn Asp Ala Ser Ala Val Pro Ile Gln Phe Ser Asn Gly Ser
145                 150                 155                 160
```

```
Gln Ser Ile Leu Leu Pro Asn Val Ile Ile Met Gly Ala Glu Pro Asp
                165                 170                 175

Leu Phe Glu Thr Asn Ser Ser Asn Ile Ser Leu Arg Asn Asn Tyr Met
            180                 185                 190

Pro Ser Asn His Gly Phe Gly Ser Ile Ala Ile Val Thr Phe Ser Pro
        195                 200                 205

Glu Tyr Ser Phe Arg Phe Lys Asp Asn Ser Met Asn Glu Phe Ile Gln
    210                 215                 220

Asp Pro Ala Leu Thr Leu Met His Glu Leu Ile His Ser Leu His Gly
225                 230                 235                 240

Leu Tyr Gly Ala Lys Gly Ile Thr Thr Lys Tyr Thr Ile Thr Gln Lys
                245                 250                 255

Gln Asn Pro Leu Ile Thr Asn Ile Arg Gly Thr Asn Ile Glu Glu Phe
            260                 265                 270

Leu Thr Phe Gly Gly Thr Asp Leu Asn Ile Ile Thr Ser Ala Gln Ser
        275                 280                 285

Asn Asp Ile Tyr Thr Asn Leu Leu Ala Asp Tyr Lys Lys Ile Ala Ser
    290                 295                 300

Lys Leu Ser Lys Val Gln Val Ser Asn Pro Leu Leu Asn Pro Tyr Lys
305                 310                 315                 320

Asp Val Phe Glu Ala Lys Tyr Gly Leu Asp Lys Asp Ala Ser Gly Ile
                325                 330                 335

Tyr Ser Val Asn Ile Asn Lys Phe Asn Asp Ile Phe Lys Lys Leu Tyr
            340                 345                 350

Ser Phe Thr Glu Phe Asp Leu Ala Thr Lys Phe Gln Val Lys Cys Arg
        355                 360                 365

Gln Thr Tyr Ile Gly Gln Tyr Lys Tyr Phe Lys Leu Ser Asn Leu Leu
    370                 375                 380

Asn Asp Ser Ile Tyr Asn Ile Ser Glu Gly Tyr Asn Ile Asn Asn Leu
385                 390                 395                 400

Lys Val Asn Phe Arg Gly Gln Asn Ala Asn Leu Asn Pro Arg Ile Ile
                405                 410                 415

Thr Pro Ile Thr Gly Arg Gly Leu Val Lys Lys Ile Ile Arg Phe Cys
            420                 425                 430

Lys Asn Ile Val Ser Val Lys Gly Ile Arg
        435                 440


<210> SEQ ID NO 22
<211> LENGTH: 456
<212> TYPE: PRT
<213> ORGANISM: Artificial Sequence
<220> FEATURE:
<223> OTHER INFORMATION: BoNT/F Light chain Amino Acid Sequence with
      hexahistidine

<400> SEQUENCE: 22

Met Gly Ser Ser His His His His His His Ser Ser Gly Leu Val Pro
1               5                   10                  15

Arg Gly Ser His Met Pro Val Ala Ile Asn Ser Phe Asn Tyr Asn Asp
            20                  25                  30

Pro Val Asn Asp Asp Thr Ile Leu Tyr Met Gln Ile Pro Tyr Glu Glu
        35                  40                  45

Lys Ser Lys Lys Tyr Tyr Lys Ala Phe Glu Ile Met Arg Asn Val Trp
    50                  55                  60

Ile Ile Pro Glu Arg Asn Thr Ile Gly Thr Asn Pro Ser Asp Phe Asp
65                  70                  75                  80
```

-continued

Pro Pro Ala Ser Leu Lys Asn Gly Ser Ser Ala Tyr Tyr Asp Pro Asn
85 90 95

Tyr Leu Thr Thr Asp Ala Glu Lys Asp Arg Tyr Leu Lys Thr Thr Ile
100 105 110

Lys Leu Phe Lys Arg Ile Asn Ser Asn Pro Ala Gly Lys Val Leu Leu
115 120 125

Gln Glu Ile Ser Tyr Ala Lys Pro Tyr Leu Gly Asn Asp His Thr Pro
130 135 140

Ile Asp Glu Phe Ser Pro Val Thr Arg Thr Thr Ser Val Asn Ile Lys
145 150 155 160

Leu Ser Thr Asn Val Glu Ser Ser Met Leu Leu Asn Leu Leu Val Leu
165 170 175

Gly Ala Gly Pro Asp Ile Phe Glu Ser Cys Cys Tyr Pro Val Arg Lys
180 185 190

Leu Ile Asp Pro Asp Val Val Tyr Asp Pro Ser Asn Tyr Gly Phe Gly
195 200 205

Ser Ile Asn Ile Val Thr Phe Ser Pro Glu Tyr Glu Tyr Thr Phe Asn
210 215 220

Asp Ile Ser Gly Gly His Asn Ser Ser Thr Glu Ser Phe Ile Ala Asp
225 230 235 240

Pro Ala Ile Ser Leu Ala His Glu Leu Ile His Ala Leu His Gly Leu
245 250 255

Tyr Gly Ala Arg Gly Val Thr Tyr Glu Glu Thr Ile Glu Val Lys Gln
260 265 270

Ala Pro Leu Met Ile Ala Glu Lys Pro Ile Arg Leu Glu Glu Phe Leu
275 280 285

Thr Phe Gly Gly Gln Asp Leu Asn Ile Ile Thr Ser Ala Met Lys Glu
290 295 300

Lys Ile Tyr Asn Asn Leu Leu Ala Asn Tyr Glu Lys Ile Ala Thr Arg
305 310 315 320

Leu Ser Glu Val Asn Ser Ala Pro Pro Glu Tyr Asp Ile Asn Glu Tyr
325 330 335

Lys Asp Tyr Phe Gln Trp Lys Tyr Gly Leu Asp Lys Asn Ala Asp Gly
340 345 350

Ser Tyr Thr Val Asn Glu Asn Lys Phe Asn Glu Ile Tyr Lys Lys Leu
355 360 365

Tyr Ser Phe Thr Glu Ser Asp Leu Ala Asn Lys Phe Lys Val Lys Cys
370 375 380

Arg Asn Thr Tyr Phe Ile Lys Tyr Glu Phe Leu Lys Val Pro Asn Leu
385 390 395 400

Leu Asp Asp Asp Ile Tyr Thr Val Ser Glu Gly Phe Asn Ile Gly Asn
405 410 415

Leu Ala Val Asn Asn Arg Gly Gln Ser Ile Lys Leu Asn Pro Lys Ile
420 425 430

Ile Asp Ser Ile Pro Asp Lys Gly Leu Val Glu Lys Ile Val Lys Phe
435 440 445

Cys Lys Ser Val Ile Pro Arg Lys
450 455

<210> SEQ ID NO 23
<211> LENGTH: 461
<212> TYPE: PRT
<213> ORGANISM: Artificial Sequence
<220> FEATURE:

-continued

<223> OTHER INFORMATION: BoNT/G Light chain Amino Acid Sequence with
hexahistidine

<400> SEQUENCE: 23

```
Met Gly Ser Ser His His His His His His Ser Ser Gly Leu Val Pro
1               5                   10                  15

Arg Gly Ser His Met Pro Val Asn Ile Lys Phe Asn Tyr Asn Asp Pro
            20                  25                  30

Ile Asn Asn Asp Asp Ile Ile Met Met Glu Pro Phe Asn Asp Pro Gly
        35                  40                  45

Pro Gly Thr Tyr Tyr Lys Ala Phe Arg Ile Ile Asp Arg Ile Trp Ile
    50                  55                  60

Val Pro Glu Arg Phe Thr Tyr Gly Phe Gln Pro Asp Gln Phe Asn Ala
65                  70                  75                  80

Ser Thr Gly Val Phe Ser Lys Asp Val Tyr Glu Tyr Tyr Asp Pro Thr
                85                  90                  95

Tyr Leu Lys Thr Asp Ala Glu Lys Asp Lys Phe Leu Lys Thr Met Ile
            100                 105                 110

Lys Leu Phe Asn Arg Ile Asn Ser Lys Pro Ser Gly Gln Arg Leu Leu
        115                 120                 125

Asp Met Ile Val Asp Ala Ile Pro Tyr Leu Gly Asn Ala Ser Thr Pro
    130                 135                 140

Pro Asp Lys Phe Ala Ala Asn Val Ala Asn Val Ser Ile Asn Lys Lys
145                 150                 155                 160

Ile Ile Gln Pro Gly Ala Glu Asp Gln Ile Lys Gly Leu Met Thr Asn
                165                 170                 175

Leu Ile Ile Phe Gly Pro Gly Pro Val Leu Ser Asp Asn Phe Thr Asp
            180                 185                 190

Ser Met Ile Met Asn Gly His Ser Pro Ile Ser Glu Gly Phe Gly Ala
        195                 200                 205

Arg Met Met Ile Arg Phe Cys Pro Ser Cys Leu Asn Val Phe Asn Asn
    210                 215                 220

Val Gln Glu Asn Lys Asp Thr Ser Ile Phe Ser Arg Arg Ala Tyr Phe
225                 230                 235                 240

Ala Asp Pro Ala Leu Thr Leu Met His Glu Leu Ile His Val Leu His
                245                 250                 255

Gly Leu Tyr Gly Ile Lys Ile Ser Asn Leu Pro Ile Thr Pro Asn Thr
            260                 265                 270

Lys Glu Phe Phe Met Gln His Ser Asp Pro Val Gln Ala Glu Glu Leu
        275                 280                 285

Tyr Thr Phe Gly Gly His Asp Pro Ser Val Ile Ser Pro Ser Thr Asp
    290                 295                 300

Met Asn Ile Tyr Asn Lys Ala Leu Gln Asn Phe Gln Asp Ile Ala Asn
305                 310                 315                 320

Arg Leu Asn Ile Val Ser Ser Ala Gln Gly Ser Gly Ile Asp Ile Ser
                325                 330                 335

Leu Tyr Lys Gln Ile Tyr Lys Asn Lys Tyr Asp Phe Val Glu Asp Pro
            340                 345                 350

Asn Gly Lys Tyr Ser Val Asp Lys Asp Lys Phe Asp Lys Leu Tyr Lys
        355                 360                 365

Ala Leu Met Phe Gly Phe Thr Glu Thr Asn Leu Ala Gly Glu Tyr Gly
    370                 375                 380

Ile Lys Thr Arg Tyr Ser Tyr Phe Ser Glu Tyr Leu Pro Pro Ile Lys
385                 390                 395                 400
```

```
Thr Glu Lys Leu Leu Asp Asn Thr Ile Tyr Thr Gln Asn Glu Gly Phe
                405                 410                 415

Asn Ile Ala Ser Lys Asn Leu Lys Thr Glu Phe Asn Gly Gln Asn Lys
            420                 425                 430

Ala Val Asn Lys Glu Ala Tyr Glu Glu Ile Ser Leu Glu His Leu Val
        435                 440                 445

Ile Tyr Arg Ile Ala Met Cys Lys Pro Val Met Tyr Lys
    450                 455                 460


<210> SEQ ID NO 24
<211> LENGTH: 1437
<212> TYPE: DNA
<213> ORGANISM: Artificial Sequence
<220> FEATURE:
<223> OTHER INFORMATION: BoNT/A Light chain cDNA Sequence with
      hexahistidine

<400> SEQUENCE: 24

atgggcagca gccatcatca tcatcatcac agcagcggcc tggtgccgcg cggcagccat     60

atgatgccct ttgtcaacaa acagttcaac tacaaggacc cagttaatgg agtagacatc    120

gcatatatca agattcccaa cgctggccag atgcaacccg ttaaggcatt taaaatccat    180

aacaaaatct gggttatccc agagcgggat accttcacca accccgagga gggcgatctg    240

aacccccgc cggaggcgaa gcaggtccca gtgagctact acgatagcac ctacctcagc    300

accgacaacg agaaggacaa ctacctcaaa ggagtcacga agttgttcga gagaatctac    360

tccacagacc tcggccgcat gcttctaacc agcattgtgc gtggcattcc cttttggggc    420

ggctctacca tcgacacaga gctgaaggtg atagacacca actgcatcaa cgtaatccag    480

cctgacggca gctaccgaag cgaggagctt aacctggtga tcatcggccc ttccgccgat    540

atcatccaat tcgagtgcaa gagcttcggc cacgaggtcc tgaacctcac ccggaacggc    600

tatggaagca cccagtacat aagattcagc cctgacttca ccttcgggtt tgaggagagc    660

ttggaggtcg acacaaaccc cctgctggga gccgggaagt tcgccactga cccagccgtg    720

actctggcac acgagctgat ccacgccggt caccgcctgt acggcatagc tataaaccca    780

aacagggtgt tcaaagtgaa caccaacgct tactatgaaa tgagcggcct ggaggtgagc    840

ttcgaggagc tgagaacgtt cgggggacat gatgctaaat ttatcgacag cctgcaggag    900

aacgagttca ggctgtacta ctacaataag ttcaaggata tagcgagcac tctgaacaag    960

gccaagtcca tcgtaggcac tactgcatcc ctccagtata tgaagaatgt gttcaaagag   1020

aaatacctgc tgagcgagga taccagcggt aagttcagcg tggataagct taagttcgac   1080

aagctgtata agatgctcac cgaaatctac accgaggata atttcgttaa gttcttcaag   1140

gtcctgaacc ggaagaccta cctgaacttc gacaaggccg tgttcaagat caacatcgtg   1200

cctaaagtga actacaccat ctacgacggg tttaacctga ggaacaccaa cctggccgct   1260

aacttcaacg ggcagaacac agagatcaac aacatgaatt tcacgaagtt gaagaacttc   1320

accggactgt ttgagttcta caaattgctg tgtgtgcgcg ggatcatcac tagcaagacc   1380

aagagccttg acaaaggcta caacaagtga ctcgagcacc accaccacca ccactga      1437


<210> SEQ ID NO 25
<211> LENGTH: 1413
<212> TYPE: DNA
<213> ORGANISM: Artificial Sequence
<220> FEATURE:
<223> OTHER INFORMATION: BoNT/B Light chain cDNA Sequence with
```

hexahistidine

<400> SEQUENCE: 25
atgggcagca gccatcatca tcatcatcac agcagcggcc tggtgccgcg cggcagccat 60
atgatgccag ttacaataaa taattttaat tataatgatc ctattgataa taataatatt 120
attatgatgg agcctccatt tgcgagaggt acggggagat attataaagc ttttaaaatc 180
acagatcgta tttggataat accggaaaga tatacttttg gatataaacc tgaggatttt 240
aataaaagtt ccggtatttt taatagagat gtttgtgaat attatgatcc agattactta 300
aatactaatg ataaaaagaa tatattttta caaacaatga tcaagttatt taatagaatc 360
aaatcaaaac cattgggtga aaagttatta gagatgatta taaatggtat accttatctt 420
ggagatagac gtgttccact cgaagagttt aacacaaaca ttgctagtgt aactgttaat 480
aaattaatca gtaatccagg agaagtggag cgaaaaaaag gtattttcgc aaatttaata 540
atatttggac ctgggccagt tttaaatgaa aatgagacta tagatatagg tatacaaaat 600
cattttgcat caagggaagg cttcgggggt ataatgcaaa tgaagttttg cccagaatat 660
gtaagcgtat ttaataatgt tcaagaaaac aaaggcgcaa gtatatttaa tagacgtgga 720
tatttttcag atccagcctt gatattaatg catgaactta tacatgtttt acatggatta 780
tatggcatta aagtagatga tttaccaatt gtaccaaatg aaaaaaaatt ttttatgcaa 840
tctacagatg ctatacaggc agaagaacta tatacatttg gaggacaaga tcccagcatc 900
ataactcctt ctacggataa aagtatctat gataaagttt tgcaaaattt tagagggata 960
gttgatagac ttaacaaggt tttagtttgc atatcagatc ctaacattaa tattaatata 1020
tataaaaata aatttaaaga taaatataaa ttcgttgaag attctgaggg aaaatatagt 1080
atagatgtag aaagttttga taaattatat aaaagcttaa tgtttggttt tacagaaact 1140
aatatagcag aaaattataa aataaaaact agagcttctt attttagtga ttccttacca 1200
ccagtaaaaa taaaaaattt attagataat gaaatctata ctatagagga agggtttaat 1260
atatctgata aagatatgga aaaagaatat agaggtcaga ataaagctat aaataaacaa 1320
gcttatgaag aaattagcaa ggagcatttg gctgtatata agatacaaat gtgtaaaagt 1380
gttaaactcg agcaccacca ccaccaccac tga 1413

<210> SEQ ID NO 26
<211> LENGTH: 1437
<212> TYPE: DNA
<213> ORGANISM: Artificial Sequence
<220> FEATURE:
<223> OTHER INFORMATION: BoNT/C Light chain cDNA Sequence with
hexahistidine

<400> SEQUENCE: 26
atgggcagca gccatcatca tcatcatcac agcagcggcc tggtgccgcg cggcagccat 60
atgatgccaa taacaattaa caactttaat tattcagatc ctgttgataa taaaaatatt 120
ttatatttag atactcattt aaatacacta gctaatgagc ctgaaaaagc ctttcgcatt 180
acaggaaata tatgggtaat acctgataga ttttcaagaa attctaatcc aaatttaaat 240
aaacctcctc gagttacaag ccctaaaagt ggttattatg atcctaatta tttgagtact 300
gattctgaca aagatacatt tttaaaagaa attataaagt tatttaaaag aattaattct 360
agagaaatag gagaagaatt aatatataga ctttcgacag atataccctt tcctgggaat 420
aacaatactc caattaatac ttttgatttt gatgtagatt ttaacagtgt tgatgttaaa 480
actagacaag gtaacaactg ggttaaaact ggtagcataa atcctagtgt tataataact 540
ggacctagag aaaacattat agatccagaa acttctacgt ttaaattaac taacaatact 600
tttgcggcac aagaaggatt tggtgcttta tcaataattt caatatcacc tagatttatg 660
ctaacatata gtaatgcaac taatgatgta ggagagggta gattttctaa gtctgaattt 720
tgcatggatc caatactaat tttaatgcat gaacttaatc atgcaatgca taatttatat 780
ggaatagcta taccaaatga tcaaacaatt tcatctgtaa ctagtaatat tttttattct 840
caatataatg tgaaattaga gtatgcagaa atatatgcat ttggaggtcc aactatagac 900
cttattccta aaagtgcaag gaaatatttt gaggaaaagg cattggatta ttatagatct 960
atagctaaaa gacttaatag tataactact gcaaatcctt caagctttaa taaatatata 1020
ggggaatata aacagaaact tattagaaag tatagattcg tagtagaatc ttcaggtgaa 1080
gttacagtaa atcgtaataa gtttgttgag ttatataatg aacttacaca aatatttaca 1140
gaatttaact acgctaaaat atataatgta caaaatagga aaatatatct ttcaaatgta 1200
tatactccgg ttacggcgaa tatattagac gataatgttt atgatataca aaatggattt 1260
aatataccta aaagtaattt aaatgtacta tttatgggtc aaaatttatc tcgaaatcca 1320
gcattaagaa aagtcaatcc tgaaaatatg ctttatttat ttacaaaatt ttgtcataaa 1380
gcaatagatg gtagatcatt atataataaa ctcgagcacc accaccacca ccactga 1437

<210> SEQ ID NO 27
<211> LENGTH: 1416
<212> TYPE: DNA
<213> ORGANISM: Artificial Sequence
<220> FEATURE:
<223> OTHER INFORMATION: BoNT/D Light chain cDNA Sequence with hexahistidine

<400> SEQUENCE: 27
atgggcagca gccatcatca tcatcatcac agcagcggcc tggtgccgcg cggcagccat 60
atgatgacat ggccagtaaa agattttaat tatagtgatc ctgttaatga caatgatata 120
ttatatttaa gaataccaca aaataagtta attactacac ctgtaaaagc ttttatgatt 180
actcaaaata tttgggtaat accagaaaga ttttcatcag atactaatcc aagtttaagt 240
aaaccgccca gacctacttc aaagtatcaa agttattatg atcctagtta tttatctact 300
gatgaacaaa aagatacatt tttaaaaggg attataaaat tatttaaaag aattaatgaa 360
agagatatag gaaaaaaatt aataaattat ttagtagttg gttcaccttt tatgggagat 420
tcaagtacgc ctgaagatac atttgatttt acacgtcata ctactaatat tgcagttgaa 480
aagtttgaaa atggtagttg gaaagtaaca aatattataa caccaagtgt attgatattt 540
ggaccacttc ctaatatatt agactataca gcatccctta cattgcaagg acaacaatca 600
aatccatcat ttgaagggtt tggaacatta tctatactaa aagtagcacc tgaatttttg 660
ttaacattta gtgatgtaac atctaatcaa agttcagctg tattaggcaa atctatattt 720
tgtatggatc cagtaatagc tttaatgcat gagttaacac attctttgca tcaattatat 780
ggaataaata taccatctga taaaaggatt cgtccacaag ttagcgaggg atttttctct 840
caagatggac ccaacgtaca atttgaggaa ttatatacat ttggaggatt agatgttgaa 900
ataatacctc aaattgaaag atcacaatta agagaaaaag cattaggtca ctataaagat 960
atagcgaaaa gacttaataa tattaataaa actattcctt ctagttggat tagtaatata 1020
gataaatata aaaaaatatt ttctgaaaag tataattttg ataaagataa tacaggaaat 1080
tttgttgtaa atattgataa attcaatagc ttatattcag acttgactaa tgttatgtca 1140
gaagttgttt attcttcgca atataatgtt aaaaacagga ctcattattt ttcaaggcat 1200
tatctacctg tatttgcaaa tatattagat gataatattt atactataag agatggtttt 1260
aatttaacaa ataaaggttt taatatagaa aattcgggtc agaatataga aaggaatcct 1320
gcactacaaa agcttagttc agaaagtgta gtagatttat ttacaaaagt atgtttaaga 1380
ttaacaaaac tcgagcacca ccaccaccac cactga 1416

<210> SEQ ID NO 28
<211> LENGTH: 1356
<212> TYPE: DNA
<213> ORGANISM: Artificial Sequence
<220> FEATURE:
<223> OTHER INFORMATION: BoNT/E Light chain cDNA Sequence with hexahistidine

<400> SEQUENCE: 28
atgggcagca gccatcatca tcatcatcac agcagcggcc tggtgccgcg cggcagccat 60
atgatgccaa caattaatag ttttaattat aatgatcctg ttaataatag aacaatttta 120
tatattaaac caggcggttg tcaacaattt tataaatcat ttaatattat gaaaaatatt 180
tggataattc cagagagaaa tgtaattggt acaattcccc aagattttct tccgcctact 240
tcattgaaaa atggagatag tagttattat gaccctaatt atttacaaag tgatcaagaa 300
aaggataaat tttaaaaaat agtcacaaaa atatttaata gaataaatga taatctttca 360
ggaaggattt tattagaaga actgtcaaaa gctaatccat atttaggaaa tgataatact 420
ccagatggtg acttcattat taatgatgca tcagcagttc caattcaatt ctcaaatggt 480
agccaaagca tactattacc taatgttatt ataatgggag cagagcctga tttatttgaa 540
actaacagtt ccaatatttc tctaagaaat aattatatgc caagcaatca cggttttgga 600
tcaatagcta tagtaacatt ctcacctgaa tattctttta gatttaaaga taatagtatg 660
aatgaattta ttcaagatcc tgctcttaca ttaatgcatg aattaataca ttcattacat 720
ggactatatg ggctaaagg gattactaca aagtatacta taacacaaaa acaaaatccc 780
ctaataacaa atataagagg tacaaatatt gaagaattct taacttttgg aggtactgat 840
ttaaacatta ttactagtgc tcagtccaat gatatctata ctaatcttct agctgattat 900
aaaaaaatag cgtctaaact tagcaaagta caagtatcta atccactact taatccttat 960
aaagatgttt ttgaagcaaa gtatggatta gataaagatg ctagcggaat ttattcggta 1020
aatataaaca aatttaatga tatttttaaa aaattataca gctttacgga atttgattta 1080
gcaactaaat ttcaagttaa atgtaggcaa acttatattg gacagtataa atacttcaaa 1140
ctttcaaact tgttaaatga ttctatttat aatatatcag aaggctataa tataaataat 1200
ttaaaggtaa attttagagg acagaatgca aatttaaatc ctagaattat tacaccaatt 1260
acaggtagag gactagtaaa aaaaatcatt agattttgta aaaatattgt ttctgtaaaa 1320
ggcataaggc tcgagcacca ccaccaccac cactga 1356

<210> SEQ ID NO 29
<211> LENGTH: 1398
<212> TYPE: DNA
<213> ORGANISM: Artificial Sequence
<220> FEATURE:
<223> OTHER INFORMATION: BoNT/F Light chain cDNA Sequence with hexahistidine

<400> SEQUENCE: 29

-continued atgggcagca gccatcatca tcatcatcac agcagcggcc tggtgccgcg cggcagccat 60
atgatgccag ttgcaataaa tagttttaat tataatgacc ctgttaatga tgatacaatt 120
ttatacatgc agataccata tgaagaaaaa agtaaaaaat attataaagc ttttgagatt 180
atgcgtaatg tttggataat tcctgagaga aatacaatag gaacgaatcc tagtgatttt 240
gatccaccgg cttcattaaa gaacggaagc agtgcttatt atgatcctaa ttatttaacc 300
actgatgctg aaaaagatag atatttaaaa acaacgataa aattatttaa gagaattaat 360
agtaatcctg cagggaaagt tttgttacaa gaaatatcat atgctaaacc atatttagga 420
aatgaccaca cgccaattga tgaattctct ccagttacta gaactacaag tgttaatata 480
aaattatcaa ctaatgttga aagttcaatg ttattgaatc ttcttgtatt gggagcagga 540
cctgatatat ttgaaagttg ttgttacccc gttagaaaac taatagatcc agatgtagtt 600
tatgatccaa gtaattatgg ttttggatca attaatatcg tgacattttc acctgagtat 660
gaatatactt ttaatgatat tagtggaggg cataatagta gtacagaatc atttattgca 720
gatcctgcaa tttcactagc tcatgaattg atacatgcac tgcatggatt atacggggct 780
aggggagtta cttatgaaga gactatagaa gtaaagcaag cacctcttat gatagccgaa 840
aaacccataa ggctagaaga atttttaacc tttggaggtc aggatttaaa tattattact 900
agtgctatga aggaaaaaat atataacaat cttttagcta actatgaaaa aatagctact 960
agacttagtg aagttaatag tgctcctcct gaatatgata ttaatgaata taaagattat 1020
tttcaatgga agtatgggct agataaaaat gctgatggaa gttatactgt aaatgaaaat 1080
aaatttaatg aaatttataa aaaattatat agttttacag agagtgactt agcaaataaa 1140
tttaaagtaa aatgtagaaa tacttatttt attaaatatg aatttttaaa agttccaaat 1200
ttgttagatg atgatattta tactgtatca gaggggttta atataggtaa tttagcagta 1260
aacaatcgcg gacaaagtat aaagttaaat cctaaaatta ttgattccat tccagataaa 1320
ggtctagtag aaaagatcgt taaattttgt aagagcgtta ttcctagaaa actcgagcac 1380
caccaccacc accactga 1398

<210> SEQ ID NO 30
<211> LENGTH: 1416
<212> TYPE: DNA
<213> ORGANISM: Artificial Sequence
<220> FEATURE:
<223> OTHER INFORMATION: BoNT/G Light chain cDNA Sequence with hexahistidine
<220> FEATURE:
<221> NAME/KEY: misc_feature
<222> LOCATION: (83)..(83)
<223> OTHER INFORMATION: n is a, c, g, or t

<400> SEQUENCE: 30
atgggcagca gccatcatca tcatcatcac agcagcggcc tggtgccgcg cggcagccat 60
atgatgccag ttaatataaa aanctttaat tataatgacc ctattaataa tgatgacatt 120
attatgatgg aaccattcaa tgacccaggg ccaggaacat attataaagc ttttaggatt 180
atagatcgta tttggatagt accagaaagg tttacttatg gatttcaacc tgaccaattt 240
aatgccagta caggagtttt tagtaaagat gtctacgaat attacgatcc aacttattta 300
aaaaccgatg ctgaaaaaga taaattttta aaaacaatga ttaaattatt taatagaatt 360
aattcaaaac catcaggaca gagattactg gatatgatag tagatgctat accttatctt 420
ggaaatgcat ctacaccgcc cgacaaattt gcagcaaatg ttgcaaatgt atctattaat 480

```
aaaaaaatta tccaacctgg agctgaagat caaataaaag gtttaatgac aaatttaata    540

atatttggac caggaccagt tctaagtgat aattttactg atagtatgat tatgaatggc    600

cattccccaa tatcagaagg atttggtgca agaatgatga taagattttg tcctagttgt    660

ttaaatgtat ttaataatgt tcaggaaaat aaagatacat ctatatttag tagacgcgcg    720

tattttgcag atccagctct aacgttaatg catgaactta tacatgtgtt acatggatta    780

tatggaatta agataagtaa tttaccaatt actccaaata caaaagaatt tttcatgcaa    840

catagcgatc ctgtacaagc agaagaacta tatacattcg gaggacatga tcctagtgtt    900

ataagtcctt ctacggatat gaatatttat aataaagcgt tacaaaattt tcaagatata    960

gctaataggc ttaatattgt ttcaagtgcc caagggagtg gaattgatat ttccttatat   1020

aaacaaatat ataaaaataa atatgatttt gttgaagatc ctaatggaaa atatagtgta   1080

gataaggata agtttgataa attatataag gccttaatgt ttggctttac tgaaactaat   1140

ctagctggtg aatatggaat aaaaactagg tattcttatt ttagtgaata tttgccaccg   1200

ataaaaactg aaaaattgtt agacaataca atttatactc aaaatgaagg ctttaacata   1260

gctagtaaaa atctcaaaac ggaatttaat ggtcagaata aggcggtaaa taaagaggct   1320

tatgaagaaa tcagcctaga acatctcgtt atatatagaa tagcaatgtg caagcctgta   1380

atgtacaaac tcgagcacca ccaccaccac cactga                             1416
```

```
<210> SEQ ID NO 31
<211> LENGTH: 461
<212> TYPE: PRT
<213> ORGANISM: Artificial Sequence
<220> FEATURE:
<223> OTHER INFORMATION: TD1-BoNT/A Light chain Amino Acid Sequence

<400> SEQUENCE: 31

Met Lys Ala Met Ile Asn Ile Asn Lys Phe Leu Asn Gln Cys Pro Phe
1               5                   10                  15

Val Asn Lys Gln Phe Asn Tyr Lys Asp Pro Val Asn Gly Val Asp Ile
            20                  25                  30

Ala Tyr Ile Lys Ile Pro Asn Ala Gly Gln Met Gln Pro Val Lys Ala
        35                  40                  45

Phe Lys Ile His Asn Lys Ile Trp Val Ile Pro Glu Arg Asp Thr Phe
    50                  55                  60

Thr Asn Pro Glu Glu Gly Asp Leu Asn Pro Pro Pro Glu Ala Lys Gln
65                  70                  75                  80

Val Pro Val Ser Tyr Tyr Asp Ser Thr Tyr Leu Ser Thr Asp Asn Glu
                85                  90                  95

Lys Asp Asn Tyr Leu Lys Gly Val Thr Lys Leu Phe Glu Arg Ile Tyr
            100                 105                 110

Ser Thr Asp Leu Gly Arg Met Leu Leu Thr Ser Ile Val Arg Gly Ile
        115                 120                 125

Pro Phe Trp Gly Gly Ser Thr Ile Asp Thr Glu Leu Lys Val Ile Asp
    130                 135                 140

Thr Asn Cys Ile Asn Val Ile Gln Pro Asp Gly Ser Tyr Arg Ser Glu
145                 150                 155                 160

Glu Leu Asn Leu Val Ile Ile Gly Pro Ser Ala Asp Ile Ile Gln Phe
                165                 170                 175

Glu Cys Lys Ser Phe Gly His Glu Val Leu Asn Leu Thr Arg Asn Gly
            180                 185                 190
```

Tyr Gly Ser Thr Gln Tyr Ile Arg Phe Ser Pro Asp Phe Thr Phe Gly
195 200 205

Phe Glu Glu Ser Leu Glu Val Asp Thr Asn Pro Leu Leu Gly Ala Gly
210 215 220

Lys Phe Ala Thr Asp Pro Ala Val Thr Leu Ala His Glu Leu Ile His
225 230 235 240

Ala Gly His Arg Leu Tyr Gly Ile Ala Ile Asn Pro Asn Arg Val Phe
245 250 255

Lys Val Asn Thr Asn Ala Tyr Tyr Glu Met Ser Gly Leu Glu Val Ser
260 265 270

Phe Glu Glu Leu Arg Thr Phe Gly Gly His Asp Ala Lys Phe Ile Asp
275 280 285

Ser Leu Gln Glu Asn Glu Phe Arg Leu Tyr Tyr Tyr Asn Lys Phe Lys
290 295 300

Asp Ile Ala Ser Thr Leu Asn Lys Ala Lys Ser Ile Val Gly Thr Thr
305 310 315 320

Ala Ser Leu Gln Tyr Met Lys Asn Val Phe Lys Glu Lys Tyr Leu Leu
325 330 335

Ser Glu Asp Thr Ser Gly Lys Phe Ser Val Asp Lys Leu Lys Phe Asp
340 345 350

Lys Leu Tyr Lys Met Leu Thr Glu Ile Tyr Thr Glu Asp Asn Phe Val
355 360 365

Lys Phe Phe Lys Val Leu Asn Arg Lys Thr Tyr Leu Asn Phe Asp Lys
370 375 380

Ala Val Phe Lys Ile Asn Ile Val Pro Lys Val Asn Tyr Thr Ile Tyr
385 390 395 400

Asp Gly Phe Asn Leu Arg Asn Thr Asn Leu Ala Ala Asn Phe Asn Gly
405 410 415

Gln Asn Thr Glu Ile Asn Asn Met Asn Phe Thr Lys Leu Lys Asn Phe
420 425 430

Thr Gly Leu Phe Glu Phe Tyr Lys Leu Leu Cys Val Arg Gly Ile Ile
435 440 445

Thr Ser Lys Thr Lys Ser Leu Asp Lys Gly Tyr Asn Lys
450 455 460

<210> SEQ ID NO 32
<211> LENGTH: 454
<212> TYPE: PRT
<213> ORGANISM: Artificial Sequence
<220> FEATURE:
<223> OTHER INFORMATION: TD1-BoNT/B Light chain Amino Acid Sequence

<400> SEQUENCE: 32

Met Lys Ala Met Ile Asn Ile Asn Lys Phe Leu Asn Gln Cys Pro Val
1 5 10 15

Thr Ile Asn Asn Phe Asn Tyr Asn Asp Pro Ile Asp Asn Asn Asn Ile
20 25 30

Ile Met Met Glu Pro Pro Phe Ala Arg Gly Thr Gly Arg Tyr Tyr Lys
35 40 45

Ala Phe Lys Ile Thr Asp Arg Ile Trp Ile Ile Pro Glu Arg Tyr Thr
50 55 60

Phe Gly Tyr Lys Pro Glu Asp Phe Asn Lys Ser Ser Gly Ile Phe Asn
65 70 75 80

Arg Asp Val Cys Glu Tyr Tyr Asp Pro Asp Tyr Leu Asn Thr Asn Asp
85 90 95

-continued

```
Lys Lys Asn Ile Phe Leu Gln Thr Met Ile Lys Leu Phe Asn Arg Ile
            100                 105                 110

Lys Ser Lys Pro Leu Gly Glu Lys Leu Leu Glu Met Ile Ile Asn Gly
        115                 120                 125

Ile Pro Tyr Leu Gly Asp Arg Arg Val Pro Leu Glu Glu Phe Asn Thr
    130                 135                 140

Asn Ile Ala Ser Val Thr Val Asn Lys Leu Ile Ser Asn Pro Gly Glu
145                 150                 155                 160

Val Glu Arg Lys Lys Gly Ile Phe Ala Asn Leu Ile Ile Phe Gly Pro
                165                 170                 175

Gly Pro Val Leu Asn Glu Asn Glu Thr Ile Asp Ile Gly Ile Gln Asn
            180                 185                 190

His Phe Ala Ser Arg Glu Gly Phe Gly Gly Ile Met Gln Met Lys Phe
        195                 200                 205

Cys Pro Glu Tyr Val Ser Val Phe Asn Asn Val Gln Glu Asn Lys Gly
    210                 215                 220

Ala Ser Ile Phe Asn Arg Arg Gly Tyr Phe Ser Asp Pro Ala Leu Ile
225                 230                 235                 240

Leu Met His Glu Leu Ile His Val Leu His Gly Leu Tyr Gly Ile Lys
                245                 250                 255

Val Asp Asp Leu Pro Ile Val Pro Asn Glu Lys Lys Phe Phe Met Gln
            260                 265                 270

Ser Thr Asp Ala Ile Gln Ala Glu Glu Leu Tyr Thr Phe Gly Gly Gln
        275                 280                 285

Asp Pro Ser Ile Ile Thr Pro Ser Thr Asp Lys Ser Ile Tyr Asp Lys
    290                 295                 300

Val Leu Gln Asn Phe Arg Gly Ile Val Asp Arg Leu Asn Lys Val Leu
305                 310                 315                 320

Val Cys Ile Ser Asp Pro Asn Ile Asn Ile Asn Ile Tyr Lys Asn Lys
                325                 330                 335

Phe Lys Asp Lys Tyr Lys Phe Val Glu Asp Ser Glu Gly Lys Tyr Ser
            340                 345                 350

Ile Asp Val Glu Ser Phe Asp Lys Leu Tyr Lys Ser Leu Met Phe Gly
        355                 360                 365

Phe Thr Glu Thr Asn Ile Ala Glu Asn Tyr Lys Ile Lys Thr Arg Ala
    370                 375                 380

Ser Tyr Phe Ser Asp Ser Leu Pro Pro Val Lys Ile Lys Asn Leu Leu
385                 390                 395                 400

Asp Asn Glu Ile Tyr Thr Ile Glu Glu Gly Phe Asn Ile Ser Asp Lys
                405                 410                 415

Asp Met Glu Lys Glu Tyr Arg Gly Gln Asn Lys Ala Ile Asn Lys Gln
            420                 425                 430

Ala Tyr Glu Glu Ile Ser Lys Glu His Leu Ala Val Tyr Lys Ile Gln
        435                 440                 445

Met Cys Lys Ser Val Lys
    450
```

<210> SEQ ID NO 33
<211> LENGTH: 462
<212> TYPE: PRT
<213> ORGANISM: Artificial Sequence
<220> FEATURE:
<223> OTHER INFORMATION: TD1-BoNT/C Light chain Amino Acid Sequence

<400> SEQUENCE: 33

-continued

```
Met Lys Ala Met Ile Asn Ile Asn Lys Phe Leu Asn Gln Cys Pro Ile
1               5                   10                  15

Thr Ile Asn Asn Phe Asn Tyr Ser Asp Pro Val Asp Asn Lys Asn Ile
            20                  25                  30

Leu Tyr Leu Asp Thr His Leu Asn Thr Leu Ala Asn Glu Pro Glu Lys
        35                  40                  45

Ala Phe Arg Ile Thr Gly Asn Ile Trp Val Ile Pro Asp Arg Phe Ser
    50                  55                  60

Arg Asn Ser Asn Pro Asn Leu Asn Lys Pro Pro Arg Val Thr Ser Pro
65                  70                  75                  80

Lys Ser Gly Tyr Tyr Asp Pro Asn Tyr Leu Ser Thr Asp Ser Asp Lys
                85                  90                  95

Asp Pro Phe Leu Lys Glu Ile Ile Lys Leu Phe Lys Arg Ile Asn Ser
            100                 105                 110

Arg Glu Ile Gly Glu Glu Leu Ile Tyr Arg Leu Ser Thr Asp Ile Pro
        115                 120                 125

Phe Pro Gly Asn Asn Asn Thr Pro Ile Asn Thr Phe Asp Phe Asp Val
    130                 135                 140

Asp Phe Asn Ser Val Asp Val Lys Thr Arg Gln Gly Asn Asn Trp Val
145                 150                 155                 160

Lys Thr Gly Ser Ile Asn Pro Ser Val Ile Ile Thr Gly Pro Arg Glu
                165                 170                 175

Asn Ile Ile Asp Pro Glu Thr Ser Thr Phe Lys Leu Thr Asn Asn Thr
            180                 185                 190

Phe Ala Ala Gln Glu Gly Phe Gly Ala Leu Ser Ile Ile Ser Ile Ser
        195                 200                 205

Pro Arg Phe Met Leu Thr Tyr Ser Asn Ala Thr Asn Asp Val Gly Glu
    210                 215                 220

Gly Arg Phe Ser Lys Ser Glu Phe Cys Met Asp Pro Ile Leu Ile Leu
225                 230                 235                 240

Met His Glu Leu Asn His Ala Met His Asn Leu Tyr Gly Ile Ala Ile
                245                 250                 255

Pro Asn Asp Gln Thr Ile Ser Ser Val Thr Ser Asn Ile Phe Tyr Ser
            260                 265                 270

Gln Tyr Asn Val Lys Leu Glu Tyr Ala Glu Ile Tyr Ala Phe Gly Gly
        275                 280                 285

Pro Thr Ile Asp Leu Ile Pro Lys Ser Ala Arg Lys Tyr Phe Glu Glu
    290                 295                 300

Lys Ala Leu Asp Tyr Tyr Arg Ser Ile Ala Lys Arg Leu Asn Ser Ile
305                 310                 315                 320

Thr Thr Ala Asn Pro Ser Ser Phe Asn Lys Tyr Ile Gly Glu Tyr Lys
                325                 330                 335

Gln Lys Leu Ile Arg Lys Tyr Arg Phe Val Val Glu Ser Ser Gly Glu
            340                 345                 350

Val Thr Val Asn Arg Asn Lys Phe Val Glu Leu Tyr Asn Glu Leu Thr
        355                 360                 365

Gln Ile Phe Thr Glu Phe Asn Tyr Ala Lys Ile Tyr Asn Val Gln Asn
    370                 375                 380

Arg Lys Ile Tyr Leu Ser Asn Val Tyr Thr Pro Val Thr Ala Asn Ile
385                 390                 395                 400

Leu Asp Asp Asn Val Tyr Asp Ile Gln Asn Gly Phe Asn Ile Pro Lys
                405                 410                 415

Ser Asn Leu Asn Val Leu Phe Met Gly Gln Asn Leu Ser Arg Asn Pro
```

```
            420                 425                 430

Ala Leu Arg Lys Val Asn Pro Glu Asn Met Leu Tyr Leu Phe Thr Lys
        435                 440                 445

Phe Cys His Lys Ala Ile Asp Gly Arg Ser Leu Tyr Asn Lys
    450                 455                 460


<210> SEQ ID NO 34
<211> LENGTH: 455
<212> TYPE: PRT
<213> ORGANISM: Artificial Sequence
<220> FEATURE:
<223> OTHER INFORMATION: TD1-BoNT/D Light chain Amino Acid Sequence

<400> SEQUENCE: 34

Met Lys Ala Met Ile Asn Ile Asn Lys Phe Leu Asn Gln Cys Thr Trp
1               5                   10                  15

Pro Val Lys Asp Phe Asn Tyr Ser Asp Pro Val Asn Asp Asn Asp Ile
            20                  25                  30

Leu Tyr Leu Arg Ile Pro Gln Asn Lys Leu Ile Thr Thr Pro Val Lys
        35                  40                  45

Ala Phe Met Ile Thr Gln Asn Ile Trp Val Ile Pro Glu Arg Phe Ser
    50                  55                  60

Ser Asp Thr Asn Pro Ser Leu Ser Lys Pro Pro Arg Pro Thr Ser Lys
65                  70                  75                  80

Tyr Gln Ser Tyr Tyr Asp Pro Ser Tyr Leu Ser Thr Asp Glu Gln Lys
                85                  90                  95

Asp Thr Phe Leu Lys Gly Ile Ile Lys Leu Phe Lys Arg Ile Asn Glu
            100                 105                 110

Arg Asp Ile Gly Lys Lys Leu Ile Asn Tyr Leu Val Val Gly Ser Pro
        115                 120                 125

Phe Met Gly Asp Ser Ser Thr Pro Glu Asp Thr Phe Asp Phe Thr Arg
    130                 135                 140

His Thr Thr Asn Ile Ala Val Glu Lys Phe Glu Asn Gly Ser Trp Lys
145                 150                 155                 160

Val Thr Asn Ile Ile Thr Pro Ser Val Leu Ile Phe Gly Pro Leu Pro
                165                 170                 175

Asn Ile Leu Asp Tyr Thr Ala Ser Leu Thr Leu Gln Gly Gln Gln Ser
            180                 185                 190

Asn Pro Ser Phe Glu Gly Phe Gly Thr Leu Ser Ile Leu Lys Val Ala
        195                 200                 205

Pro Glu Phe Leu Leu Thr Phe Ser Asp Val Thr Ser Asn Gln Ser Ser
    210                 215                 220

Ala Val Leu Gly Lys Ser Ile Phe Cys Met Asp Pro Val Ile Ala Leu
225                 230                 235                 240

Met His Glu Leu Thr His Ser Leu His Gln Leu Tyr Gly Ile Asn Ile
                245                 250                 255

Pro Ser Asp Lys Arg Ile Arg Pro Gln Val Ser Glu Gly Phe Phe Ser
            260                 265                 270

Gln Asp Gly Pro Asn Val Gln Phe Glu Glu Leu Tyr Thr Phe Gly Gly
        275                 280                 285

Leu Asp Val Glu Ile Ile Pro Gln Ile Glu Arg Ser Gln Leu Arg Glu
    290                 295                 300

Lys Ala Leu Gly His Tyr Lys Asp Ile Ala Lys Arg Leu Asn Asn Ile
305                 310                 315                 320

Asn Lys Thr Ile Pro Ser Ser Trp Ile Ser Asn Ile Asp Lys Tyr Lys
```

```
                325                 330                 335

Lys Ile Phe Ser Glu Lys Tyr Asn Phe Asp Lys Asp Asn Thr Gly Asn
            340                 345                 350

Phe Val Val Asn Ile Asp Lys Phe Asn Ser Leu Tyr Ser Asp Leu Thr
        355                 360                 365

Asn Val Met Ser Glu Val Val Tyr Ser Ser Gln Tyr Asn Val Lys Asn
    370                 375                 380

Arg Thr His Tyr Phe Ser Arg His Tyr Leu Pro Val Phe Ala Asn Ile
385                 390                 395                 400

Leu Asp Asp Asn Ile Tyr Thr Ile Arg Asp Gly Phe Asn Leu Thr Asn
                405                 410                 415

Lys Gly Phe Asn Ile Glu Asn Ser Gly Gln Asn Ile Glu Arg Asn Pro
            420                 425                 430

Ala Leu Gln Lys Leu Ser Ser Glu Ser Val Val Asp Leu Phe Thr Lys
        435                 440                 445

Val Cys Leu Arg Leu Thr Lys
    450                 455


<210> SEQ ID NO 35
<211> LENGTH: 435
<212> TYPE: PRT
<213> ORGANISM: Artificial Sequence
<220> FEATURE:
<223> OTHER INFORMATION: TD1-BoNT/E Light chain Amino Acid Sequence

<400> SEQUENCE: 35

Met Lys Ala Met Ile Asn Ile Asn Lys Phe Leu Asn Gln Cys Pro Thr
1               5                   10                  15

Ile Asn Ser Phe Asn Tyr Asn Asp Pro Val Asn Asn Arg Thr Ile Leu
            20                  25                  30

Tyr Ile Lys Pro Gly Gly Cys Gln Gln Phe Tyr Lys Ser Phe Asn Ile
        35                  40                  45

Met Lys Asn Ile Trp Ile Ile Pro Glu Arg Asn Val Ile Gly Thr Ile
    50                  55                  60

Pro Gln Asp Phe Leu Pro Pro Thr Ser Leu Lys Asn Gly Asp Ser Ser
65                  70                  75                  80

Tyr Tyr Asp Pro Asn Tyr Leu Gln Ser Asp Gln Glu Lys Asp Lys Phe
                85                  90                  95

Leu Lys Ile Val Thr Lys Ile Phe Asn Arg Ile Asn Asp Asn Leu Ser
            100                 105                 110

Gly Arg Ile Leu Leu Glu Glu Leu Ser Lys Ala Asn Pro Tyr Leu Gly
        115                 120                 125

Asn Asp Asn Thr Pro Asp Gly Asp Phe Ile Ile Asn Asp Ala Ser Ala
    130                 135                 140

Val Pro Ile Gln Phe Ser Asn Gly Ser Gln Ser Ile Leu Leu Pro Asn
145                 150                 155                 160

Val Ile Ile Met Gly Ala Glu Pro Asp Leu Phe Glu Thr Asn Ser Ser
                165                 170                 175

Asn Ile Ser Leu Arg Asn Asn Tyr Met Pro Ser Asn His Gly Phe Gly
            180                 185                 190

Ser Ile Ala Ile Val Thr Phe Ser Pro Glu Tyr Ser Phe Arg Phe Lys
        195                 200                 205

Asp Asn Ser Met Asn Glu Phe Ile Gln Asp Pro Ala Leu Thr Leu Met
    210                 215                 220

His Glu Leu Ile His Ser Leu His Gly Leu Tyr Gly Ala Lys Gly Ile
```

-continued

```
225                 230                 235                 240

Thr Thr Lys Tyr Thr Ile Thr Gln Lys Gln Asn Pro Leu Ile Thr Asn
                245                 250                 255

Ile Arg Gly Thr Asn Ile Glu Glu Phe Leu Thr Phe Gly Gly Thr Asp
            260                 265                 270

Leu Asn Ile Ile Thr Ser Ala Gln Ser Asn Asp Ile Tyr Thr Asn Leu
        275                 280                 285

Leu Ala Asp Tyr Lys Lys Ile Ala Ser Lys Leu Ser Lys Val Gln Val
    290                 295                 300

Ser Asn Pro Leu Leu Asn Pro Tyr Lys Asp Val Phe Glu Ala Lys Tyr
305                 310                 315                 320

Gly Leu Asp Lys Asp Ala Ser Gly Ile Tyr Ser Val Asn Ile Asn Lys
                325                 330                 335

Phe Asn Asp Ile Phe Lys Lys Leu Tyr Ser Phe Thr Glu Phe Asp Leu
            340                 345                 350

Ala Thr Lys Phe Gln Val Lys Cys Arg Gln Thr Tyr Ile Gly Gln Tyr
        355                 360                 365

Lys Tyr Phe Lys Leu Ser Asn Leu Leu Asn Asp Ser Ile Tyr Asn Ile
    370                 375                 380

Ser Glu Gly Tyr Asn Ile Asn Asn Leu Lys Val Asn Phe Arg Gly Gln
385                 390                 395                 400

Asn Ala Asn Leu Asn Pro Arg Ile Ile Thr Pro Ile Thr Gly Arg Gly
                405                 410                 415

Leu Val Lys Lys Ile Ile Arg Phe Cys Lys Asn Ile Val Ser Val Lys
            420                 425                 430

Gly Ile Arg
        435


<210> SEQ ID NO 36
<211> LENGTH: 449
<212> TYPE: PRT
<213> ORGANISM: Artificial Sequence
<220> FEATURE:
<223> OTHER INFORMATION: TD1-BoNT/F Light chain Amino Acid Sequence

<400> SEQUENCE: 36

Met Lys Ala Met Ile Asn Ile Asn Lys Phe Leu Asn Gln Cys Pro Val
1               5                   10                  15

Ala Ile Asn Ser Phe Asn Tyr Asn Asp Pro Val Asn Asp Asp Thr Ile
            20                  25                  30

Leu Tyr Met Gln Ile Pro Tyr Glu Glu Lys Ser Lys Lys Tyr Tyr Lys
        35                  40                  45

Ala Phe Glu Ile Met Arg Asn Val Trp Ile Ile Pro Glu Arg Asn Thr
    50                  55                  60

Ile Gly Thr Asn Pro Ser Asp Phe Asp Pro Pro Ala Ser Leu Lys Asn
65                  70                  75                  80

Gly Ser Ser Ala Tyr Tyr Asp Pro Asn Tyr Leu Thr Thr Asp Ala Glu
                85                  90                  95

Lys Asp Arg Tyr Leu Lys Thr Thr Ile Lys Leu Phe Lys Arg Ile Asn
            100                 105                 110

Ser Asn Pro Ala Gly Lys Val Leu Leu Gln Glu Ile Ser Tyr Ala Lys
        115                 120                 125

Pro Tyr Leu Gly Asn Asp His Thr Pro Ile Asp Glu Phe Ser Pro Val
    130                 135                 140

Thr Arg Thr Thr Ser Val Asn Ile Lys Leu Ser Thr Asn Val Glu Ser
```

145 150 155 160

Ser Met Leu Leu Asn Leu Leu Val Leu Gly Ala Gly Pro Asp Ile Phe
165 170 175

Glu Ser Cys Cys Tyr Pro Val Arg Lys Leu Ile Asp Pro Asp Val Val
180 185 190

Tyr Asp Pro Ser Asn Tyr Gly Phe Gly Ser Ile Asn Ile Val Thr Phe
195 200 205

Ser Pro Glu Tyr Glu Tyr Thr Phe Asn Asp Ile Ser Gly Gly His Asn
210 215 220

Ser Ser Thr Glu Ser Phe Ile Ala Asp Pro Ala Ile Ser Leu Ala His
225 230 235 240

Glu Leu Ile His Ala Leu His Gly Leu Tyr Gly Ala Arg Gly Val Thr
245 250 255

Tyr Glu Glu Thr Ile Glu Val Lys Gln Ala Pro Leu Met Ile Ala Glu
260 265 270

Lys Pro Ile Arg Leu Glu Glu Phe Leu Thr Phe Gly Gly Gln Asp Leu
275 280 285

Asn Ile Ile Thr Ser Ala Met Lys Glu Lys Ile Tyr Asn Asn Leu Leu
290 295 300

Ala Asn Tyr Glu Lys Ile Ala Thr Arg Leu Ser Glu Val Asn Ser Ala
305 310 315 320

Pro Pro Glu Tyr Asp Ile Asn Glu Tyr Lys Asp Tyr Phe Gln Trp Lys
325 330 335

Tyr Gly Leu Asp Lys Asn Ala Asp Gly Ser Tyr Thr Val Asn Glu Asn
340 345 350

Lys Phe Asn Glu Ile Tyr Lys Lys Leu Tyr Ser Phe Thr Glu Ser Asp
355 360 365

Leu Ala Asn Lys Phe Lys Val Lys Cys Arg Asn Thr Tyr Phe Ile Lys
370 375 380

Tyr Glu Phe Leu Lys Val Pro Asn Leu Leu Asp Asp Asp Ile Tyr Thr
385 390 395 400

Val Ser Glu Gly Phe Asn Ile Gly Asn Leu Ala Val Asn Asn Arg Gly
405 410 415

Gln Ser Ile Lys Leu Asn Pro Lys Ile Ile Asp Ser Ile Pro Asp Lys
420 425 430

Gly Leu Val Glu Lys Ile Val Lys Phe Cys Lys Ser Val Ile Pro Arg
435 440 445

Lys

<210> SEQ ID NO 37
<211> LENGTH: 454
<212> TYPE: PRT
<213> ORGANISM: Artificial Sequence
<220> FEATURE:
<223> OTHER INFORMATION: TD1-BoNT/G Light chain Amino Acid Sequence

<400> SEQUENCE: 37

Met Lys Ala Met Ile Asn Ile Asn Lys Phe Leu Asn Gln Cys Pro Val
1 5 10 15

Asn Ile Lys Phe Asn Tyr Asn Asp Pro Ile Asn Asn Asp Asp Ile Ile
20 25 30

Met Met Glu Pro Phe Asn Asp Pro Gly Pro Gly Thr Tyr Tyr Lys Ala
35 40 45

Phe Arg Ile Ile Asp Arg Ile Trp Ile Val Pro Glu Arg Phe Thr Tyr
50 55 60

```
Gly Phe Gln Pro Asp Gln Phe Asn Ala Ser Thr Gly Val Phe Ser Lys
65                  70                  75                  80

Asp Val Tyr Glu Tyr Tyr Asp Pro Thr Tyr Leu Lys Thr Asp Ala Glu
                85                  90                  95

Lys Asp Lys Phe Leu Lys Thr Met Ile Lys Leu Phe Asn Arg Ile Asn
            100                 105                 110

Ser Lys Pro Ser Gly Gln Arg Leu Leu Asp Met Ile Val Asp Ala Ile
        115                 120                 125

Pro Tyr Leu Gly Asn Ala Ser Thr Pro Pro Asp Lys Phe Ala Ala Asn
    130                 135                 140

Val Ala Asn Val Ser Ile Asn Lys Lys Ile Ile Gln Pro Gly Ala Glu
145                 150                 155                 160

Asp Gln Ile Lys Gly Leu Met Thr Asn Leu Ile Ile Phe Gly Pro Gly
                165                 170                 175

Pro Val Leu Ser Asp Asn Phe Thr Asp Ser Met Ile Met Asn Gly His
            180                 185                 190

Ser Pro Ile Ser Glu Gly Phe Gly Ala Arg Met Met Ile Arg Phe Cys
        195                 200                 205

Pro Ser Cys Leu Asn Val Phe Asn Asn Val Gln Glu Asn Lys Asp Thr
    210                 215                 220

Ser Ile Phe Ser Arg Arg Ala Tyr Phe Ala Asp Pro Ala Leu Thr Leu
225                 230                 235                 240

Met His Glu Leu Ile His Val Leu His Gly Leu Tyr Gly Ile Lys Ile
                245                 250                 255

Ser Asn Leu Pro Ile Thr Pro Asn Thr Lys Glu Phe Phe Met Gln His
            260                 265                 270

Ser Asp Pro Val Gln Ala Glu Glu Leu Tyr Thr Phe Gly Gly His Asp
        275                 280                 285

Pro Ser Val Ile Ser Pro Ser Thr Asp Met Asn Ile Tyr Asn Lys Ala
    290                 295                 300

Leu Gln Asn Phe Gln Asp Ile Ala Asn Arg Leu Asn Ile Val Ser Ser
305                 310                 315                 320

Ala Gln Gly Ser Gly Ile Asp Ile Ser Leu Tyr Lys Gln Ile Tyr Lys
                325                 330                 335

Asn Lys Tyr Asp Phe Val Glu Asp Pro Asn Gly Lys Tyr Ser Val Asp
            340                 345                 350

Lys Asp Lys Phe Asp Lys Leu Tyr Lys Ala Leu Met Phe Gly Phe Thr
        355                 360                 365

Glu Thr Asn Leu Ala Gly Glu Tyr Gly Ile Lys Thr Arg Tyr Ser Tyr
    370                 375                 380

Phe Ser Glu Tyr Leu Pro Pro Ile Lys Thr Glu Lys Leu Leu Asp Asn
385                 390                 395                 400

Thr Ile Tyr Thr Gln Asn Glu Gly Phe Asn Ile Ala Ser Lys Asn Leu
                405                 410                 415

Lys Thr Glu Phe Asn Gly Gln Asn Lys Ala Val Asn Lys Glu Ala Tyr
            420                 425                 430

Glu Glu Ile Ser Leu Glu His Leu Val Ile Tyr Arg Ile Ala Met Cys
        435                 440                 445

Lys Pro Val Met Tyr Lys
    450
```

<210> SEQ ID NO 38
<211> LENGTH: 461

<212> TYPE: PRT
<213> ORGANISM: Artificial Sequence
<220> FEATURE:
<223> OTHER INFORMATION: BoNT/A Light chain-TD1r Amino Acid Sequence

<400> SEQUENCE: 38

```
Met Pro Phe Val Asn Lys Gln Phe Asn Tyr Lys Asp Pro Val Asn Gly
1               5                   10                  15

Val Asp Ile Ala Tyr Ile Lys Ile Pro Asn Ala Gly Gln Met Gln Pro
            20                  25                  30

Val Lys Ala Phe Lys Ile His Asn Lys Ile Trp Val Ile Pro Glu Arg
        35                  40                  45

Asp Thr Phe Thr Asn Pro Glu Glu Gly Asp Leu Asn Pro Pro Pro Glu
    50                  55                  60

Ala Lys Gln Val Pro Val Ser Tyr Tyr Asp Ser Thr Tyr Leu Ser Thr
65                  70                  75                  80

Asp Asn Glu Lys Asp Asn Tyr Leu Lys Gly Val Thr Lys Leu Phe Glu
                85                  90                  95

Arg Ile Tyr Ser Thr Asp Leu Gly Arg Met Leu Leu Thr Ser Ile Val
            100                 105                 110

Arg Gly Ile Pro Phe Trp Gly Gly Ser Thr Ile Asp Thr Glu Leu Lys
        115                 120                 125

Val Ile Asp Thr Asn Cys Ile Asn Val Ile Gln Pro Asp Gly Ser Tyr
    130                 135                 140

Arg Ser Glu Glu Leu Asn Leu Val Ile Ile Gly Pro Ser Ala Asp Ile
145                 150                 155                 160

Ile Gln Phe Glu Cys Lys Ser Phe Gly His Glu Val Leu Asn Leu Thr
                165                 170                 175

Arg Asn Gly Tyr Gly Ser Thr Gln Tyr Ile Arg Phe Ser Pro Asp Phe
            180                 185                 190

Thr Phe Gly Phe Glu Glu Ser Leu Glu Val Asp Thr Asn Pro Leu Leu
        195                 200                 205

Gly Ala Gly Lys Phe Ala Thr Asp Pro Ala Val Thr Leu Ala His Glu
    210                 215                 220

Leu Ile His Ala Gly His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
                245                 250                 255

Glu Val Ser Phe Glu Glu Leu Arg Thr Phe Gly Gly His Asp Ala Lys
            260                 265                 270

Phe Ile Asp Ser Leu Gln Glu Asn Glu Phe Arg Leu Tyr Tyr Tyr Asn
        275                 280                 285

Lys Phe Lys Asp Ile Ala Ser Thr Leu Asn Lys Ala Lys Ser Ile Val
    290                 295                 300

Gly Thr Thr Ala Ser Leu Gln Tyr Met Lys Asn Val Phe Lys Glu Lys
305                 310                 315                 320

Tyr Leu Leu Ser Glu Asp Thr Ser Gly Lys Phe Ser Val Asp Lys Leu
                325                 330                 335

Lys Phe Asp Lys Leu Tyr Lys Met Leu Thr Glu Ile Tyr Thr Glu Asp
            340                 345                 350

Asn Phe Val Lys Phe Phe Lys Val Leu Asn Arg Lys Thr Tyr Leu Asn
        355                 360                 365

Phe Asp Lys Ala Val Phe Lys Ile Asn Ile Val Pro Lys Val Asn Tyr
    370                 375                 380
```

-continued

```
Thr Ile Tyr Asp Gly Phe Asn Leu Arg Asn Thr Asn Leu Ala Ala Asn
385                 390                 395                 400

Phe Asn Gly Gln Asn Thr Glu Ile Asn Asn Met Asn Phe Thr Lys Leu
                405                 410                 415

Lys Asn Phe Thr Gly Leu Phe Glu Phe Tyr Lys Leu Leu Cys Val Arg
            420                 425                 430

Gly Ile Ile Thr Ser Lys Thr Lys Ser Leu Asp Lys Gly Tyr Asn Lys
        435                 440                 445

Cys Gln Asn Leu Phe Lys Asn Ile Asn Ile Met Ala Lys
    450                 455                 460


<210> SEQ ID NO 39
<211> LENGTH: 454
<212> TYPE: PRT
<213> ORGANISM: Artificial Sequence
<220> FEATURE:
<223> OTHER INFORMATION: BoNT/B Light chain-TD1r Amino Acid Sequence

<400> SEQUENCE: 39

Met Pro Val Thr Ile Asn Asn Phe Asn Tyr Asn Asp Pro Ile Asp Asn
1               5                   10                  15

Asn Asn Ile Ile Met Met Glu Pro Pro Phe Ala Arg Gly Thr Gly Arg
            20                  25                  30

Tyr Tyr Lys Ala Phe Lys Ile Thr Asp Arg Ile Trp Ile Ile Pro Glu
        35                  40                  45

Arg Tyr Thr Phe Gly Tyr Lys Pro Glu Asp Phe Asn Lys Ser Ser Gly
    50                  55                  60

Ile Phe Asn Arg Asp Val Cys Glu Tyr Tyr Asp Pro Asp Tyr Leu Asn
65                  70                  75                  80

Thr Asn Asp Lys Lys Asn Ile Phe Leu Gln Thr Met Ile Lys Leu Phe
                85                  90                  95

Asn Arg Ile Lys Ser Lys Pro Leu Gly Glu Lys Leu Leu Glu Met Ile
            100                 105                 110

Ile Asn Gly Ile Pro Tyr Leu Gly Asp Arg Arg Val Pro Leu Glu Glu
        115                 120                 125

Phe Asn Thr Asn Ile Ala Ser Val Thr Val Asn Lys Leu Ile Ser Asn
    130                 135                 140

Pro Gly Glu Val Glu Arg Lys Lys Gly Ile Phe Ala Asn Leu Ile Ile
145                 150                 155                 160

Phe Gly Pro Gly Pro Val Leu Asn Glu Asn Glu Thr Ile Asp Ile Gly
                165                 170                 175

Ile Gln Asn His Phe Ala Ser Arg Glu Gly Phe Gly Gly Ile Met Gln
            180                 185                 190

Met Lys Phe Cys Pro Glu Tyr Val Ser Val Phe Asn Asn Val Gln Glu
        195                 200                 205

Asn Lys Gly Ala Ser Ile Phe Asn Arg Arg Gly Tyr Phe Ser Asp Pro
    210                 215                 220

Ala Leu Ile Leu Met His Glu Leu Ile His Val Leu His Gly Leu Tyr
225                 230                 235                 240

Gly Ile Lys Val Asp Asp Leu Pro Ile Val Pro Asn Glu Lys Lys Phe
                245                 250                 255

Phe Met Gln Ser Thr Asp Ala Ile Gln Ala Glu Glu Leu Tyr Thr Phe
            260                 265                 270

Gly Gly Gln Asp Pro Ser Ile Ile Thr Pro Ser Thr Asp Lys Ser Ile
        275                 280                 285
```

```
Tyr Asp Lys Val Leu Gln Asn Phe Arg Gly Ile Val Asp Arg Leu Asn
    290                 295                 300

Lys Val Leu Val Cys Ile Ser Asp Pro Asn Ile Asn Ile Asn Ile Tyr
305                 310                 315                 320

Lys Asn Lys Phe Lys Asp Lys Tyr Lys Phe Val Glu Asp Ser Glu Gly
                325                 330                 335

Lys Tyr Ser Ile Asp Val Glu Ser Phe Asp Lys Leu Tyr Lys Ser Leu
            340                 345                 350

Met Phe Gly Phe Thr Glu Thr Asn Ile Ala Glu Asn Tyr Lys Ile Lys
        355                 360                 365

Thr Arg Ala Ser Tyr Phe Ser Asp Ser Leu Pro Pro Val Lys Ile Lys
    370                 375                 380

Asn Leu Leu Asp Asn Glu Ile Tyr Thr Ile Glu Glu Gly Phe Asn Ile
385                 390                 395                 400

Ser Asp Lys Asp Met Glu Lys Glu Tyr Arg Gly Gln Asn Lys Ala Ile
                405                 410                 415

Asn Lys Gln Ala Tyr Glu Glu Ile Ser Lys Glu His Leu Ala Val Tyr
            420                 425                 430

Lys Ile Gln Met Cys Lys Ser Val Lys Cys Gln Asn Leu Phe Lys Asn
        435                 440                 445

Ile Asn Ile Met Ala Lys
    450


<210> SEQ ID NO 40
<211> LENGTH: 462
<212> TYPE: PRT
<213> ORGANISM: Artificial Sequence
<220> FEATURE:
<223> OTHER INFORMATION: BoNT/C Light chain-TD1r Amino Acid Sequence

<400> SEQUENCE: 40

Met Pro Ile Thr Ile Asn Asn Phe Asn Tyr Ser Asp Pro Val Asp Asn
1               5                   10                  15

Lys Asn Ile Leu Tyr Leu Asp Thr His Leu Asn Thr Leu Ala Asn Glu
            20                  25                  30

Pro Glu Lys Ala Phe Arg Ile Thr Gly Asn Ile Trp Val Ile Pro Asp
        35                  40                  45

Arg Phe Ser Arg Asn Ser Asn Pro Asn Leu Asn Lys Pro Pro Arg Val
    50                  55                  60

Thr Ser Pro Lys Ser Gly Tyr Tyr Asp Pro Asn Tyr Leu Ser Thr Asp
65                  70                  75                  80

Ser Asp Lys Asp Pro Phe Leu Lys Glu Ile Ile Lys Leu Phe Lys Arg
                85                  90                  95

Ile Asn Ser Arg Glu Ile Gly Glu Glu Leu Ile Tyr Arg Leu Ser Thr
            100                 105                 110

Asp Ile Pro Phe Pro Gly Asn Asn Asn Thr Pro Ile Asn Thr Phe Asp
        115                 120                 125

Phe Asp Val Asp Phe Asn Ser Val Asp Val Lys Thr Arg Gln Gly Asn
    130                 135                 140

Asn Trp Val Lys Thr Gly Ser Ile Asn Pro Ser Val Ile Ile Thr Gly
145                 150                 155                 160

Pro Arg Glu Asn Ile Ile Asp Pro Glu Thr Ser Thr Phe Lys Leu Thr
                165                 170                 175

Asn Asn Thr Phe Ala Ala Gln Glu Gly Phe Gly Ala Leu Ser Ile Ile
            180                 185                 190
```

```
Ser Ile Ser Pro Arg Phe Met Leu Thr Tyr Ser Asn Ala Thr Asn Asp
        195                 200                 205

Val Gly Glu Gly Arg Phe Ser Lys Ser Glu Phe Cys Met Asp Pro Ile
    210                 215                 220

Leu Ile Leu Met His Glu Leu Asn His Ala Met His Asn Leu Tyr Gly
225                 230                 235                 240

Ile Ala Ile Pro Asn Asp Gln Thr Ile Ser Ser Val Thr Ser Asn Ile
                245                 250                 255

Phe Tyr Ser Gln Tyr Asn Val Lys Leu Glu Tyr Ala Glu Ile Tyr Ala
            260                 265                 270

Phe Gly Gly Pro Thr Ile Asp Leu Ile Pro Lys Ser Ala Arg Lys Tyr
        275                 280                 285

Phe Glu Glu Lys Ala Leu Asp Tyr Tyr Arg Ser Ile Ala Lys Arg Leu
    290                 295                 300

Asn Ser Ile Thr Thr Ala Asn Pro Ser Ser Phe Asn Lys Tyr Ile Gly
305                 310                 315                 320

Glu Tyr Lys Gln Lys Leu Ile Arg Lys Tyr Arg Phe Val Val Glu Ser
                325                 330                 335

Ser Gly Glu Val Thr Val Asn Arg Asn Lys Phe Val Glu Leu Tyr Asn
            340                 345                 350

Glu Leu Thr Gln Ile Phe Thr Glu Phe Asn Tyr Ala Lys Ile Tyr Asn
        355                 360                 365

Val Gln Asn Arg Lys Ile Tyr Leu Ser Asn Val Tyr Thr Pro Val Thr
    370                 375                 380

Ala Asn Ile Leu Asp Asp Asn Val Tyr Asp Ile Gln Asn Gly Phe Asn
385                 390                 395                 400

Ile Pro Lys Ser Asn Leu Asn Val Leu Phe Met Gly Gln Asn Leu Ser
                405                 410                 415

Arg Asn Pro Ala Leu Arg Lys Val Asn Pro Glu Asn Met Leu Tyr Leu
            420                 425                 430

Phe Thr Lys Phe Cys His Lys Ala Ile Asp Gly Arg Ser Leu Tyr Asn
        435                 440                 445

Lys Cys Gln Asn Leu Phe Lys Asn Ile Asn Ile Met Ala Lys
    450                 455                 460


<210> SEQ ID NO 41
<211> LENGTH: 455
<212> TYPE: PRT
<213> ORGANISM: Artificial Sequence
<220> FEATURE:
<223> OTHER INFORMATION: BoNT/D Light chain-TD1r Amino Acid Sequence

<400> SEQUENCE: 41

Met Thr Trp Pro Val Lys Asp Phe Asn Tyr Ser Asp Pro Val Asn Asp
1               5                   10                  15

Asn Asp Ile Leu Tyr Leu Arg Ile Pro Gln Asn Lys Leu Ile Thr Thr
            20                  25                  30

Pro Val Lys Ala Phe Met Ile Thr Gln Asn Ile Trp Val Ile Pro Glu
        35                  40                  45

Arg Phe Ser Ser Asp Thr Asn Pro Ser Leu Ser Lys Pro Pro Arg Pro
    50                  55                  60

Thr Ser Lys Tyr Gln Ser Tyr Tyr Asp Pro Ser Tyr Leu Ser Thr Asp
65                  70                  75                  80

Glu Gln Lys Asp Thr Phe Leu Lys Gly Ile Ile Lys Leu Phe Lys Arg
                85                  90                  95
```

-continued

```
Ile Asn Glu Arg Asp Ile Gly Lys Lys Leu Ile Asn Tyr Leu Val Val
            100                 105                 110

Gly Ser Pro Phe Met Gly Asp Ser Ser Thr Pro Glu Asp Thr Phe Asp
        115                 120                 125

Phe Thr Arg His Thr Thr Asn Ile Ala Val Glu Lys Phe Glu Asn Gly
    130                 135                 140

Ser Trp Lys Val Thr Asn Ile Ile Thr Pro Ser Val Leu Ile Phe Gly
145                 150                 155                 160

Pro Leu Pro Asn Ile Leu Asp Tyr Thr Ala Ser Leu Thr Leu Gln Gly
                165                 170                 175

Gln Gln Ser Asn Pro Ser Phe Glu Gly Phe Gly Thr Leu Ser Ile Leu
            180                 185                 190

Lys Val Ala Pro Glu Phe Leu Leu Thr Phe Ser Asp Val Thr Ser Asn
        195                 200                 205

Gln Ser Ser Ala Val Leu Gly Lys Ser Ile Phe Cys Met Asp Pro Val
    210                 215                 220

Ile Ala Leu Met His Glu Leu Thr His Ser Leu His Gln Leu Tyr Gly
225                 230                 235                 240

Ile Asn Ile Pro Ser Asp Lys Arg Ile Arg Pro Gln Val Ser Glu Gly
                245                 250                 255

Phe Phe Ser Gln Asp Gly Pro Asn Val Gln Phe Glu Glu Leu Tyr Thr
            260                 265                 270

Phe Gly Gly Leu Asp Val Glu Ile Ile Pro Gln Ile Glu Arg Ser Gln
        275                 280                 285

Leu Arg Glu Lys Ala Leu Gly His Tyr Lys Asp Ile Ala Lys Arg Leu
    290                 295                 300

Asn Asn Ile Asn Lys Thr Ile Pro Ser Ser Trp Ile Ser Asn Ile Asp
305                 310                 315                 320

Lys Tyr Lys Lys Ile Phe Ser Glu Lys Tyr Asn Phe Asp Lys Asp Asn
                325                 330                 335

Thr Gly Asn Phe Val Val Asn Ile Asp Lys Phe Asn Ser Leu Tyr Ser
            340                 345                 350

Asp Leu Thr Asn Val Met Ser Glu Val Val Tyr Ser Ser Gln Tyr Asn
        355                 360                 365

Val Lys Asn Arg Thr His Tyr Phe Ser Arg His Tyr Leu Pro Val Phe
    370                 375                 380

Ala Asn Ile Leu Asp Asp Asn Ile Tyr Thr Ile Arg Asp Gly Phe Asn
385                 390                 395                 400

Leu Thr Asn Lys Gly Phe Asn Ile Glu Asn Ser Gly Gln Asn Ile Glu
                405                 410                 415

Arg Asn Pro Ala Leu Gln Lys Leu Ser Ser Glu Ser Val Val Asp Leu
            420                 425                 430

Phe Thr Lys Val Cys Leu Arg Leu Thr Lys Cys Gln Asn Leu Phe Lys
        435                 440                 445

Asn Ile Asn Ile Met Ala Lys
    450                 455
```

<210> SEQ ID NO 42
<211> LENGTH: 435
<212> TYPE: PRT
<213> ORGANISM: Artificial Sequence
<220> FEATURE:
<223> OTHER INFORMATION: BoNT/E Light chain-TD1r Amino Acid Sequence

<400> SEQUENCE: 42

-continued

```
Met Pro Thr Ile Asn Ser Phe Asn Tyr Asn Asp Pro Val Asn Asn Arg
1               5                   10                  15

Thr Ile Leu Tyr Ile Lys Pro Gly Gly Cys Gln Gln Phe Tyr Lys Ser
            20                  25                  30

Phe Asn Ile Met Lys Asn Ile Trp Ile Ile Pro Glu Arg Asn Val Ile
        35                  40                  45

Gly Thr Ile Pro Gln Asp Phe Leu Pro Pro Thr Ser Leu Lys Asn Gly
    50                  55                  60

Asp Ser Ser Tyr Tyr Asp Pro Asn Tyr Leu Gln Ser Asp Gln Glu Lys
65                  70                  75                  80

Asp Lys Phe Leu Lys Ile Val Thr Lys Ile Phe Asn Arg Ile Asn Asp
                85                  90                  95

Asn Leu Ser Gly Arg Ile Leu Leu Glu Glu Leu Ser Lys Ala Asn Pro
            100                 105                 110

Tyr Leu Gly Asn Asp Asn Thr Pro Asp Gly Asp Phe Ile Ile Asn Asp
        115                 120                 125

Ala Ser Ala Val Pro Ile Gln Phe Ser Asn Gly Ser Gln Ser Ile Leu
    130                 135                 140

Leu Pro Asn Val Ile Ile Met Gly Ala Glu Pro Asp Leu Phe Glu Thr
145                 150                 155                 160

Asn Ser Ser Asn Ile Ser Leu Arg Asn Asn Tyr Met Pro Ser Asn His
                165                 170                 175

Gly Phe Gly Ser Ile Ala Ile Val Thr Phe Ser Pro Glu Tyr Ser Phe
            180                 185                 190

Arg Phe Lys Asp Asn Ser Met Asn Glu Phe Ile Gln Asp Pro Ala Leu
        195                 200                 205

Thr Leu Met His Glu Leu Ile His Ser Leu His Gly Leu Tyr Gly Ala
    210                 215                 220

Lys Gly Ile Thr Thr Lys Tyr Thr Ile Thr Gln Lys Gln Asn Pro Leu
225                 230                 235                 240

Ile Thr Asn Ile Arg Gly Thr Asn Ile Glu Glu Phe Leu Thr Phe Gly
                245                 250                 255

Gly Thr Asp Leu Asn Ile Ile Thr Ser Ala Gln Ser Asn Asp Ile Tyr
            260                 265                 270

Thr Asn Leu Leu Ala Asp Tyr Lys Lys Ile Ala Ser Lys Leu Ser Lys
        275                 280                 285

Val Gln Val Ser Asn Pro Leu Leu Asn Pro Tyr Lys Asp Val Phe Glu
    290                 295                 300

Ala Lys Tyr Gly Leu Asp Lys Asp Ala Ser Gly Ile Tyr Ser Val Asn
305                 310                 315                 320

Ile Asn Lys Phe Asn Asp Ile Phe Lys Lys Leu Tyr Ser Phe Thr Glu
                325                 330                 335

Phe Asp Leu Ala Thr Lys Phe Gln Val Lys Cys Arg Gln Thr Tyr Ile
            340                 345                 350

Gly Gln Tyr Lys Tyr Phe Lys Leu Ser Asn Leu Leu Asn Asp Ser Ile
        355                 360                 365

Tyr Asn Ile Ser Glu Gly Tyr Asn Ile Asn Asn Leu Lys Val Asn Phe
    370                 375                 380

Arg Gly Gln Asn Ala Asn Leu Asn Pro Arg Ile Ile Thr Pro Ile Thr
385                 390                 395                 400

Gly Arg Gly Leu Val Lys Lys Ile Ile Arg Phe Cys Lys Asn Ile Val
                405                 410                 415

Ser Val Lys Gly Ile Arg Cys Gln Asn Leu Phe Lys Asn Ile Asn Ile
```

```
            420                 425                 430

Met Ala Lys
        435


<210> SEQ ID NO 43
<211> LENGTH: 449
<212> TYPE: PRT
<213> ORGANISM: Artificial Sequence
<220> FEATURE:
<223> OTHER INFORMATION: BoNT/F Light chain-TD1r Amino Acid Sequence

<400> SEQUENCE: 43

Met Pro Val Ala Ile Asn Ser Phe Asn Tyr Asn Asp Pro Val Asn Asp
1               5                   10                  15

Asp Thr Ile Leu Tyr Met Gln Ile Pro Tyr Glu Glu Lys Ser Lys Lys
            20                  25                  30

Tyr Tyr Lys Ala Phe Glu Ile Met Arg Asn Val Trp Ile Ile Pro Glu
        35                  40                  45

Arg Asn Thr Ile Gly Thr Asn Pro Ser Asp Phe Asp Pro Pro Ala Ser
    50                  55                  60

Leu Lys Asn Gly Ser Ser Ala Tyr Tyr Asp Pro Asn Tyr Leu Thr Thr
65                  70                  75                  80

Asp Ala Glu Lys Asp Arg Tyr Leu Lys Thr Thr Ile Lys Leu Phe Lys
                85                  90                  95

Arg Ile Asn Ser Asn Pro Ala Gly Lys Val Leu Leu Gln Glu Ile Ser
            100                 105                 110

Tyr Ala Lys Pro Tyr Leu Gly Asn Asp His Thr Pro Ile Asp Glu Phe
        115                 120                 125

Ser Pro Val Thr Arg Thr Thr Ser Val Asn Ile Lys Leu Ser Thr Asn
    130                 135                 140

Val Glu Ser Ser Met Leu Leu Asn Leu Leu Val Leu Gly Ala Gly Pro
145                 150                 155                 160

Asp Ile Phe Glu Ser Cys Cys Tyr Pro Val Arg Lys Leu Ile Asp Pro
                165                 170                 175

Asp Val Val Tyr Asp Pro Ser Asn Tyr Gly Phe Gly Ser Ile Asn Ile
            180                 185                 190

Val Thr Phe Ser Pro Glu Tyr Glu Tyr Thr Phe Asn Asp Ile Ser Gly
        195                 200                 205

Gly His Asn Ser Ser Thr Glu Ser Phe Ile Ala Asp Pro Ala Ile Ser
    210                 215                 220

Leu Ala His Glu Leu Ile His Ala Leu His Gly Leu Tyr Gly Ala Arg
225                 230                 235                 240

Gly Val Thr Tyr Glu Glu Thr Ile Glu Val Lys Gln Ala Pro Leu Met
                245                 250                 255

Ile Ala Glu Lys Pro Ile Arg Leu Glu Glu Phe Leu Thr Phe Gly Gly
            260                 265                 270

Gln Asp Leu Asn Ile Ile Thr Ser Ala Met Lys Glu Lys Ile Tyr Asn
        275                 280                 285

Asn Leu Leu Ala Asn Tyr Glu Lys Ile Ala Thr Arg Leu Ser Glu Val
    290                 295                 300

Asn Ser Ala Pro Pro Glu Tyr Asp Ile Asn Glu Tyr Lys Asp Tyr Phe
305                 310                 315                 320

Gln Trp Lys Tyr Gly Leu Asp Lys Asn Ala Asp Gly Ser Tyr Thr Val
                325                 330                 335

Asn Glu Asn Lys Phe Asn Glu Ile Tyr Lys Lys Leu Tyr Ser Phe Thr
```

```
            340                 345                 350

Glu Ser Asp Leu Ala Asn Lys Phe Lys Val Lys Cys Arg Asn Thr Tyr
        355                 360                 365

Phe Ile Lys Tyr Glu Phe Leu Lys Val Pro Asn Leu Leu Asp Asp Asp
    370                 375                 380

Ile Tyr Thr Val Ser Glu Gly Phe Asn Ile Gly Asn Leu Ala Val Asn
385                 390                 395                 400

Asn Arg Gly Gln Ser Ile Lys Leu Asn Pro Lys Ile Ile Asp Ser Ile
                405                 410                 415

Pro Asp Lys Gly Leu Val Glu Lys Ile Val Lys Phe Cys Lys Ser Val
            420                 425                 430

Ile Pro Arg Lys Cys Gln Asn Leu Phe Lys Asn Ile Asn Ile Met Ala
        435                 440                 445

Lys


<210> SEQ ID NO 44
<211> LENGTH: 454
<212> TYPE: PRT
<213> ORGANISM: Artificial Sequence
<220> FEATURE:
<223> OTHER INFORMATION: BoNT/G Light chain-TD1r Amino Acid Sequence

<400> SEQUENCE: 44

Met Pro Val Asn Ile Lys Phe Asn Tyr Asn Asp Pro Ile Asn Asn Asp
1               5                   10                  15

Asp Ile Ile Met Met Glu Pro Phe Asn Asp Pro Gly Pro Gly Thr Tyr
            20                  25                  30

Tyr Lys Ala Phe Arg Ile Ile Asp Arg Ile Trp Ile Val Pro Glu Arg
        35                  40                  45

Phe Thr Tyr Gly Phe Gln Pro Asp Gln Phe Asn Ala Ser Thr Gly Val
    50                  55                  60

Phe Ser Lys Asp Val Tyr Glu Tyr Tyr Asp Pro Thr Tyr Leu Lys Thr
65                  70                  75                  80

Asp Ala Glu Lys Asp Lys Phe Leu Lys Thr Met Ile Lys Leu Phe Asn
                85                  90                  95

Arg Ile Asn Ser Lys Pro Ser Gly Gln Arg Leu Leu Asp Met Ile Val
            100                 105                 110

Asp Ala Ile Pro Tyr Leu Gly Asn Ala Ser Thr Pro Pro Asp Lys Phe
        115                 120                 125

Ala Ala Asn Val Ala Asn Val Ser Ile Asn Lys Lys Ile Ile Gln Pro
    130                 135                 140

Gly Ala Glu Asp Gln Ile Lys Gly Leu Met Thr Asn Leu Ile Ile Phe
145                 150                 155                 160

Gly Pro Gly Pro Val Leu Ser Asp Asn Phe Thr Asp Ser Met Ile Met
                165                 170                 175

Asn Gly His Ser Pro Ile Ser Glu Gly Phe Gly Ala Arg Met Met Ile
            180                 185                 190

Arg Phe Cys Pro Ser Cys Leu Asn Val Phe Asn Asn Val Gln Glu Asn
        195                 200                 205

Lys Asp Thr Ser Ile Phe Ser Arg Arg Ala Tyr Phe Ala Asp Pro Ala
    210                 215                 220

Leu Thr Leu Met His Glu Leu Ile His Val Leu His Gly Leu Tyr Gly
225                 230                 235                 240

Ile Lys Ile Ser Asn Leu Pro Ile Thr Pro Asn Thr Lys Glu Phe Phe
                245                 250                 255
```

```
Met Gln His Ser Asp Pro Val Gln Ala Glu Glu Leu Tyr Thr Phe Gly
            260                 265                 270

Gly His Asp Pro Ser Val Ile Ser Pro Ser Thr Asp Met Asn Ile Tyr
        275                 280                 285

Asn Lys Ala Leu Gln Asn Phe Gln Asp Ile Ala Asn Arg Leu Asn Ile
    290                 295                 300

Val Ser Ser Ala Gln Gly Ser Gly Ile Asp Ile Ser Leu Tyr Lys Gln
305                 310                 315                 320

Ile Tyr Lys Asn Lys Tyr Asp Phe Val Glu Asp Pro Asn Gly Lys Tyr
                325                 330                 335

Ser Val Asp Lys Asp Lys Phe Asp Lys Leu Tyr Lys Ala Leu Met Phe
            340                 345                 350

Gly Phe Thr Glu Thr Asn Leu Ala Gly Glu Tyr Gly Ile Lys Thr Arg
        355                 360                 365

Tyr Ser Tyr Phe Ser Glu Tyr Leu Pro Pro Ile Lys Thr Glu Lys Leu
    370                 375                 380

Leu Asp Asn Thr Ile Tyr Thr Gln Asn Glu Gly Phe Asn Ile Ala Ser
385                 390                 395                 400

Lys Asn Leu Lys Thr Glu Phe Asn Gly Gln Asn Lys Ala Val Asn Lys
                405                 410                 415

Glu Ala Tyr Glu Glu Ile Ser Leu Glu His Leu Val Ile Tyr Arg Ile
            420                 425                 430

Ala Met Cys Lys Pro Val Met Tyr Lys Cys Gln Asn Leu Phe Lys Asn
        435                 440                 445

Ile Asn Ile Met Ala Lys
    450


<210> SEQ ID NO 45
<211> LENGTH: 469
<212> TYPE: PRT
<213> ORGANISM: Artificial Sequence
<220> FEATURE:
<223> OTHER INFORMATION: TD1-BoNT/A Light chain Amino Acid Sequence with
      hexahistidine

<400> SEQUENCE: 45

Met Lys Ala Met Ile Asn Ile Asn Lys Phe Leu Asn Gln Cys Pro Phe
1               5                   10                  15

Val Asn Lys Gln Phe Asn Tyr Lys Asp Pro Val Asn Gly Val Asp Ile
            20                  25                  30

Ala Tyr Ile Lys Ile Pro Asn Ala Gly Gln Met Gln Pro Val Lys Ala
        35                  40                  45

Phe Lys Ile His Asn Lys Ile Trp Val Ile Pro Glu Arg Asp Thr Phe
    50                  55                  60

Thr Asn Pro Glu Glu Gly Asp Leu Asn Pro Pro Pro Glu Ala Lys Gln
65                  70                  75                  80

Val Pro Val Ser Tyr Tyr Asp Ser Thr Tyr Leu Ser Thr Asp Asn Glu
                85                  90                  95

Lys Asp Asn Tyr Leu Lys Gly Val Thr Lys Leu Phe Glu Arg Ile Tyr
            100                 105                 110

Ser Thr Asp Leu Gly Arg Met Leu Leu Thr Ser Ile Val Arg Gly Ile
        115                 120                 125

Pro Phe Trp Gly Gly Ser Thr Ile Asp Thr Glu Leu Lys Val Ile Asp
    130                 135                 140

Thr Asn Cys Ile Asn Val Ile Gln Pro Asp Gly Ser Tyr Arg Ser Glu
```

145 150 155 160

Glu Leu Asn Leu Val Ile Ile Gly Pro Ser Ala Asp Ile Ile Gln Phe
165 170 175

Glu Cys Lys Ser Phe Gly His Glu Val Leu Asn Leu Thr Arg Asn Gly
180 185 190

Tyr Gly Ser Thr Gln Tyr Ile Arg Phe Ser Pro Asp Phe Thr Phe Gly
195 200 205

Phe Glu Glu Ser Leu Glu Val Asp Thr Asn Pro Leu Leu Gly Ala Gly
210 215 220

Lys Phe Ala Thr Asp Pro Ala Val Thr Leu Ala His Glu Leu Ile His
225 230 235 240

Ala Gly His Arg Leu Tyr Gly Ile Ala Ile Asn Pro Asn Arg Val Phe
245 250 255

Lys Val Asn Thr Asn Ala Tyr Tyr Glu Met Ser Gly Leu Glu Val Ser
260 265 270

Phe Glu Glu Leu Arg Thr Phe Gly Gly His Asp Ala Lys Phe Ile Asp
275 280 285

Ser Leu Gln Glu Asn Glu Phe Arg Leu Tyr Tyr Tyr Asn Lys Phe Lys
290 295 300

Asp Ile Ala Ser Thr Leu Asn Lys Ala Lys Ser Ile Val Gly Thr Thr
305 310 315 320

Ala Ser Leu Gln Tyr Met Lys Asn Val Phe Lys Glu Lys Tyr Leu Leu
325 330 335

Ser Glu Asp Thr Ser Gly Lys Phe Ser Val Asp Lys Leu Lys Phe Asp
340 345 350

Lys Leu Tyr Lys Met Leu Thr Glu Ile Tyr Thr Glu Asp Asn Phe Val
355 360 365

Lys Phe Phe Lys Val Leu Asn Arg Lys Thr Tyr Leu Asn Phe Asp Lys
370 375 380

Ala Val Phe Lys Ile Asn Ile Val Pro Lys Val Asn Tyr Thr Ile Tyr
385 390 395 400

Asp Gly Phe Asn Leu Arg Asn Thr Asn Leu Ala Ala Asn Phe Asn Gly
405 410 415

Gln Asn Thr Glu Ile Asn Asn Met Asn Phe Thr Lys Leu Lys Asn Phe
420 425 430

Thr Gly Leu Phe Glu Phe Tyr Lys Leu Leu Cys Val Arg Gly Ile Ile
435 440 445

Thr Ser Lys Thr Lys Ser Leu Asp Lys Gly Tyr Asn Lys Leu Glu His
450 455 460

His His His His His
465

<210> SEQ ID NO 46
<211> LENGTH: 462
<212> TYPE: PRT
<213> ORGANISM: Artificial Sequence
<220> FEATURE:
<223> OTHER INFORMATION: TD1-BoNT/B Light chain Amino Acid Sequence with hexahistidine

<400> SEQUENCE: 46

Met Lys Ala Met Ile Asn Ile Asn Lys Phe Leu Asn Gln Cys Pro Val
1 5 10 15

Thr Ile Asn Asn Phe Asn Tyr Asn Asp Pro Ile Asp Asn Asn Asn Ile
20 25 30

-continued

```
Ile Met Met Glu Pro Pro Phe Ala Arg Gly Thr Gly Arg Tyr Tyr Lys
        35                  40                  45

Ala Phe Lys Ile Thr Asp Arg Ile Trp Ile Ile Pro Glu Arg Tyr Thr
    50                  55                  60

Phe Gly Tyr Lys Pro Glu Asp Phe Asn Lys Ser Ser Gly Ile Phe Asn
65                  70                  75                  80

Arg Asp Val Cys Glu Tyr Tyr Asp Pro Asp Tyr Leu Asn Thr Asn Asp
                85                  90                  95

Lys Lys Asn Ile Phe Leu Gln Thr Met Ile Lys Leu Phe Asn Arg Ile
            100                 105                 110

Lys Ser Lys Pro Leu Gly Glu Lys Leu Leu Glu Met Ile Ile Asn Gly
        115                 120                 125

Ile Pro Tyr Leu Gly Asp Arg Arg Val Pro Leu Glu Glu Phe Asn Thr
    130                 135                 140

Asn Ile Ala Ser Val Thr Val Asn Lys Leu Ile Ser Asn Pro Gly Glu
145                 150                 155                 160

Val Glu Arg Lys Lys Gly Ile Phe Ala Asn Leu Ile Ile Phe Gly Pro
                165                 170                 175

Gly Pro Val Leu Asn Glu Asn Glu Thr Ile Asp Ile Gly Ile Gln Asn
            180                 185                 190

His Phe Ala Ser Arg Glu Gly Phe Gly Gly Ile Met Gln Met Lys Phe
        195                 200                 205

Cys Pro Glu Tyr Val Ser Val Phe Asn Asn Val Gln Glu Asn Lys Gly
    210                 215                 220

Ala Ser Ile Phe Asn Arg Arg Gly Tyr Phe Ser Asp Pro Ala Leu Ile
225                 230                 235                 240

Leu Met His Glu Leu Ile His Val Leu His Gly Leu Tyr Gly Ile Lys
                245                 250                 255

Val Asp Asp Leu Pro Ile Val Pro Asn Glu Lys Lys Phe Phe Met Gln
            260                 265                 270

Ser Thr Asp Ala Ile Gln Ala Glu Glu Leu Tyr Thr Phe Gly Gly Gln
        275                 280                 285

Asp Pro Ser Ile Ile Thr Pro Ser Thr Asp Lys Ser Ile Tyr Asp Lys
    290                 295                 300

Val Leu Gln Asn Phe Arg Gly Ile Val Asp Arg Leu Asn Lys Val Leu
305                 310                 315                 320

Val Cys Ile Ser Asp Pro Asn Ile Asn Ile Asn Ile Tyr Lys Asn Lys
                325                 330                 335

Phe Lys Asp Lys Tyr Lys Phe Val Glu Asp Ser Glu Gly Lys Tyr Ser
            340                 345                 350

Ile Asp Val Glu Ser Phe Asp Lys Leu Tyr Lys Ser Leu Met Phe Gly
        355                 360                 365

Phe Thr Glu Thr Asn Ile Ala Glu Asn Tyr Lys Ile Lys Thr Arg Ala
    370                 375                 380

Ser Tyr Phe Ser Asp Ser Leu Pro Pro Val Lys Ile Lys Asn Leu Leu
385                 390                 395                 400

Asp Asn Glu Ile Tyr Thr Ile Glu Glu Gly Phe Asn Ile Ser Asp Lys
                405                 410                 415

Asp Met Glu Lys Glu Tyr Arg Gly Gln Asn Lys Ala Ile Asn Lys Gln
            420                 425                 430

Ala Tyr Glu Glu Ile Ser Lys Glu His Leu Ala Val Tyr Lys Ile Gln
        435                 440                 445

Met Cys Lys Ser Val Lys Leu Glu His His His His His His
```

450 455 460

<210> SEQ ID NO 47
<211> LENGTH: 470
<212> TYPE: PRT
<213> ORGANISM: Artificial Sequence
<220> FEATURE:
<223> OTHER INFORMATION: TD1-BoNT/C Light chain Amino Acid Sequence with hexahistidine

<400> SEQUENCE: 47

Met Lys Ala Met Ile Asn Ile Asn Lys Phe Leu Asn Gln Cys Pro Ile
1 5 10 15

Thr Ile Asn Asn Phe Asn Tyr Ser Asp Pro Val Asp Asn Lys Asn Ile
20 25 30

Leu Tyr Leu Asp Thr His Leu Asn Thr Leu Ala Asn Glu Pro Glu Lys
35 40 45

Ala Phe Arg Ile Thr Gly Asn Ile Trp Val Ile Pro Asp Arg Phe Ser
50 55 60

Arg Asn Ser Asn Pro Asn Leu Asn Lys Pro Pro Arg Val Thr Ser Pro
65 70 75 80

Lys Ser Gly Tyr Tyr Asp Pro Asn Tyr Leu Ser Thr Asp Ser Asp Lys
85 90 95

Asp Pro Phe Leu Lys Glu Ile Ile Lys Leu Phe Lys Arg Ile Asn Ser
100 105 110

Arg Glu Ile Gly Glu Glu Leu Ile Tyr Arg Leu Ser Thr Asp Ile Pro
115 120 125

Phe Pro Gly Asn Asn Asn Thr Pro Ile Asn Thr Phe Asp Phe Asp Val
130 135 140

Asp Phe Asn Ser Val Asp Val Lys Thr Arg Gln Gly Asn Asn Trp Val
145 150 155 160

Lys Thr Gly Ser Ile Asn Pro Ser Val Ile Ile Thr Gly Pro Arg Glu
165 170 175

Asn Ile Ile Asp Pro Glu Thr Ser Thr Phe Lys Leu Thr Asn Asn Thr
180 185 190

Phe Ala Ala Gln Glu Gly Phe Gly Ala Leu Ser Ile Ile Ser Ile Ser
195 200 205

Pro Arg Phe Met Leu Thr Tyr Ser Asn Ala Thr Asn Asp Val Gly Glu
210 215 220

Gly Arg Phe Ser Lys Ser Glu Phe Cys Met Asp Pro Ile Leu Ile Leu
225 230 235 240

Met His Glu Leu Asn His Ala Met His Asn Leu Tyr Gly Ile Ala Ile
245 250 255

Pro Asn Asp Gln Thr Ile Ser Ser Val Thr Ser Asn Ile Phe Tyr Ser
260 265 270

Gln Tyr Asn Val Lys Leu Glu Tyr Ala Glu Ile Tyr Ala Phe Gly Gly
275 280 285

Pro Thr Ile Asp Leu Ile Pro Lys Ser Ala Arg Lys Tyr Phe Glu Glu
290 295 300

Lys Ala Leu Asp Tyr Tyr Arg Ser Ile Ala Lys Arg Leu Asn Ser Ile
305 310 315 320

Thr Thr Ala Asn Pro Ser Ser Phe Asn Lys Tyr Ile Gly Glu Tyr Lys
325 330 335

Gln Lys Leu Ile Arg Lys Tyr Arg Phe Val Val Glu Ser Ser Gly Glu
340 345 350

```
Val Thr Val Asn Arg Asn Lys Phe Val Glu Leu Tyr Asn Glu Leu Thr
        355                 360                 365

Gln Ile Phe Thr Glu Phe Asn Tyr Ala Lys Ile Tyr Asn Val Gln Asn
    370                 375                 380

Arg Lys Ile Tyr Leu Ser Asn Val Tyr Thr Pro Val Thr Ala Asn Ile
385                 390                 395                 400

Leu Asp Asp Asn Val Tyr Asp Ile Gln Asn Gly Phe Asn Ile Pro Lys
                405                 410                 415

Ser Asn Leu Asn Val Leu Phe Met Gly Gln Asn Leu Ser Arg Asn Pro
            420                 425                 430

Ala Leu Arg Lys Val Asn Pro Glu Asn Met Leu Tyr Leu Phe Thr Lys
        435                 440                 445

Phe Cys His Lys Ala Ile Asp Gly Arg Ser Leu Tyr Asn Lys Leu Glu
    450                 455                 460

His His His His His His
465                 470


<210> SEQ ID NO 48
<211> LENGTH: 463
<212> TYPE: PRT
<213> ORGANISM: Artificial Sequence
<220> FEATURE:
<223> OTHER INFORMATION: TD1-BoNT/D Light chain Amino Acid Sequence with
      hexahistidine

<400> SEQUENCE: 48

Met Lys Ala Met Ile Asn Ile Asn Lys Phe Leu Asn Gln Cys Thr Trp
1               5                   10                  15

Pro Val Lys Asp Phe Asn Tyr Ser Asp Pro Val Asn Asp Asn Asp Ile
            20                  25                  30

Leu Tyr Leu Arg Ile Pro Gln Asn Lys Leu Ile Thr Thr Pro Val Lys
        35                  40                  45

Ala Phe Met Ile Thr Gln Asn Ile Trp Val Ile Pro Glu Arg Phe Ser
    50                  55                  60

Ser Asp Thr Asn Pro Ser Leu Ser Lys Pro Pro Arg Pro Thr Ser Lys
65                  70                  75                  80

Tyr Gln Ser Tyr Tyr Asp Pro Ser Tyr Leu Ser Thr Asp Glu Gln Lys
                85                  90                  95

Asp Thr Phe Leu Lys Gly Ile Ile Lys Leu Phe Lys Arg Ile Asn Glu
            100                 105                 110

Arg Asp Ile Gly Lys Lys Leu Ile Asn Tyr Leu Val Val Gly Ser Pro
        115                 120                 125

Phe Met Gly Asp Ser Ser Thr Pro Glu Asp Thr Phe Asp Phe Thr Arg
    130                 135                 140

His Thr Thr Asn Ile Ala Val Glu Lys Phe Glu Asn Gly Ser Trp Lys
145                 150                 155                 160

Val Thr Asn Ile Ile Thr Pro Ser Val Leu Ile Phe Gly Pro Leu Pro
                165                 170                 175

Asn Ile Leu Asp Tyr Thr Ala Ser Leu Thr Leu Gln Gly Gln Gln Ser
            180                 185                 190

Asn Pro Ser Phe Glu Gly Phe Gly Thr Leu Ser Ile Leu Lys Val Ala
        195                 200                 205

Pro Glu Phe Leu Leu Thr Phe Ser Asp Val Thr Ser Asn Gln Ser Ser
    210                 215                 220

Ala Val Leu Gly Lys Ser Ile Phe Cys Met Asp Pro Val Ile Ala Leu
225                 230                 235                 240
```

```
Met His Glu Leu Thr His Ser Leu His Gln Leu Tyr Gly Ile Asn Ile
                245                 250                 255

Pro Ser Asp Lys Arg Ile Arg Pro Gln Val Ser Glu Gly Phe Phe Ser
            260                 265                 270

Gln Asp Gly Pro Asn Val Gln Phe Glu Glu Leu Tyr Thr Phe Gly Gly
        275                 280                 285

Leu Asp Val Glu Ile Ile Pro Gln Ile Glu Arg Ser Gln Leu Arg Glu
    290                 295                 300

Lys Ala Leu Gly His Tyr Lys Asp Ile Ala Lys Arg Leu Asn Asn Ile
305                 310                 315                 320

Asn Lys Thr Ile Pro Ser Ser Trp Ile Ser Asn Ile Asp Lys Tyr Lys
                325                 330                 335

Lys Ile Phe Ser Glu Lys Tyr Asn Phe Asp Lys Asp Asn Thr Gly Asn
            340                 345                 350

Phe Val Val Asn Ile Asp Lys Phe Asn Ser Leu Tyr Ser Asp Leu Thr
        355                 360                 365

Asn Val Met Ser Glu Val Val Tyr Ser Ser Gln Tyr Asn Val Lys Asn
    370                 375                 380

Arg Thr His Tyr Phe Ser Arg His Tyr Leu Pro Val Phe Ala Asn Ile
385                 390                 395                 400

Leu Asp Asp Asn Ile Tyr Thr Ile Arg Asp Gly Phe Asn Leu Thr Asn
                405                 410                 415

Lys Gly Phe Asn Ile Glu Asn Ser Gly Gln Asn Ile Glu Arg Asn Pro
            420                 425                 430

Ala Leu Gln Lys Leu Ser Ser Glu Ser Val Val Asp Leu Phe Thr Lys
        435                 440                 445

Val Cys Leu Arg Leu Thr Lys Leu Glu His His His His His His
    450                 455                 460


<210> SEQ ID NO 49
<211> LENGTH: 443
<212> TYPE: PRT
<213> ORGANISM: Artificial Sequence
<220> FEATURE:
<223> OTHER INFORMATION: TD1-BoNT/E Light chain Amino Acid Sequence with
      hexahistidine

<400> SEQUENCE: 49

Met Lys Ala Met Ile Asn Ile Asn Lys Phe Leu Asn Gln Cys Pro Thr
1               5                   10                  15

Ile Asn Ser Phe Asn Tyr Asn Asp Pro Val Asn Asn Arg Thr Ile Leu
            20                  25                  30

Tyr Ile Lys Pro Gly Gly Cys Gln Gln Phe Tyr Lys Ser Phe Asn Ile
        35                  40                  45

Met Lys Asn Ile Trp Ile Ile Pro Glu Arg Asn Val Ile Gly Thr Ile
    50                  55                  60

Pro Gln Asp Phe Leu Pro Pro Thr Ser Leu Lys Asn Gly Asp Ser Ser
65                  70                  75                  80

Tyr Tyr Asp Pro Asn Tyr Leu Gln Ser Asp Gln Glu Lys Asp Lys Phe
                85                  90                  95

Leu Lys Ile Val Thr Lys Ile Phe Asn Arg Ile Asn Asp Asn Leu Ser
            100                 105                 110

Gly Arg Ile Leu Leu Glu Glu Leu Ser Lys Ala Asn Pro Tyr Leu Gly
        115                 120                 125

Asn Asp Asn Thr Pro Asp Gly Asp Phe Ile Ile Asn Asp Ala Ser Ala
```

-continued

```
    130                 135                 140

Val Pro Ile Gln Phe Ser Asn Gly Ser Gln Ser Ile Leu Leu Pro Asn
145                 150                 155                 160

Val Ile Ile Met Gly Ala Glu Pro Asp Leu Phe Glu Thr Asn Ser Ser
                165                 170                 175

Asn Ile Ser Leu Arg Asn Asn Tyr Met Pro Ser Asn His Gly Phe Gly
            180                 185                 190

Ser Ile Ala Ile Val Thr Phe Ser Pro Glu Tyr Ser Phe Arg Phe Lys
        195                 200                 205

Asp Asn Ser Met Asn Glu Phe Ile Gln Asp Pro Ala Leu Thr Leu Met
    210                 215                 220

His Glu Leu Ile His Ser Leu His Gly Leu Tyr Gly Ala Lys Gly Ile
225                 230                 235                 240

Thr Thr Lys Tyr Thr Ile Thr Gln Lys Gln Asn Pro Leu Ile Thr Asn
                245                 250                 255

Ile Arg Gly Thr Asn Ile Glu Glu Phe Leu Thr Phe Gly Gly Thr Asp
            260                 265                 270

Leu Asn Ile Ile Thr Ser Ala Gln Ser Asn Asp Ile Tyr Thr Asn Leu
        275                 280                 285

Leu Ala Asp Tyr Lys Lys Ile Ala Ser Lys Leu Ser Lys Val Gln Val
    290                 295                 300

Ser Asn Pro Leu Leu Asn Pro Tyr Lys Asp Val Phe Glu Ala Lys Tyr
305                 310                 315                 320

Gly Leu Asp Lys Asp Ala Ser Gly Ile Tyr Ser Val Asn Ile Asn Lys
                325                 330                 335

Phe Asn Asp Ile Phe Lys Lys Leu Tyr Ser Phe Thr Glu Phe Asp Leu
            340                 345                 350

Ala Thr Lys Phe Gln Val Lys Cys Arg Gln Thr Tyr Ile Gly Gln Tyr
        355                 360                 365

Lys Tyr Phe Lys Leu Ser Asn Leu Leu Asn Asp Ser Ile Tyr Asn Ile
    370                 375                 380

Ser Glu Gly Tyr Asn Ile Asn Asn Leu Lys Val Asn Phe Arg Gly Gln
385                 390                 395                 400

Asn Ala Asn Leu Asn Pro Arg Ile Ile Thr Pro Ile Thr Gly Arg Gly
                405                 410                 415

Leu Val Lys Lys Ile Ile Arg Phe Cys Lys Asn Ile Val Ser Val Lys
            420                 425                 430

Gly Ile Arg Leu Glu His His His His His His
        435                 440


<210> SEQ ID NO 50
<211> LENGTH: 457
<212> TYPE: PRT
<213> ORGANISM: Artificial Sequence
<220> FEATURE:
<223> OTHER INFORMATION: TD1-BoNT/F Light chain Amino Acid Sequence with
      hexahistidine

<400> SEQUENCE: 50

Met Lys Ala Met Ile Asn Ile Asn Lys Phe Leu Asn Gln Cys Pro Val
1               5                   10                  15

Ala Ile Asn Ser Phe Asn Tyr Asn Asp Pro Val Asn Asp Asp Thr Ile
            20                  25                  30

Leu Tyr Met Gln Ile Pro Tyr Glu Glu Lys Ser Lys Lys Tyr Tyr Lys
        35                  40                  45
```

-continued

```
Ala Phe Glu Ile Met Arg Asn Val Trp Ile Ile Pro Glu Arg Asn Thr
    50                  55                  60

Ile Gly Thr Asn Pro Ser Asp Phe Asp Pro Pro Ala Ser Leu Lys Asn
65                  70                  75                  80

Gly Ser Ser Ala Tyr Tyr Asp Pro Asn Tyr Leu Thr Thr Asp Ala Glu
                85                  90                  95

Lys Asp Arg Tyr Leu Lys Thr Thr Ile Lys Leu Phe Lys Arg Ile Asn
            100                 105                 110

Ser Asn Pro Ala Gly Lys Val Leu Leu Gln Glu Ile Ser Tyr Ala Lys
        115                 120                 125

Pro Tyr Leu Gly Asn Asp His Thr Pro Ile Asp Glu Phe Ser Pro Val
    130                 135                 140

Thr Arg Thr Thr Ser Val Asn Ile Lys Leu Ser Thr Asn Val Glu Ser
145                 150                 155                 160

Ser Met Leu Leu Asn Leu Leu Val Leu Gly Ala Gly Pro Asp Ile Phe
                165                 170                 175

Glu Ser Cys Cys Tyr Pro Val Arg Lys Leu Ile Asp Pro Asp Val Val
            180                 185                 190

Tyr Asp Pro Ser Asn Tyr Gly Phe Gly Ser Ile Asn Ile Val Thr Phe
        195                 200                 205

Ser Pro Glu Tyr Glu Tyr Thr Phe Asn Asp Ile Ser Gly Gly His Asn
    210                 215                 220

Ser Ser Thr Glu Ser Phe Ile Ala Asp Pro Ala Ile Ser Leu Ala His
225                 230                 235                 240

Glu Leu Ile His Ala Leu His Gly Leu Tyr Gly Ala Arg Gly Val Thr
                245                 250                 255

Tyr Glu Glu Thr Ile Glu Val Lys Gln Ala Pro Leu Met Ile Ala Glu
            260                 265                 270

Lys Pro Ile Arg Leu Glu Glu Phe Leu Thr Phe Gly Gly Gln Asp Leu
        275                 280                 285

Asn Ile Ile Thr Ser Ala Met Lys Glu Lys Ile Tyr Asn Asn Leu Leu
    290                 295                 300

Ala Asn Tyr Glu Lys Ile Ala Thr Arg Leu Ser Glu Val Asn Ser Ala
305                 310                 315                 320

Pro Pro Glu Tyr Asp Ile Asn Glu Tyr Lys Asp Tyr Phe Gln Trp Lys
                325                 330                 335

Tyr Gly Leu Asp Lys Asn Ala Asp Gly Ser Tyr Thr Val Asn Glu Asn
            340                 345                 350

Lys Phe Asn Glu Ile Tyr Lys Lys Leu Tyr Ser Phe Thr Glu Ser Asp
        355                 360                 365

Leu Ala Asn Lys Phe Lys Val Lys Cys Arg Asn Thr Tyr Phe Ile Lys
    370                 375                 380

Tyr Glu Phe Leu Lys Val Pro Asn Leu Leu Asp Asp Asp Ile Tyr Thr
385                 390                 395                 400

Val Ser Glu Gly Phe Asn Ile Gly Asn Leu Ala Val Asn Asn Arg Gly
                405                 410                 415

Gln Ser Ile Lys Leu Asn Pro Lys Ile Ile Asp Ser Ile Pro Asp Lys
            420                 425                 430

Gly Leu Val Glu Lys Ile Val Lys Phe Cys Lys Ser Val Ile Pro Arg
        435                 440                 445

Lys Leu Glu His His His His His His
    450                 455
```

-continued

<210> SEQ ID NO 51
<211> LENGTH: 462
<212> TYPE: PRT
<213> ORGANISM: Artificial Sequence
<220> FEATURE:
<223> OTHER INFORMATION: TD1-BoNT/G Light chain Amino Acid Sequence with hexahistidine

<400> SEQUENCE: 51

```
Met Lys Ala Met Ile Asn Ile Asn Lys Phe Leu Asn Gln Cys Pro Val
1               5                   10                  15

Asn Ile Lys Phe Asn Tyr Asn Asp Pro Ile Asn Asn Asp Asp Ile Ile
            20                  25                  30

Met Met Glu Pro Phe Asn Asp Pro Gly Pro Gly Thr Tyr Tyr Lys Ala
        35                  40                  45

Phe Arg Ile Ile Asp Arg Ile Trp Ile Val Pro Glu Arg Phe Thr Tyr
    50                  55                  60

Gly Phe Gln Pro Asp Gln Phe Asn Ala Ser Thr Gly Val Phe Ser Lys
65                  70                  75                  80

Asp Val Tyr Glu Tyr Tyr Asp Pro Thr Tyr Leu Lys Thr Asp Ala Glu
                85                  90                  95

Lys Asp Lys Phe Leu Lys Thr Met Ile Lys Leu Phe Asn Arg Ile Asn
            100                 105                 110

Ser Lys Pro Ser Gly Gln Arg Leu Leu Asp Met Ile Val Asp Ala Ile
        115                 120                 125

Pro Tyr Leu Gly Asn Ala Ser Thr Pro Pro Asp Lys Phe Ala Ala Asn
    130                 135                 140

Val Ala Asn Val Ser Ile Asn Lys Lys Ile Ile Gln Pro Gly Ala Glu
145                 150                 155                 160

Asp Gln Ile Lys Gly Leu Met Thr Asn Leu Ile Ile Phe Gly Pro Gly
                165                 170                 175

Pro Val Leu Ser Asp Asn Phe Thr Asp Ser Met Ile Met Asn Gly His
            180                 185                 190

Ser Pro Ile Ser Glu Gly Phe Gly Ala Arg Met Met Ile Arg Phe Cys
        195                 200                 205

Pro Ser Cys Leu Asn Val Phe Asn Asn Val Gln Glu Asn Lys Asp Thr
    210                 215                 220

Ser Ile Phe Ser Arg Arg Ala Tyr Phe Ala Asp Pro Ala Leu Thr Leu
225                 230                 235                 240

Met His Glu Leu Ile His Val Leu His Gly Leu Tyr Gly Ile Lys Ile
                245                 250                 255

Ser Asn Leu Pro Ile Thr Pro Asn Thr Lys Glu Phe Phe Met Gln His
            260                 265                 270

Ser Asp Pro Val Gln Ala Glu Glu Leu Tyr Thr Phe Gly Gly His Asp
        275                 280                 285

Pro Ser Val Ile Ser Pro Ser Thr Asp Met Asn Ile Tyr Asn Lys Ala
    290                 295                 300

Leu Gln Asn Phe Gln Asp Ile Ala Asn Arg Leu Asn Ile Val Ser Ser
305                 310                 315                 320

Ala Gln Gly Ser Gly Ile Asp Ile Ser Leu Tyr Lys Gln Ile Tyr Lys
                325                 330                 335

Asn Lys Tyr Asp Phe Val Glu Asp Pro Asn Gly Lys Tyr Ser Val Asp
            340                 345                 350

Lys Asp Lys Phe Asp Lys Leu Tyr Lys Ala Leu Met Phe Gly Phe Thr
        355                 360                 365
```

-continued

```
Glu Thr Asn Leu Ala Gly Glu Tyr Gly Ile Lys Thr Arg Tyr Ser Tyr
    370                 375                 380

Phe Ser Glu Tyr Leu Pro Pro Ile Lys Thr Glu Lys Leu Leu Asp Asn
385                 390                 395                 400

Thr Ile Tyr Thr Gln Asn Glu Gly Phe Asn Ile Ala Ser Lys Asn Leu
                405                 410                 415

Lys Thr Glu Phe Asn Gly Gln Asn Lys Ala Val Asn Lys Glu Ala Tyr
            420                 425                 430

Glu Glu Ile Ser Leu Glu His Leu Val Ile Tyr Arg Ile Ala Met Cys
        435                 440                 445

Lys Pro Val Met Tyr Lys Leu Glu His His His His His His
    450                 455                 460


<210> SEQ ID NO 52
<211> LENGTH: 481
<212> TYPE: PRT
<213> ORGANISM: Artificial Sequence
<220> FEATURE:
<223> OTHER INFORMATION: BoNT/A Light chain-TD1r Amino Acid Sequence
      with hexahistidine

<400> SEQUENCE: 52

Met Gly Ser Ser His His His His His His Ser Ser Gly Leu Val Pro
1               5                   10                  15

Arg Gly Ser His Met Pro Phe Val Asn Lys Gln Phe Asn Tyr Lys Asp
            20                  25                  30

Pro Val Asn Gly Val Asp Ile Ala Tyr Ile Lys Ile Pro Asn Ala Gly
        35                  40                  45

Gln Met Gln Pro Val Lys Ala Phe Lys Ile His Asn Lys Ile Trp Val
    50                  55                  60

Ile Pro Glu Arg Asp Thr Phe Thr Asn Pro Glu Glu Gly Asp Leu Asn
65                  70                  75                  80

Pro Pro Pro Glu Ala Lys Gln Val Pro Val Ser Tyr Tyr Asp Ser Thr
                85                  90                  95

Tyr Leu Ser Thr Asp Asn Glu Lys Asp Asn Tyr Leu Lys Gly Val Thr
            100                 105                 110

Lys Leu Phe Glu Arg Ile Tyr Ser Thr Asp Leu Gly Arg Met Leu Leu
        115                 120                 125

Thr Ser Ile Val Arg Gly Ile Pro Phe Trp Gly Gly Ser Thr Ile Asp
    130                 135                 140

Thr Glu Leu Lys Val Ile Asp Thr Asn Cys Ile Asn Val Ile Gln Pro
145                 150                 155                 160

Asp Gly Ser Tyr Arg Ser Glu Glu Leu Asn Leu Val Ile Ile Gly Pro
                165                 170                 175

Ser Ala Asp Ile Ile Gln Phe Glu Cys Lys Ser Phe Gly His Glu Val
            180                 185                 190

Leu Asn Leu Thr Arg Asn Gly Tyr Gly Ser Thr Gln Tyr Ile Arg Phe
        195                 200                 205

Ser Pro Asp Phe Thr Phe Gly Phe Glu Glu Ser Leu Glu Val Asp Thr
    210                 215                 220

Asn Pro Leu Leu Gly Ala Gly Lys Phe Ala Thr Asp Pro Ala Val Thr
225                 230                 235                 240

Leu Ala His Glu Leu Ile His Ala Gly His Arg Leu Tyr Gly Ile Ala
                245                 250                 255

Ile Asn Pro Asn Arg Val Phe Lys Val Asn Thr Asn Ala Tyr Tyr Glu
            260                 265                 270
```

```
Met Ser Gly Leu Glu Val Ser Phe Glu Glu Leu Arg Thr Phe Gly Gly
        275                 280                 285

His Asp Ala Lys Phe Ile Asp Ser Leu Gln Glu Asn Glu Phe Arg Leu
    290                 295                 300

Tyr Tyr Tyr Asn Lys Phe Lys Asp Ile Ala Ser Thr Leu Asn Lys Ala
305                 310                 315                 320

Lys Ser Ile Val Gly Thr Thr Ala Ser Leu Gln Tyr Met Lys Asn Val
                325                 330                 335

Phe Lys Glu Lys Tyr Leu Leu Ser Glu Asp Thr Ser Gly Lys Phe Ser
            340                 345                 350

Val Asp Lys Leu Lys Phe Asp Lys Leu Tyr Lys Met Leu Thr Glu Ile
        355                 360                 365

Tyr Thr Glu Asp Asn Phe Val Lys Phe Phe Lys Val Leu Asn Arg Lys
    370                 375                 380

Thr Tyr Leu Asn Phe Asp Lys Ala Val Phe Lys Ile Asn Ile Val Pro
385                 390                 395                 400

Lys Val Asn Tyr Thr Ile Tyr Asp Gly Phe Asn Leu Arg Asn Thr Asn
                405                 410                 415

Leu Ala Ala Asn Phe Asn Gly Gln Asn Thr Glu Ile Asn Asn Met Asn
            420                 425                 430

Phe Thr Lys Leu Lys Asn Phe Thr Gly Leu Phe Glu Phe Tyr Lys Leu
        435                 440                 445

Leu Cys Val Arg Gly Ile Ile Thr Ser Lys Thr Lys Ser Leu Asp Lys
    450                 455                 460

Gly Tyr Asn Lys Cys Gln Asn Leu Phe Lys Asn Ile Asn Ile Met Ala
465                 470                 475                 480

Lys


<210> SEQ ID NO 53
<211> LENGTH: 474
<212> TYPE: PRT
<213> ORGANISM: Artificial Sequence
<220> FEATURE:
<223> OTHER INFORMATION: BoNT/B Light chain-TD1r Amino Acid Sequence
      with hexahistidine

<400> SEQUENCE: 53

Met Gly Ser Ser His His His His His His Ser Ser Gly Leu Val Pro
1               5                   10                  15

Arg Gly Ser His Met Pro Val Thr Ile Asn Asn Phe Asn Tyr Asn Asp
            20                  25                  30

Pro Ile Asp Asn Asn Asn Ile Ile Met Met Glu Pro Pro Phe Ala Arg
        35                  40                  45

Gly Thr Gly Arg Tyr Tyr Lys Ala Phe Lys Ile Thr Asp Arg Ile Trp
    50                  55                  60

Ile Ile Pro Glu Arg Tyr Thr Phe Gly Tyr Lys Pro Glu Asp Phe Asn
65                  70                  75                  80

Lys Ser Ser Gly Ile Phe Asn Arg Asp Val Cys Glu Tyr Tyr Asp Pro
                85                  90                  95

Asp Tyr Leu Asn Thr Asn Asp Lys Lys Asn Ile Phe Leu Gln Thr Met
            100                 105                 110

Ile Lys Leu Phe Asn Arg Ile Lys Ser Lys Pro Leu Gly Glu Lys Leu
        115                 120                 125

Leu Glu Met Ile Ile Asn Gly Ile Pro Tyr Leu Gly Asp Arg Arg Val
    130                 135                 140
```

```
Pro Leu Glu Glu Phe Asn Thr Asn Ile Ala Ser Val Thr Val Asn Lys
145                 150                 155                 160

Leu Ile Ser Asn Pro Gly Glu Val Glu Arg Lys Lys Gly Ile Phe Ala
                165                 170                 175

Asn Leu Ile Ile Phe Gly Pro Gly Pro Val Leu Asn Glu Asn Glu Thr
            180                 185                 190

Ile Asp Ile Gly Ile Gln Asn His Phe Ala Ser Arg Glu Gly Phe Gly
        195                 200                 205

Gly Ile Met Gln Met Lys Phe Cys Pro Glu Tyr Val Ser Val Phe Asn
    210                 215                 220

Asn Val Gln Glu Asn Lys Gly Ala Ser Ile Phe Asn Arg Arg Gly Tyr
225                 230                 235                 240

Phe Ser Asp Pro Ala Leu Ile Leu Met His Glu Leu Ile His Val Leu
                245                 250                 255

His Gly Leu Tyr Gly Ile Lys Val Asp Asp Leu Pro Ile Val Pro Asn
            260                 265                 270

Glu Lys Lys Phe Phe Met Gln Ser Thr Asp Ala Ile Gln Ala Glu Glu
        275                 280                 285

Leu Tyr Thr Phe Gly Gly Gln Asp Pro Ser Ile Ile Thr Pro Ser Thr
    290                 295                 300

Asp Lys Ser Ile Tyr Asp Lys Val Leu Gln Asn Phe Arg Gly Ile Val
305                 310                 315                 320

Asp Arg Leu Asn Lys Val Leu Val Cys Ile Ser Asp Pro Asn Ile Asn
                325                 330                 335

Ile Asn Ile Tyr Lys Asn Lys Phe Lys Asp Lys Tyr Lys Phe Val Glu
            340                 345                 350

Asp Ser Glu Gly Lys Tyr Ser Ile Asp Val Glu Ser Phe Asp Lys Leu
        355                 360                 365

Tyr Lys Ser Leu Met Phe Gly Phe Thr Glu Thr Asn Ile Ala Glu Asn
    370                 375                 380

Tyr Lys Ile Lys Thr Arg Ala Ser Tyr Phe Ser Asp Ser Leu Pro Pro
385                 390                 395                 400

Val Lys Ile Lys Asn Leu Leu Asp Asn Glu Ile Tyr Thr Ile Glu Glu
                405                 410                 415

Gly Phe Asn Ile Ser Asp Lys Asp Met Glu Lys Glu Tyr Arg Gly Gln
            420                 425                 430

Asn Lys Ala Ile Asn Lys Gln Ala Tyr Glu Glu Ile Ser Lys Glu His
        435                 440                 445

Leu Ala Val Tyr Lys Ile Gln Met Cys Lys Ser Val Lys Cys Gln Asn
    450                 455                 460

Leu Phe Lys Asn Ile Asn Ile Met Ala Lys
465                 470


<210> SEQ ID NO 54
<211> LENGTH: 482
<212> TYPE: PRT
<213> ORGANISM: Artificial Sequence
<220> FEATURE:
<223> OTHER INFORMATION: BoNT/C Light chain-TD1r Amino Acid Sequence
      with hexahistidine

<400> SEQUENCE: 54

Met Gly Ser Ser His His His His His His Ser Ser Gly Leu Val Pro
1               5                   10                  15

Arg Gly Ser His Met Pro Ile Thr Ile Asn Asn Phe Asn Tyr Ser Asp
```

-continued

```
            20                  25                  30

Pro Val Asp Asn Lys Asn Ile Leu Tyr Leu Asp Thr His Leu Asn Thr
        35                  40                  45

Leu Ala Asn Glu Pro Glu Lys Ala Phe Arg Ile Thr Gly Asn Ile Trp
    50                  55                  60

Val Ile Pro Asp Arg Phe Ser Arg Asn Ser Asn Pro Asn Leu Asn Lys
65                  70                  75                  80

Pro Pro Arg Val Thr Ser Pro Lys Ser Gly Tyr Tyr Asp Pro Asn Tyr
                85                  90                  95

Leu Ser Thr Asp Ser Asp Lys Asp Pro Phe Leu Lys Glu Ile Ile Lys
            100                 105                 110

Leu Phe Lys Arg Ile Asn Ser Arg Glu Ile Gly Glu Glu Leu Ile Tyr
        115                 120                 125

Arg Leu Ser Thr Asp Ile Pro Phe Pro Gly Asn Asn Asn Thr Pro Ile
    130                 135                 140

Asn Thr Phe Asp Phe Asp Val Asp Phe Asn Ser Val Asp Val Lys Thr
145                 150                 155                 160

Arg Gln Gly Asn Asn Trp Val Lys Thr Gly Ser Ile Asn Pro Ser Val
                165                 170                 175

Ile Ile Thr Gly Pro Arg Glu Asn Ile Ile Asp Pro Glu Thr Ser Thr
            180                 185                 190

Phe Lys Leu Thr Asn Asn Thr Phe Ala Ala Gln Glu Gly Phe Gly Ala
        195                 200                 205

Leu Ser Ile Ile Ser Ile Ser Pro Arg Phe Met Leu Thr Tyr Ser Asn
    210                 215                 220

Ala Thr Asn Asp Val Gly Glu Gly Arg Phe Ser Lys Ser Glu Phe Cys
225                 230                 235                 240

Met Asp Pro Ile Leu Ile Leu Met His Glu Leu Asn His Ala Met His
                245                 250                 255

Asn Leu Tyr Gly Ile Ala Ile Pro Asn Asp Gln Thr Ile Ser Ser Val
            260                 265                 270

Thr Ser Asn Ile Phe Tyr Ser Gln Tyr Asn Val Lys Leu Glu Tyr Ala
        275                 280                 285

Glu Ile Tyr Ala Phe Gly Gly Pro Thr Ile Asp Leu Ile Pro Lys Ser
    290                 295                 300

Ala Arg Lys Tyr Phe Glu Glu Lys Ala Leu Asp Tyr Tyr Arg Ser Ile
305                 310                 315                 320

Ala Lys Arg Leu Asn Ser Ile Thr Thr Ala Asn Pro Ser Ser Phe Asn
                325                 330                 335

Lys Tyr Ile Gly Glu Tyr Lys Gln Lys Leu Ile Arg Lys Tyr Arg Phe
            340                 345                 350

Val Val Glu Ser Ser Gly Glu Val Thr Val Asn Arg Asn Lys Phe Val
        355                 360                 365

Glu Leu Tyr Asn Glu Leu Thr Gln Ile Phe Thr Glu Phe Asn Tyr Ala
    370                 375                 380

Lys Ile Tyr Asn Val Gln Asn Arg Lys Ile Tyr Leu Ser Asn Val Tyr
385                 390                 395                 400

Thr Pro Val Thr Ala Asn Ile Leu Asp Asp Asn Val Tyr Asp Ile Gln
                405                 410                 415

Asn Gly Phe Asn Ile Pro Lys Ser Asn Leu Asn Val Leu Phe Met Gly
            420                 425                 430

Gln Asn Leu Ser Arg Asn Pro Ala Leu Arg Lys Val Asn Pro Glu Asn
        435                 440                 445
```

```
Met Leu Tyr Leu Phe Thr Lys Phe Cys His Lys Ala Ile Asp Gly Arg
    450                 455                 460

Ser Leu Tyr Asn Lys Cys Gln Asn Leu Phe Lys Asn Ile Asn Ile Met
465                 470                 475                 480

Ala Lys


<210> SEQ ID NO 55
<211> LENGTH: 475
<212> TYPE: PRT
<213> ORGANISM: Artificial Sequence
<220> FEATURE:
<223> OTHER INFORMATION: BoNT/D Light chain-TD1r Amino Acid Sequence
      with hexahistidine

<400> SEQUENCE: 55

Met Gly Ser Ser His His His His His His Ser Ser Gly Leu Val Pro
1               5                   10                  15

Arg Gly Ser His Met Thr Trp Pro Val Lys Asp Phe Asn Tyr Ser Asp
            20                  25                  30

Pro Val Asn Asp Asn Asp Ile Leu Tyr Leu Arg Ile Pro Gln Asn Lys
        35                  40                  45

Leu Ile Thr Thr Pro Val Lys Ala Phe Met Ile Thr Gln Asn Ile Trp
    50                  55                  60

Val Ile Pro Glu Arg Phe Ser Ser Asp Thr Asn Pro Ser Leu Ser Lys
65                  70                  75                  80

Pro Pro Arg Pro Thr Ser Lys Tyr Gln Ser Tyr Tyr Asp Pro Ser Tyr
                85                  90                  95

Leu Ser Thr Asp Glu Gln Lys Asp Thr Phe Leu Lys Gly Ile Ile Lys
            100                 105                 110

Leu Phe Lys Arg Ile Asn Glu Arg Asp Ile Gly Lys Lys Leu Ile Asn
        115                 120                 125

Tyr Leu Val Val Gly Ser Pro Phe Met Gly Asp Ser Ser Thr Pro Glu
    130                 135                 140

Asp Thr Phe Asp Phe Thr Arg His Thr Thr Asn Ile Ala Val Glu Lys
145                 150                 155                 160

Phe Glu Asn Gly Ser Trp Lys Val Thr Asn Ile Ile Thr Pro Ser Val
                165                 170                 175

Leu Ile Phe Gly Pro Leu Pro Asn Ile Leu Asp Tyr Thr Ala Ser Leu
            180                 185                 190

Thr Leu Gln Gly Gln Gln Ser Asn Pro Ser Phe Glu Gly Phe Gly Thr
        195                 200                 205

Leu Ser Ile Leu Lys Val Ala Pro Glu Phe Leu Leu Thr Phe Ser Asp
    210                 215                 220

Val Thr Ser Asn Gln Ser Ser Ala Val Leu Gly Lys Ser Ile Phe Cys
225                 230                 235                 240

Met Asp Pro Val Ile Ala Leu Met His Glu Leu Thr His Ser Leu His
                245                 250                 255

Gln Leu Tyr Gly Ile Asn Ile Pro Ser Asp Lys Arg Ile Arg Pro Gln
            260                 265                 270

Val Ser Glu Gly Phe Phe Ser Gln Asp Gly Pro Asn Val Gln Phe Glu
        275                 280                 285

Glu Leu Tyr Thr Phe Gly Gly Leu Asp Val Glu Ile Ile Pro Gln Ile
    290                 295                 300

Glu Arg Ser Gln Leu Arg Glu Lys Ala Leu Gly His Tyr Lys Asp Ile
305                 310                 315                 320
```

```
Ala Lys Arg Leu Asn Asn Ile Asn Lys Thr Ile Pro Ser Ser Trp Ile
                325                 330                 335

Ser Asn Ile Asp Lys Tyr Lys Lys Ile Phe Ser Glu Lys Tyr Asn Phe
            340                 345                 350

Asp Lys Asp Asn Thr Gly Asn Phe Val Val Asn Ile Asp Lys Phe Asn
        355                 360                 365

Ser Leu Tyr Ser Asp Leu Thr Asn Val Met Ser Glu Val Val Tyr Ser
    370                 375                 380

Ser Gln Tyr Asn Val Lys Asn Arg Thr His Tyr Phe Ser Arg His Tyr
385                 390                 395                 400

Leu Pro Val Phe Ala Asn Ile Leu Asp Asp Asn Ile Tyr Thr Ile Arg
                405                 410                 415

Asp Gly Phe Asn Leu Thr Asn Lys Gly Phe Asn Ile Glu Asn Ser Gly
            420                 425                 430

Gln Asn Ile Glu Arg Asn Pro Ala Leu Gln Lys Leu Ser Ser Glu Ser
        435                 440                 445

Val Val Asp Leu Phe Thr Lys Val Cys Leu Arg Leu Thr Lys Cys Gln
    450                 455                 460

Asn Leu Phe Lys Asn Ile Asn Ile Met Ala Lys
465                 470                 475


<210> SEQ ID NO 56
<211> LENGTH: 455
<212> TYPE: PRT
<213> ORGANISM: Artificial Sequence
<220> FEATURE:
<223> OTHER INFORMATION: BoNT/E Light chain-TD1r Amino Acid Sequence
      with hexahistidine

<400> SEQUENCE: 56

Met Gly Ser Ser His His His His His His Ser Ser Gly Leu Val Pro
1               5                   10                  15

Arg Gly Ser His Met Pro Thr Ile Asn Ser Phe Asn Tyr Asn Asp Pro
            20                  25                  30

Val Asn Asn Arg Thr Ile Leu Tyr Ile Lys Pro Gly Gly Cys Gln Gln
        35                  40                  45

Phe Tyr Lys Ser Phe Asn Ile Met Lys Asn Ile Trp Ile Ile Pro Glu
    50                  55                  60

Arg Asn Val Ile Gly Thr Ile Pro Gln Asp Phe Leu Pro Pro Thr Ser
65                  70                  75                  80

Leu Lys Asn Gly Asp Ser Ser Tyr Tyr Asp Pro Asn Tyr Leu Gln Ser
                85                  90                  95

Asp Gln Glu Lys Asp Lys Phe Leu Lys Ile Val Thr Lys Ile Phe Asn
            100                 105                 110

Arg Ile Asn Asp Asn Leu Ser Gly Arg Ile Leu Leu Glu Glu Leu Ser
        115                 120                 125

Lys Ala Asn Pro Tyr Leu Gly Asn Asp Asn Thr Pro Asp Gly Asp Phe
    130                 135                 140

Ile Ile Asn Asp Ala Ser Ala Val Pro Ile Gln Phe Ser Asn Gly Ser
145                 150                 155                 160

Gln Ser Ile Leu Leu Pro Asn Val Ile Ile Met Gly Ala Glu Pro Asp
                165                 170                 175

Leu Phe Glu Thr Asn Ser Ser Asn Ile Ser Leu Arg Asn Asn Tyr Met
            180                 185                 190

Pro Ser Asn His Gly Phe Gly Ser Ile Ala Ile Val Thr Phe Ser Pro
```

```
        195                 200                 205

Glu Tyr Ser Phe Arg Phe Lys Asp Asn Ser Met Asn Glu Phe Ile Gln
    210                 215                 220

Asp Pro Ala Leu Thr Leu Met His Glu Leu Ile His Ser Leu His Gly
225                 230                 235                 240

Leu Tyr Gly Ala Lys Gly Ile Thr Thr Lys Tyr Thr Ile Thr Gln Lys
                245                 250                 255

Gln Asn Pro Leu Ile Thr Asn Ile Arg Gly Thr Asn Ile Glu Glu Phe
            260                 265                 270

Leu Thr Phe Gly Gly Thr Asp Leu Asn Ile Ile Thr Ser Ala Gln Ser
        275                 280                 285

Asn Asp Ile Tyr Thr Asn Leu Leu Ala Asp Tyr Lys Lys Ile Ala Ser
    290                 295                 300

Lys Leu Ser Lys Val Gln Val Ser Asn Pro Leu Leu Asn Pro Tyr Lys
305                 310                 315                 320

Asp Val Phe Glu Ala Lys Tyr Gly Leu Asp Lys Asp Ala Ser Gly Ile
                325                 330                 335

Tyr Ser Val Asn Ile Asn Lys Phe Asn Asp Ile Phe Lys Lys Leu Tyr
            340                 345                 350

Ser Phe Thr Glu Phe Asp Leu Ala Thr Lys Phe Gln Val Lys Cys Arg
        355                 360                 365

Gln Thr Tyr Ile Gly Gln Tyr Lys Tyr Phe Lys Leu Ser Asn Leu Leu
    370                 375                 380

Asn Asp Ser Ile Tyr Asn Ile Ser Glu Gly Tyr Asn Ile Asn Asn Leu
385                 390                 395                 400

Lys Val Asn Phe Arg Gly Gln Asn Ala Asn Leu Asn Pro Arg Ile Ile
                405                 410                 415

Thr Pro Ile Thr Gly Arg Gly Leu Val Lys Lys Ile Ile Arg Phe Cys
            420                 425                 430

Lys Asn Ile Val Ser Val Lys Gly Ile Arg Cys Gln Asn Leu Phe Lys
        435                 440                 445

Asn Ile Asn Ile Met Ala Lys
    450                 455


<210> SEQ ID NO 57
<211> LENGTH: 469
<212> TYPE: PRT
<213> ORGANISM: Artificial Sequence
<220> FEATURE:
<223> OTHER INFORMATION: BoNT/F Light chain-TD1r Amino Acid Sequence
      with hexahistidine

<400> SEQUENCE: 57

Met Gly Ser Ser His His His His His His Ser Ser Gly Leu Val Pro
1               5                   10                  15

Arg Gly Ser His Met Pro Val Ala Ile Asn Ser Phe Asn Tyr Asn Asp
            20                  25                  30

Pro Val Asn Asp Asp Thr Ile Leu Tyr Met Gln Ile Pro Tyr Glu Glu
        35                  40                  45

Lys Ser Lys Lys Tyr Tyr Lys Ala Phe Glu Ile Met Arg Asn Val Trp
    50                  55                  60

Ile Ile Pro Glu Arg Asn Thr Ile Gly Thr Asn Pro Ser Asp Phe Asp
65                  70                  75                  80

Pro Pro Ala Ser Leu Lys Asn Gly Ser Ser Ala Tyr Tyr Asp Pro Asn
                85                  90                  95
```

-continued

```
Tyr Leu Thr Thr Asp Ala Glu Lys Asp Arg Tyr Leu Lys Thr Thr Ile
            100                 105                 110

Lys Leu Phe Lys Arg Ile Asn Ser Asn Pro Ala Gly Lys Val Leu Leu
        115                 120                 125

Gln Glu Ile Ser Tyr Ala Lys Pro Tyr Leu Gly Asn Asp His Thr Pro
    130                 135                 140

Ile Asp Glu Phe Ser Pro Val Thr Arg Thr Thr Ser Val Asn Ile Lys
145                 150                 155                 160

Leu Ser Thr Asn Val Glu Ser Ser Met Leu Leu Asn Leu Leu Val Leu
                165                 170                 175

Gly Ala Gly Pro Asp Ile Phe Glu Ser Cys Cys Tyr Pro Val Arg Lys
            180                 185                 190

Leu Ile Asp Pro Asp Val Val Tyr Asp Pro Ser Asn Tyr Gly Phe Gly
        195                 200                 205

Ser Ile Asn Ile Val Thr Phe Ser Pro Glu Tyr Glu Tyr Thr Phe Asn
    210                 215                 220

Asp Ile Ser Gly Gly His Asn Ser Ser Thr Glu Ser Phe Ile Ala Asp
225                 230                 235                 240

Pro Ala Ile Ser Leu Ala His Glu Leu Ile His Ala Leu His Gly Leu
                245                 250                 255

Tyr Gly Ala Arg Gly Val Thr Tyr Glu Glu Thr Ile Glu Val Lys Gln
            260                 265                 270

Ala Pro Leu Met Ile Ala Glu Lys Pro Ile Arg Leu Glu Glu Phe Leu
        275                 280                 285

Thr Phe Gly Gly Gln Asp Leu Asn Ile Ile Thr Ser Ala Met Lys Glu
    290                 295                 300

Lys Ile Tyr Asn Asn Leu Leu Ala Asn Tyr Glu Lys Ile Ala Thr Arg
305                 310                 315                 320

Leu Ser Glu Val Asn Ser Ala Pro Pro Glu Tyr Asp Ile Asn Glu Tyr
                325                 330                 335

Lys Asp Tyr Phe Gln Trp Lys Tyr Gly Leu Asp Lys Asn Ala Asp Gly
            340                 345                 350

Ser Tyr Thr Val Asn Glu Asn Lys Phe Asn Glu Ile Tyr Lys Lys Leu
        355                 360                 365

Tyr Ser Phe Thr Glu Ser Asp Leu Ala Asn Lys Phe Lys Val Lys Cys
    370                 375                 380

Arg Asn Thr Tyr Phe Ile Lys Tyr Glu Phe Leu Lys Val Pro Asn Leu
385                 390                 395                 400

Leu Asp Asp Asp Ile Tyr Thr Val Ser Glu Gly Phe Asn Ile Gly Asn
                405                 410                 415

Leu Ala Val Asn Asn Arg Gly Gln Ser Ile Lys Leu Asn Pro Lys Ile
            420                 425                 430

Ile Asp Ser Ile Pro Asp Lys Gly Leu Val Glu Lys Ile Val Lys Phe
        435                 440                 445

Cys Lys Ser Val Ile Pro Arg Lys Cys Gln Asn Leu Phe Lys Asn Ile
    450                 455                 460

Asn Ile Met Ala Lys
465
```

<210> SEQ ID NO 58
<211> LENGTH: 474
<212> TYPE: PRT
<213> ORGANISM: Artificial Sequence
<220> FEATURE:
<223> OTHER INFORMATION: BoNT/G Light chain-TD1r Amino Acid Sequence with hexahistidine

<400> SEQUENCE: 58

Met Gly Ser Ser His His His His His His Ser Ser Gly Leu Val Pro
1 5 10 15

Arg Gly Ser His Met Pro Val Asn Ile Lys Phe Asn Tyr Asn Asp Pro
20 25 30

Ile Asn Asn Asp Asp Ile Ile Met Met Glu Pro Phe Asn Asp Pro Gly
35 40 45

Pro Gly Thr Tyr Tyr Lys Ala Phe Arg Ile Ile Asp Arg Ile Trp Ile
50 55 60

Val Pro Glu Arg Phe Thr Tyr Gly Phe Gln Pro Asp Gln Phe Asn Ala
65 70 75 80

Ser Thr Gly Val Phe Ser Lys Asp Val Tyr Glu Tyr Tyr Asp Pro Thr
85 90 95

Tyr Leu Lys Thr Asp Ala Glu Lys Asp Lys Phe Leu Lys Thr Met Ile
100 105 110

Lys Leu Phe Asn Arg Ile Asn Ser Lys Pro Ser Gly Gln Arg Leu Leu
115 120 125

Asp Met Ile Val Asp Ala Ile Pro Tyr Leu Gly Asn Ala Ser Thr Pro
130 135 140

Pro Asp Lys Phe Ala Ala Asn Val Ala Asn Val Ser Ile Asn Lys Lys
145 150 155 160

Ile Ile Gln Pro Gly Ala Glu Asp Gln Ile Lys Gly Leu Met Thr Asn
165 170 175

Leu Ile Ile Phe Gly Pro Gly Pro Val Leu Ser Asp Asn Phe Thr Asp
180 185 190

Ser Met Ile Met Asn Gly His Ser Pro Ile Ser Glu Gly Phe Gly Ala
195 200 205

Arg Met Met Ile Arg Phe Cys Pro Ser Cys Leu Asn Val Phe Asn Asn
210 215 220

Val Gln Glu Asn Lys Asp Thr Ser Ile Phe Ser Arg Arg Ala Tyr Phe
225 230 235 240

Ala Asp Pro Ala Leu Thr Leu Met His Glu Leu Ile His Val Leu His
245 250 255

Gly Leu Tyr Gly Ile Lys Ile Ser Asn Leu Pro Ile Thr Pro Asn Thr
260 265 270

Lys Glu Phe Phe Met Gln His Ser Asp Pro Val Gln Ala Glu Glu Leu
275 280 285

Tyr Thr Phe Gly Gly His Asp Pro Ser Val Ile Ser Pro Ser Thr Asp
290 295 300

Met Asn Ile Tyr Asn Lys Ala Leu Gln Asn Phe Gln Asp Ile Ala Asn
305 310 315 320

Arg Leu Asn Ile Val Ser Ser Ala Gln Gly Ser Gly Ile Asp Ile Ser
325 330 335

Leu Tyr Lys Gln Ile Tyr Lys Asn Lys Tyr Asp Phe Val Glu Asp Pro
340 345 350

Asn Gly Lys Tyr Ser Val Asp Lys Asp Lys Phe Asp Lys Leu Tyr Lys
355 360 365

Ala Leu Met Phe Gly Phe Thr Glu Thr Asn Leu Ala Gly Glu Tyr Gly
370 375 380

Ile Lys Thr Arg Tyr Ser Tyr Phe Ser Glu Tyr Leu Pro Pro Ile Lys
385 390 395 400

-continued

```
Thr Glu Lys Leu Leu Asp Asn Thr Ile Tyr Thr Gln Asn Glu Gly Phe
                405                 410                 415

Asn Ile Ala Ser Lys Asn Leu Lys Thr Glu Phe Asn Gly Gln Asn Lys
            420                 425                 430

Ala Val Asn Lys Glu Ala Tyr Glu Glu Ile Ser Leu Glu His Leu Val
        435                 440                 445

Ile Tyr Arg Ile Ala Met Cys Lys Pro Val Met Tyr Lys Cys Gln Asn
    450                 455                 460

Leu Phe Lys Asn Ile Asn Ile Met Ala Lys
465                 470


<210> SEQ ID NO 59
<211> LENGTH: 1386
<212> TYPE: DNA
<213> ORGANISM: Artificial Sequence
<220> FEATURE:
<223> OTHER INFORMATION: TD1-BoNT/A Light chain cDNA Sequence

<400> SEQUENCE: 59

atgaaggcca tgatcaatat taacaagttc ttaaatcaat gtccctttgt caacaaacag      60

ttcaactaca aggacccagt taatggagta gacatcgcat atatcaagat tcccaacgct     120

ggccagatgc aacccgttaa ggcatttaaa atccataaca aaatctgggt tatcccagag     180

cgggatacct tcaccaaccc cgaggagggc gatctgaacc ccccgccgga ggcgaagcag     240

gtcccagtga gctactacga tagcacctac ctcagcaccg acaacgagaa ggacaactac     300

ctcaaaggag tcacgaagtt gttcgagaga atctactcca cagacctcgg ccgcatgctt     360

ctaaccagca ttgtgcgtgg cattcccttt tggggcggct ctaccatcga cacagagctg     420

aaggtgatag acaccaactg catcaacgta atccagcctg acggcagcta ccgaagcgag     480

gagcttaacc tggtgatcat cggccccttcc gccgatatca tccaattcga gtgcaagagc     540

ttcggccacg aggtcctgaa cctcacccgg aacggctatg gaagcaccca gtacataaga     600

ttcagccctg acttcacctt cgggtttgag gagagcttgg aggtcgacac aaaccccctg     660

ctgggagccg ggaagttcgc cactgaccca gccgtgactc tggcacacga gctgatccac     720

gccggtcacc gcctgtacgg catagctata aacccaaaca gggtgttcaa agtgaacacc     780

aacgcttact atgaaatgag cggcctggag gtgagcttcg aggagctgag aacgttcggg     840

ggacatgatg ctaaatttat cgacagcctg caggagaacg agttcaggct gtactactac     900

aataagttca aggatatagc gagcactctg aacaaggcca agtccatcgt aggcactact     960

gcatccctcc agtatatgaa gaatgtgttc aaagagaaat acctgctgag cgaggatacc    1020

agcggtaagt tcagcgtgga taagcttaag ttcgacaagc tgtataagat gctcaccgaa    1080

atctacaccg aggataattt cgttaagttc ttcaaggtcc tgaaccggaa gacctacctg    1140

aacttcgaca aggccgtgtt caagatcaac atcgtgccta aagtgaacta caccatctac    1200

gacgggttta acctgaggaa caccaacctg gccgctaact tcaacgggca gaacacagag    1260

atcaacaaca tgaatttcac gaagttgaag aacttcaccg gactgtttga gttctacaaa    1320

ttgctgtgtg tgcgcgggat catcactagc aagaccaaga gccttgacaa aggctacaac    1380

aagtga                                                                1386


<210> SEQ ID NO 60
<211> LENGTH: 1362
<212> TYPE: DNA
<213> ORGANISM: Artificial Sequence
<220> FEATURE:
```

<223> OTHER INFORMATION: TD1-BoNT/B Light chain cDNA Sequence

<400> SEQUENCE: 60

```
atgaaggcca tgatcaatat taacaagttc ttaaatcaat gtccagttac aataaataat     60
tttaattata atgatcctat tgataataat aatattatta tgatggagcc tccatttgcg    120
agaggtacgg ggagatatta taaagctttt aaaatcacag atcgtatttg gataataccg    180
gaaagatata cttttggata taaacctgag gattttaata aaagttccgg tatttttaat    240
agagatgttt gtgaatatta tgatccagat tacttaaata ctaatgataa aaagaatata    300
tttttacaaa caatgatcaa gttatttaat agaatcaaat caaaaccatt gggtgaaaag    360
ttattagaga tgattataaa tggtatacct tatcttggag atagacgtgt tccactcgaa    420
gagtttaaca caaacattgc tagtgtaact gttaataaat taatcagtaa tccaggagaa    480
gtggagcgaa aaaaaggtat tttcgcaaat ttaataatat ttggacctgg gccagtttta    540
aatgaaaatg agactataga tataggtata caaaatcatt ttgcatcaag ggaaggcttc    600
gggggtataa tgcaaatgaa gttttgccca gaatatgtaa gcgtatttaa taatgttcaa    660
gaaaacaaag gcgcaagtat atttaataga cgtggatatt tttcagatcc agccttgata    720
ttaatgcatg aacttataca tgttttacat ggattatatg gcattaaagt agatgattta    780
ccaattgtac caaatgaaaa aaaatttttt atgcaatcta cagatgctat acaggcagaa    840
gaactatata catttggagg acaagatccc agcatcataa ctccttctac ggataaaagt    900
atctatgata aagttttgca aaattttaga gggatagttg atagacttaa caaggtttta    960
gtttgcatat cagatcctaa cattaatatt aatatatata aaaataaatt taaagataaa   1020
tataaattcg ttgaagattc tgagggaaaa tatagtatag atgtagaaag ttttgataaa   1080
ttatataaaa gcttaatgtt tggttttaca gaaactaata tagcagaaaa ttataaaata   1140
aaaactagag cttcttattt tagtgattcc ttaccaccag taaaaataaa aaatttatta   1200
gataatgaaa tctatactat agaggaaggg tttaatatat ctgataaaga tatggaaaaa   1260
gaatatagag gtcagaataa agctataaat aaacaagctt atgaagaaat tagcaaggag   1320
catttggctg tatataagat acaaatgtgt aaaagtgtta aa                      1362
```

<210> SEQ ID NO 61
<211> LENGTH: 1386
<212> TYPE: DNA
<213> ORGANISM: Artificial Sequence
<220> FEATURE:
<223> OTHER INFORMATION: TD1-BoNT/C Light chain cDNA Sequence

<400> SEQUENCE: 61

```
atgaaggcca tgatcaatat taacaagttc ttaaatcaat gtccaataac aattaacaac     60
tttaattatt cagatcctgt tgataataaa aatattttat atttagatac tcatttaaat    120
acactagcta atgagcctga aaaagccttt cgcattacag gaaatatatg ggtaatacct    180
gatagatttt caagaaattc taatccaaat ttaaataaac ctcctcgagt tacaagccct    240
aaaagtggtt attatgatcc taattatttg agtactgatt ctgacaaaga tacattttta    300
aaagaaatta taaagttatt taaaagaatt aattctagag aaataggaga agaattaata    360
tatagacttt cgacagatat accctttcct gggaataaca atactccaat taatactttt    420
gattttgatg tagattttaa cagtgttgat gttaaaacta gacaaggtaa caactgggtt    480
aaaactggta gcataaatcc tagtgttata ataactggac ctagagaaaa cattatagat    540
ccagaaactt ctacgtttaa attaactaac aatacttttg cggcacaaga aggatttggt    600
```

```
gctttatcaa taatttcaat atcacctaga tttatgctaa catatagtaa tgcaactaat    660

gatgtaggag agggtagatt ttctaagtct gaattttgca tggatccaat actaatttta    720

atgcatgaac ttaatcatgc aatgcataat ttatatggaa tagctatacc aaatgatcaa    780

acaatttcat ctgtaactag taatattttt tattctcaat ataatgtgaa attagagtat    840

gcagaaatat atgcatttgg aggtccaact atagacctta ttcctaaaag tgcaaggaaa    900

tattttgagg aaaaggcatt ggattattat agatctatag ctaaaagact taatagtata    960

actactgcaa atccttcaag ctttaataaa tatatagggg aatataaaca gaaacttatt   1020

agaaagtata gattcgtagt agaatcttca ggtgaagtta cagtaaatcg taataagttt   1080

gttgagttat ataatgaact tacacaaata tttacagaat ttaactacgc taaaatatat   1140

aatgtacaaa ataggaaaat atatctttca aatgtatata ctccggttac ggcgaatata   1200

ttagacgata atgtttatga tatacaaaat ggatttaata tacctaaaag taatttaaat   1260

gtactattta tgggtcaaaa tttatctcga aatccagcat taagaaaagt caatcctgaa   1320

aatatgcttt atttatttac aaaattttgt cataaagcaa tagatggtag atcattatat   1380

aataaa                                                              1386
```

<210> SEQ ID NO 62
<211> LENGTH: 1365
<212> TYPE: DNA
<213> ORGANISM: Artificial Sequence
<220> FEATURE:
<223> OTHER INFORMATION: TD1-BoNT/D Light chain cDNA Sequence

<400> SEQUENCE: 62

```
atgaaggcca tgatcaatat taacaagttc ttaaatcaat gtacatggcc agtaaaagat     60

tttaattata gtgatcctgt taatgacaat gatatattat atttaagaat accacaaaat    120

aagttaatta ctacacctgt aaaagctttt atgattactc aaaatatttg ggtaatacca    180

gaaagatttt catcagatac taatccaagt ttaagtaaac cgcccagacc tacttcaaag    240

tatcaaagtt attatgatcc tagttattta tctactgatg aacaaaaaga tacattttta    300

aaagggatta taaaattatt taaaagaatt aatgaaagag atataggaaa aaaattaata    360

aattatttag tagttggttc accttttatg ggagattcaa gtacgcctga agatacattt    420

gattttacac gtcatactac taatattgca gttgaaaagt ttgaaaatgg tagttggaaa    480

gtaacaaata ttataacacc aagtgtattg atatttggac cacttcctaa tatattagac    540

tatacagcat cccttacatt gcaaggacaa caatcaaatc catcatttga agggtttgga    600

acattatcta tactaaaagt agcacctgaa tttttgttaa catttagtga tgtaacatct    660

aatcaaagtt cagctgtatt aggcaaatct atattttgta tggatccagt aatagcttta    720

atgcatgagt taacacattc tttgcatcaa ttatatggaa taaatatacc atctgataaa    780

aggattcgtc cacaagttag cgagggattt ttctctcaag atggacccaa cgtacaattt    840

gaggaattat atacatttgg aggattagat gttgaaataa tacctcaaat tgaaagatca    900

caattaagag aaaaagcatt aggtcactat aaagatatag cgaaaagact taataatatt    960

aataaaacta ttccttctag ttggattagt aatatagata aatataaaaa aatattttct   1020

gaaaagtata attttgataa agataataca ggaaattttg ttgtaaatat tgataaattc   1080

aatagcttat attcagactt gactaatgtt atgtcagaag ttgtttattc ttcgcaatat   1140

aatgttaaaa acaggactca ttatttttca aggcattatc tacctgtatt tgcaaatata   1200
```

ttagatgata atatttatac tataagagat ggttttaatt taacaaataa aggttttaat 1260
atagaaaatt cgggtcagaa tatagaaagg aatcctgcac tacaaaagct tagttcagaa 1320
agtgtagtag atttatttac aaaagtatgt ttaagattaa caaaa 1365

<210> SEQ ID NO 63
<211> LENGTH: 1305
<212> TYPE: DNA
<213> ORGANISM: Artificial Sequence
<220> FEATURE:
<223> OTHER INFORMATION: TD1-BoNT/E Light chain cDNA Sequence

<400> SEQUENCE: 63
atgaaggcca tgatcaatat taacaagttc ttaaatcaat gtccaacaat taatagtttt 60
aattataatg atcctgttaa taatagaaca attttatata ttaaaccagg cggttgtcaa 120
caattttata aatcatttaa tattatgaaa aatatttgga taattccaga gagaaatgta 180
attggtacaa ttccccaaga ttttcttccg cctacttcat tgaaaaatgg agatagtagt 240
tattatgacc ctaattattt acaaagtgat caagaaaagg ataaattttt aaaaatagtc 300
acaaaaatat ttaatagaat aaatgataat ctttcaggaa ggatttttatt agaagaactg 360 tcaaaagcta atccatattt aggaaatgat aatactccag atggtgactt cattattaat 420
gatgcatcag cagttccaat tcaattctca aatggtagcc aaagcatact attacctaat 480
gttattataa tgggagcaga gcctgattta tttgaaacta acagttccaa tatttctcta 540
agaaataatt atatgccaag caatcacggt tttggatcaa tagctatagt aacattctca 600
cctgaatatt cttttagatt taaagataat agtatgaatg aatttattca agatcctgct 660
cttacattaa tgcatgaatt aatacattca ttacatggac tatatggggc taaagggatt 720
actacaaagt atactataac acaaaaacaa aatcccctaa taacaaatat aagaggtaca 780
aatattgaag aattcttaac ttttggaggt actgatttaa acattattac tagtgctcag 840
tccaatgata tctatactaa tcttctagct gattataaaa aaatagcgtc taaacttagc 900
aaagtacaag tatctaatcc actacttaat ccttataaag atgtttttga agcaaagtat 960
ggattagata aagatgctag cggaatttat tcggtaaata taaacaaatt taatgatatt 1020
tttaaaaaat tatacagctt tacggaattt gatttagcaa ctaaatttca agttaaatgt 1080
aggcaaactt atattggaca gtataaatac ttcaaacttt caaacttgtt aaatgattct 1140
atttataata tatcagaagg ctataatata aataatttaa aggtaaattt tagaggacag 1200
aatgcaaatt taaatcctag aattattaca ccaattacag gtagaggact agtaaaaaaa 1260
atcattagat tttgtaaaaa tattgtttct gtaaaaggca taagg 1305

<210> SEQ ID NO 64
<211> LENGTH: 1347
<212> TYPE: DNA
<213> ORGANISM: Artificial Sequence
<220> FEATURE:
<223> OTHER INFORMATION: TD1-BoNT/F Light chain cDNA Sequence

<400> SEQUENCE: 64
atgaaggcca tgatcaatat taacaagttc ttaaatcaat gtccagttgc aataaatagt 60
tttaattata atgaccctgt taatgatgat acaattttat acatgcagat accatatgaa 120
gaaaaaagta aaaaatatta taaagctttt gagattatgc gtaatgtttg gataattcct 180
gagagaaata caataggaac gaatcctagt gattttgatc caccggcttc attaaagaac 240
ggaagcagtg cttattatga tcctaattat ttaaccactg atgctgaaaa agatagatat 300

```
ttaaaaacaa cgataaaatt atttaagaga attaatagta atcctgcagg gaaagttttg    360

ttacaagaaa tatcatatgc taaaccatat ttaggaaatg accacacgcc aattgatgaa    420

ttctctccag ttactagaac tacaagtgtt aatataaaat tatcaactaa tgttgaaagt    480

tcaatgttat tgaatcttct tgtattggga gcaggacctg atatatttga aagttgttgt    540

taccccgtta gaaaactaat agatccagat gtagtttatg atccaagtaa ttatggtttt    600

ggatcaatta atatcgtgac attttcacct gagtatgaat atacttttaa tgatattagt    660

ggagggcata atagtagtac agaatcattt attgcagatc ctgcaatttc actagctcat    720

gaattgatac atgcactgca tggattatac ggggctaggg gagttactta tgaagagact    780

atagaagtaa agcaagcacc tcttatgata gccgaaaaac ccataaggct agaagaattt    840

ttaacctttg gaggtcagga tttaaatatt attactagtg ctatgaagga aaaaatatat    900

aacaatcttt tagctaacta tgaaaaaata gctactagac ttagtgaagt taatagtgct    960

cctcctgaat atgatattaa tgaatataaa gattattttc aatggaagta tgggctagat   1020

aaaaatgctg atggaagtta tactgtaaat gaaaataaat ttaatgaaat ttataaaaaa   1080

ttatatagtt ttacagagag tgacttagca aataaattta aagtaaaatg tagaaatact   1140

tattttatta aatatgaatt tttaaaagtt ccaaatttgt tagatgatga tatttatact   1200

gtatcagagg ggtttaatat aggtaattta gcagtaaaca atcgcggaca aagtataaag   1260

ttaaatccta aaattattga ttccattcca gataaaggtc tagtagaaaa gatcgttaaa   1320

ttttgtaaga gcgttattcc tagaaaa                                      1347
```

<210> SEQ ID NO 65
<211> LENGTH: 1365
<212> TYPE: DNA
<213> ORGANISM: Artificial Sequence
<220> FEATURE:
<223> OTHER INFORMATION: TD1-BoNT/G Light chain cDNA Sequence
<220> FEATURE:
<221> NAME/KEY: misc_feature
<222> LOCATION: (59)..(59)
<223> OTHER INFORMATION: n is a, c, g, or t

<400> SEQUENCE: 65

```
atgaaggcca tgatcaatat taacaagttc ttaaatcaat gtccagttaa tataaaaanc     60

tttaattata atgaccctat taataatgat gacattatta tgatggaacc attcaatgac    120

ccagggccag gaacatatta taaagctttt aggattatag atcgtatttg gatagtacca    180

gaaaggttta cttatggatt tcaacctgac caatttaatg ccagtacagg agtttttagt    240

aaagatgtct acgaatatta cgatccaact tatttaaaaa ccgatgctga aaaagataaa    300

tttttaaaaa caatgattaa attatttaat agaattaatt caaaaccatc aggacagaga    360

ttactggata tgatagtaga tgctatacct tatcttggaa atgcatctac accgcccgac    420

aaatttgcag caaatgttgc aaatgtatct attaataaaa aaattatcca acctggagct    480

gaagatcaaa taaaaggttt aatgacaaat ttaataatat ttggaccagg accagttcta    540

agtgataatt ttactgatag tatgattatg aatggccatt ccccaatatc agaaggattt    600

ggtgcaagaa tgatgataag attttgtcct agttgtttaa atgtatttaa taatgttcag    660

gaaaataaag atacatctat atttagtaga cgcgcgtatt ttgcagatcc agctctaacg    720

ttaatgcatg aacttataca tgtgttacat ggattatatg gaattaagat aagtaattta    780

ccaattactc caaatacaaa agaatttttc atgcaacata gcgatcctgt acaagcagaa    840
```

```
gaactatata cattcggagg acatgatcct agtgttataa gtccttctac ggatatgaat    900

atttataata aagcgttaca aaattttcaa gatatagcta ataggcttaa tattgtttca    960

agtgcccaag ggagtggaat tgatatttcc ttatataaac aaatatataa aaataaatat   1020

gattttgttg aagatcctaa tggaaaatat agtgtagata aggataagtt tgataaatta   1080

tataaggcct taatgtttgg ctttactgaa actaatctag ctggtgaata tggaataaaa   1140

actaggtatt cttattttag tgaatatttg ccaccgataa aaactgaaaa attgttagac   1200

aatacaattt atactcaaaa tgaaggcttt aacatagcta gtaaaaatct caaaacggaa   1260

tttaatggtc agaataaggc ggtaaataaa gaggcttatg aagaaatcag cctagaacat   1320

ctcgttatat atagaatagc aatgtgcaag cctgtaatgt acaaa                   1365
```

<210> SEQ ID NO 66
<211> LENGTH: 1386
<212> TYPE: DNA
<213> ORGANISM: Artificial Sequence
<220> FEATURE:
<223> OTHER INFORMATION: BoNT/A Light chain-TD1r cDNA Sequence

<400> SEQUENCE: 66

```
atgccctttg tcaacaaaca gttcaactac aaggacccag ttaatggagt agacatcgca     60

tatatcaaga ttcccaacgc tggccagatg caacccgtta aggcatttaa aatccataac    120

aaaatctggg ttatcccaga gcgggatacc ttcaccaacc ccgaggaggg cgatctgaac    180

cccccgccgg aggcgaagca ggtcccagtg agctactacg atagcaccta cctcagcacc    240

gacaacgaga aggacaacta cctcaaagga gtcacgaagt tgttcgagag aatctactcc    300

acagacctcg gccgcatgct tctaaccagc attgtgcgtg gcattccctt ttggggcggc    360

tctaccatcg acacagagct gaaggtgata gacaccaact gcatcaacgt aatccagcct    420

gacggcagct accgaagcga ggagcttaac ctggtgatca tcggcccttc cgccgatatc    480

atccaattcg agtgcaagag cttcggccac gaggtcctga acctcacccg gaacggctat    540

ggaagcaccc agtacataag attcagccct gacttcacct tcgggtttga ggagagcttg    600

gaggtcgaca caaacccct gctgggagcc gggaagttcg ccactgaccc agccgtgact    660

ctggcacacg agctgatcca cgccggtcac cgcctgtacg gcatagctat aaacccaaac    720

agggtgttca aagtgaacac caacgcttac tatgaaatga gcggcctgga ggtgagcttc    780

gaggagctga gaacgttcgg gggacatgat gctaaattta tcgacagcct gcaggagaac    840

gagttcaggc tgtactacta caataagttc aaggatatag cgagcactct gaacaaggcc    900

aagtccatcg taggcactac tgcatccctc cagtatatga agaatgtgtt caaagagaaa    960

tacctgctga gcgaggatac cagcggtaag ttcagcgtgg ataagcttaa gttcgacaag   1020

ctgtataaga tgctcaccga aatctacacc gaggataatt tcgttaagtt cttcaaggtc   1080

ctgaaccgga agacctacct gaacttcgac aaggccgtgt tcaagatcaa catcgtgcct   1140

aaagtgaact acaccatcta cgacgggttt aacctgagga acaccaacct ggccgctaac   1200

ttcaacgggc agaacacaga gatcaacaac atgaatttca cgaagttgaa gaacttcacc   1260

ggactgtttg agttctacaa attgctgtgt gtgcgcggga tcatcactag caagaccaag   1320

agccttgaca aaggctacaa caagtgatgt caaaatttat tcaagaacat taatatcatg   1380

gccaag                                                              1386
```

<210> SEQ ID NO 67
<211> LENGTH: 1362

<212> TYPE: DNA
<213> ORGANISM: Artificial Sequence
<220> FEATURE:
<223> OTHER INFORMATION: BoNT/B Light chain-TD1r cDNA Sequence

<400> SEQUENCE: 67
atgccagtta caataaataa ttttaattat aatgatccta ttgataataa taatattatt 60
atgatggagc ctccatttgc gagaggtacg gggagatatt ataaagcttt taaaatcaca 120
gatcgtattt ggataatacc ggaaagatat acttttggat ataaacctga ggattttaat 180
aaaagttccg gtatttttaa tagagatgtt tgtgaatatt atgatccaga ttacttaaat 240
actaatgata aaaagaatat atttttacaa acaatgatca agttatttaa tagaatcaaa 300
tcaaaaccat tgggtgaaaa gttattagag atgattataa atggtatacc ttatcttgga 360
gatagacgtg ttccactcga agagtttaac acaaacattg ctagtgtaac tgttaataaa 420
ttaatcagta atccaggaga agtggagcga aaaaaaggta ttttcgcaaa tttaataata 480
tttggacctg ggccagtttt aaatgaaaat gagactatag atataggtat acaaaatcat 540
tttgcatcaa gggaaggctt cggggggtata atgcaaatga agttttgccc agaatatgta 600
agcgtattta ataatgttca agaaaacaaa ggcgcaagta tatttaatag acgtggatat 660
ttttcagatc cagccttgat attaatgcat gaacttatac atgttttaca tggattatat 720
ggcattaaag tagatgattt accaattgta ccaaatgaaa aaaaattttt tatgcaatct 780
acagatgcta tacaggcaga agaactatat acatttggag gacaagatcc cagcatcata 840
actccttcta cggataaaag tatctatgat aaagttttgc aaaattttag agggatagtt 900
gatagactta acaaggtttt agtttgcata tcagatccta acattaatat taatatatat 960
aaaaataaat ttaaagataa atataaattc gttgaagatt ctgagggaaa atatagtata 1020
gatgtagaaa gttttgataa attatataaa agcttaatgt ttggttttac agaaactaat 1080
atagcagaaa attataaaat aaaaactaga gcttcttatt ttagtgattc cttaccacca 1140
gtaaaaataa aaaatttatt agataatgaa atctatacta tagaggaagg gtttaatata 1200
tctgataaag atatggaaaa agaatataga ggtcagaata aagctataaa taaacaagct 1260
tatgaagaaa ttagcaagga gcatttggct gtatataaga tacaaatgtg taaaagtgtt 1320
aaatgtcaaa atttattcaa gaacattaat atcatggcca ag 1362

<210> SEQ ID NO 68
<211> LENGTH: 1386
<212> TYPE: DNA
<213> ORGANISM: Artificial Sequence
<220> FEATURE:
<223> OTHER INFORMATION: BoNT/C Light chain-TD1r cDNA Sequence

<400> SEQUENCE: 68
atgccaataa caattaacaa ctttaattat tcagatcctg ttgataataa aaatatttta 60
tatttagata ctcatttaaa tacactagct aatgagcctg aaaaagcctt tcgcattaca 120
ggaaatatat gggtaatacc tgatagattt tcaagaaatt ctaatccaaa tttaaataaa 180
cctcctcgag ttacaagccc taaaagtggt tattatgatc ctaattattt gagtactgat 240
tctgacaaag atacattttt aaaagaaatt ataaagttat ttaaaagaat taattctaga 300
gaaataggag aagaattaat atatagactt tcgacagata taccctttcc tgggaataac 360
aatactccaa ttaatacttt tgattttgat gtagatttta acagtgttga tgttaaaact 420
agacaaggta acaactgggt taaaactggt agcataaatc ctagtgttat aataactgga 480

-continued

```
cctagagaaa acattataga tccagaaact tctacgttta aattaactaa caatactttt    540

gcggcacaag aaggatttgg tgctttatca ataatttcaa tatcacctag atttatgcta    600

acatatagta atgcaactaa tgatgtagga gagggtagat tttctaagtc tgaattttgc    660

atggatccaa tactaatttt aatgcatgaa cttaatcatg caatgcataa tttatatgga    720

atagctatac caaatgatca aacaatttca tctgtaacta gtaatatttt ttattctcaa    780

tataatgtga aattagagta tgcagaaata tatgcatttg gaggtccaac tatagacctt    840

attcctaaaa gtgcaaggaa atattttgag gaaaaggcat tggattatta tagatctata    900

gctaaaagac ttaatagtat aactactgca aatccttcaa gctttaataa atatataggg    960

gaatataaac agaaacttat tagaaagtat agattcgtag tagaatcttc aggtgaagtt   1020

acagtaaatc gtaataagtt tgttgagtta tataatgaac ttacacaaat atttacagaa   1080

tttaactacg ctaaaatata taatgtacaa aataggaaaa tatatctttc aaatgtatat   1140

actccggtta cggcgaatat attagacgat aatgtttatg atatacaaaa tggatttaat   1200

atacctaaaa gtaatttaaa tgtactattt atgggtcaaa atttatctcg aaatccagca   1260

ttaagaaaag tcaatcctga aaatatgctt tatttattta caaaattttg tcataaagca   1320

atagatggta gatcattata taataaatgt caaaatttat tcaagaacat taatatcatg   1380

gccaag                                                               1386
```

```
<210> SEQ ID NO 69
<211> LENGTH: 1365
<212> TYPE: DNA
<213> ORGANISM: Artificial Sequence
<220> FEATURE:
<223> OTHER INFORMATION: BoNT/D Light chain-TD1r cDNA Sequence

<400> SEQUENCE: 69
```

```
atgacatggc cagtaaaaga ttttaattat agtgatcctg ttaatgacaa tgatatatta     60

tatttaagaa taccacaaaa taagttaatt actacacctg taaaagcttt tatgattact    120

caaaatattt gggtaatacc agaaagattt tcatcagata ctaatccaag tttaagtaaa    180

ccgcccagac ctacttcaaa gtatcaaagt tattatgatc ctagttattt atctactgat    240

gaacaaaaag atacattttt aaaagggatt ataaaattat ttaaaagaat taatgaaaga    300

gatataggaa aaaaattaat aaattattta gtagttggtt cacctttttat gggagattca    360

agtacgcctg aagatacatt tgattttaca cgtcatacta ctaatattgc agttgaaaag    420

tttgaaaatg gtagttggaa agtaacaaat attataacac caagtgtatt gatatttgga    480

ccacttccta atatattaga ctatacagca tcccttacat tgcaaggaca acaatcaaat    540

ccatcatttg aagggtttgg aacattatct atactaaaag tagcacctga atttttgtta    600

acatttagtg atgtaacatc taatcaaagt tcagctgtat taggcaaatc tatattttgt    660

atggatccag taatagcttt aatgcatgag ttaacacatt ctttgcatca attatatgga    720

ataaatatac catctgataa aaggattcgt ccacaagtta gcgagggatt tttctctcaa    780

gatggaccca acgtacaatt tgaggaatta tatacatttg gaggattaga tgttgaaata    840

atacctcaaa ttgaaagatc acaattaaga gaaaaagcat taggtcacta taaagatata    900

gcgaaaagac ttaataatat taataaaact attccttcta gttggattag taatatagat    960

aaatataaaa aaatattttc tgaaaagtat aattttgata aagataatac aggaaatttt   1020

gttgtaaata ttgataaatt caatagctta tattcagact tgactaatgt tatgtcagaa   1080

gttgtttatt cttcgcaata taatgttaaa aacaggactc attatttttc aaggcattat   1140
```

ctacctgtat ttgcaaatat attagatgat aatatttata ctataagaga tggttttaat 1200
ttaacaaata aaggttttaa tatagaaaat tcgggtcaga atatagaaag gaatcctgca 1260
ctacaaaagc ttagttcaga aagtgtagta gatttattta caaaagtatg tttaagatta 1320
acaaaatgtc aaaatttatt caagaacatt aatatcatgg ccaag 1365

<210> SEQ ID NO 70
<211> LENGTH: 1305
<212> TYPE: DNA
<213> ORGANISM: Artificial Sequence
<220> FEATURE:
<223> OTHER INFORMATION: BoNT/E Light chain-TD1r cDNA Sequence

<400> SEQUENCE: 70
atgccaacaa ttaatagttt taattataat gatcctgtta ataatagaac aattttatat 60
attaaaccag gcggttgtca acaattttat aaatcattta atattatgaa aaatatttgg 120
ataattccag agagaaatgt aattggtaca attccccaag attttcttcc gcctacttca 180
ttgaaaaatg gagatagtag ttattatgac cctaattatt tacaaagtga tcaagaaaag 240
gataaatttt taaaaatagt cacaaaaata tttaatagaa taaatgataa tctttcagga 300
aggattttat tagaagaact gtcaaaagct aatccatatt taggaaatga taatactcca 360
gatggtgact tcattattaa tgatgcatca gcagttccaa ttcaattctc aaatggtagc 420
caaagcatac tattacctaa tgttattata atgggagcag agcctgattt atttgaaact 480
aacagttcca atatttctct aagaaataat tatatgccaa gcaatcacgg ttttggatca 540
atagctatag taacattctc acctgaatat tcttttagat ttaaagataa tagtatgaat 600
gaatttattc aagatcctgc tcttacatta atgcatgaat taatacattc attacatgga 660
ctatatgggg ctaaagggat tactacaaag tatactataa cacaaaaaca aaatccccta 720
ataacaaata taagaggtac aaatattgaa gaattcttaa cttttggagg tactgattta 780
aacattatta ctagtgctca gtccaatgat atctatacta atcttctagc tgattataaa 840
aaaatagcgt ctaaacttag caaagtacaa gtatctaatc cactacttaa tccttataaa 900
gatgtttttg aagcaaagta tggattagat aaagatgcta gcggaattta ttcggtaaat 960
ataaacaaat ttaatgatat ttttaaaaaa ttatacagct ttacggaatt tgatttagca 1020
actaaatttc aagttaaatg taggcaaact tatattggac agtataaata cttcaaactt 1080
tcaaacttgt taaatgattc tatttataat atatcagaag gctataatat aaataattta 1140
aaggtaaatt ttagaggaca gaatgcaaat ttaaatccta gaattattac accaattaca 1200
ggtagaggac tagtaaaaaa aatcattaga ttttgtaaaa atattgtttc tgtaaaaggc 1260
ataaggtgtc aaaatttatt caagaacatt aatatcatgg ccaag 1305

<210> SEQ ID NO 71
<211> LENGTH: 1347
<212> TYPE: DNA
<213> ORGANISM: Artificial Sequence
<220> FEATURE:
<223> OTHER INFORMATION: BoNT/F Light chain-TD1r cDNA Sequence

<400> SEQUENCE: 71
atgccagttg caataaatag ttttaattat aatgaccctg ttaatgatga tacaatttta 60
tacatgcaga taccatatga agaaaaaagt aaaaaatatt ataaagcttt tgagattatg 120
cgtaatgttt ggataattcc tgagagaaat acaataggaa cgaatcctag tgattttgat 180

```
ccaccggctt cattaaagaa cggaagcagt gcttattatg atcctaatta tttaaccact    240

gatgctgaaa aagatagata tttaaaaaca acgataaaat tatttaagag aattaatagt    300

aatcctgcag ggaaagtttt gttacaagaa atatcatatg ctaaaccata tttaggaaat    360

gaccacacgc caattgatga attctctcca gttactagaa ctacaagtgt taatataaaa    420

ttatcaacta atgttgaaag ttcaatgtta ttgaatcttc ttgtattggg agcaggacct    480

gatatatttg aaagttgttg ttaccccgtt agaaaactaa tagatccaga tgtagtttat    540

gatccaagta attatggttt tggatcaatt aatatcgtga cattttcacc tgagtatgaa    600

tatactttta atgatattag tggagggcat aatagtagta cagaatcatt tattgcagat    660

cctgcaattt cactagctca tgaattgata catgcactgc atggattata cggggctagg    720

ggagttactt atgaagagac tatagaagta aagcaagcac ctcttatgat agccgaaaaa    780

cccataaggc tagaagaatt tttaaccttt ggaggtcagg atttaaatat tattactagt    840

gctatgaagg aaaaaatata taacaatctt ttagctaact atgaaaaaat agctactaga    900

cttagtgaag ttaatagtgc tcctcctgaa tatgatatta atgaatataa agattatttt    960

caatggaagt atgggctaga taaaaatgct gatggaagtt atactgtaaa tgaaaataaa   1020

tttaatgaaa tttataaaaa attatatagt tttacagaga gtgacttagc aaataaattt   1080

aaagtaaaat gtagaaatac ttattttatt aaatatgaat ttttaaaagt tccaaatttg   1140

ttagatgatg atatttatac tgtatcagag ggtttaata taggtaattt agcagtaaac   1200

aatcgcggac aaagtataaa gttaaatcct aaaattattg attccattcc agataaaggt   1260

ctagtagaaa agatcgttaa attttgtaag agcgttattc ctagaaaatg tcaaaattta   1320

ttcaagaaca ttaatatcat ggccaag                                     1347
```

<210> SEQ ID NO 72
<211> LENGTH: 1365
<212> TYPE: DNA
<213> ORGANISM: Artificial Sequence
<220> FEATURE:
<223> OTHER INFORMATION: BoNT/G Light chain-TD1r cDNA Sequence
<220> FEATURE:
<221> NAME/KEY: misc_feature
<222> LOCATION: (20)..(20)
<223> OTHER INFORMATION: n is a, c, g, or t

<400> SEQUENCE: 72

```
atgccagtta atataaaaan ctttaattat aatgacccta ttaataatga tgacattatt     60

atgatggaac cattcaatga cccagggcca ggaacatatt ataaagcttt taggattata    120

gatcgtattt ggatagtacc agaaaggttt acttatggat ttcaacctga ccaatttaat    180

gccagtacag gagtttttag taaagatgtc tacgaatatt acgatccaac ttatttaaaa    240

accgatgctg aaaaagataa atttttaaaa acaatgatta aattatttaa tagaattaat    300

tcaaaaccat caggacagag attactggat atgatagtag atgctatacc ttatcttgga    360

aatgcatcta caccgcccga caaatttgca gcaaatgttg caaatgtatc tattaataaa    420

aaaattatcc aacctggagc tgaagatcaa ataaaaggtt taatgacaaa tttaataata    480

tttggaccag gaccagttct aagtgataat tttactgata gtatgattat gaatggccat    540

tccccaatat cagaaggatt tggtgcaaga atgatgataa gattttgtcc tagttgttta    600

aatgtattta ataatgttca ggaaaataaa gatacatcta tatttagtag acgcgcgtat    660

tttgcagatc cagctctaac gttaatgcat gaacttatac atgtgttaca tggattatat    720

ggaattaaga taagtaattt accaattact ccaaatacaa aagaattttt catgcaacat    780
```

-continued

```
agcgatcctg tacaagcaga agaactatat acattcggag gacatgatcc tagtgttata    840

agtccttcta cggatatgaa tatttataat aaagcgttac aaaattttca agatatagct    900

aataggctta atattgtttc aagtgcccaa gggagtggaa ttgatatttc cttatataaa    960

caaatatata aaaataaata tgattttgtt gaagatccta atggaaaata tagtgtagat   1020

aaggataagt ttgataaatt atataaggcc ttaatgtttg gctttactga aactaatcta   1080

gctggtgaat atggaataaa aactaggtat tcttatttta gtgaatattt gccaccgata   1140

aaaactgaaa aattgttaga caatacaatt tatactcaaa atgaaggctt taacatagct   1200

agtaaaaatc tcaaaacgga atttaatggt cagaataagg cggtaaataa agaggcttat   1260

gaagaaatca gcctagaaca tctcgttata tatagaatag caatgtgcaa gcctgtaatg   1320

tacaaatgtc aaaatttatt caagaacatt aatatcatgg ccaag                   1365
```

<210> SEQ ID NO 73
<211> LENGTH: 1413
<212> TYPE: DNA
<213> ORGANISM: Artificial Sequence
<220> FEATURE:
<223> OTHER INFORMATION: TD1-BoNT/A Light chain cDNA Sequence with hexahistidine

<400> SEQUENCE: 73

```
atgaaggcca tgatcaatat taacaagttc ttaaatcaat gtccctttgt caacaaacag     60

ttcaactaca aggacccagt taatggagta gacatcgcat atatcaagat tcccaacgct    120

ggccagatgc aacccgttaa ggcatttaaa atccataaca aaatctgggt tatcccagag    180

cgggatacct tcaccaaccc cgaggagggc gatctgaacc ccccgccgga ggcgaagcag    240

gtcccagtga gctactacga tagcacctac ctcagcaccg acaacgagaa ggacaactac    300

ctcaaaggag tcacgaagtt gttcgagaga atctactcca cagacctcgg ccgcatgctt    360

ctaaccagca ttgtgcgtgg cattcccttt tggggcggct ctaccatcga cacagagctg    420

aaggtgatag acaccaactg catcaacgta atccagcctg acggcagcta ccgaagcgag    480

gagcttaacc tggtgatcat cggccccttcc gccgatatca tccaattcga gtgcaagagc    540

ttcggccacg aggtcctgaa cctcacccgg aacggctatg gaagcaccca gtacataaga    600

ttcagccctg acttcacctt cgggtttgag gagagcttgg aggtcgacac aaaccccctg    660

ctgggagccg ggaagttcgc cactgaccca gccgtgactc tggcacacga gctgatccac    720

gccggtcacc gcctgtacgg catagctata aacccaaaca gggtgttcaa agtgaacacc    780

aacgcttact atgaaatgag cggcctggag gtgagcttcg aggagctgag aacgttcggg    840

ggacatgatg ctaaatttat cgacagcctg caggagaacg agttcaggct gtactactac    900

aataagttca aggatatagc gagcactctg aacaaggcca agtccatcgt aggcactact    960

gcatccctcc agtatatgaa gaatgtgttc aaagagaaat acctgctgag cgaggatacc   1020

agcggtaagt tcagcgtgga taagcttaag ttcgacaagc tgtataagat gctcaccgaa   1080

atctacaccg aggataattt cgttaagttc ttcaaggtcc tgaaccggaa gacctacctg   1140

aacttcgaca aggccgtgtt caagatcaac atcgtgccta aagtgaacta caccatctac   1200

gacgggttta acctgaggaa caccaacctg gccgctaact tcaacgggca gaacacagag   1260

atcaacaaca tgaatttcac gaagttgaag aacttcaccg gactgtttga gttctacaaa   1320

ttgctgtgtg tgcgcgggat catcactagc aagaccaaga gccttgacaa aggctacaac   1380

aagtgactcg agcaccacca ccaccaccac tga                                1413
```

<210> SEQ ID NO 74
<211> LENGTH: 1389
<212> TYPE: DNA
<213> ORGANISM: Artificial Sequence
<220> FEATURE:
<223> OTHER INFORMATION: TD1-BoNT/B Light chain cDNA Sequence with hexahistidine

<400> SEQUENCE: 74

```
atgaaggcca tgatcaatat taacaagttc ttaaatcaat gtccagttac aataaataat     60
tttaattata atgatcctat tgataataat aatattatta tgatggagcc tccatttgcg    120
agaggtacgg ggagatatta taaagctttt aaaatcacag atcgtatttg gataataccg    180
gaaagatata cttttggata taaacctgag gattttaata aaagttccgg tatttttaat    240
agagatgttt gtgaatatta tgatccagat tacttaaata ctaatgataa aaagaatata    300
tttttacaaa caatgatcaa gttatttaat agaatcaaat caaaaccatt gggtgaaaag    360
ttattagaga tgattataaa tggtatacct tatcttggag atagacgtgt tccactcgaa    420
gagtttaaca caaacattgc tagtgtaact gttaataaat taatcagtaa tccaggagaa    480
gtggagcgaa aaaaaggtat tttcgcaaat ttaataatat ttggacctgg gccagtttta    540
aatgaaaatg agactataga tataggtata caaaatcatt ttgcatcaag ggaaggcttc    600
gggggtataa tgcaaatgaa gttttgccca gaatatgtaa gcgtatttaa taatgttcaa    660
gaaaacaaag gcgcaagtat atttaataga cgtggatatt tttcagatcc agccttgata    720
ttaatgcatg aacttataca tgttttacat ggattatatg gcattaaagt agatgattta    780
ccaattgtac caaatgaaaa aaaatttttt atgcaatcta cagatgctat acaggcagaa    840
gaactatata catttggagg acaagatccc agcatcataa ctccttctac ggataaaagt    900
atctatgata aagttttgca aaattttaga gggatagttg atagacttaa caaggtttta    960
gtttgcatat cagatcctaa cattaatatt aatatatata aaaataaatt taaagataaa   1020
tataaattcg ttgaagattc tgagggaaaa tatagtatag atgtagaaag ttttgataaa   1080
ttatataaaa gcttaatgtt tggttttaca gaaactaata tagcagaaaa ttataaaata   1140
aaaactagag cttcttattt tagtgattcc ttaccaccag taaaaataaa aaatttatta   1200
gataatgaaa tctatactat agaggaaggg tttaatatat ctgataaaga tatggaaaaa   1260
gaatatagag gtcagaataa agctataaat aaacaagctt atgaagaaat tagcaaggag   1320
catttggctg tatataagat acaaatgtgt aaaagtgtta aactcgagca ccaccaccac   1380
caccactga                                                           1389
```

<210> SEQ ID NO 75
<211> LENGTH: 1413
<212> TYPE: DNA
<213> ORGANISM: Artificial Sequence
<220> FEATURE:
<223> OTHER INFORMATION: TD1-BoNT/C Light chain cDNA Sequence with hexahistidine

<400> SEQUENCE: 75

```
atgaaggcca tgatcaatat taacaagttc ttaaatcaat gtccaataac aattaacaac     60
tttaattatt cagatcctgt tgataataaa aatattttat atttagatac tcatttaaat    120
acactagcta atgagcctga aaaagccttt cgcattacag gaaatatatg ggtaatacct    180
gatagatttt caagaaattc taatccaaat ttaaataaac ctcctcgagt tacaagccct    240
```

```
aaaagtggtt attatgatcc taattatttg agtactgatt ctgacaaaga tacattttta    300

aaagaaatta taaagttatt taaaagaatt aattctagag aaataggaga agaattaata    360

tatagacttt cgacagatat accctttcct gggaataaca atactccaat taatactttt    420

gattttgatg tagattttaa cagtgttgat gttaaaacta gacaaggtaa caactgggtt    480

aaaactggta gcataaatcc tagtgttata ataactggac ctagagaaaa cattatagat    540

ccagaaactt ctacgtttaa attaactaac aatacttttg cggcacaaga aggatttggt    600

gctttatcaa taatttcaat atcacctaga tttatgctaa catatagtaa tgcaactaat    660

gatgtaggag agggtagatt ttctaagtct gaattttgca tggatccaat actaatttta    720

atgcatgaac ttaatcatgc aatgcataat ttatatggaa tagctatacc aaatgatcaa    780

acaatttcat ctgtaactag taatattttt tattctcaat ataatgtgaa attagagtat    840

gcagaaatat atgcatttgg aggtccaact atagacctta ttcctaaaag tgcaaggaaa    900

tattttgagg aaaaggcatt ggattattat agatctatag ctaaaagact taatagtata    960

actactgcaa atccttcaag ctttaataaa tatatagggg aatataaaca gaaacttatt   1020

agaaagtata gattcgtagt agaatcttca ggtgaagtta cagtaaatcg taataagttt   1080

gttgagttat ataatgaact tacacaaata tttacagaat ttaactacgc taaaatatat   1140

aatgtacaaa ataggaaaat atatctttca aatgtatata ctccggttac ggcgaatata   1200

ttagacgata atgtttatga tatacaaaat ggatttaata tacctaaaag taatttaaat   1260

gtactattta tgggtcaaaa tttatctcga aatccagcat taagaaaagt caatcctgaa   1320

aatatgcttt atttatttac aaaattttgt cataaagcaa tagatggtag atcattatat   1380

aataaactcg agcaccacca ccaccaccac tga                                1413
```

<210> SEQ ID NO 76
<211> LENGTH: 1392
<212> TYPE: DNA
<213> ORGANISM: Artificial Sequence
<220> FEATURE:
<223> OTHER INFORMATION: TD1-BoNT/D Light chain cDNA Sequence with hexahistidine

<400> SEQUENCE: 76

```
atgaaggcca tgatcaatat taacaagttc ttaaatcaat gtacatggcc agtaaaagat     60

tttaattata gtgatcctgt taatgacaat gatatattat atttaagaat accacaaaat    120

aagttaatta ctacacctgt aaaagctttt atgattactc aaaatatttg ggtaatacca    180

gaaagatttt catcagatac taatccaagt ttaagtaaac cgcccagacc tacttcaaag    240

tatcaaagtt attatgatcc tagttattta tctactgatg aacaaaaaga tacattttta    300

aaagggatta taaaattatt taaaagaatt aatgaaagag atataggaaa aaaattaata    360

aattatttag tagttggttc accttttatg ggagattcaa gtacgcctga agatacattt    420

gattttacac gtcatactac taatattgca gttgaaaagt ttgaaaatgg tagttggaaa    480

gtaacaaata ttataacacc aagtgtattg atatttggac cacttcctaa tatattagac    540

tatacagcat cccttacatt gcaaggacaa caatcaaatc catcatttga agggtttgga    600

acattatcta tactaaaagt agcacctgaa tttttgttaa catttagtga tgtaacatct    660

aatcaaagtt cagctgtatt aggcaaatct atattttgta tggatccagt aatagcttta    720

atgcatgagt taacacattc tttgcatcaa ttatatggaa taaatatacc atctgataaa    780

aggattcgtc cacaagttag cgagggattt ttctctcaag atggacccaa cgtacaattt    840
```

-continued

```
gaggaattat atacatttgg aggattagat gttgaaataa tacctcaaat tgaaagatca     900

caattaagag aaaaagcatt aggtcactat aaagatatag cgaaaagact taataatatt     960

aataaaacta ttccttctag ttggattagt aatatagata aatataaaaa aatattttct    1020

gaaaagtata attttgataa agataataca ggaaattttg ttgtaaatat tgataaattc    1080

aatagcttat attcagactt gactaatgtt atgtcagaag ttgtttattc ttcgcaatat    1140

aatgttaaaa acaggactca ttatttttca aggcattatc tacctgtatt tgcaaatata    1200

ttagatgata atatttatac tataagagat ggttttaatt taacaaataa aggttttaat    1260

atagaaaatt cgggtcagaa tatagaaagg aatcctgcac tacaaaagct tagttcagaa    1320

agtgtagtag atttatttac aaaagtatgt ttaagattaa caaaactcga gcaccaccac    1380

caccaccact ga                                                        1392
```

<210> SEQ ID NO 77
<211> LENGTH: 1332
<212> TYPE: DNA
<213> ORGANISM: Artificial Sequence
<220> FEATURE:
<223> OTHER INFORMATION: TD1-BoNT/E Light chain cDNA Sequence with hexahistidine

<400> SEQUENCE: 77

```
atgaaggcca tgatcaatat taacaagttc ttaaatcaat gtccaacaat taatagtttt      60

aattataatg atcctgttaa taatagaaca attttatata ttaaaccagg cggttgtcaa     120

caattttata aatcatttaa tattatgaaa aatatttgga taattccaga gagaaatgta     180

attggtacaa ttccccaaga ttttcttccg cctacttcat tgaaaaatgg agatagtagt     240

tattatgacc ctaattattt acaaagtgat caagaaaagg ataaattttt aaaaatagtc     300

acaaaaatat ttaatagaat aaatgataat ctttcaggaa ggattttatt agaagaactg     360

tcaaaagcta atccatattt aggaaatgat aatactccag atggtgactt cattattaat     420

gatgcatcag cagttccaat tcaattctca aatggtagcc aaagcatact attacctaat     480

gttattataa tgggagcaga gcctgattta tttgaaacta acagttccaa tatttctcta     540

agaaataatt atatgccaag caatcacggt tttggatcaa tagctatagt aacattctca     600

cctgaatatt cttttagatt taaagataat agtatgaatg aatttattca agatcctgct     660

cttacattaa tgcatgaatt aatacattca ttacatggac tatatggggc taaagggatt     720

actacaaagt atactataac acaaaaacaa aatcccctaa taacaaatat aagaggtaca     780

aatattgaag aattcttaac ttttggaggt actgatttaa acattattac tagtgctcag     840

tccaatgata tctatactaa tcttctagct gattataaaa aaatagcgtc taaacttagc     900

aaagtacaag tatctaatcc actacttaat ccttataaag atgtttttga agcaaagtat     960

ggattagata aagatgctag cggaatttat tcggtaaata taaacaaatt taatgatatt    1020

tttaaaaaat tatacagctt tacggaattt gatttagcaa ctaaatttca agttaaatgt    1080

aggcaaactt atattggaca gtataaatac ttcaaacttt caaacttgtt aaatgattct    1140

atttataata tatcagaagg ctataatata aataatttaa aggtaaattt tagaggacag    1200

aatgcaaatt taaatcctag aattattaca ccaattacag gtagaggact agtaaaaaaa    1260

atcattagat tttgtaaaaa tattgtttct gtaaaaggca taaggctcga gcaccaccac    1320

caccaccact ga                                                        1332
```

<210> SEQ ID NO 78

<211> LENGTH: 1374
<212> TYPE: DNA
<213> ORGANISM: Artificial Sequence
<220> FEATURE:
<223> OTHER INFORMATION: TD1-BoNT/F Light chain cDNA Sequence with hexahistidine

<400> SEQUENCE: 78
atgaaggcca tgatcaatat taacaagttc ttaaatcaat gtccagttgc aataaatagt 60
tttaattata atgaccctgt taatgatgat acaattttat acatgcagat accatatgaa 120
gaaaaaagta aaaaatatta taaagctttt gagattatgc gtaatgtttg gataattcct 180
gagagaaata caataggaac gaatcctagt gattttgatc caccggcttc attaaagaac 240
ggaagcagtg cttattatga tcctaattat ttaaccactg atgctgaaaa agatagatat 300
ttaaaaacaa cgataaaatt atttaagaga attaatagta atcctgcagg gaaagttttg 360
ttacaagaaa tatcatatgc taaaccatat ttaggaaatg accacacgcc aattgatgaa 420
ttctctccag ttactagaac tacaagtgtt aatataaaat tatcaactaa tgttgaaagt 480
tcaatgttat tgaatcttct tgtattggga gcaggacctg atatatttga aagttgttgt 540
taccccgtta gaaaactaat agatccagat gtagtttatg atccaagtaa ttatggtttt 600
ggatcaatta atatcgtgac attttcacct gagtatgaat atacttttaa tgatattagt 660
ggagggcata atagtagtac agaatcattt attgcagatc ctgcaatttc actagctcat 720
gaattgatac atgcactgca tggattatac ggggctaggg gagttactta tgaagagact 780
atagaagtaa agcaagcacc tcttatgata gccgaaaaac ccataaggct agaagaattt 840
ttaacctttg gaggtcagga tttaaatatt attactagtg ctatgaagga aaaaatatat 900
aacaatcttt tagctaacta tgaaaaaata gctactagac ttagtgaagt taatagtgct 960
cctcctgaat atgatattaa tgaatataaa gattattttc aatggaagta tgggctagat 1020
aaaaatgctg atggaagtta tactgtaaat gaaaataaat ttaatgaaat ttataaaaaa 1080
ttatatagtt ttacagagag tgacttagca aataaattta aagtaaaatg tagaaatact 1140
tattttatta aatatgaatt tttaaaagtt ccaaatttgt tagatgatga tatttatact 1200
gtatcagagg ggtttaatat aggtaattta gcagtaaaca atcgcggaca aagtataaag 1260
ttaaatccta aaattattga ttccattcca gataaaggtc tagtagaaaa gatcgttaaa 1320
ttttgtaaga gcgttattcc tagaaaactc gagcaccacc accaccacca ctga 1374

<210> SEQ ID NO 79
<211> LENGTH: 1392
<212> TYPE: DNA
<213> ORGANISM: Artificial Sequence
<220> FEATURE:
<223> OTHER INFORMATION: TD1-BoNT/G Light chain cDNA Sequence with hexahistidine
<220> FEATURE:
<221> NAME/KEY: misc_feature
<222> LOCATION: (59)..(59)
<223> OTHER INFORMATION: n is a, c, g, or t

<400> SEQUENCE: 79
atgaaggcca tgatcaatat taacaagttc ttaaatcaat gtccagttaa tataaaaanc 60
tttaattata atgaccctat taataatgat gacattatta tgatggaacc attcaatgac 120
ccagggccag gaacatatta taaagctttt aggattatag atcgtatttg gatagtacca 180
gaaaggttta cttatggatt tcaacctgac caatttaatg ccagtacagg agtttttagt 240
aaagatgtct acgaatatta cgatccaact tatttaaaaa ccgatgctga aaaagataaa 300

```
tttttaaaaa caatgattaa attatttaat agaattaatt caaaaccatc aggacagaga    360

ttactggata tgatagtaga tgctatacct tatcttggaa atgcatctac accgcccgac    420

aaatttgcag caaatgttgc aaatgtatct attaataaaa aaattatcca acctggagct    480

gaagatcaaa taaaaggttt aatgacaaat ttaataatat ttggaccagg accagttcta    540

agtgataatt ttactgatag tatgattatg aatggccatt ccccaatatc agaaggattt    600

ggtgcaagaa tgatgataag attttgtcct agttgtttaa atgtatttaa taatgttcag    660

gaaaataaag atacatctat atttagtaga cgcgcgtatt ttgcagatcc agctctaacg    720

ttaatgcatg aacttataca tgtgttacat ggattatatg gaattaagat aagtaattta    780

ccaattactc caaatacaaa agaatttttc atgcaacata gcgatcctgt acaagcagaa    840

gaactatata cattcggagg acatgatcct agtgttataa gtccttctac ggatatgaat    900

atttataata aagcgttaca aaattttcaa gatatagcta ataggcttaa tattgtttca    960

agtgcccaag ggagtggaat tgatatttcc ttatataaac aaatatataa aaataaatat   1020

gattttgttg aagatcctaa tggaaaatat agtgtagata aggataagtt tgataaatta   1080

tataaggcct taatgtttgg ctttactgaa actaatctag ctggtgaata tggaataaaa   1140

actaggtatt cttattttag tgaatatttg ccaccgataa aaactgaaaa attgttagac   1200

aatacaattt atactcaaaa tgaaggcttt aacatagcta gtaaaaatct caaaacggaa   1260

tttaatggtc agaataaggc ggtaaataaa gaggcttatg aagaaatcag cctagaacat   1320

ctcgttatat atagaatagc aatgtgcaag cctgtaatgt acaaactcga gcaccaccac   1380

caccaccact ga                                                       1392
```

<210> SEQ ID NO 80
<211> LENGTH: 1446
<212> TYPE: DNA
<213> ORGANISM: Artificial Sequence
<220> FEATURE:
<223> OTHER INFORMATION: BoNT/A Light chain-TD1r cDNA Sequence with hexahistidine

<400> SEQUENCE: 80

```
atgggcagca gccatcatca tcatcatcac agcagcggcc tggtgccgcg cggcagccat     60

atgccctttg tcaacaaaca gttcaactac aaggacccag ttaatggagt agacatcgca    120

tatatcaaga ttcccaacgc tggccagatg caacccgtta aggcatttaa aatccataac    180

aaaatctggg ttatcccaga gcgggatacc ttcaccaacc ccgaggaggg cgatctgaac    240

cccccgccgg aggcgaagca ggtcccagtg agctactacg atagcaccta cctcagcacc    300

gacaacgaga aggacaacta cctcaaagga gtcacgaagt tgttcgagag aatctactcc    360

acagacctcg gccgcatgct tctaaccagc attgtgcgtg gcattccctt ttggggcggc    420

tctaccatcg acacagagct gaaggtgata gacaccaact gcatcaacgt aatccagcct    480

gacggcagct accgaagcga ggagcttaac ctggtgatca tcggcccttc cgccgatatc    540

atccaattcg agtgcaagag cttcggccac gaggtcctga acctcacccg gaacggctat    600

ggaagcaccc agtacataag attcagccct gacttcacct tcgggtttga ggagagcttg    660

gaggtcgaca caaacccccct gctgggagcc gggaagttcg ccactgaccc agccgtgact    720

ctggcacacg agctgatcca cgccggtcac cgcctgtacg gcatagctat aaacccaaac    780

agggtgttca aagtgaacac caacgcttac tatgaaatga gcggcctgga ggtgagcttc    840

gaggagctga gaacgttcgg gggacatgat gctaaattta tcgacagcct gcaggagaac    900
```

gagttcaggc tgtactacta caataagttc aaggatatag cgagcactct gaacaaggcc 960
aagtccatcg taggcactac tgcatccctc cagtatatga agaatgtgtt caaagagaaa 1020
tacctgctga gcgaggatac cagcggtaag ttcagcgtgg ataagcttaa gttcgacaag 1080
ctgtataaga tgctcaccga aatctacacc gaggataatt tcgttaagtt cttcaaggtc 1140
ctgaaccgga agacctacct gaacttcgac aaggccgtgt tcaagatcaa catcgtgcct 1200
aaagtgaact acaccatcta cgacgggttt aacctgagga acaccaacct ggccgctaac 1260
ttcaacgggc agaacacaga gatcaacaac atgaatttca cgaagttgaa gaacttcacc 1320
ggactgtttg agttctacaa attgctgtgt gtgcgcggga tcatcactag caagaccaag 1380
agccttgaca aaggctacaa caagtgatgt caaaatttat tcaagaacat taatatcatg 1440
gccaag 1446

<210> SEQ ID NO 81
<211> LENGTH: 1422
<212> TYPE: DNA
<213> ORGANISM: Artificial Sequence
<220> FEATURE:
<223> OTHER INFORMATION: BoNT/B Light chain-TD1r cDNA Sequence with hexahistidine

<400> SEQUENCE: 81
atgggcagca gccatcatca tcatcatcac agcagcggcc tggtgccgcg cggcagccat 60
atgccagtta caataaataa ttttaattat aatgatccta ttgataataa taatattatt 120
atgatggagc ctccatttgc gagaggtacg gggagatatt ataaagcttt taaaatcaca 180
gatcgtattt ggataatacc ggaaagatat acttttggat ataaacctga ggattttaat 240
aaaagttccg gtatttttaa tagagatgtt tgtgaatatt atgatccaga ttacttaaat 300
actaatgata aaaagaatat atttttacaa acaatgatca agttatttaa tagaatcaaa 360
tcaaaaccat tgggtgaaaa gttattagag atgattataa atggtatacc ttatcttgga 420
gatagacgtg ttccactcga agagtttaac acaaacattg ctagtgtaac tgttaataaa 480
ttaatcagta atccaggaga agtggagcga aaaaaaggta ttttcgcaaa tttaataata 540
tttggacctg ggccagtttt aaatgaaaat gagactatag atataggtat acaaaatcat 600
tttgcatcaa gggaaggctt cgggggtata atgcaaatga agttttgccc agaatatgta 660
agcgtattta ataatgttca agaaaacaaa ggcgcaagta tatttaatag acgtggatat 720
ttttcagatc cagccttgat attaatgcat gaacttatac atgttttaca tggattatat 780
ggcattaaag tagatgattt accaattgta ccaaatgaaa aaaaattttt tatgcaatct 840
acagatgcta tacaggcaga agaactatat acatttggag gacaagatcc cagcatcata 900
actccttcta cggataaaag tatctatgat aaagttttgc aaaattttag agggatagtt 960
gatagactta acaaggtttt agtttgcata tcagatccta acattaatat taatatatat 1020
aaaaataaat ttaaagataa atataaattc gttgaagatt ctgagggaaa atatagtata 1080
gatgtagaaa gttttgataa attatataaa agcttaatgt ttggttttac agaaactaat 1140
atagcagaaa attataaaat aaaaactaga gcttcttatt ttagtgattc cttaccacca 1200
gtaaaaataa aaaatttatt agataatgaa atctatacta tagaggaagg gtttaatata 1260
tctgataaag atatggaaaa agaatataga ggtcagaata aagctataaa taaacaagct 1320
tatgaagaaa ttagcaagga gcatttggct gtatataaga tacaaatgtg taaaagtgtt 1380
aaatgtcaaa atttattcaa gaacattaat atcatggcca ag 1422

-continued

<210> SEQ ID NO 82
<211> LENGTH: 1446
<212> TYPE: DNA
<213> ORGANISM: Artificial Sequence
<220> FEATURE:
<223> OTHER INFORMATION: BoNT/C Light chain-TD1r cDNA Sequence with hexahistidine

<400> SEQUENCE: 82

```
atgggcagca gccatcatca tcatcatcac agcagcggcc tggtgccgcg cggcagccat     60
atgccaataa caattaacaa ctttaattat tcagatcctg ttgataataa aaatatttta    120
tatttagata ctcatttaaa tacactagct aatgagcctg aaaaagcctt tcgcattaca    180
ggaaatatat gggtaatacc tgatagattt tcaagaaatt ctaatccaaa tttaaataaa    240
cctcctcgag ttacaagccc taaaagtggt tattatgatc ctaattattt gagtactgat    300
tctgacaaag atacattttt aaaagaaatt ataaagttat ttaaaagaat taattctaga    360
gaaataggag aagaattaat atatagactt tcgacagata taccctttcc tgggaataac    420
aatactccaa ttaatacttt tgattttgat gtagatttta acagtgttga tgttaaaact    480
agacaaggta acaactgggt taaaactggt agcataaatc ctagtgttat aataactgga    540
cctagagaaa acattataga tccagaaact tctacgttta aattaactaa caatactttt    600
gcggcacaag aaggatttgg tgctttatca ataatttcaa tatcacctag atttatgcta    660
acatatagta atgcaactaa tgatgtagga gagggtagat ttctaagtc tgaattttgc     720
atggatccaa tactaatttt aatgcatgaa cttaatcatg caatgcataa tttatatgga    780
atagctatac caaatgatca aacaatttca tctgtaacta gtaatatttt ttattctcaa    840
tataatgtga aattagagta tgcagaaata tatgcatttg gaggtccaac tatagacctt    900
attcctaaaa gtgcaaggaa atattttgag gaaaaggcat tggattatta tagatctata    960
gctaaaagac ttaatagtat aactactgca aatccttcaa gctttaataa atatataggg   1020
gaatataaac agaaacttat tagaaagtat agattcgtag tagaatcttc aggtgaagtt   1080
acagtaaatc gtaataagtt tgttgagtta tataatgaac ttacacaaat atttacagaa   1140
tttaactacg ctaaaatata taatgtacaa aataggaaaa tatatctttc aaatgtatat   1200
actccggtta cggcgaatat attagacgat aatgtttatg atatacaaaa tggatttaat   1260
atacctaaaa gtaatttaaa tgtactattt atgggtcaaa atttatctcg aaatccagca   1320
ttaagaaaag tcaatcctga aaatatgctt tatttattta caaaattttg tcataaagca   1380
atagatggta gatcattata taataaatgt caaaatttat tcaagaacat taatatcatg   1440
gccaag                                                              1446
```

<210> SEQ ID NO 83
<211> LENGTH: 1425
<212> TYPE: DNA
<213> ORGANISM: Artificial Sequence
<220> FEATURE:
<223> OTHER INFORMATION: BoNT/D Light chain-TD1r cDNA Sequence with hexahistidine

<400> SEQUENCE: 83

```
atgggcagca gccatcatca tcatcatcac agcagcggcc tggtgccgcg cggcagccat     60
atgacatggc cagtaaaaga ttttaattat agtgatcctg ttaatgacaa tgatatatta    120
tatttaagaa taccacaaaa taagttaatt actacacctg taaaagcttt tatgattact    180
```

```
caaaatattt gggtaatacc agaaagattt tcatcagata ctaatccaag tttaagtaaa    240

ccgcccagac ctacttcaaa gtatcaaagt tattatgatc ctagttattt atctactgat    300

gaacaaaaag atacattttt aaaagggatt ataaaattat ttaaaagaat taatgaaaga    360

gatataggaa aaaaattaat aaattattta gtagttggtt caccttttat gggagattca    420

agtacgcctg aagatacatt tgattttaca cgtcatacta ctaatattgc agttgaaaag    480

tttgaaaatg gtagttggaa agtaacaaat attataaacac caagtgtatt gatatttgga    540

ccacttccta atatattaga ctatacagca tcccttacat tgcaaggaca acaatcaaat    600

ccatcatttg aagggtttgg aacattatct atactaaaag tagcacctga atttttgtta    660

acatttagtg atgtaacatc taatcaaagt tcagctgtat taggcaaatc tatattttgt    720

atggatccag taatagcttt aatgcatgag ttaacacatt ctttgcatca attatatgga    780

ataaatatac catctgataa aaggattcgt ccacaagtta gcgagggatt tttctctcaa    840

gatggaccca acgtacaatt tgaggaatta tatacatttg gaggattaga tgttgaaata    900

atacctcaaa ttgaaagatc acaattaaga gaaaaagcat taggtcacta taaagatata    960

gcgaaaagac ttaataatat taataaaact attccttcta gttggattag taatatagat   1020

aaatataaaa aaatattttc tgaaaagtat aatttgata aagataatac aggaaatttt   1080

gttgtaaata ttgataaatt caatagctta tattcagact tgactaatgt tatgtcagaa   1140

gttgtttatt cttcgcaata taatgttaaa aacaggactc attatttttc aaggcattat   1200

ctacctgtat ttgcaaatat attagatgat aatatttata ctataagaga tggttttaat   1260

ttaacaaata aaggttttaa tatagaaaat tcgggtcaga atatagaaag gaatcctgca   1320

ctacaaaagc ttagttcaga aagtgtagta gatttattta caaaagtatg tttaagatta   1380

acaaaatgtc aaaatttatt caagaacatt aatatcatgg ccaag                  1425
```

<210> SEQ ID NO 84
<211> LENGTH: 1365
<212> TYPE: DNA
<213> ORGANISM: Artificial Sequence
<220> FEATURE:
<223> OTHER INFORMATION: BoNT/E Light chain-TD1r cDNA Sequence with hexahistidine

<400> SEQUENCE: 84

```
atgggcagca gccatcatca tcatcatcac agcagcggcc tggtgccgcg cggcagccat     60

atgccaacaa ttaatagttt taattataat gatcctgtta ataatagaac aattttatat    120

attaaaccag gcggttgtca acaattttat aaatcattta atattatgaa aaatatttgg    180

ataattccag agagaaatgt aattggtaca attccccaag attttcttcc gcctacttca    240

ttgaaaaatg gagatagtag ttattatgac cctaattatt tacaaagtga tcaagaaaag    300

gataaatttt taaaaatagt cacaaaaata tttaatagaa taaatgataa tctttcagga    360

aggattttat tagaagaact gtcaaaagct aatccatatt taggaaatga taatactcca    420

gatggtgact tcattattaa tgatgcatca gcagttccaa ttcaattctc aaatggtagc    480

caaagcatac tattacctaa tgttattata atgggagcag agcctgattt atttgaaact    540

aacagttcca atatttctct aagaaataat tatatgccaa gcaatcacgg ttttggatca    600

atagctatag taacattctc acctgaatat tcttttagat ttaaagataa tagtatgaat    660

gaatttattc aagatcctgc tcttacatta atgcatgaat taatacattc attacatgga    720

ctatatgggg ctaaagggat tactacaaag tatactataa cacaaaaaca aaatccccta    780
```

```
ataacaaata taagaggtac aaatattgaa gaattcttaa cttttggagg tactgattta    840

aacattatta ctagtgctca gtccaatgat atctatacta atcttctagc tgattataaa    900

aaaatagcgt ctaaacttag caaagtacaa gtatctaatc cactacttaa tccttataaa    960

gatgtttttg aagcaaagta tggattagat aaagatgcta gcggaattta ttcggtaaat   1020

ataaacaaat ttaatgatat ttttaaaaaa ttatacagct ttacggaatt tgatttagca   1080

actaaatttc aagttaaatg taggcaaact tatattggac agtataaata cttcaaactt   1140

tcaaacttgt taaatgattc tatttataat atatcagaag gctataatat aaataattta   1200

aaggtaaatt ttagaggaca gaatgcaaat ttaaatccta gaattattac accaattaca   1260

ggtagaggac tagtaaaaaa aatcattaga ttttgtaaaa atattgtttc tgtaaaaggc   1320

ataaggtgtc aaaatttatt caagaacatt aatatcatgg ccaag                   1365
```

<210> SEQ ID NO 85
<211> LENGTH: 1407
<212> TYPE: DNA
<213> ORGANISM: Artificial Sequence
<220> FEATURE:
<223> OTHER INFORMATION: BoNT/F Light chain-TD1r cDNA Sequence with hexahistidine

<400> SEQUENCE: 85

```
atgggcagca gccatcatca tcatcatcac agcagcggcc tggtgccgcg cggcagccat     60

atgccagttg caataaatag ttttaattat aatgaccctg ttaatgatga tacaatttta    120

tacatgcaga taccatatga agaaaaaagt aaaaaatatt ataaagcttt tgagattatg    180

cgtaatgttt ggataattcc tgagagaaat acaataggaa cgaatcctag tgattttgat    240

ccaccggctt cattaaagaa cggaagcagt gcttattatg atcctaatta tttaaccact    300

gatgctgaaa aagatagata tttaaaaaca acgataaaat tatttaagag aattaatagt    360

aatcctgcag ggaaagtttt gttacaagaa atatcatatg ctaaaccata tttaggaaat    420

gaccacacgc caattgatga attctctcca gttactagaa ctacaagtgt taatataaaa    480

ttatcaacta atgttgaaag ttcaatgtta ttgaatcttc ttgtattggg agcaggacct    540

gatatatttg aaagttgttg ttaccccgtt agaaaactaa tagatccaga tgtagtttat    600

gatccaagta attatggttt tggatcaatt aatatcgtga cattttcacc tgagtatgaa    660

tatactttta atgatattag tggagggcat aatagtagta cagaatcatt tattgcagat    720

cctgcaattt cactagctca tgaattgata catgcactgc atggattata cggggctagg    780

ggagttactt atgaagagac tatagaagta aagcaagcac ctcttatgat agccgaaaaa    840

cccataaggc tagaagaatt tttaaccttt ggaggtcagg atttaaatat tattactagt    900

gctatgaagg aaaaaatata taacaatctt ttagctaact atgaaaaaat agctactaga    960

cttagtgaag ttaatagtgc tcctcctgaa tatgatatta atgaatataa agattatttt   1020

caatggaagt atgggctaga taaaaatgct gatggaagtt atactgtaaa tgaaaataaa   1080

tttaatgaaa tttataaaaa attatatagt tttacagaga gtgacttagc aaataaattt   1140

aaagtaaaat gtagaaatac ttattttatt aaatatgaat ttttaaaagt tccaaatttg   1200

ttagatgatg atatttatac tgtatcagag ggtttaata taggtaattt agcagtaaac    1260

aatcgcggac aaagtataaa gttaaatcct aaaattattg attccattcc agataaaggt   1320

ctagtagaaa agatcgttaa attttgtaag agcgttattc ctagaaaatg tcaaaattta   1380

ttcaagaaca ttaatatcat ggccaag                                       1407
```

<210> SEQ ID NO 86
<211> LENGTH: 1425
<212> TYPE: DNA
<213> ORGANISM: Artificial Sequence
<220> FEATURE:
<223> OTHER INFORMATION: BoNT/G Light chain-TD1r cDNA Sequence with hexahistidine
<220> FEATURE:
<221> NAME/KEY: misc_feature
<222> LOCATION: (80)..(80)
<223> OTHER INFORMATION: n is a, c, g, or t

<400> SEQUENCE: 86
atgggcagca gccatcatca tcatcatcac agcagcggcc tggtgccgcg cggcagccat 60
atgccagtta atataaaaan ctttaattat aatgacccta ttaataatga tgacattatt 120
atgatggaac cattcaatga cccagggcca ggaacatatt ataaagcttt taggattata 180
gatcgtattt ggatagtacc agaaaggttt acttatggat ttcaacctga ccaatttaat 240
gccagtacag gagtttttag taaagatgtc tacgaatatt acgatccaac ttatttaaaa 300
accgatgctg aaaaagataa atttttaaaa acaatgatta aattatttaa tagaattaat 360
tcaaaaccat caggacagag attactggat atgatagtag atgctatacc ttatcttgga 420
aatgcatcta caccgcccga caaatttgca gcaaatgttg caaatgtatc tattaataaa 480
aaaattatcc aacctggagc tgaagatcaa ataaaaggtt taatgacaaa tttaataata 540
tttggaccag gaccagttct aagtgataat tttactgata gtatgattat gaatggccat 600
tccccaatat cagaaggatt tggtgcaaga atgatgataa gattttgtcc tagttgttta 660
aatgtattta ataatgttca ggaaaataaa gatacatcta tatttagtag acgcgcgtat 720
tttgcagatc cagctctaac gttaatgcat gaacttatac atgtgttaca tggattatat 780
ggaattaaga taagtaattt accaattact ccaaatacaa aagaattttt catgcaacat 840
agcgatcctg tacaagcaga agaactatat acattcggag gacatgatcc tagtgttata 900
agtccttcta cggatatgaa tatttataat aaagcgttac aaaattttca agatatagct 960
aataggctta atattgtttc aagtgcccaa gggagtggaa ttgatatttc cttatataaa 1020
caaatatata aaaataaata tgattttgtt gaagatccta atggaaaata tagtgtagat 1080
aaggataagt ttgataaatt atataaggcc ttaatgtttg gctttactga aactaatcta 1140
gctggtgaat atggaataaa aactaggtat tcttatttta gtgaatattt gccaccgata 1200
aaaactgaaa aattgttaga caatacaatt tatactcaaa atgaaggctt taacatagct 1260
agtaaaaatc tcaaaacgga atttaatggt cagaataagg cggtaaataa agaggcttat 1320
gaagaaatca gcctagaaca tctcgttata tatagaatag caatgtgcaa gcctgtaatg 1380
tacaaatgtc aaaatttatt caagaacatt aatatcatgg ccaag 1425

<210> SEQ ID NO 87
<211> LENGTH: 34
<212> TYPE: DNA
<213> ORGANISM: Artificial Sequence
<220> FEATURE:
<223> OTHER INFORMATION: BoNT/A Light chain Forward Primer Sequence

<400> SEQUENCE: 87
ggaattccat atgccctttg tcaacaaaca gttc 34

<210> SEQ ID NO 88
<211> LENGTH: 30
<212> TYPE: DNA

-continued

```
<213> ORGANISM: Artificial Sequence
<220> FEATURE:
<223> OTHER INFORMATION: BoNT/A Light chain Reverse Primer Sequence

<400> SEQUENCE: 88

ccgctcgagc ttgttgtagc ctttgtcaag                                  30


<210> SEQ ID NO 89
<211> LENGTH: 73
<212> TYPE: DNA
<213> ORGANISM: Artificial Sequence
<220> FEATURE:
<223> OTHER INFORMATION: TD1-BoNT/A Light chain Forward Primer Sequence

<400> SEQUENCE: 89

ggaattccat atgaaggcca tgatcaatat taacaagttc ttaaatcaat gtccctttgt     60

caacaaacag ttc                                                        73


<210> SEQ ID NO 90
<211> LENGTH: 60
<212> TYPE: DNA
<213> ORGANISM: Artificial Sequence
<220> FEATURE:
<223> OTHER INFORMATION: TD1-BoNT/A Light chain Reverse Primer Sequence

<400> SEQUENCE: 90

cttgacaaag gctacaacaa gcaccaccac cacagcggcg gtggtatgtg actcgagcgg     60
```

CELL PENETRATING PEPTIDE, CONJUGATE THEREOF WITH BOTULINUM TOXIN, AND USE THEREOF

CROSS-REFERENCE TO RELATED APPLICATIONS

This application claims priority to and the benefit of U.S. Provisional Patent Application No. 62/004,426, filed on May 29, 2014 and International Patent Application No. PCT/KR2015/005434, filed on May 29, 2015, the disclosure of which is incorporated herein by reference in its entirety.

TECHNICAL FIELD

The present invention relates to a novel cell-penetrating peptide, a cell-penetrating botulinum toxin recombinant protein in which a cell-penetrating peptide is conjugated with one end of the light chain of botulinum toxin, and uses thereof.

BACKGROUND ART

Botulinum toxin is a neurotoxin produced by the Gram-positive anaerobic bacterium *Clostridium botulinum*, which grows in spoiled canned goods or spoiled meat. Botulinum toxin is classified into 8 types of neurotoxins, seven types (A, B, C, D, E, F, G) of which may induce neuronal paralysis. Botulinum toxin has a size of approximately 150 kDa, and forms a complex of a botulinum toxin protein and a non-toxin protein. The size of each complex is formed to have a size up to 900 kDa according to the type of neurotoxin. Action type and target, and an activity duration may vary according to botulinum toxin type, and the botulinum toxin type A is known as one of the deadly biological agents.

Botulinum toxin causes paralysis by blocking a signal inducing muscle convulsion or contraction, and due to this function, is used for medical treatment or cosmetic purposes, since approved by the FDA in 1989. For medical treatment, botulinum toxin is used as an injection for a medical purpose to treat a neuromuscular disorder such as strabismus, torticollis or blepharospasm, for a cosmetological purpose to reduce wrinkles, frown or glabellar lines and a square jaw, and for other purposes to treat hyperhidrosis or migraines. While it has been reported that botulinum toxin has side effects including dysphagia, voice change, dry mouth and blurred vision, since no death directly caused by botulinum toxin has been reported yet, if properly used, botulinum toxin is evaluated as a very safe drug. However, the use of botulinum toxin is restricted in the cases of a person who has hypersensitivity to the drug or a musculoskeletal disease, or a pregnant or breastfeeding woman.

In current applications of botulinum toxin, the duration of botulinum toxin injected into skin tissue lasts approximately 3 to 6 months, and when signal transduction between a nerve and a muscle is blocked by botulinum toxin, a new dendrite is produced to reduce a neuronal paralysis effect caused by botulinum toxin, and thus a regular treatment is needed. Also, when botulinum toxin is repeatedly administered, an antibody to the botulinum toxin is produced in vivo, and thus its effect is reduced.

Also, since muscle paralysis caused by such botulinum toxin is mostly induced by injections, a variety of research has been conducted to find a different, effective delivery means that can provide convenience to a user, which however is still inadequate.

Meanwhile, a body structure which is always in contact with an external environment, that is, skin, plays an important role as a protective barrier that prevents release of body fluids and infection, and water loss, and is composed of the epidermis, the dermis and subcutaneous tissue. The cornified layer of the epidermis is present at the outermost part of the skin, and prevents skin dryness by inhibiting the loss of water and electrolytes out of the skin and provides an environment facilitating normal biochemical metabolism of the skin. Also, the skin cornified layer plays an important role to protect the body from external physical damage and chemicals, and prevent dermal invasion by bacteria, molds, or viruses.

There are three absorption paths through the skin including absorption through the cornified layer, absorption through follicles and sebaceous glands, and absorption through sweat glands, and the delivery of active materials through the skin has numerous limitations in terms of the structural and physical characteristics of the skin. Particularly, the skin cornified layer has a compact structure at the outermost layer of the skin due to the natural death of keratinocytes, which are the main component cells of the skin, and exhibits an acidity of approximately pH 5 due to sweat and a variety of lipid ingredients. To pass through such a barrier of the cornified layer, it has been reported that the active material should generally have a molecular weight as small as 1,000 or less, and have lipophilic characteristics.

While low molecular weight synthetic compounds or natural materials which are frequently used as cosmetic and medical ingredients are known to be easily delivered into cells, since macromolecules such as proteins, peptides and nucleic acids are difficult to penetrate a cell membrane having a bilayer lipid membrane structure due to the size of a molecular weight and hydrophilicity, it has been known that, due to the intrinsic characteristics of the cornified layer that substantially constitutes the skin barrier, low molecular weight materials have extremely low penetration efficiency, and high molecular weight materials have an even lower penetration efficiency.

Therefore, for the transdermal delivery of botulinum toxin, a carrier which can deliver botulinum toxin through the skin barrier is needed. As a method of amplifying the efficiency of transmitting the small molecules and macromolecules through a cell plasma membrane, a protein transduction domain (PTD) may be applied. First, widely known PTDs are PTDs such as HIV-Tat, antennapedia, etc., which are known as positive-charged short peptides to deliver DNA, RNA, lipids, carbohydrates, compounds or viruses as well as proteins into cells. It has been reported that the PTDs are receptor-independent, and penetrate the cell membrane according to a mechanism such as endocytosis or phagocytosis. As a long history of such a PTD, a variety of applications using the PTD have been attempted, but it has been known that there is no successful development case so far. In the HIV-Tat-derived PTD, a peptide is derived from a virus, there is a problem in terms of safety, and particularly, when such transduction domains of the PTD family are independently used, it is known that an intracellular transduction rate is rapidly decreased at a low concentration of 2 to 5 μM or less according to the type of transduction domain. Also, it also has been reported that, when a protein having a molecular weight of 30,000 Da or more is conjugated to a PTD to be transduced into a cell, most of the PTD-protein conjugates tend to be transduced into the cell in the form of an endosome through endocytosis, and it has been reported that the endosome combines with a lysosome in the cytoplasm, and thus most of the PTD-protein conjugates are degraded by a hydrolase present in the lysosome, and only some undamaged PTD-protein conjugates are released into the cytoplasm. Accordingly, for dermal transduction of a functional protein using a PTD, a large amount of PTD-protein conjugates are needed to express expected efficacy, and will bring about an undesirable result in terms of economic feasibility.

To solve such a problem of the PTD and increase a pharmacological value, a hydrophobic or amphiphatic peptide having different characteristics from a conventional PTD, a macromolecule transduction domain (MTD; Korean Patent No. 10-1258279) was developed. An MTD is a novel cell-penetrating peptide, which has enhanced efficiency of delivering a material into cells, and has a different structure and different electrostatic properties, compared with a PTD. Unlike a PTD, in the intracellular transduction process of a MTD, endocytosis and energy are not needed, and the rigidity and integrity of the cell membrane act as important factors. Therefore, it has been suggested that direct interaction with the cell membrane is critical for the intracellular transduction process of an MTD. Such a cell membrane penetrating phenomenon of a peptide may increase a development value as a novel therapeutic drug by intracellular transduction of a therapeutic protein, or a nucleic acid material such as DNA or siRNA, which is difficult to be used as a drug because of a short in vivo half life or difficult cell membrane penetration. Also, compared with a conventional cell-penetrating peptide, which is a HIV-Tat-derived peptide, it is determined that a MTD has high availability in development of botulinum toxin as an external agent due to high efficiency of delivering a cargo material such as a compound, a peptide or a protein.

Also, as an amount of a light chain or light chain derivative of skin-penetrating and a nerve terminus cell-penetrating botulinum toxin, which is sought in the present invention, should be limited to a concentration of 1 to 10 ppm in order to ensure safety even through a toxicity attenuation process, it seems that it is inappropriate that a PTD is used as a skin- and neuronal cell-penetrating means, and to overcome this problem, there are demands for utilizing a MTD which has both skin barrier-penetrating and neuronal cell-penetrating potential and concentration-dependently penetrates the skin barrier even at low concentrations, or developing a novel MTD having the above-mentioned characteristics.

DISCLOSURE

Technical Problem

The present invention is directed to providing a novel cell-penetrating peptide derived from a heavy chain translocation domain of botulinum toxin and capable of mediating intracellular delivery of a biologically active molecule, wherein the cell-penetrating peptide is designed to effectively transmit a botulinum toxin protein which is difficult to be delivered through the skin because of a molecular weight and the intrinsic characteristics of a skin cornified layer as described above, and to deliver the transmitted botulinum toxin protein to a neuronal cell present in skin tissue.

The present invention is also directed to providing a cell-penetrating botulinum toxin recombinant protein in which the cell-penetrating peptide is conjugated with one or both termini of the light chain of botulinum toxin.

The present invention is also directed to providing a composition comprising the botulinum toxin recombinant protein as an active ingredient, and more particularly, a composition which facilitates transdermal delivery of the cell-penetrating botulinum toxin recombinant protein, and is able to be topically used for various dermatological treatments and a cosmetological purpose.

However, technological problems resolved by the present invention are not limited to the above-described problems, and other problems which are not mentioned will be more clearly understood by those of ordinary skill in the art with reference to the following descriptions.

Technical Solution

The present invention provides a peptide for mediating intracellular delivery of a biologically active molecule, which is a cell-penetrating peptide consisting of an amino acid sequence of SEQ. ID. NO: 1.

The present invention provides a polynucleotide encoding the peptide.

In one exemplary embodiment of the present invention, the polynucleotide may consist of a nucleotide sequence of SEQ. ID. NO: 2.

The present invention provides a cell-penetrating botulinum toxin recombinant protein in which the cell-penetrating peptide consisting of the amino acid sequence of SEQ. ID. NO: 1 is conjugated with one or both termini of the light chain of botulinum toxin.

In one exemplary embodiment of the present invention, the botulinum toxin recombinant protein may consist of an amino acid sequence selected from the group consisting of SEQ. ID. NO: 31 to SEQ. ID. NO: 58.

In another exemplary embodiment of the present invention, the light chain of botulinum toxin may consist of an amino acid sequence selected from the group consisting of SEQ. ID. NO: 3 to SEQ. ID. NO: 9.

In still another exemplary embodiment of the present invention, the light chain of botulinum toxin may further comprise a hexahistidine tag at one terminus.

In yet another exemplary embodiment of the present invention, the light chain of botulinum toxin may be selected from the group consisting of botulinum toxin serotypes A, B, C, D, E, F and G.

In yet another exemplary embodiment of the present invention, the conjugation may be conjugation of the cell-penetrating peptide to a carboxyl terminus or an amino terminus of the light chain of botulinum toxin, or both termini thereof.

In yet another exemplary embodiment of the present invention, the conjugation may be achieved by a peptide bond or a covalent bond.

The present invention provides a polynucleotide encoding the cell-penetrating botulinum toxin recombinant protein.

In one exemplary embodiment of the present invention, the polynucleotide may consist of a nucleotide sequence selected from the group consisting of SEQ. ID. NO: 59 to SEQ. ID. NO: 86.

The present invention provides a recombinant expression vector comprising the polynucleotide.

In one exemplary embodiment of the present invention, the recombinant expression vector may comprise an affinity tag selected from the group consisting of His, HAT, FLAG, c-myc, SBP, a chitin-conjugated domain, glutathione-S transferase and a maltose-conjugated protein.

The present invention provides a bacterium transformed by the recombinant expression vector.

The present invention provides a pharmaceutical composition which comprises the cell-penetrating botulinum toxin recombinant protein and a pharmaceutically acceptable carrier to treat a disease selected from the group consisting of facial spasms, eyelid spasms, torticollis (斜頸), blepharospasm, cervical dystonia, oropharynx dystonia, spasmodic dysphonia, migraines, pruritis ani and hyperhidrosis.

In one exemplary embodiment of the present invention, the pharmaceutical composition may be used for transdermal administration.

The present invention provides a composition for an external dermal agent, which comprises the cell-penetrating botulinum toxin recombinant protein as an active ingredient.

The present invention provides a cosmetic composition comprising the cell-penetrating botulinum toxin recombinant protein as an active ingredient.

In one exemplary embodiment of the present invention, the composition may be applied to improve wrinkles, a square jaw and a sharp jaw, injuries, skin softening, scars, acne, pores, elasticity or keloids.

The present invention provides a method for treating a disease selected from the group consisting of facial spasms, eyelid spasms, torticollis (斜頸), blepharospasm, cervical dystonia, oropharynx dystonia, spasmodic dysphonia, migraines, pruritis ani and hyperhidrosis, the method comprises transdermally administering the cell-penetrating botulinum toxin recombinant protein into a subject.

The present invention provides a method for improving wrinkles, a square jaw and sharp jaw, injuries, skin softening, scars, acne, pores, elasticity or keloids, which comprises transdermally administering the cell-penetrating botulinum toxin recombinant protein into a subject.

The present invention provides a use of the cell-penetrating botulinum toxin recombinant protein to treat a disease selected from the group consisting of facial spasms, eyelid spasms, torticollis (斜頸), blepharospasm, cervical dystonia, oropharynx dystonia, spasmodic dysphonia, migraines, pruritis ani and hyperhidrosis.

The present invention provides a use of the cell-penetrating botulinum toxin recombinant protein to improve wrinkles, a square jaw and a sharp jaw, injuries, skin softening, scars, acne, pores, elasticity or keloid symptoms.

The present invention provides a method for producing a cell-penetrating botulinum toxin recombinant protein, which comprises culturing the transformed bacteria.

Advantageous Effects

Botulinum toxin causes paralysis by blocking signals inducing muscle convulsion or contraction. Today, due to such muscle paralysis caused by botulinum toxin, botulinum toxin is applied in medical treatments for blepharospasm, spasticity, migraines, temporomandibular disorder, hyperhidrosis, etc., and esthetic and cosmetological fields for wrinkle improvement, pore reduction, acne, elasticity enhancement, and square jaw reduction. However, since there is no effective means for transdermal delivery until now, generally, people who want to obtain such effects have relied on only injections. For this reason, a non-injectable topical application of botulinum toxin will be a more safe and preferable, therapeutic alternative. Accordingly, a cell-penetrating peptide-botulinum toxin recombinant protein of the present invention can pass through the multiple layers of the skin and neuronal cells and cleave a SNARE protein of the neuronal cells, and thus can exhibit its activity, and since the recombinant protein is considerably smaller than general botulinum toxin, the probability of producing an antibody can be significantly reduced, and thus reduced efficacy according to formation of a neutralizing antibody can be reduced.

Also, as the cell-penetrating peptide-botulinum toxin recombinant protein of the present invention can be transdermally delivered, the cell-penetrating peptide-botulinum toxin recombinant protein has the intrinsic efficacy of botulinum toxin and expanded accessibility, and thus can be effectively used as a topical agonist for treating various diseases, and aesthetic and/or cosmetological purposes.

Also, while even several picograms (pg) of botulinum toxin type A expresses serious toxicity, the cell-penetrating botulinum toxin of the present invention is subjected to toxicity attenuation to express toxicity at a microgram (μg) level, and thus can guarantee sufficient safety from the toxicity of botulinum toxin.

DESCRIPTION OF DRAWINGS

FIG. 1 is a table showing the characteristics of a cell-penetrating peptide TD1.

FIG. 2 illustrates the structure of the cell-penetrating peptide TD1.

FIG. 13 shows the results of safety and skin irritation tests of a cell-penetrating botulinum toxin recombinant protein TD1-Lc formulated as a cosmetic agent, evaluated by a contract research organization.

FIGS. 14*a*, 14*b* and 14*c* show clinical efficacy of the cell-penetrating botulinum toxin recombinant protein TD1-Lc formulated as a cosmetic agent, evaluated by a contract research organization.

MODES OF THE INVENTION

Figure 3A:
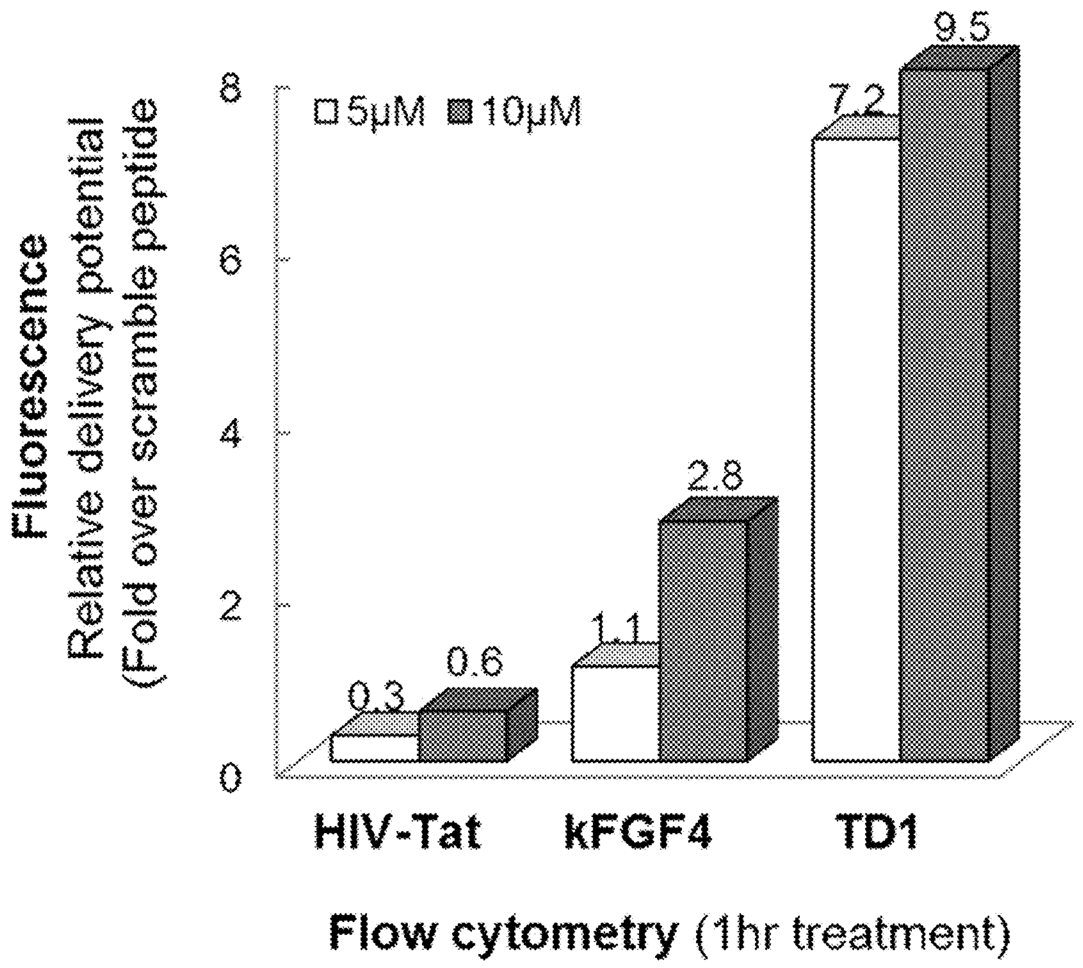
FIGS. 3*a* and 3*b* show an in vitro penetration potentials of the cell-penetrating peptide TD1 with respect to keratinocytes (HaCaT cells), assessed by flow cytometry.

The present invention provides a novel cell-penetrating peptide, and a composition and method for transdermally delivering the light chain of botulinum toxin using the same. According to the present invention, it was determined that the developed novel cell-penetrating peptide TD1 is appropriate as a transduction system capable of transdermally administering the light chain of botulinum toxin by topical application of a suitable agent.

While expressed as one polypeptide, botulinum toxin is divided into a heavy (H) chain of approximately 100 kDa and a light (L) chain of approximately 50 kDa through reconfiguration after expression, which are linked by a disulfide bond. The H chain is linked to a neuronal cell receptor to allow the entry of botulinum toxin into cells by endocytosis. The light chain of botulinum toxin which has entered the cells is released from an endosome and then transported into the cytoplasm. Botulinum toxin cleaves a SNARE protein in the cytoplasm to inhibit acetylcholine release, leading to muscle paralysis. Therefore, the acetylcholine release from the neuronal cell may be inhibited only by the L chain, and the H chain and the L chain may each independently function. Based on this, there was an attempt to develop a transdermal delivery system only using the L chain having a muscle paralyzing effect.

However, the separated light chain of botulinum toxin having a molecular weight of 50 kDa cannot pass through the cell membrane, and thus is not able to properly function by itself. Generally, to exhibit a specific botulinum toxin activity by delivering the light chain of botulinum toxin into the cytoplasm of the neuronal cell, the aid of the heavy chain of botulinum toxin of approximately 100 kDa is definitely needed. The heavy chain of botulinum toxin consists of two domains, for example, a receptor-conjugated domain of a neuronal cell membrane and a translocation domain integrated into the cell membrane to facilitate translocation of the light chain.

In the present invention, as a result of studying a method for efficiently delivering botulinum toxin, more particularly, the light chain of botulinum toxin into the skin and to a neuronal cell, a novel cell-penetrating peptide facilitating intracellular transduction was developed by structural analysis of the heavy chain of botulinum toxin.

First, the sequence of a protein-conjugated site which has a chance to be developed as a cell-penetrating peptide was extracted and selected by in silico analysis of the three-dimensional structure of the translocation domain of the heavy chain of botulinum toxin. Subsequently, a simulation process including removing or substituting an amino acid to give penetration potential to a sequence selected by comparison with the sequence of a peptide derived from a signal protein involved in release of several proteins or a viral protein, and a conventional macromolecule transduction domain (MTD; Korean Patent No. 10-1258279) passing through the cell membrane to mediate the transmission of a macromolecule such as a protein into the cell was performed several times. The peptide was increased in cell membrane accessibility by placement of an amphiphatic, polar amino acid, improved in physical properties and solubility, and obtained suitable hydrophobicity for penetration into the cell membrane by addition of a non-polar amino acid, thereby developing a novel cell-penetrating peptide, and it was confirmed that the novel cell-penetrating peptide has penetration potentials with respect to both of human keratinocytes and neuronal cells, and thus the present invention was completed.

Therefore, the present invention provides a novel cell-penetrating peptide, and more particularly, a peptide capable of mediating intracellular delivery of a biologically active molecule, which is a cell-penetrating peptide consisting of an amino acid sequence of SEQ. ID. NO: 1.

In the present invention, the novel cell-penetrating peptide is a peptide capable of mediating the intracellular delivery of a biologically active molecule, and called "TD1."

The cell-penetrating peptide TD1 of the present invention:

1) consists of 13 amino acids;

2) has a molecular weight of approximately 1537 Da;

3) has a theoretical pI of 9.31; and 4) is an amphiphatic peptide having a hydrophobic amino acid composition in fragments of 60% or more;

5) has an instability index of 49.65 analyzed using a ProtParam program (refer to web.expacy.org/protparam) to evaluate sequence stability;

6) has an aliphatic index of 97.69 to evaluate the total volume of a molecule;

7) is improved in aggregation of the peptide as the grand average of hydropathicity (GRAVY) is evaluated as 0; and 8) has a sequence having an SVM value of −0.15 according to an analysis for predicting the cell-penetrating peptide based on a support vector machine (SVM) classification algorithm.

In the present invention, the cell-penetrating peptide itself may not have a defined enzymatic or biological therapeutic activity, but serves as a carrier facilitating intracellular transduction through the cell membrane. The peptide may be attached to the N- or C-terminus and both termini of a cargo translocated into a cell, and may be attached to each terminus in a forward or reverse direction. Also, the peptide according to the present invention is preferably a monomer, but the present invention is not limited there to, and may be a dimer or a polymer. Moreover, the peptide of the present invention may be a peptide comprising an amino acid sequence of SEQ. ID. NO: 1 as the minimum unit. Cell membrane accessibility, penetration potential and physical properties may be changed by adding one or more amino acids to one or both termini of the peptide sequence TD1 according to the present invention. Preferably, the amino acids are selected to have a hydrophobicity ranging from 25% to 75%, and a sequence having hydrophilicity may be further added when agglomeration occurs in the process of purifying the recombinant protein.

In another aspect of the present invention, the present invention provides a polynucleotide encoding the peptide. That is, the polynucleotide may encode a cell-penetrating peptide consisting of an amino acid sequence of SEQ. ID. NO: 1, and may consist of a nucleotide sequence of SEQ. ID. NO: 2, but the present invention is not limited thereto.

The polynucleotide according to the present invention may be RNA or DNA, and the DNA includes cDNA and synthetic DNA. The DNA may be a single- or double-stranded. The single-stranded DNA may be a coding strand or non-coding (antisense) strand. The coding sequence may be the same as or different from the nucleotide sequence of SEQ. ID. NO: 2. The coding sequence is obtained by degeneracy or redundancy of a genetic code, and may encode the same polypeptide.

In one exemplary embodiment of the present invention, it was confirmed that all of keratinocytes (HaCaT cells), neuroblastoma cells (SiMa cells and U-87 MG cells) and HeLa cells exhibit a considerably excellent cell penetration potential of the cell-penetrating peptide TD1 according to the present invention (refer to Examples 2 and 3).

In another aspect of the present invention, the present invention provides a cell-penetrating botulinum toxin recombinant protein in which a cell-penetrating peptide consisting of an amino acid sequence of SEQ. ID. NO: 1 is conjugated to one or both termini of the light chain of botulinum toxin.

In the present invention, the term "cell-penetrating botulinum toxin recombinant protein" refers to a conjugate comprising a novel cell-penetrating peptide TD1 and the light chain of botulinum toxin, which are chemically linked by a peptide bond or covalent bond. That is, the cell-penetrating botulinum toxin recombinant protein delivers the light chain of botulinum toxin into a cell with high efficiency by conjugating a specific cell-penetrating peptide with the light chain of botulinum toxin, which is a macromolecule that is difficult to be introduced into the cell, to give a cell penetrating potential. Here, the conjugation may be made between the cell-penetrating peptide and a carboxyl terminus, an amino terminus or both termini of the light chain of botulinum toxin.

In the present invention, the term "botulinum toxin" refers to a known type of botulinum toxin, whether subsequently found to be produced by a bacterium or a recombination technique or comprising manipulated variants or a conjugated protein.

In the present invention, the light chain of botulinum toxin may be selected from the group consisting of the botulinum toxin serotypes A, B, C, D, E, F and G. Here, the light chain of botulinum toxin may consist of an amino acid sequence selected from the group consisting of SEQ. ID. NO: 3 to SEQ. ID. NO: 9. Also, a hexahistidine tag may be further comprised at one terminus.

In the present invention, the light chain of botulinum toxin may alternatively be a botulinum toxin derivative, that is, a compound having a botulinum toxin activity but one or more variations in a random part or a sequence. For example, compared to light chain proteins of the seven serotypes of botulinum toxins, the light chain of botulinum toxin may be varied by deletion, modification, replacement or chimeric fusion in an amino acid sequence to maintain an endopeptidase activity of the light chain, reinforce the characteristic or reduce a side effect. Also, the light chain of botulinum toxin prepared by recombination or chemical synthesis or a part thereof may be used.

In the present invention, the cell-penetrating botulinum toxin recombinant protein may consist of an amino acid sequence selected from the group consisting of SEQ. ID. NO: 31 to SEQ. ID. NO: 58, and a polynucleotide encoding the recombinant protein may consist of a nucleotide sequence selected from the group consisting of SEQ. ID. NO: 59 to SEQ. ID. NO: 86, but the present invention is not limited thereto.

In another exemplary embodiment of the present invention, it was confirmed that the cell-penetrating botulinum toxin recombinant protein according to the present invention exhibits a remarkably excellent cell penetration potential with respect to keratinocytes (HaCaT cells), neuroblastoma cells (SiMa cells and U-87 MG cells) and a synthetic skin substitute (Strat-M™) (refer to Examples 6 and 7).

In still another aspect of the present invention, the present invention provides a recombinant expression vector comprising a polynucleotide encoding the cell-penetrating botulinum toxin recombinant protein.

In the present invention, the term "recombinant expression vector" refers to a vector capable of expressing a target protein or target DNA in suitable host cells, which is a gene construct comprising essential regulatory factors operably linked to express a gene insert.

In the present invention, the term "operably linked" refers to functional linkage of a nucleic acid expression regulatory sequence with a nucleic acid sequence encoding a target protein or RNA to perform a general function. For example, a promoter may be operably linked to a nucleic acid sequence encoding a protein or RNA to affect the expression of the coding nucleic acid sequence. The operable linkage with the recombinant expression vector may be achieved using a gene recombination technique well known in the art, and site-specific DNA cleavage and ligation use enzymes generally known in the art.

The expression vector which can be used in the present invention includes a plasma vector, a cosmid vector, a bacteriophage vector or a virus vector, but the present invention is not limited thereto. A variety of suitable expression vectors may be prepared to comprise a signal sequence or leader sequence for membrane targeting or release, in addition to an expression regulatory sequence such as a promoter, an operator, an initiation codon, a termination codon, a polyadenylation signal or an enhancer according to a purpose. The promoter of the expression vector may be constitutive or inducible. Also, the expression vector may comprise a selective marker for selecting host cells containing a vector, and comprise a replication origin in the case of a replicable expression vector. Also, the expression vector may also comprise an affinity tag selected from the group consisting of His, HAT, FLAG, c-myc, SBP, a chitin-conjugated domain, glutathion-S transferase and a maltose-conjugated protein.

In yet another aspect of the present invention, the present invention provides a transformed bacterium transformed by the recombinant expression vector.

In yet another aspect of the present invention, the present invention provides a method for producing a cell-penetrating botulinum toxin recombinant protein, which includes culturing the transformed bacteria.

The production method is performed by culturing the transformed bacteria in a suitable medium under suitable conditions to express a polynucleotide encoding the cell-penetrating botulinum toxin recombinant protein of the present invention in the recombinant expression vector introduced into the transformed bacteria of the present invention. The method for expressing a recombinant protein by culturing the transformed bacteria is known in the art, and for example, the method may induce protein expression by inoculating a suitable medium for growing transformed bacteria with transformed bacteria to culture an inoculant, and culturing the inoculant in a culture medium under suitable conditions, for example, in the presence of a gene expression inducer, such as isopropyl-β-D-thiogalactoside (IPTG). After the culture, substantially pure recombinant proteins may be collected from the cultured product. In the present invention, the term "substantially pure" means that the sequences of the recombinant protein of the present invention and the polynucleotide encoding the recombinant protein do not substantially include another protein derived from host cells.

The collecting of the recombinant proteins expressed from the transformed bacteria may be performed by various isolation and purification methods known in the art, and following centrifugation of a cell lysate, to conventionally remove cell debris, culture impurities, etc., precipitation, for example, salting-out (ammonium sulfate precipitation and sodium sulfate precipitation), solvent precipitation (protein fraction precipitation using acetone, ethanol or isopropyl alcohol), dialysis, electrophoresis, or various column chromatography may be performed. As the chromatography, ion-exchange chromatography, gel-filtration chromatography, HPLC, reverse-HPLC, adsorption chromatography, affinity column chromatography and ultrafiltration may be used alone or in combination thereof.

Meanwhile, the recombinant protein expressed in the bacteria transformed by the recombinant expression vector may be divided into a soluble fraction and an insoluble fraction according to the characteristic of a protein when the protein is isolated. When most of the expressed proteins are in the soluble fraction, the proteins may be easily isolated and purified by the above-described method, but when most of the expressed proteins are present in the insoluble fraction, that is, an inclusion body, the proteins may be dissolved with a solution containing a protein denaturant such as urea or a surfactant as much as possible, centrifuged and then purified by dialysis, electrophoresis and column chromatography charged with various types of resins. Here, since the protein structure is changed by the solution containing a protein denaturant and loses its activity, desalting and refolding steps are needed in the process of purifying the protein from the insoluble fraction. That is, in the desalting and refolding steps, dialysis and dilution steps using a protein denaturant-free solution or a centrifugation step using a filter may be performed. Also, even in the process of purifying the protein from the solution fraction, when a salt concentration in the solution used in the purification is high, such desalting and refolding steps may be performed.

Figure 8:
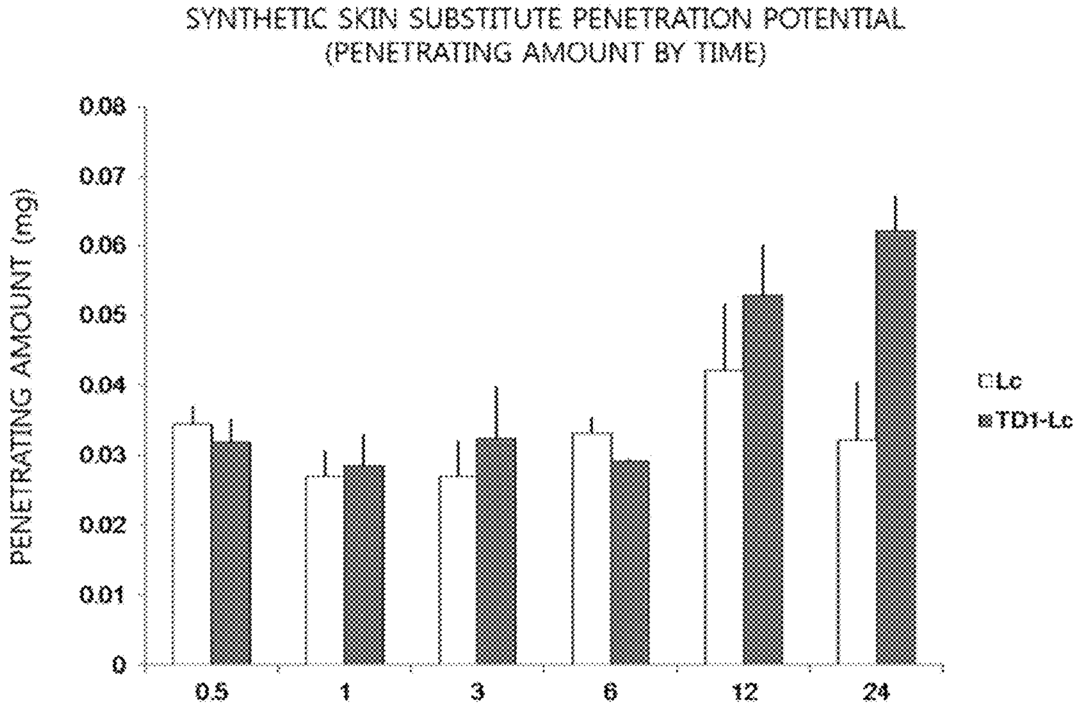
FIG. 8 shows the penetration potential of the cell-penetrating botulinum toxin recombinant protein TD1-Lc with respect to a synthetic skin substitute.
Figure 9:
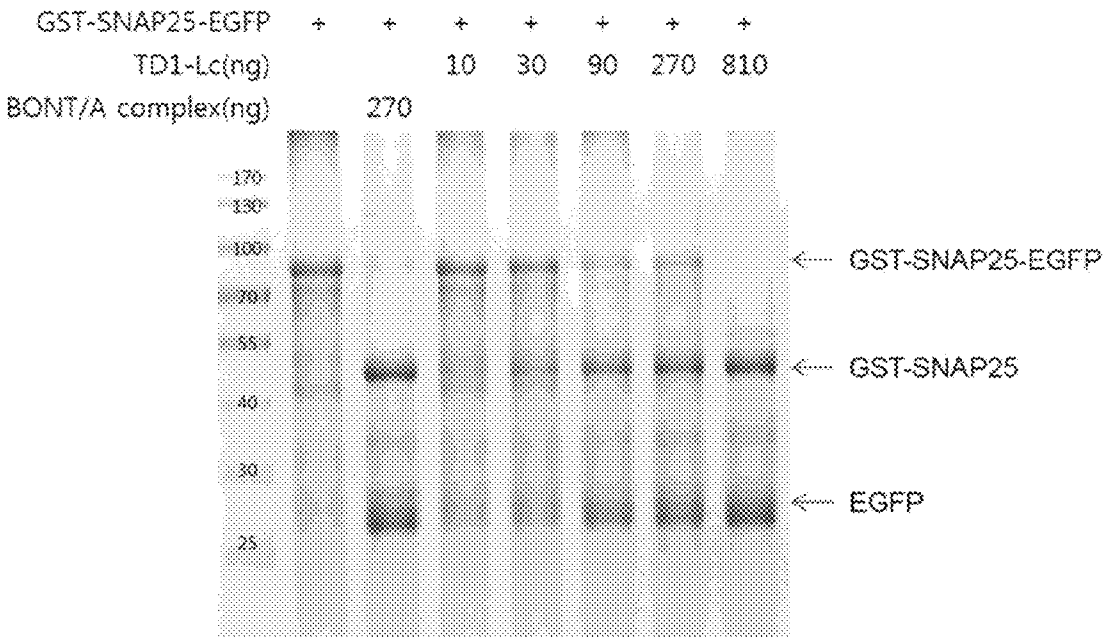
FIG. 9 shows an in vitro SNAP25 cleavage activity of the purified cell-penetrating botulinum toxin recombinant protein TD1-Lc, assessed by SDS-PAGE.

Meanwhile, in yet another exemplary embodiment of the present invention, as a result of evaluating the efficacy of the cell-penetrating botulinum toxin recombinant protein according to the present invention, it was confirmed that, even the cell-penetrating botulinum toxin recombinant protein (TD1-Lc) according to the present invention has the activity of botulinum toxin, and the same function as botulinum toxin (refer to FIGS. 8 and 9). Also, it was confirmed that human keratinocytes (HaCaT cells) and neuroblastoma cells (SiMa cells) do not exhibit cytotoxicity (refer to Example 10), but also exhibit high stability (refer to Example 11) as well. Therefore, the cell-penetrating botulinum toxin recombinant protein (TD1-Lc) according to the present invention may be more effectively used as a topical agonist for treatment of various diseases, and aesthetic and/or cosmetological purposes.

Therefore, in yet another aspect of the present invention, the present invention provides a pharmaceutical composition for treating a disease selected from the group consisting of facial spasms, eyelid spasms, torticollis (斜頸), blepharospasm, cervical dystonia, oropharynx dystonia, spasmodic dysphonia, migraines, pruritis ani and hyperhidrosis, which comprises a cell-penetrating botulinum toxin recombinant protein as an active ingredient. The pharmaceutical composition of the present invention may further comprise a pharmaceutically acceptable carrier, as well as the cell-penetrating botulinum toxin recombinant protein as an active ingredient. Here, the pharmaceutically acceptable carrier included in the pharmaceutical composition of the present invention may be saline, buffered saline, water, glycerol or ethanol, but the present invention is not limited thereto, and all of the suitable agents known in the art are able to be used.

In yet another aspect of the present invention, the present invention provides a composition for an external dermal agent or a cosmetic composition, which comprises a botulinum toxin recombinant protein as an active ingredient. The composition may be applied to reduce wrinkles, a square jaw and a sharp jaw, to treat injuries, to soften the skin, to treat scars, acne and pores, to raise elasticity or to treat a keloid symptom, but the present invention is not limited thereto. An effective amount of the composition according to the present invention may be delivered to induce paralysis in muscles or pre-structures beneath the skin to reduce or lessen contractions, or to give different desired cosmetological effects.

In yet another exemplary embodiment of the present invention, as a result of evaluating the wrinkle improving efficacy of the cell-penetrating botulinum toxin recombinant protein according to the present invention, it was confirmed that the cell-penetrating botulinum toxin recombinant protein helps to improve nasolabial fold and skin elasticity when continuously used for 4 weeks (refer to Example 13).

The cosmetic composition of the present invention may be prepared in any formulation which is conventionally prepared in the art, for example, a solution, a suspension, an emulsion, a paste, a gel, a cream, a lotion, a powder, a soap, a surfactant-containing cleansing, oil, a powder foundation, an emulsion foundation, or wax foundation, but the present invention is not limited thereto. More specifically, the cosmetic composition may be prepared in the formulation of a softener, a nourishing toner, a nutrient cream, a massage cream, an essence, an eye cream, a cleansing cream, a cleansing foam, a cleansing water, a pack or a powder.

A cosmetologically effective carrier contained in the cosmetic composition of the present invention may be a carrier conventionally used in the art. When the formulation of the present invention is a paste, a cream or a gel, animal oil, vegetable oil, wax, paraffin, starch, tragacanth, a cellulose derivative, polyethylene glycol, silicone, bentonite, silica, talc or zinc oxide may be used as a carrier ingredient.

When the formulation of the present invention is a solution or an emulsion, a solvent, a solubilizer or an emulsifier is used as a carrier ingredient, and for example, water, ethanol, isopropanol, ethyl carbonate, ethyl acetate, benzyl alcohol, benzyl benzoate, propylene glycol, 1,3-butylglycol oil, glycerol aliphatic ester, polyethylene glycol or sorbitan aliphatic ester is used.

When the formulation of the present invention is a suspension, a liquid diluent such as water, ethanol or propylene glycol, a suspension such as ethoxylated isostearyl alcohol, polyoxyethylene sorbitol ester or polyoxyethylene sorbitan ester, microcrystalline cellulose, aluminum methahydroxide, bentonite, agar or tragacanth may be used as a carrier ingredient.

When the formulation of the present invention is a surfactant-containing cleansing product, as a carrier ingredient, an aliphatic alcohol sulfate, an aliphatic alcohol ether sulfate, a sulfosuccinic monoester, isethionate, an imidazolinium derivative, methyltaurate, sarcosinate, an aliphatic amide ether sulfate, alkylamidobetaine, an aliphatic alcohol, aliphatic glyceride, aliphatic diethanolamide, vegetable oil, a lanolin derivative or ethoxylated glycerol ester of fatty acids may be used.

The cosmetic composition of the present invention may include ingredients conventionally used in a cosmetic composition, in addition to the active ingredient and the carrier ingredient, and the ingredients may be, for example, a moisturizer, an antioxidant, a fragrance, a filler, a thickening agent, a dye, a coloring agent, a surfactant, natural or synthetic oil, a preservative, a penetration agent, a wettable powder, an antifungal agent, an emulsifier solvent, a softening agent, a deodorant, and a wax. The cosmetic composition of the present invention may selectively include other ingredients comprising plant extracts, a conditioning agent, a pigment or a whitening agent, a UV protector, a wetting agent, vitamin and a derivative thereof, conventionally used in the products as such.

In yet another aspect of the present invention, the present invention provides a method for treating a disease selected from the group consisting of facial spasms, eyelid spasms, torticollis (斜頸), blepharospasm, cervical dystonia, oropharynx dystonia, spasmodic dysphonia, migraines, pruritis ani and hyperhidrosis or a method for improving wrinkles, reduction of a square jaw and a sharp jaw, injuries, skin softening, scars, acne, pores, elasticity or keloids, which includes locally administering the cell-penetrating botulinum toxin recombinant protein to a subject. In the present invention, the term "subject" refers to a target needing the treatment of a disease or skin improvement, and more specifically, a mammal such as a human or a non-human primate, a mouse, a rat, a dog, a cat, a horse or a cow.

The term "local administration" used in the present invention refers to direct administration of a drug onto an animal body or into the body that requires a biological effect of the drug, or around the region. The local administration excludes systemic administration such as intravenous administration or oral administration. The "topical administration" is included as a type of the local administration for applying a pharmaceutical agent to the human skin. The composition of the present invention may be transdermally administered to give dermatologically and cosmetologically desired effects.

In the composition of the present invention, a total effective amount of the recombinant protein of the present invention may be administered to a patient in a single dose or may be administered to a patient in multiple doses according to a fractionated treatment protocol, and the content of the active ingredient may vary according to the severity of symptoms. This is sufficient to bring about desired muscle paralysis or biological or aesthetic effects, but refers to an intrinsically safe amount. However, an effective administration amount of the recombinant protein may be determined by considering various factors such as a patient's age, weight, health condition, sex, disease severity, diet and excretion rate as well as a drug administration route and the number of treatments.

Hereinafter, to aid understanding of the present invention, exemplary examples will be provided. However, the following examples are merely provided to more easily understand the present invention, and the scope of the present invention is not limited to the following examples.

EXAMPLES

Example 1. Construction of Novel Cell-Penetrating Peptide

Novel skin-penetrating and cell-penetrating peptides capable of implementing transdermal delivery of the light chain of botulinum toxin were developed. First, structures and functions of the heavy chain and the light chain of botulinum toxin were analyzed, and a sequence was selected based on the fact that the heavy chain plays an important role in penetration of botulinum toxin type A into neuronal cells. Also, compared with a conventional MTD sequence, a novel cell-penetrating peptide consisting of an amino acid sequence of SEQ. ID. NO: 1 was designed through a process of increasing the cell membrane accessibility by the placement of an amphiphatic, polar amino acid, improving physical properties and solubility, and providing suitable hydrophobicity for cell membrane penetration by addition of a non-polar amino acid. The cell-penetrating peptide designed as described above was named TD1, and the characteristics and structure thereof were analyzed using a ProtParam program (web.expacy.org/protparam), and the results are shown in FIG. 1 and FIG. 2.

Example 2. Confirmation of In Vitro Cell-Penetration Potential of Cell-Penetrating Peptide TD1 Using Flow Cytometry To confirm the penetration potential of the novel cell-penetrating peptide TD1 constructed according to Example 1 with respect to skin cells and neuronal cells, an experiment was conducted using flow cytometry. To compare the cell penetration property of the cell-penetrating peptide TD1, a previously-developed cell-penetrating peptide, kFGF4, and a representative protein translocation domain (PTD), HIV-Tat, were used as control MTDs, and each peptide sample was fluorescence-labeled with FITC and synthesized by an organization specializing in peptide synthesis (GL Biochem Ltd. (Shanghai, China)).

2-1. Quantitative Analysis of Cell Penetration Potential in Keratinocytes (HaCaT Cells)

Figure 3B:
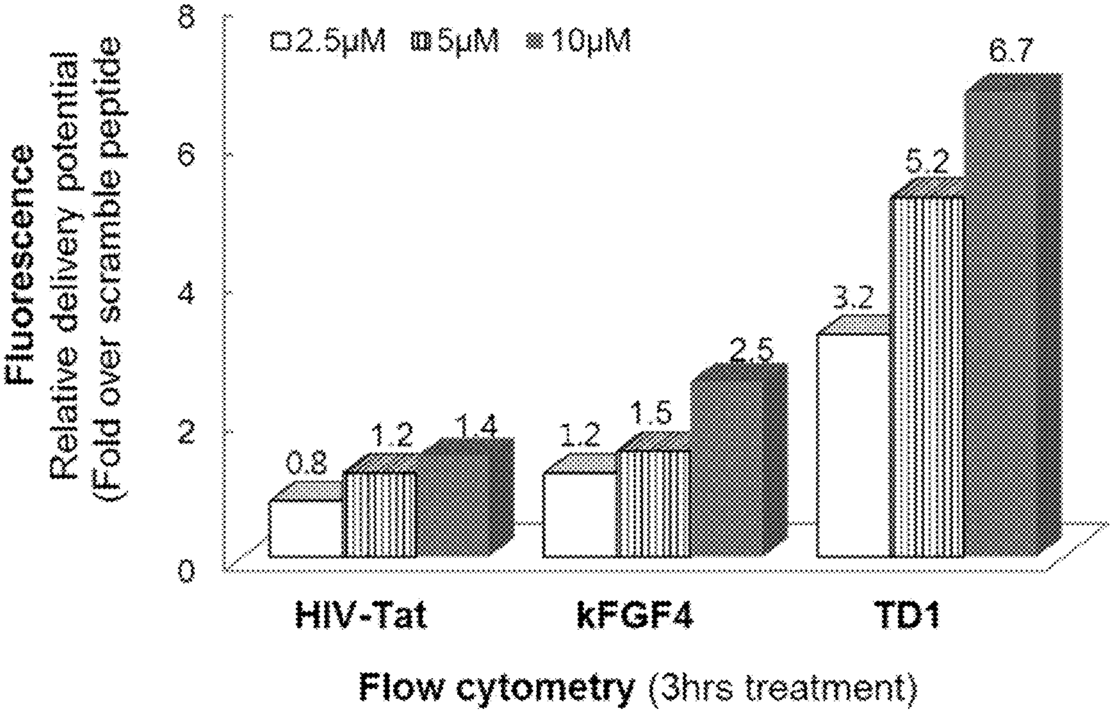

To confirm a cell penetration potential in keratinocytes, HaCaT cells, the HaCaT cells were cultured using DMEM complete media (10% FBS, 1% penicillin/streptomycin). For flow cytometry, the cells were transferred to a 12-well plate and further cultured for 16 to 24 hours. Each sample was added to the cells in a serum-free medium to which FBS was not added (hereinafter, referred to as an FBS-free medium) for 1 hour (treating concentrations: 5 μM, 10 μM) and 3 hours (treating concentrations: 2.5 μM, 5 μM, 10 μM). After the reaction, the cells were washed with DPBS twice to remove a sample residue, treated with 0.05% trypsin-EDTA, and reacted for 10 minutes while light was blocked, followed by inactivation of trypsin-EDTA using complete media. Subsequently, the cells were collected in a prepared tube, treated with 3 mL of phosphate buffered saline (PBS), and then centrifuged at 2,000 rpm for 3 minutes. Following the removal of a supernatant, 200 μL of PBS was added to each FACS tube, the cells were sufficiently resuspended to perform flow cytometry. As experimental groups, Cell only and FITC only, Scramble peptide, and HIV-Tat, and kFGF4-derived peptides were used, and compared with the Scramble peptide which is considered to have no cell penetration potential, transduction potentials of the HIV-Tat, kFGF4-derived peptide and the cell-penetrating peptide TD1 were determined. As a result, as shown in FIG. 3*a* and FIG. 3*b*, it was confirmed that, compared with the controls, the cell-penetrating peptide TD1 exhibits a remarkably excellent cell penetration potential in keratinocytes.

2-2. Quantitative Analysis of Cell Penetration Potential in Neuroblastoma Cells (SiMa Cells)

A cell penetration potential with respect to SiMa cells, which is a neuroblastoma cell line, was confirmed. The SiMa cells used a culture dish coated with gelatin (Sigma-Aldrich, G2500) due to low cell adherence with respect to the culture dish, which was prepared by applying a 0.1% gelatin solution thereto, removing the solution after 1 hour at room temperature, and then drying the dish. The SiMa cells were sub-cultured to 80% or higher confluence in RPMI1640 (10% FBS, 1% penicillin/streptomycin) as complete media. The cells were stabilized through repeated sub-cultures, and seeded at $5\times10^5$/well per 100 mm culture dish, and overnight cultured at 37° C. in a 5% $CO_2$ atmosphere in an incubator, followed by conducting an experiment.

Figure 3C:
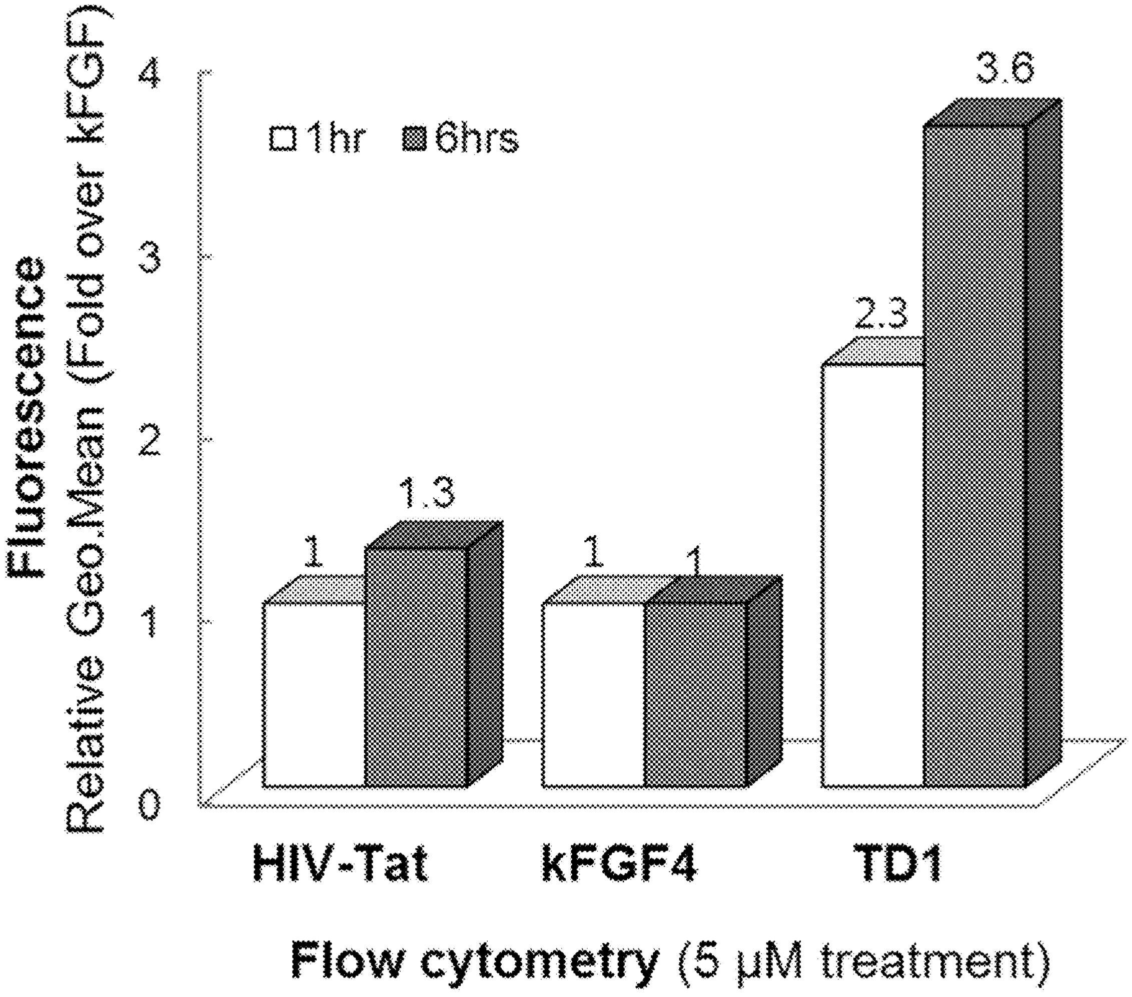
FIG. 3*c* shows an in vitro penetration potential of the cell-penetrating peptide TD1 with respect to neuroblastoma cells (SiMa cells), assessed by flow cytometry.

Each sample (reference materials: Cell only, FITC only, comparative materials: HIV-Tat & kFGF4-derived peptide, experiment material: TD1) was added to the cells in FBS-free media at 5 μM, and the cells were incubated for 1 hour and 6 hours. After the reaction, the cells were washed with DPBS twice to remove a sample residue, treated with 0.05% trypsin-EDTA, and incubated for 10 minutes while light was blocked, followed by inactivation of trypsin-EDTA using complete media. Subsequently, the cells were collected in a prepared tube, treated with 3 mL of PBS, and then centrifuged at 2,000 rpm for 3 minutes. Following the removal of a supernatant, 200 μL of PBS was added to each FACS tube, and the cells were sufficiently resuspended to perform flow cytometry. From a measured geometric mean (geo.mean) value of F1-1, compared with the kFGF4-derived peptide, transduction potentials of the HIV-Tat, kFGF4-derived peptide and the cell-penetrating peptide TD1 were determined. As a result, as shown in FIG. 3*c*, it was confirmed that, compared with the control, the cell-penetrating peptide TD1 also exhibits an excellent cell penetration potential in neuronal cells.

2-3. Quantitative Analysis of Cell Penetration Potential in Neuronal Cells (U-87 MG Cells)

Figure 3D:
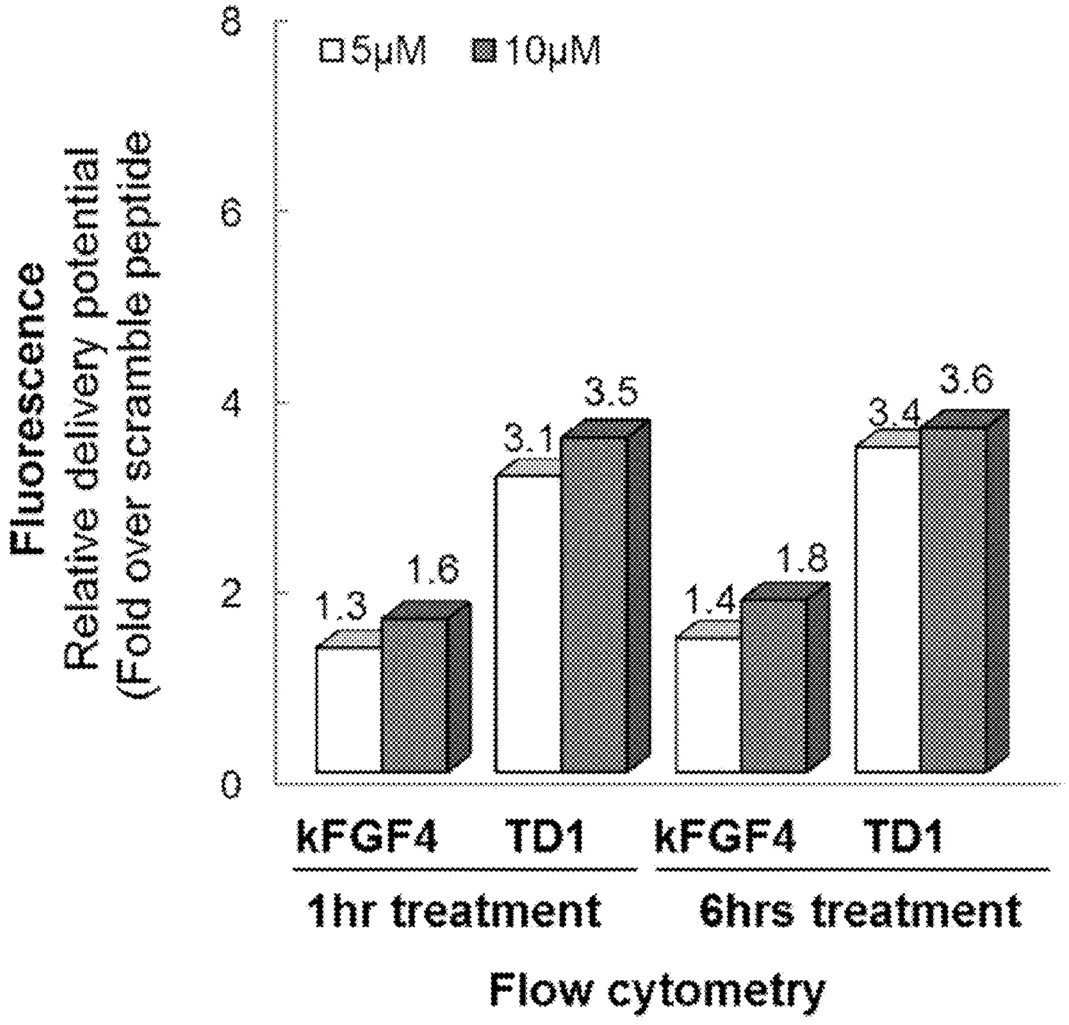
FIG. 3*d* shows an in vitro penetration potential of the cell-penetrating peptide TD1 with respect to neuronal cells (U-87MG cells), assessed by flow cytometry.

To confirm a cell penetration potential in neuronal cells (U-87 MG cells), cells were cultured using MEM complete media (10% FBS, 1% penicillin/streptomycin). For flow cytometry, the cells were seeded into a 12-well plate and cultured for 16 to 24 hours, and each sample (reference materials: Cell only, FITC only, Scramble peptide, comparative materials: kFGF4-derived peptide, experiment material: TD1) was added to the cells in FBS-free media at 5 μM and 10 μM, and then the cells were incubated for 1 hour and 6 hours, respectively. After the reaction, the cells were washed with DPBS twice to remove a sample residue, treated with 0.05% trypsin-EDTA, and incubated for 10 minutes while light is blocked, followed by inactivation of trypsin-EDTA using complete media. Subsequently, the cells were collected in a prepared tube, treated with 3 mL of PBS, and then centrifuged at 2,000 rpm for 3 minutes. Following the removal of a supernatant, 200 μL of PBS was added to each FACS tube, the cells were sufficiently resuspended to perform flow cytometry. To measure a level of FITC penetrated into the cells, an FL-1 wavelength was used, and to compensate a fluorescence value of the sample from a measured geo.mean value of F1-1, a transduction potential was determined based on the Scramble peptide value. As a result, as shown in FIG. 3*d*, it was confirmed that, compared with the kFGF4-derived peptide, which is a conventionally known cell-penetrating peptide, the cell-penetrating peptide TD1 exhibits excellent cell penetration in neuronal cells (U-87 MG cells).

2-4. Quantitative Analysis of Cell Penetration Potential in HeLa Cells

Figure 3E:
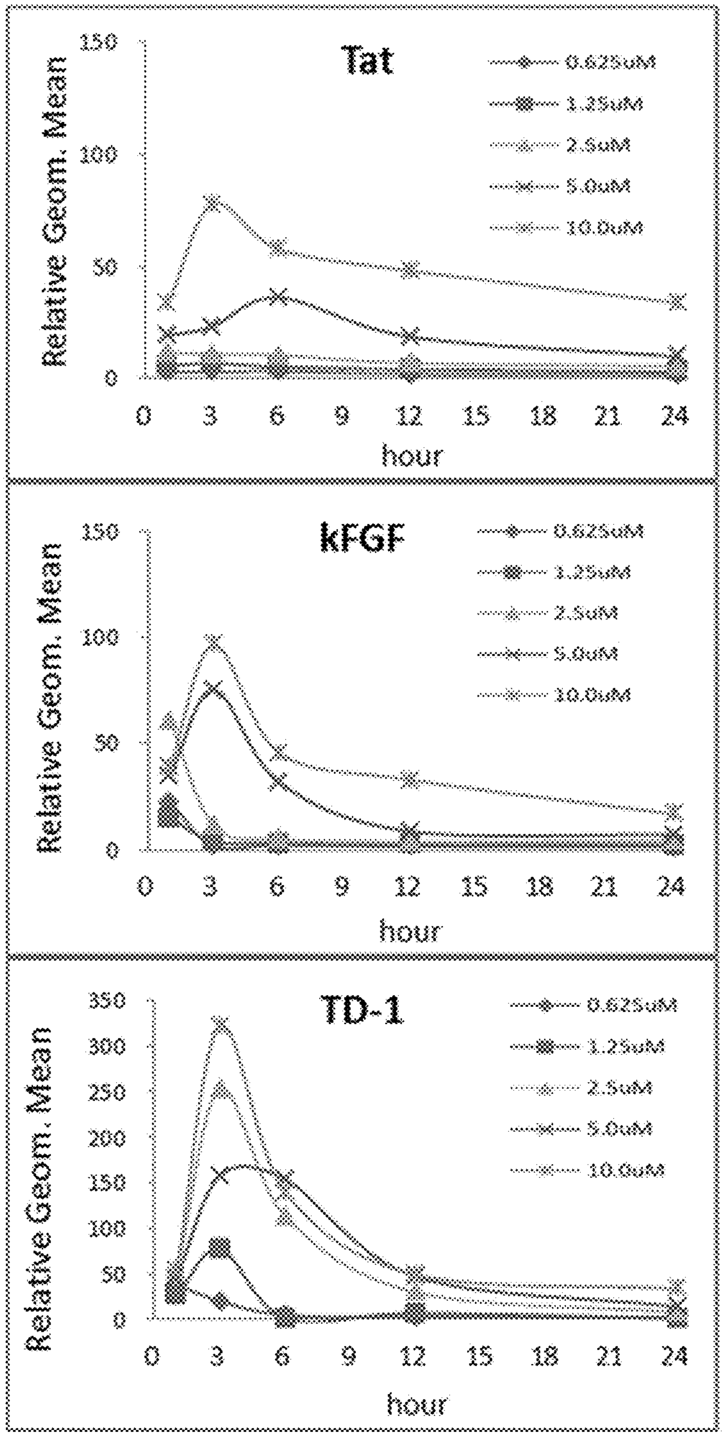
FIG. 3*e* shows an in vitro penetration potential of the cell-penetrating peptide TD1 with respect to HeLa cells, assessed by flow cytometry.

To confirm a cell penetration potential in human cervix adenocarcinoma cells (HeLa cells), the cells were cultured using MEM complete media (10% FBS, 1% penicillin/streptomycin). For flow cytometry, the cells were transferred to a 12-well plate and further cultured for 16 to 24 hours, and then treated with each sample in a FBS-free medium, followed by incubation according to time and a treating concentration of the sample. After the reaction, the cells were washed with DPBS twice to remove a sample residue, treated with 0.05% trypsin-EDTA, and incubated for 10 minutes while light was blocked, followed by inactivation of trypsin-EDTA using complete media. Subsequently, the cells were collected in a prepared tube, treated with 3 mL of PBS, and then centrifuged at 2,000 rpm for 3 minutes. Following the removal of a supernatant, 200 μL of PBS was added to each FACS tube, the cells were sufficiently resuspended to perform flow cytometry. As experimental groups, TD1, HIV-Tat and a kFGF4-derived peptide were used, and from the measured geo.mean value of F1-1, transduction potentials were determined by time and concentration. As a result, as shown in FIG. 3*e*, it can be seen that TD1 uptake occurred in the HeLa cells in a concentration-dependent manner within 12 hours, and when the concentrations of the HIV-Tat and kFGF4-derived peptide were 5 μM or higher, uptake of the HIV-the Tat and kFGF4-derived peptide significantly occurred in the HeLa cells, but the penetration amounts of the HIV-Tat and the kFGF4-derived peptide are considerably smaller than that of the TD1. Likewise, compared with the controls, it can be confirmed that the TD1 exhibits very excellent cell penetration in the HeLa cells.

Example 3. Confirmation of In Vitro Cell Penetration Potential of Cell-Penetrating Peptide TD1 Using Confocal Microscopy 3-1. Qualitative Analysis of Cell Penetration Potential in Keratinocytes (HaCaT Cell)

Figure 4A:
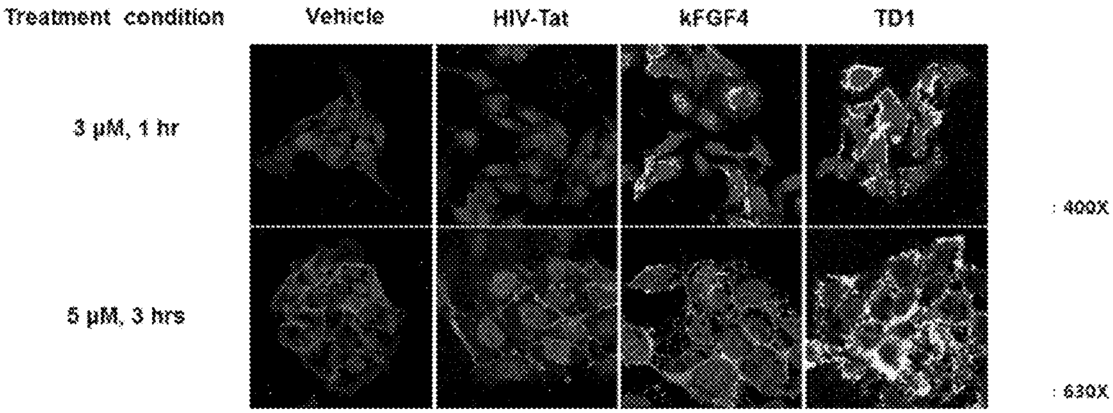
FIG. 4*a* shows an in vitro penetration potential of the cell-penetrating peptide TD1 with respect to keratinocytes (HaCaT cells), assessed by confocal microscopy.

To confirm a cell penetration potential in HaCaT cells, which is a keratinocyte cell line, cells were cultured using DMEM complete media (10% FBS, 1% penicillin/streptomycin). For microscopy, 12 mm cover glasses were flame-sterilized and added to each well of a 24-well plate, and the HaCaT cells were seeded into the plate and cultured for 16 to 24 hours. Each sample (reference materials: Vehicle, comparative materials: HIV-Tat and kFGF4-derived peptide, experiment material: TD1) was added to the cells in FBS-free media at 3 μM and 5 μM, and the cells were incubated for 1 hour and 3 hours, respectively. After the reaction, the medium was completely removed using suction, a step of adding PBS to the plate and gently agitating the plate was repeated to wash the cells, and then 200 μL of a 10% formalin solution was added to each well and gently stirred in a light blocking state for 10 minutes to fix the cells. Following the cell fixation, the fixing solution was removed, and the cells were washed with PBS twice for 10 minutes. Subsequently, counter staining was carried out with Hoechst and DAPI dye solutions at room temperature for 10 minutes while light was blocked, and following the reaction, the dye solution was removed, and the cells were washed with PBS twice. Afterward, a cover glass was retrieved, and then slowly laid down and mounted without having bubbles on the slide glass onto which a mounting solution was added dropwise. In a light blocking state, the slide glass was sufficiently dried to observe the cells using a confocal microscope (Zeiss LSM700). As a result, as shown in FIG. 4*a*, it can be confirmed that, compared with the HIV-Tat and the kFGF4-derived peptide, the TD1 exhibits excellent cell penetration in keratinocytes.

3-2. Qualitative Analysis of Cell Preparation Potential in Neuroblastoma Cells (SiMa Cells)

Figure 4B:
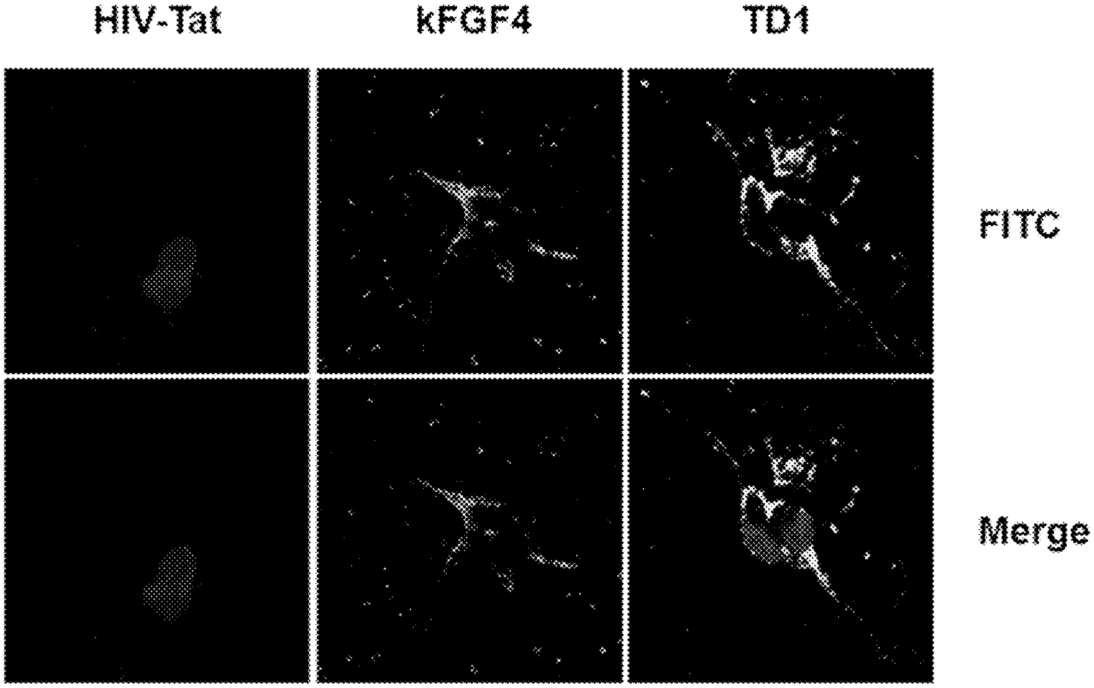
FIG. 4*b* shows an in vitro penetration potential of the cell-penetrating peptide TD1 with respect to neuroblastoma cells (SiMa cells), assessed by confocal microscopy.

To confirm a cell penetration potential with respect to a neuroblastoma cell line, SiMa cells, the cells were cultured to a 80% or higher confluence using RPMI1640 (10% FBS, 1% penicillin/streptomycin) as complete media. The cells were stabilized through repeated sub-cultures, and for microscopy, a 12 mm cover glass was flame-sterilized and added to each well of a 24-well plate, and the SiMa cells were seeded into the plate and cultured for 16 to 24 hours. Each sample (HIV-Tat, kFGF4-derived peptide, TD1) was added to the cells in a FBS-free medium at 5 μM, followed by incubation for 6 hours. After the reaction, the medium was completely removed using suction, the cells were gently stirred and washed with PBS twice, and 200 μL of a 10% formalin solution was added to each well to fix the cells in a light blocking state for 10 minutes. Following the cell fixation, the fixing solution was removed, and the cells were washed with PBS twice for 10 minutes. Subsequently, counter staining was carried out in a light blocking state at room temperature for 10 minutes. After the reaction, the dye solution was removed, and the cells were washed with PBS twice. Afterward, a cover glass was retrieved, and then slowly laid down and mounted without having bubbles on a slide glass onto which a mounting solution was added dropwise. When the slide glass was sufficiently dried in a light blocking state, the cells were observed using a confocal microscope (Zeiss LSM700). As a result, as shown in FIG. 4*b*, it can be confirmed that, compared with the kFGF4-derived peptide, the TD1 also exhibits excellent cell penetration in neuronal cells.

3-3. Qualitative Analysis of Cell Penetration Potential in Neuronal Cells (U-87 MG Cells)

Figure 4C:
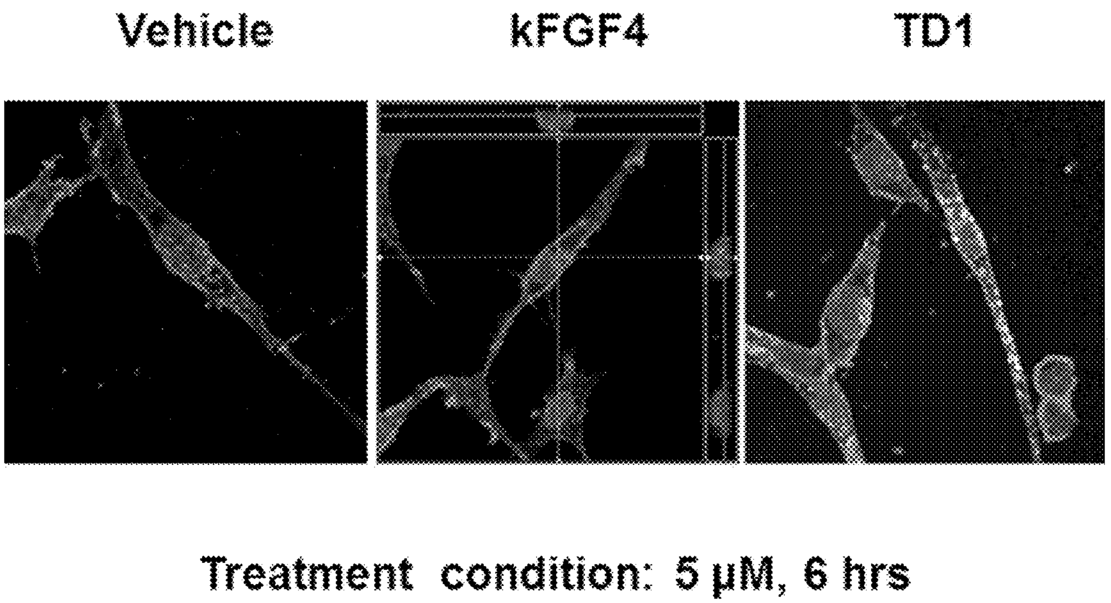
FIG. 4*c* shows an in vitro penetration potential of the cell-penetrating peptide TD1 with respect to glioblastoma cells (U-87MG cells), assessed by confocal microscopy.

To confirm a cell penetration potential in a neuronal cell line, U-87 MG cells, U-87 MG cells were cultured using DMEM complete media (10% FBS, 1% penicillin/streptomycin). For fluorescence microscopy, a 12 mm cover glass was flame-sterilized and added to each well of a 24-well plate, and the U-87 MG cells were seeded into the plate and cultured for 16 to 24 hours. Each sample (kFGF4-derived peptide, TD1) was added to the cells in an FBS-free medium at 5 μM, followed by incubation for 6 hours. After the reaction, the treated sample was removed, the cells were washed with PBS twice, 200 μL of a 10% formalin solution was added to each well to fix the cells in a light blocking state for 10 minutes. Subsequently, the fixing solution was removed, and the cells were washed with PBS twice for 10 minutes and then stained with Hoechst and DAPI dye solutions at room temperature for 10 minutes in a light blocking state. After staining, the solutions were removed, and the cells were washed with PBS twice. Then, a cover glass was retrieved and then mounted without having bubbles on the slide glass onto which a mounting solution was added dropwise. In a light blocking state, the slide glass was sufficiently dried to observe the cells using a confocal microscope (Zeiss LSM700). As a result, as shown in FIG. 4*c*, it can be visualized that, compared with the kFGF4-derived peptide, the TD1 exhibits excellent cell penetration in U-87 MG cells.

3-4. Qualitative Analysis of Cell Penetration Potential in HeLa Cells

Figure 4D:
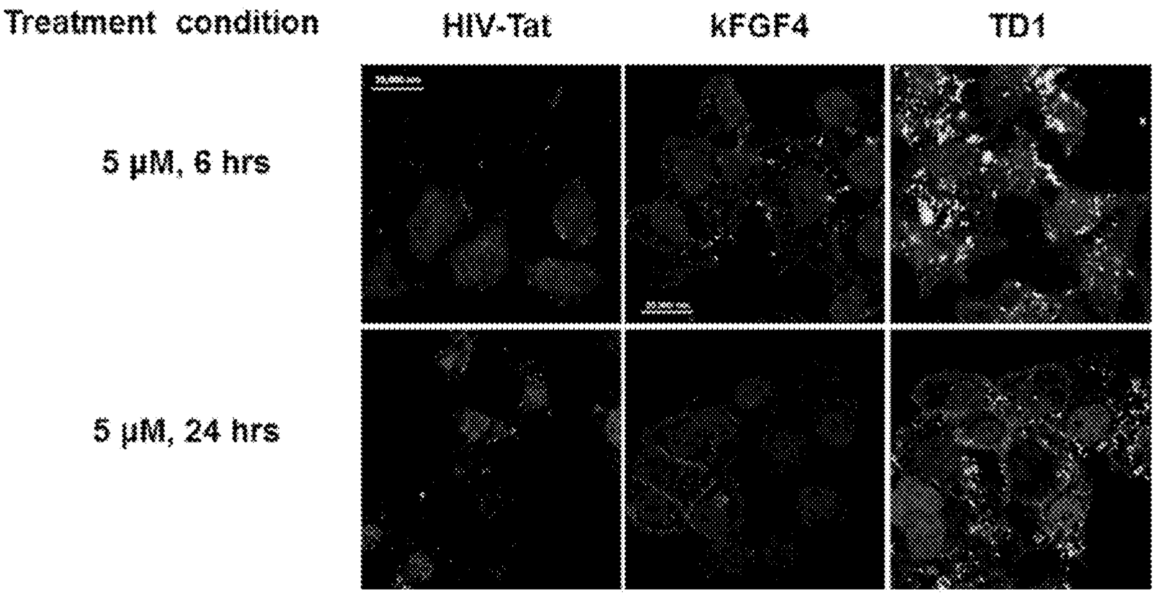
FIG. 4*d* shows an in vitro penetration potential of the cell-penetrating peptide TD1 with respect to HeLa cells, assessed by confocal microscopy.

To confirm a cell penetration potential in human cervix adenocarcinoma cells (HeLa cells), the cells were cultured using MEM complete media (10% FBS, 1% penicillin/streptomycin). For fluorescence microscopy, a 12 mm cover glass was flame-sterilized and added to each well of a 24-well plate, and the cells were seeded into the plate and cultured for 16 to 24 hours. Each sample (HIV-Tat, kFGF4-derived peptide, TD1) was added to the cells in a FBS-free medium at 5 μM for 6 to 24 hours. After the reaction, the treated sample was removed, the cells were washed with PBS twice, and 200 μL of a 10% formalin solution was added to each well to fix the cells in a light blocking state for 10 minutes. Subsequently, the fixing solution was removed, and the cells were washed with PBS twice for 10 minutes and then stained with Hoechst and DAPI dye solutions at room temperature for 10 minutes in a light blocking state. After staining, the solutions were removed, and the cells were washed with PBS twice. Subsequently, a cover glass was retrieved and then mounted without having bubbles on the slide glass onto which a mounting solution was added dropwise. In a light blocking state, the slide glass was sufficiently dried to observe the cells using a confocal microscope (Zeiss LSM700). As a result, as shown in FIG. 4*d*, it can be seen that, compared with the control, the TD1 exhibits very excellent cell penetration in HeLa cells.

Example 4. Construction of Expression Constructs for Botulinum Toxin Light Chain Protein (BoNT/A Light Chain (Lc)) and Recombinant Protein (TD1-Lc) in which MTD (TD1) and Botulinum Toxin Light Chain Protein (Lc) are Conjugated Expression constructs for a botulinum toxin type A light chain protein (Lc) and a recombinant protein in which MTD (TD1) and the botulinum toxin protein light chain protein (Lc) are conjugated were constructed. First, a codon-optimized light chain (Lc) sequence of botulinum neurotoxin type A, which was synthesized by Bioneer, was used as a template to carry out polymerase chain reaction (PCR) using primer pairs specifically designed for the template. Here, information of the primer sequences are shown in Table 1.

TABLE 1

| | |
|---|---|
| Lc Forward primer | GGAATTCCATATGCCCTTTGTCAACAAACAGTTC (SEQ. ID. NO: 87) |
| Lc Reverse primer | CCGCTCGAGCTTGTTGTAGCCTTTGTCAAG (SEQ. ID. NO: 88) |
| TD1-Lc Forward primer | GGAATTCCATATGAAGGCCATGATCAATATTAACAAGTTCTTAAATCAATGTCCCTTTGTCAACAAACAGTTC (SEQ. ID. NO: 89) |
| TD1-Lc Reverse primer | CTTGACAAAGGCTACAACAAGCACCACCACCACAGCGGCGGTGGTATGTGACTCGAGCGG (SEQ. ID. NO: 90) |

PCR was carried out with a reaction mixture containing 100 ng of codon optimized Lc as a template, a dNTP mixture having the final concentration of 0.4 mM, 1 µM of each primer, 5 µl of 10×EX taq buffered solution, and 0.25 µl of an EX taq polymerase (Takara) for the final volume of 50 µl. First, PCR conditions included thermal denaturation at 95° C. for 5 minutes, 30 cycles of reactions at 95° C. for 30 seconds, 58° C. for 1 minute, and 72° C. for 1 minute, and finally amplification at 72° C. for 8 minutes. After the reaction, electrophoresis was carried out using a 1% agarose gel (Agarose gel) to confirm amplified products, and then the amplified recombinant fragments were collected from the agarose gel and then extracted and purified using a commercially-available gel extraction kit (Intron, Korea). Each of the purified PCR products was treated with NdeI and XhoI enzymes at 37° C. for 2 hours, followed by electrophoresis using an agarose gel again. Then, each recombinant fragment digested thereby was purified using a gel extraction kit (Intron, Korea). Meanwhile, an expression vector pET-21b(+) vector (Novagen, USA), which has a histidine-tag and a T7 promoter, was digested with restriction enzymes NdeI and XhoI under the same conditions as described above, the purified recombinant fragment and the digested pET-21b(+) vector were mixed together, and then ligation was carried out by adding T4 DNA ligase (Intron, Korea) at 16° C. for 16 hours. The resulting products were transfected into E. coli DH5α-sensitive cells, thereby obtaining recombinant protein expression vectors. Through the digestion with expression enzymes NdeI and XhoI as described above and 1% agarose gel electrophoresis, it was confirmed that each recombinant fragment was properly inserted into the pET-21b(+) vector. The obtained recombinant protein expression vectors were named pET21b(+)-Lc and pET21b(+)-TD1-Lc.

Example 5. Culture and Purification of Strains for Expressing Botulinum Toxin Light Chain Protein (Lc) and Recombinant Protein (TD1-Lc) in which MTD (TD1) was Conjugated with Botulinum Toxin Light Chain Protein (Lc)

Figure 5:
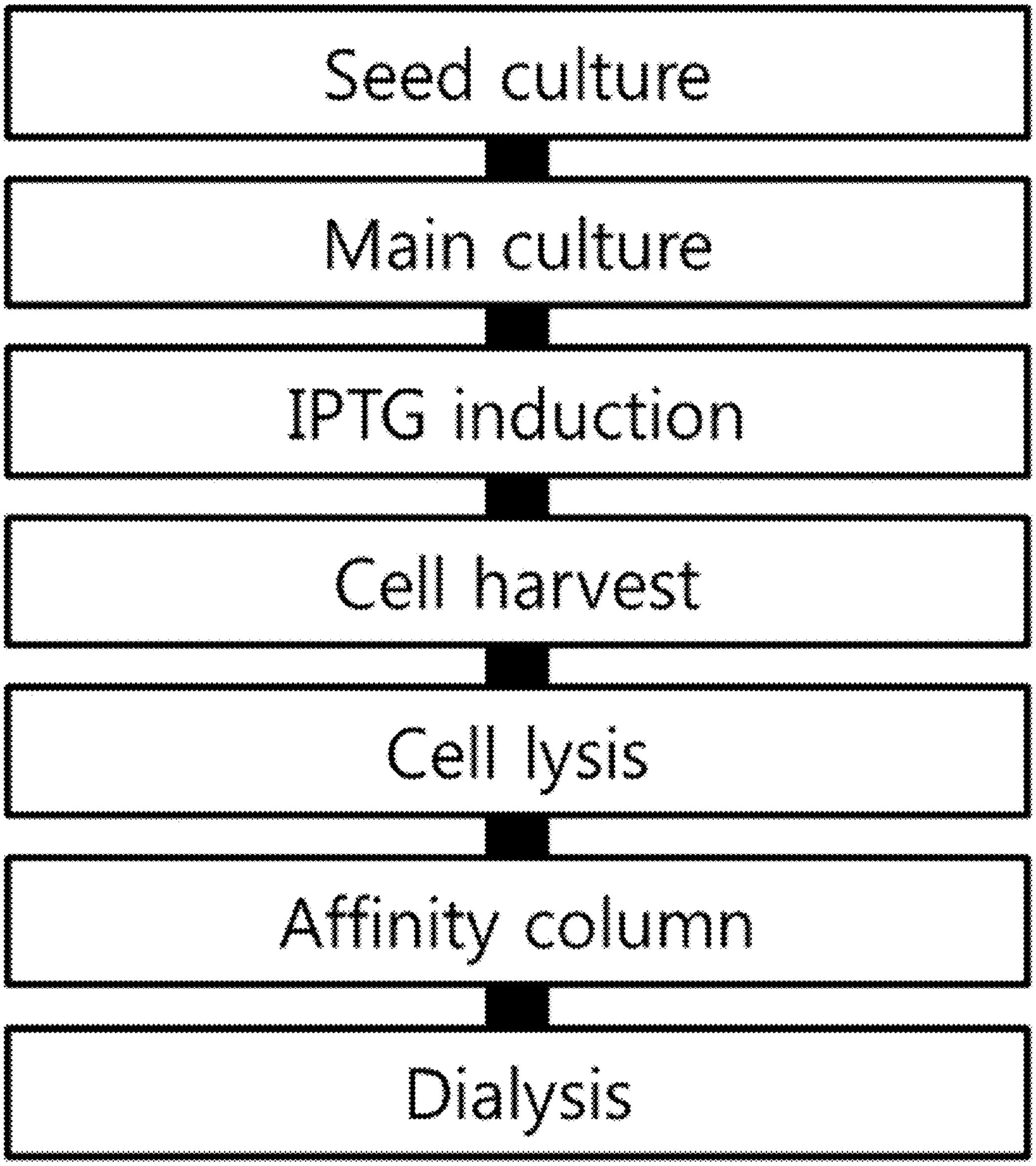
FIG. 5 is a schematic diagram illustrating a process of purifying a botulinum toxin recombinant protein TD1-Lc conjugated with a cell-penetrating peptide TD1.

A process of culturing and purifying a strain for expressing a recombinant protein according to the present invention was performed as follows, and a schematic diagram of the process is shown in FIG. 5.

5-1. Culture of Bacterial Strains

E. coli BL21 (DE3) RIL-CodonPlus was transformed with each of the recombinant expression vectors pET21b (+)-Lc and pET21b(+)-TD1-Lc by a heat shock method, and cultured in LB medium containing 50 µg/ml of ampicillin. Subsequently, the E. coli into which the recombinant protein gene was introduced was inoculated into 25 ml of LB medium, and cultured overnight at 37° C., thereby preparing a first culture solution. The first culture solution was added again to 9f of LB medium for inoculation, and cultured at 37° C. to reach an optical density at 600 nm ($OD_{600}$) of 0.4 to 0.8. Afterward, 1 mM of IPTG, which is a protein expression inducer, was added to the culture solution, and then the cells were further cultured overnight at 18° C. and centrifuged at 4° C. and 8,000 rpm for 10 minutes. Then, a supernatant was removed, thereby retrieving a cell pellet. The collected cell pellet was suspended in PBS and treated with a lysozyme, and then the cells were disrupted using a sonicator and centrifuged at 13,000 rpm for 30 minutes, thereby obtaining a soluble fraction.

5-2. Protein Purification and Purity Identification (SDS-PAGE)

The soluble fraction obtained in Example 5-1 was purified using fast protein liquid chromatography (FPLC; Bio-Rad). The soluble fraction was added to FPLC to be bound to an affinity chromatography column, and then washed with a washing buffer. Afterward, an imidazole concentration was gradually increased to obtain a purified sample, and then the sample was dialyzed using PBS or a dialysis membrane in PBS while being stirred at 4° C. for 16 to 20 hours.

Figure 6:
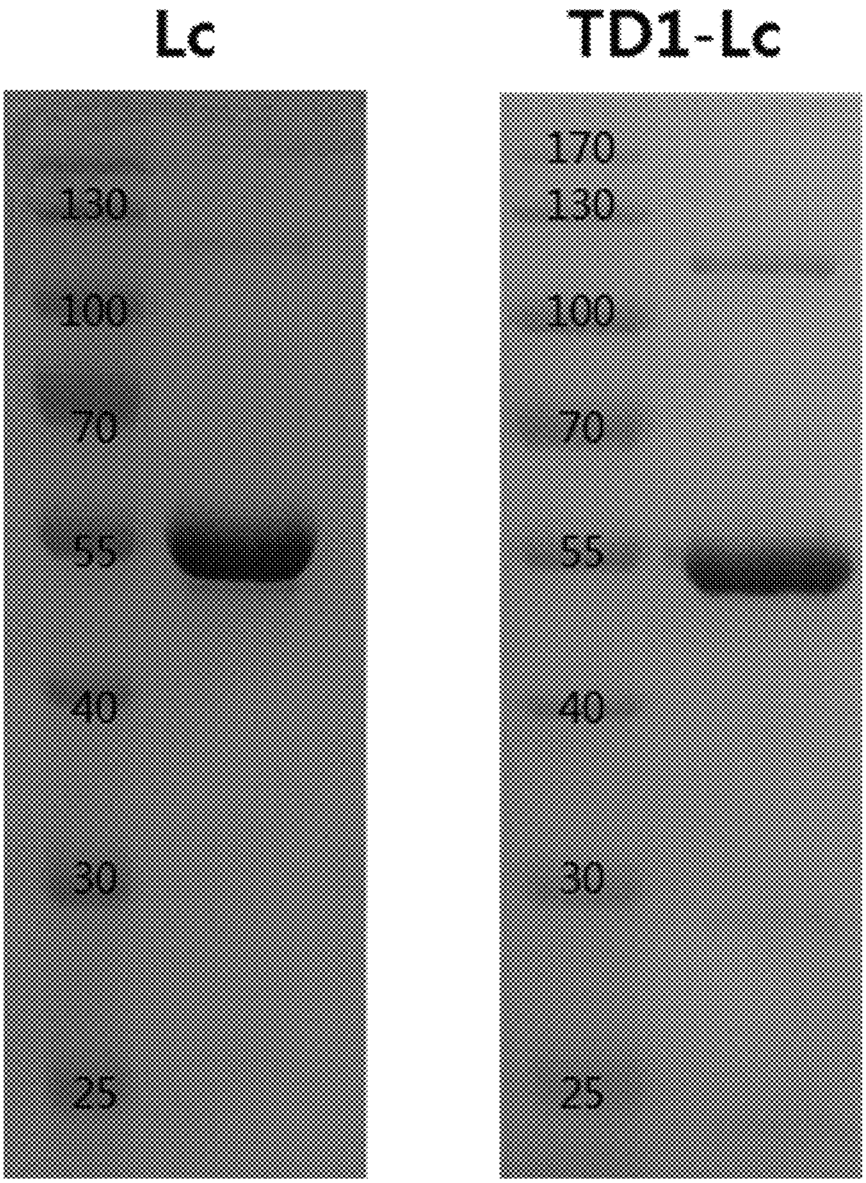
FIG. 6 shows the purity and molecular weight of the purified cell-penetrating botulinum toxin recombinant protein TD1-Lc, assessed by SDS-PAGE.

The purified sample was subjected to electrophoresis in a 12% SDS-PAGE gel to detect a purity. The gel was stained with Coomassie brilliant blue R while being gently agitated, and then destained using a destaining buffer until the band of a desired protein became clear. As a result, as shown in FIG. 6, it can be seen that the purified protein had a purity of 95% or higher using SDS-PAGE.

Example 6. Evaluation of Cell Penetration Potential of Cell-Penetrating Botulinum Toxin Recombinant Protein (TD1-Lc)

6-1. Construction of Fluorescence-Labeled Protein

To evaluate an in vitro cell penetration potential of a cell-penetrating botulinum toxin recombinant protein (TD1-Lc), a FITC-labeled protein was prepared. 10 mL of a protein suspension was prepared by mixing 50 mM boric acid and 0.1 ng/mL FITC with 0.5 µg/mL of the protein in a light blocking state, and reacting at 4° C. for 8 hours. After the reaction, dialysis was carried out by adding the protein suspension to a dialysis tube, and then replacing with DPBS at 4° C. for 3 days at 4 hour-4 hour-16 hour intervals in a light blocking state. After dialysis was completed, an FITC-labeled protein was filtered using a 0.2 µm syringe filter, and the protein obtained thereby was quantified by Bradford analysis and selectively concentrated according to a required concentration. The protein was diluted to meet the lowest concentration among the measured concentrations to measure fluorescence intensity (RFU). Based on the measured RFU, the fluorescent intensity of the FITC-conjugated protein used in verification was compared.

6-2. Confirmation of Neuronal Cell Penetration Potential Using Flow Cytometry

A cell penetration potential of the cell-penetrating botulinum toxin recombinant protein (TD1-Lc) with respect to a neuroblastoma cell line, SiMa cells, was evaluated. Since the SiMa cells had low cell adherence with respect to a culture dish, a gelatin (Sigma-Aldrich, G2500)-coated culture dish was used, and then the dish was coated with a 0.1% gelatin solution. After 1 hour at room temperature, the solution was removed, and the dish was dried. The cells were sub-cultured to 80% or higher confluence using RPMI1640 (10% FBS, 1% penicillin/streptomycin) as complete media. The cells were stabilized through repeated sub-cultures, seeded into a 100 mm culture dish at $5 \times 10^5$/well, and cultured in a 37° C., 5% $CO_2$ incubator for 16 to 20 hours to be used in the experiment.

Figure 7A:
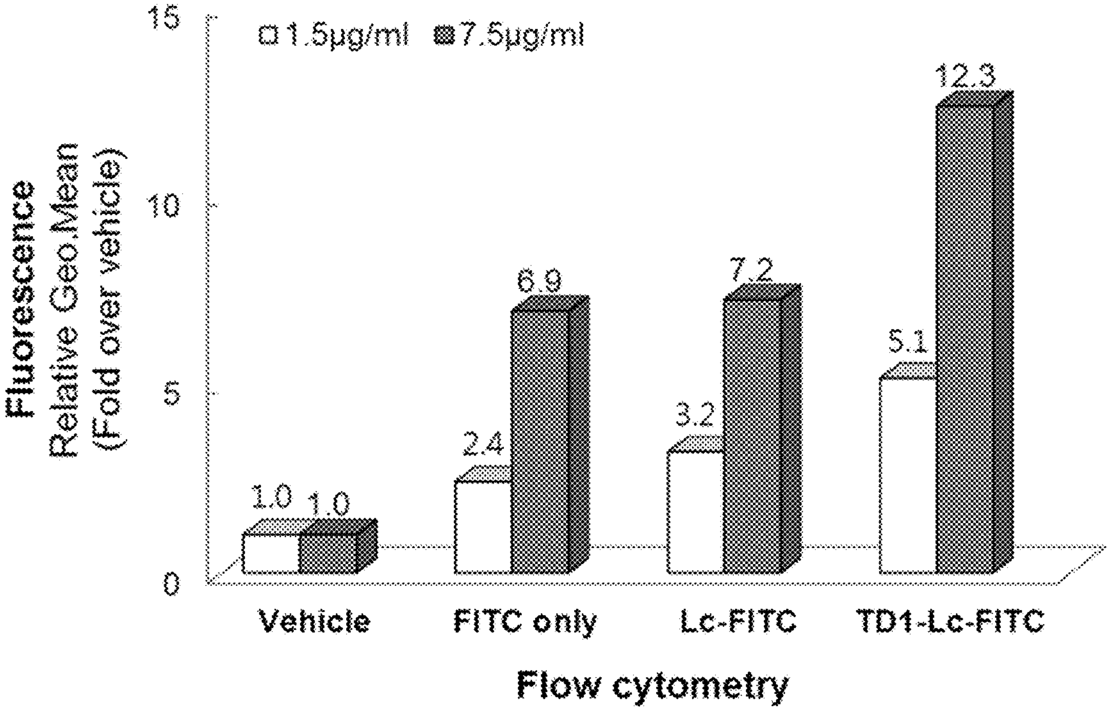
FIG. 7*a* shows an in vitro penetration potential of the cell-penetrating botulinum toxin recombinant protein TD1-Lc with respect to neuroblastoma cells (SiMa cells), assessed by flow cytometry.

Each sample (Vehicle, FITC only, Lc-FITC, TD1-Lc-FITC) was added to an FBS-free medium for 6 hours at concentrations of 1.5 µg/ml and 7.5 µg/ml. After the reaction, the cells were washed with DPBS twice to remove a sample residue, treated with 0.05% trypsin-EDTA for 10 minutes while light was blocked, and then treated with complete media to inactivate the trypsin-EDTA. Afterward, the cells were collected in a prepared tube, treated with 3 mL PBS, and then centrifuged at 2,000 rpm for 3 minutes. Following the removal of a supernatant, each FACS tube was treated with 200 µL PBS to sufficiently resuspend the cells to perform flow cytometry. To compensate a fluorescence value from a measured geo.mean value of F1-1, transduction potentials of the botulinum toxin type A light chain (LC) and the cell-penetrating botulinum toxin recombinant protein (TD1-Lc) were determined based on the Vehicle value. As a result, as shown in FIG. 7*a*, it was quantitatively confirmed that, compared with an Lc protein which does not conjugate to a cell-penetrating peptide, the cell-penetrating peptide-conjugated TD1-Lc recombinant protein exhibits considerably excellent cell penetration in neuronal cells. This is the result obtained by confirming the possibility of TD1 as the carrier of a macromolecule such as a protein on a cellular level.

Figure 7B:
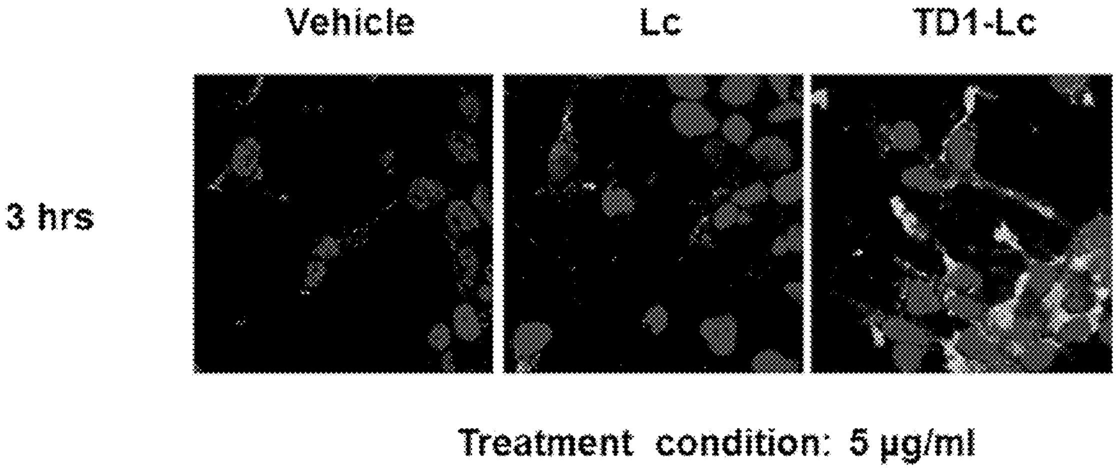
FIG. 7*b* shows an in vitro penetration potential of the cell-penetrating botulinum toxin recombinant protein TD1-Lc with respect to neuroblastoma cells (SiMa cells), assessed by confocal microscopy.

6-3. Confirmation of Neuronal Cell Penetration Potential Using Confocal Microscopy To confirm the cell penetration potential of a cell-penetrating botulinum toxin recombinant protein (TD1-Lc) with respect to a neuroblastoma cell line, SiMa cells, the SiMa cells were sub-cultured to 80% or higher confluence in RPMI1640 (10% FBS, 1% penicillin/streptomycin) as complete media. The cells were stabilized through repeated sub-cultures, and for microscopy, a 12 mm cover glass was flame-sterilized and added to each well of a 24-well plate. The SiMa cells were seeded into the plate and cultured for 16 to 24 hours. Each sample (Vehicle, Lc, TD1-Lc) was added to the cells at a concentration of 5 μg/ml in an FBS-free medium, followed by incubation for 3 hours. After the reaction, the medium was completely removed using suction, the cells were washed with PBS twice, 200 μL of 10% formalin solution was added to each well, followed by fixation of the cells for 10 minutes in a light blocking state. After the cell fixation, the fixing solution was removed, and the cells were washed with PBS twice for 10 minutes. Subsequently, after counter staining was carried out in a light blocking state at room temperature for 10 minutes, a dye solution was removed, and then the cells were washed with PBS twice. To observe the cells, a cover glass was retrieved, and then slowly laid down and mounted without having bubbles on a side glass onto which a mounting solution was added dropwise. The cover glass was sufficiently dried in a light blocking state, and the cells were observed using a confocal microscope (Zeiss LSM700). As a result, as shown in FIG. 7*b*, it was visualized that, compared with the Lc protein, the cell-penetrating peptide-conjugated TD1-Lc recombinant protein exhibits considerably excellent cell penetration in the neuronal cells.

Figure 7C:
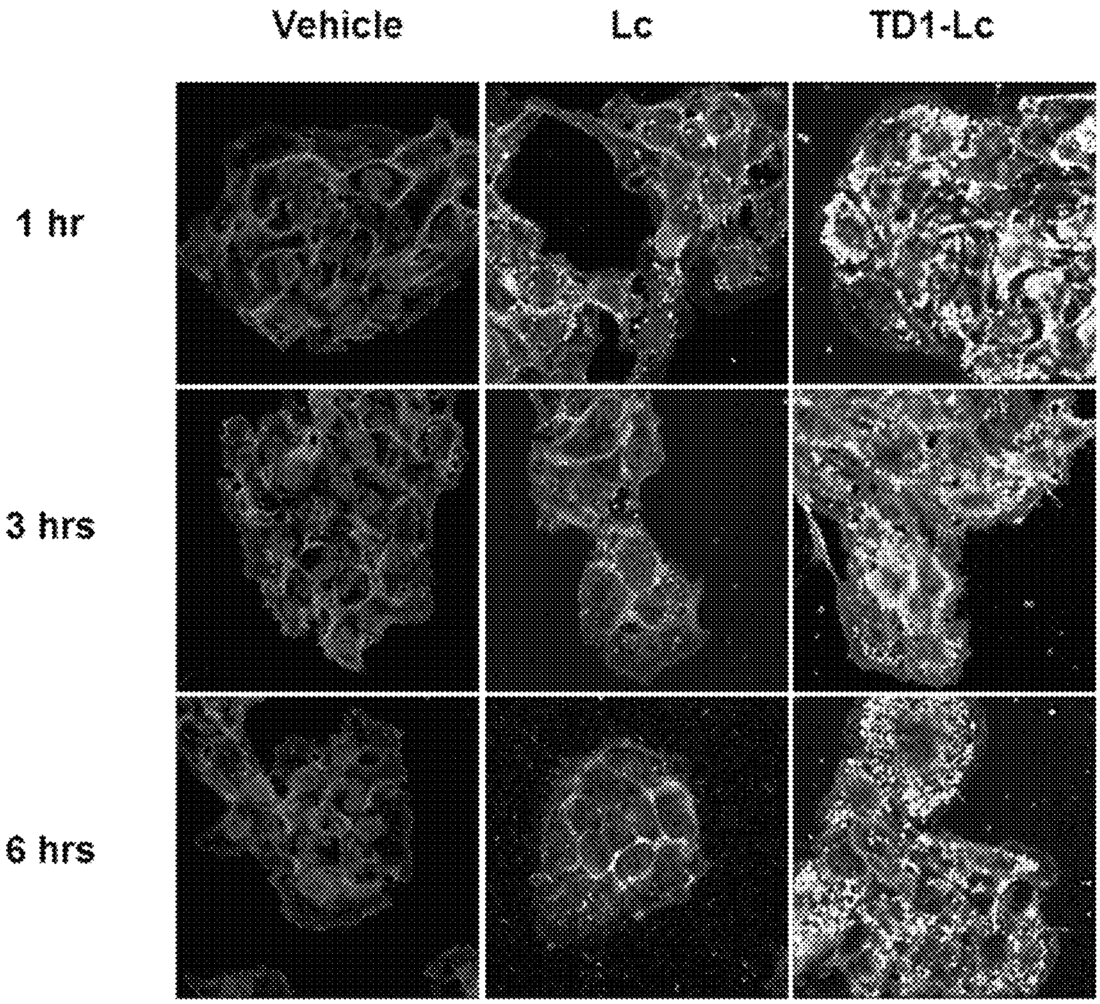
FIG. 7*c* shows an in vitro penetration potential of the cell-penetrating botulinum toxin recombinant protein TD1-Lc with respect to keratinocytes (HaCaT cells), assessed by confocal microscopy.

6-4. Confirmation of Keratinocyte Penetration Potential Using Confocal Microscopy To confirm the cell penetration potential of a cell-penetrating botulinum toxin recombinant protein (TD1-Lc) with respect to a keratinocyte cell line, HaCaT cells, the cells were cultured using DMEM complete media (10% FBS, 1% penicillin/streptomycin). For microscopy, a 12 mm cover glass was flame-sterilized and added to each well of a 24-well plate, and HaCaT cells were seeded into the plate and cultured for 16 to 24 hours. Each sample (Vehicle, Lc, TD1-Lc) was added to the cells at a concentration of 5 μM in a FBS-free medium, followed by incubation for 1 hour, 3 hours and 6 hours. After the reaction, the medium was removed from each well, the plate was washed with PBS twice, and then 200 μL of a 10% formalin solution was added to each well to fix the cells for 10 minutes in a light blocking state. Following the cell fixation, the fixing solution was removed, and the cells were washed with PBS twice for 10 minutes and counter-stained with Hoechst and DAPI dye solutions at room temperature for 10 minutes in a light blocking state. After staining, the dye solutions were removed, and the cells were washed with PBS twice. To observe the cells, a cover glass was retrieved, and then slowly laid down and mounted without having bubbles on a slide glass onto which a mounting solution was added dropwise. The slide glass was sufficiently dried in a light blocking state, and the cells were observed using a confocal microscope (Zeiss LSM700). As a result, as shown in FIG. 7*c*, it was visualized that, compared with the Lc protein, the cell-penetrating peptide-conjugated TD1-Lc recombinant protein exhibits considerably excellent cell penetration in the keratinocytes.

Example 7. Evaluation of Penetration Efficacy of Cell-Penetrating Peptide TD1-Conjugated Botulinum Toxin Recombinant Protein TD1-Lc with Respect to Synthetic Skin Substitute To evaluate skin barrier penetrating efficacy of the recombinant protein (TD1-Lc) in which a cell-penetrating peptide (TD1) is conjugated with a botulinum toxin light chain protein (Lc), the skin penetrating efficacy of a synthetic skin substitute (Strat-M™) was confirmed using an automated transdermal diffusion cell system (MicroettePlus). The synthetic skin substitute was composed of an upper layer of polyether sulfone (PES) for inhibiting absorption and a lower layer of a polyolefin which may impart absorption differentiation due to a porous structure, be easily stored and is capable of being applied to the system without pretreatment. Also, it is widely used since a penetration amount difficult to be measured in the actual skin may be quantified under a skin-like condition. To evaluate the penetrating efficacy in the prepared synthetic skin substitute, PBS was added below a vertical cell to allow the buffered solution to be conjugated with the synthetic skin substitute without an empty space, and then a sample was added above the vertical cell. 10% of the buffered solution present below the vertical cell was extracted, and then the empty space was charged with the same amount of a buffered solution, which was repeated during the reaction. After the reaction, the amount of the sample was assessed by ELISA. As a result, as shown in FIG. 8, it can be seen that a novel cell-penetrating peptide MTD-conjugated TD1-Lc had a penetration potential approximately 20% or higher than the botulinum toxin light chain protein Lc in the synthetic skin substitute. It can be seen that a degree of penetration of the synthetic skin substitute over time seemed similar until 6 hours after the reaction, but 12 to 24 hours after the reaction, the penetration potential of the TD1-Lc protein was higher.

Example 8. Evaluation of Efficacy of Cell-Penetrating Peptide TD1-Conjugated Botulinum Toxin Recombinant Protein TD1-Lc (In Vitro SNAP25 Cleavage Assay)

SNAP25 protein is a type of SNARE protein, which is cleaved by the light chain of botulinum toxin type A. Generally, to see the activity of botulinum toxin, an in vitro SNAP25 cleavage assay is used. In one exemplary embodiment, to confirm the activity of the light chain of botulinum toxin (BoNT/A Light chain (Lc)), a cleavage assay was used. 2 μl of a cleavage assay buffer (10 mM DTT, 10 mM HEPES, 10 mM NaCl & 20 uM $ZnCl_2$) was added to 2 μg of a GST-SNAP25-EGFP-conjugated protein, and a recombinant protein TD1-Lc was added at various concentrations of 10, 30, 90, 270 and 810 ng, followed by a reaction at 37° C. for 4 hours. As a positive control, 270 ng of a botulinum toxin complex (BoNT/A complex) was added, and then triple distilled water was added for a total volume of 20 μl, followed by a reaction under the same conditions as described above. The mixture in which the reaction was completed was treated with a 5× reduced buffer, heated at 100° C. for 10 minutes, and subjected to electrophoresis using a 12% SDS-PAGE gel at 80V for 20 minutes and at 120V for 1 hour. The SDS-PAGE gel was stained with a staining buffer (0.25% Coomassie brilliant blue, 45% methanol, 10% acetic acid), and then destained with a destaining buffer (30% methanol, 10% acetic acid) to confirm a protein pattern. As a result, as shown in FIG. 8, it can be confirmed the activity of botulinum toxin is maintained even in the recombinant protein of TD1-Lc. From the result, it can be expected that the recombinant protein of TD1-Lc will have the same function as botulinum toxin.

Example 9. Evaluation of In Vitro Efficacy of Cell-Penetrating Peptide TD1-Conjugated Botulinum Toxin Recombinant Protein TD1-Lc 9-1. Confirmation of SNAP25 Cleavage in Human Keratinocytes (HaCaT Cells)

Figure 10A:
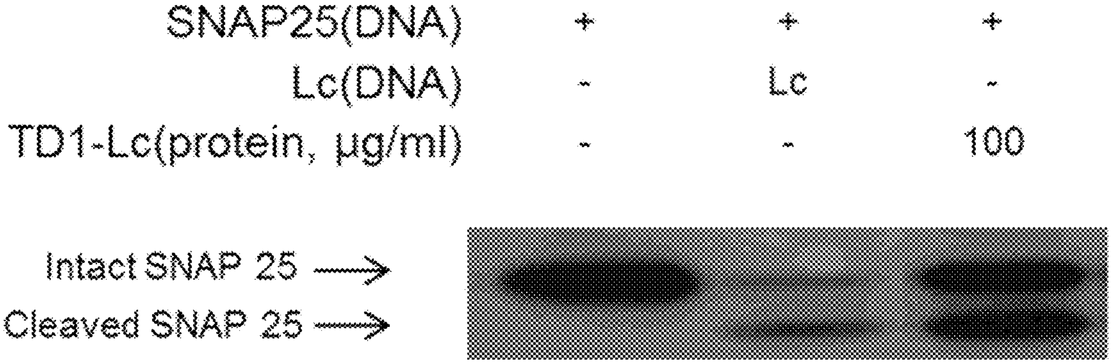
FIG. 10*a* shows an in vitro SNAP25 cleavage activity of the cell-penetrating botulinum toxin recombinant protein TD1-Lc with respect to keratinocytes (HaCaT cells).

To evaluate skin penetration and efficacy of the recombinant protein TD1-Lc in keratinocytes (HaCaT cells), an SNAP25 cleavage assay capable of confirming the efficacy according to the cleavage of the SNAP25 protein was carried out through western blotting. The keratinocytes (HaCaT cells) were cultured in a 24 well plate up to a cell density of $1\times10^4$/well for 24 hours, transfected with a pcDNA3.1-SNAP25 plasmid, and contransfected with a pcDNA3.1-Lc plasmid as a positive control. Following the overexpression of SNAP25 through 15-hour culture, a medium was transferred with an FBS-free medium and removed after 48 hours of TD1-Lc protein treatment, and then the cells were washed with PBS. Afterward, 200 μl of RIPA buffer (Intron) was added to each well to lyse the cells, and then the cells were centrifuged at 4° C. and 8,000 rpm for 10 minutes, thereby obtaining a supernatant. The obtained supernatant was mixed with a 5× reducing sample buffer, heated at 100° C. for 10 minutes, and subjected to electrophoresis using a 15% SDS-PAGE gel at 80V for 20 minutes and at 120V for 1 hour. After the electrophoresis, the gel was transferred to a PVDF membrane (Millipore, IPVH00010) at 90V for 1 hour and 10 minutes, and the transferred membrane was blocked with 5% BSA for 2 hours. Afterward, a primary antibody (Covance, SMI-81) was diluted with 5% BSA at a ratio of 1:1000, and reacted at 4° C. for 16 hours. After the reaction, the membrane was washed with PBST at 10-minute intervals three times or more, a second antibody (Millipore, AP192P) was diluted with 5% BSA at a ratio of 1:2500, followed by a further reaction for 1 hour at room temperature. After the second reaction, the membrane was washed with PBST at 10-minute intervals three times or more, treated with an ECL solution for a further reaction, transferred to a cassette, and exposed on an X-ray film in a dark room. As a result, as shown in FIG. 10*a*, when Lc is expressed in a plasmid or a plasmid is externally treated with the protein, in all cases, the SNAP25 cleavage was confirmed. That means that the externally treated protein of TD1-Lc penetrates a skin cell to cleave SNAP25 expressed therein. Therefore, it was confirmed that the recombinant protein TD1-Lc has excellent skin cell penetration and activity.

9-2. Confirmation of SANP25 Cleavage in Human Neuroblastoma Cells (SiMa Cells)

To evaluate the skin penetration and efficacy of the recombinant protein TD1-Lc in human neuroblastoma cells, SiMa cells, an SNAP25 cleavage assay capable of confirming efficacy by the cleavage of an SNAP25 protein was performed through western blotting.

Figure 10B:
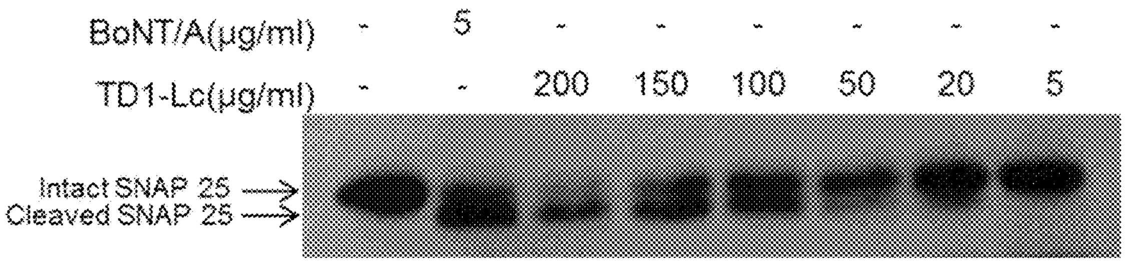
FIG. 10*b* shows an in vitro SNAP25 cleavage activity of the cell-penetrating botulinum toxin recombinant protein TD1-Lc with respect to neuroblastoma cells (SiMa cells).

First, the SiMa cells were seeded in a 24-well plate using an RPMI medium containing 10% FBS and 1% P/S at a cell density of $5\times10^5$/well. The cells were cultured overnight in an 37° C., 5% $CO_2$ incubator, the medium was exchanged with 1 ml of a differentiation medium (10% FBS, RPMI, Glutamax, 1×NEAA, 1×B27, 1×N2, 5 uM RA, 2.5 uM PUR), and then the cells were cultured for 24 hours. GT1b was added to a differentiation medium (10% FBS, RPMI, Glutamax, 1×NEAA, 1×B27, 1×N2, 5 uM RA, 2.5 uM PUR) at a concentration of 25 μg/mL, and then the medium was exchanged with 1 ml of the differentiation medium. After 24-hour culture, the medium was exchanged with 1 ml of a differentiation medium (10% FBS, RPMI, Glutamax, 1×NEAA, 1×B27, 1×N2, 5 uM RA, 2.5 uM PUR) to induce differentiation. The human neuroblastoma cells (SiMa cells) were cultured in a 24-well plate at a cell density of $5\times10^5$/well, differentiated according to a neuronal differentiation method, and then a medium was exchanged with a final differentiation medium, and after 4 hours, the cells were treated with a recombinant protein TD1-Lc. After 48 hours of the protein treatment, the medium was removed, and the cells were washed with PBS, lyzed by adding 200 μl of RIPA buffer (Intron) to each well, and centrifuged at 4° C. and 8,000 rpm for 10 minutes, thereby obtaining a supernatant. The obtained supernatant was mixed with a 5× reducing sample buffer, heated at 100° C. for 10 minutes, and subjected to electrophoresis using a 15% SDS-PAGE gel at 80V for 20 minutes, and at 120V for 1 hour. After the electrophoresis, the gel was transferred to a PVDF membrane (Millipore, IPVH00010) at 90V for 1 hour and 10 minutes, and blocked with 5% BSA for 2 hours. Afterward, a primary antibody (Covance, SMI-81) was diluted with 5% BSA at a ratio of 1:1000, and reacted at 4° C. for 16 hours. After the reaction, the membrane was washed with PBST at 10-minute intervals three times or more, a second antibody (Millipore, AP192P) was diluted with 5% BSA at a ratio of 1:2500, followed by a further reaction for 1 hour at room temperature. After the second reaction, the membrane was washed with PBST at 10-minute intervals three times or more, treated with an ECL solution for a further reaction, transferred to a cassette, and exposed on an X-ray film in a dark room. As a result, as shown in FIG. 10*b*, it was confirmed that only the TD1-Lc protein were able to effectively penetrate the human neuroblastoma cells. Therefore, it was confirmed that the TD1-Lc protein can also effectively pass through neuronal cells as well as skin cells.

Example 10. Evaluation of Skin Cell Cytotoxicity of Cell-Penetrating Peptide TD1-Conjugated Botulinum Toxin Recombinant Protein TD1-Lc 10-1. Evaluation of Cytotoxicity in Human Keratinocytes (HaCaT Cells)

Figure 11A:
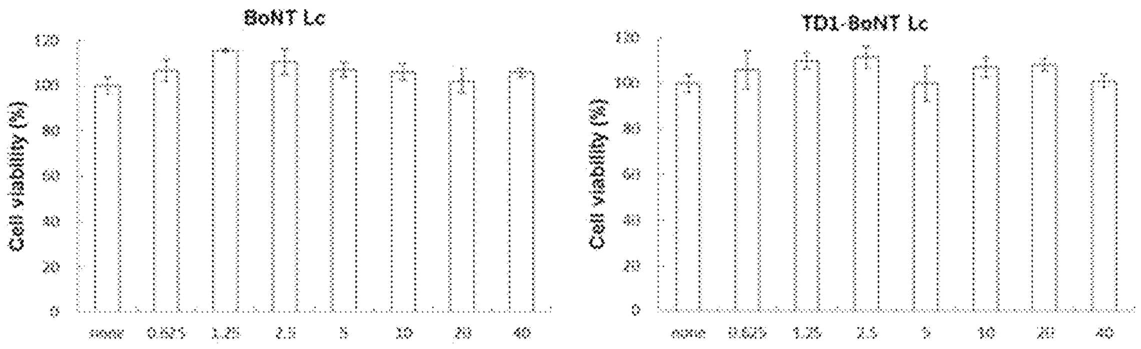
FIG. 11*a* shows the cytotoxicity of the cell-penetrating botulinum toxin recombinant protein TD1-Lc in neuroblastoma keratinocytes (HaCaT cells).

To evaluate the cytotoxicity of the recombinant protein TD1-Lc with respect to human skin cells, an MTT assay for measuring cell viability was carried out. First, keratinocytes (HaCaT cells) were cultured in a 24-well plate at a cell density of $1\times10^4$/well, and then a medium was exchanged with an FBS-free medium 4 hours before treatment with the recombinant protein TD1-Lc. The cells were treated with the protein at concentrations from 0.625 μg/ml to 40 μg/ml, reacted for 48 hours, and further reacted for 4 hours by adding 10 μl of 5 mg/ml MTT (Sigma-Aldrich). After the reaction, the culture medium was discarded, and 100 μl of DMSO was added to each sample and reacted at room temperature for 10 minutes, followed by measuring an absorbance ($OD_{570}$). As a control for the experiment, a botulinum toxin light chain protein (Lc) which is not conjugated with TD1 was used. As a result, as shown in FIG. 11*a*, it can be confirmed that the recombinant protein TD1-Lc has cell viability even at a high concentration of 40 μg/ml in the keratinocytes (HaCaT cells), and thus has no cytotoxicity.

10-2. Evaluation of Cytotoxicity in Human Neuroblastoma Cells (SiMa Cells)

Figure 11B:
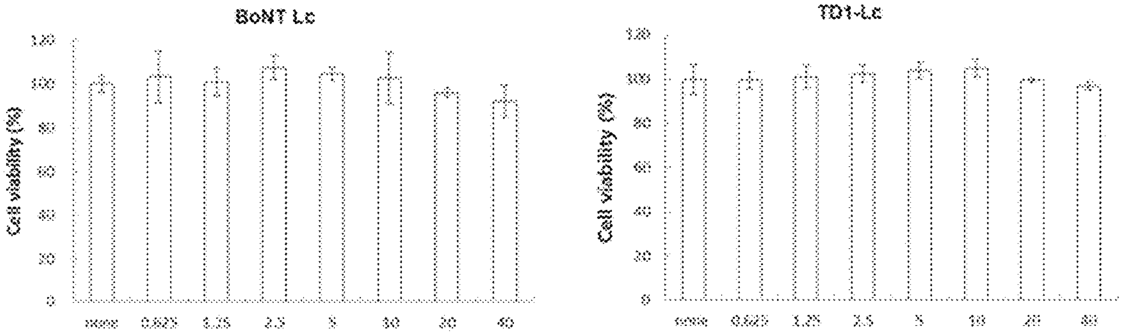
FIG. 11*b* shows the cytotoxicity of the cell-penetrating botulinum toxin recombinant protein TD1-Lc in neuroblastoma cells (SiMa cells).

To evaluate the cytotoxicity of the recombinant protein TD1-Lc with respect to human neuroblastoma cells (SiMa cells), an MTT assay for measuring cell viability was carried out. The human neuroblastoma cells (SiMa cells) were cultured in a 24-well plate at a cell density of $5\times10^5$/well, and differentiated according to a neuronal differentiation method. 4 hours after the exchange with a final differentiation medium, the recombinant protein TD1-Lc was treated. The cells were treated with the protein at concentrations of 0.625 μg/ml to 40 μg/ml to perform a reaction for 48 hours, and then further reacted for 4 hours by adding 10 μl of 5 mg/ml MTT (Sigma-Aldrich). After the reaction, the culture medium was discarded, and 100 μl of DMSO was added to each sample and reacted at room temperature for 10 minutes, followed by measuring an absorbance ($OD_{570}$). As a control for the experiment, a botulinum toxin light chain protein (Lc) which was not conjugated with TD1 was used. As a result, as shown in FIG. 11*b*, it can be confirmed that as the cell viability of the recombinant protein TD1-Lc-treated human neuroblastoma cells (SiMa cells) was maintained, cytotoxicity is not shown even at high concentrations of the recombinant protein TD1-Lc.

Figure 12:
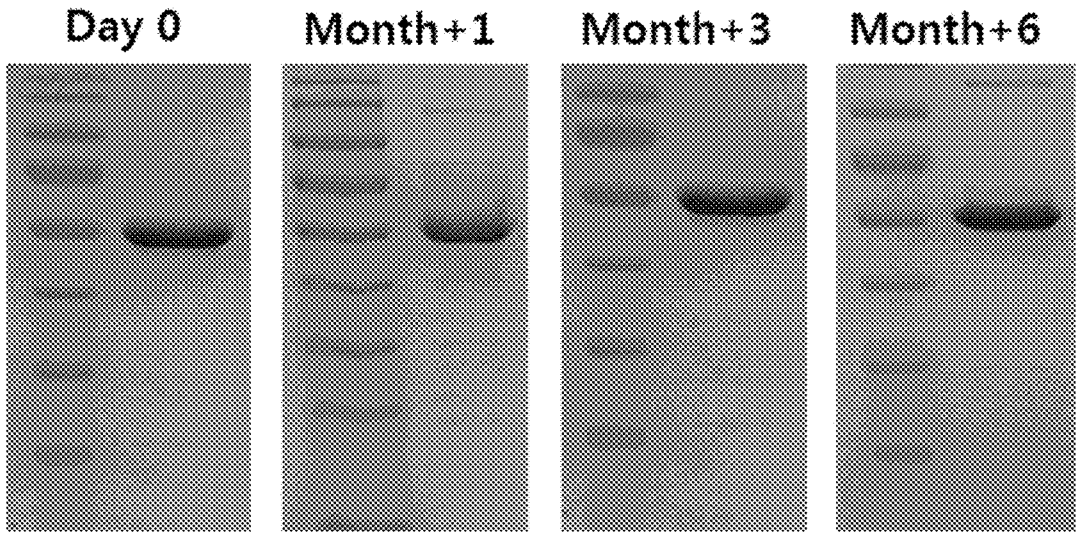
FIG. 12 shows the stability of the purified cell-penetrating botulinum toxin recombinant protein TD1-Lc according to storage period, assessed by SDS-PAGE.

Example 11. Evaluation of Stability of Cell-Penetrating Peptide TD1-Conjugated Botulinum Toxin Recombinant Protein TD1-Lc In the case of the light chain of botulinum toxin, two light chain proteins after purification forms a dimer, and the formed light chain dimer has self-cleavage activity, and shows a difference in self-cleavage activity according to a storage condition. Therefore, to confirm the stability according to a storage period of the recombinant protein TD1-Lc, a pattern change of the protein by period was confirmed by SDS-PAGE electrophoresis. The recombinant protein TD1-Lc was quantified and 10 μg was dispensed into each tube, and then stored in a −80° C. ultra-low temperature freezer. After 1, 3 and 6 months of storage, according to the passage of each period, each recombinant protein TD1-Lc was loaded in a 12% SDS-PAGE gel to perform electrophoresis, thereby confirming changes in the purity and pattern of the protein. As a result, as shown in FIG. 12, it can be confirmed that even after 6 months, the recombinant protein is stably maintained without a change in the protein pattern.

Example 12. Preparation of Cosmetic Composition of Cell-Penetrating Peptide TD1-Conjugated Botulinum Toxin Recombinant Protein TD1-Lc and Evaluation of Stability to Skin Stimulation For a clinical test of the recombinant protein TD1-Lc, a cosmetic composition was manufactured by processing the recombinant protein TD1-Lc by a liposome technique conducted by H&A Pharmachem and then processing the liposomal protein together with cosmetic ingredients.

Also, to evaluate skin irritation safety for humans, a test was conducted by I.E.C. Korea (Korea), which is the requested contract research organization (CRO). The test was performed by adding samples obtained from 31 healthy males and females to IQ chambers and attaching a patch of the samples to the skin of a subject's back, and after 48 hours, the safety with respect to human skin was determined by a dermatologist to evaluate and analyze an irritation degree. The patch method was performed as a single occlusive patch test, and an irritation degree was evaluated and analyzed by an evaluation method designed by Frosch & Kligman in accordance with the CTFA guidelines generally used in skin irritation evaluation. As test volunteers, 32 healthy adult males and females suitable for selection and exclusion criteria were selected through the medical histories of a dermatologist, who was the test manager, and researchers, interviews and visual inspections, and if necessary, palpation, but one of them dropped out. Age distribution was from 20 to 36 years old, a mean age was 25.7±5.4, and a male: female ratio was 13:18. After a single patch test for the 31 subjects who finished the test, a skin irritation degree in accordance with the evaluation criteria was determined, and the result is shown in FIG. 13. When the irritation degree is evaluated through the result of a skin irritation response, common worldwide standards applicable in the human skin irritation response have not been determined, normally, in a test for 50 or more volunteers, by data reading in a single patch test, samples showing responses in a frequency of more than 20% of the total volunteers (7 or more, which is 20% of 31 volunteers in the test) or samples showing irritation responses of +2 or higher in every data reading in more than 10% of the total volunteers may be considered as materials capable of significantly causing irritation. In this test, as skin responses were observed after patches were applied to the skin of the backs of the 31 subjects for 48 hours, it was determined that the requested samples can be safely used with respect to the skin without irritation.

Example 13. Evaluation of Wrinkle Improvement Efficacy of Cell-Penetrating Peptide TD1-Conjugated Botulinum Toxin Recombinant Protein TD1-Lc To evaluate the wrinkle improving efficacy of the recombinant protein TD1-Lc, a clinical test was performed by I.E.C. Korea (Korea), which is a contract research organization (CRO). The test was performed on 22 Korean adult female subjects having nasolabial folds and ranging in age from 30 to 59 by using one type of sample twice a day for 4 weeks by themselves at home, measuring the roughness of nasolabial folds and skin elasticity, and evaluating a skin fold reducing efficacy of the recombinant protein TD1-Lc through clinical imaging in combination with visual evaluation of nasolabial folds by a dermatologist. The roughness of nasolabial folds was measured using a PRIMOS system, and the skin elasticity was measured using a Cutometer MPA580.

The human-applied test was carried out with a priority of protecting the rights, safety and welfare of the subjects based on the content of the spirit of the Declaration of Helsinki and GCP guidelines. Researchers faithfully performed the following requirements to ensure the safety of a subject.

During the test, a test manager and test personnel should make every effort to maximize the safety of a subject, and take immediate and appropriate actions to all unusual symptoms of the skin to reduce responses to the symptoms.

During the test, when the subject reported skin irritation or an unusual symptom, which is caused by a sample, the used sample is wiped off immediately, and when the symptom is not improved, dermatological evaluation and proper treatment are given by the test manager.

When an unusual symptom occurs on the skin despite normal test procedures, proper dermatological evaluation and treatment are given.

When other abnormal skin responses occur, the test manager and the test personnel take proper actions along with dermatological evaluation, and record cases and situations in detail.

For measurement of the result, the subject visits the laboratory, takes a rest in a constant temperature and humidity room (22±2° C. 50±5%) for 15 minutes or longer to stabilize the skin which is then subjected to measurement and evaluation.

In this test, before and 4 weeks after the use of the sample, nasolabial fold regions were scanned, and skin roughness parameters were analyzed using a PRIMOS system. The parameters expressing skin roughness are as follows.

Ra: arithmetic average (average roughness)

Rmax: Maximum peak to valley roughness (maximum roughness)

R3z: Arithmetic mean third height

Rt: distance between the highest and the lowest points

Rz: Average maximum height (10 point height)

Skin elasticity was evaluated by measuring elasticity (elastic restoring force) in a pore region of the cheek using a Cutometer. A process including suction at a pressure of 400 mb for 2 seconds and release for 2 seconds was repeated three times, and to increase reproducibility of the measurement results, pretension time was set to 0.1 second. When the skin was suctioned and released, the parameters obtained from the measurement values through the suction and release of the skin are to be interpreted as follows.

R5: Net elasticity of the skin without viscous deformation

R7: Portion of the elasticity compared to the complete curve

The visual evaluation of nasolabial folds were carried out through visual observation of a state of the left or right nasolabial fold of each subject by a dermatologist before (D+0) and 4 weeks (D+28) after the use of the sample in accordance with a photographic scale.

Before and after the use of the sample, statistical significance of nasolabial fold roughness, skin elasticity and the visual evaluation by a dermatologist was examined, and when there were significant changes in the roughness of nasolabial folds, skin elasticity parameters and the visual evaluation on the nasolabial fold by the dermatologist before and after the use of the sample, it was concluded that the nasolabial fold or elasticity was improved.

As a statistical analysis program, SPSS 14.0 was used, and as a result of machine measurement, the Shapiro-Wilk test for data normality was carried out. All of the 22 subjects were determined as suitable subjects, and tests on all of the subjects were completed until the final visits, thereby obtaining effective data from the final 22 subjects (average age: 46.1).

Figure 15:
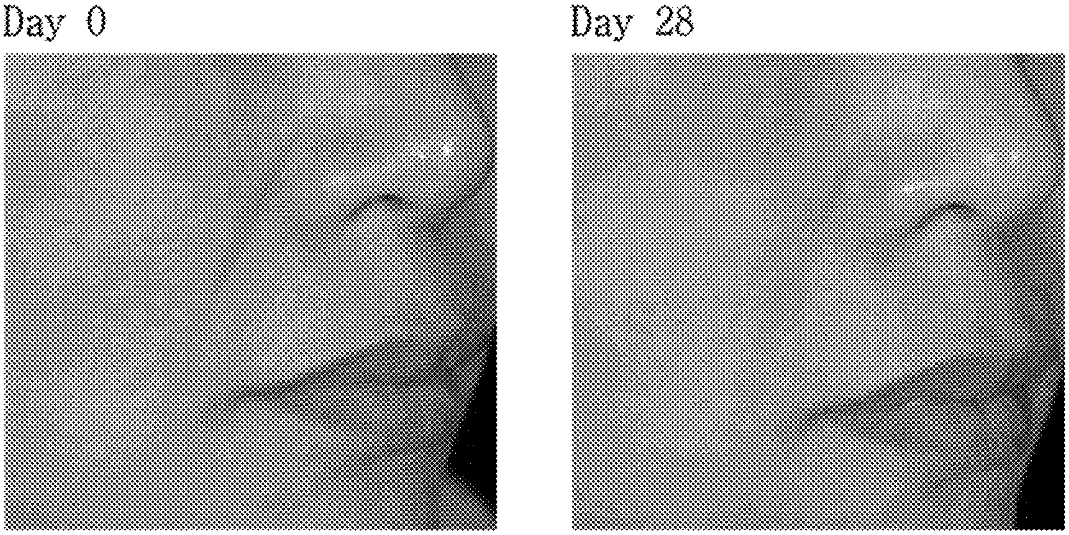
FIG. 15 shows clinical efficacy of the cell-penetrating botulinum toxin recombinant protein TD1-Lc formulated as a cosmetic agent with respect to nasolabial folds, evaluated by a contract research organization.

As a result, as shown in FIG. 14*a,* 4 weeks after the use of the sample, Ra, Rmax, R3z, Rz and Rt parameters expressing the skin roughness at the nasolabial fold region were significantly reduced, which means that the nasolabial fold was improved. Also, as shown in FIG. 14*b,* 4 weeks after the use of the sample, it was shown that R5 and R7 parameters expressing skin elasticity were significantly increased, which means that the skin elasticity was improved. The visual evaluation of the nasolabial folds also showed that the nasolabial folds were significantly reduced 4 weeks after the use of the sample, as shown in FIG. 14*c,* and the wrinkle reducing efficacy can be visually confirmed as shown in FIG. 15.

Therefore, according to the evaluation of the skin improving efficacy of a TD1-conjugated botulinum toxin recombinant protein TD1-Lc through clinical tests, it was confirmed that when the sample was continuously used for 4 weeks, it is effective in improvement of the nasolabial folds and the skin elasticity. This shows that, as the topically-applied cell-penetrating botulinum toxin recombinant protein (TD1-Lc) is effectively transdermally delivered, it provides significant efficacy in reducing fine wrinkles and deep wrinkles in the skin.

It would be understood by those of ordinary skill in the art that the above descriptions of the present invention are exemplary, and the example embodiments disclosed herein can be easily modified into other specific forms without changing the technical spirit or essential features of the present invention. Therefore, it should be interpreted that the example embodiments described above are exemplary in all aspects, and are not limitative.

INDUSTRIAL APPLICABILITY

As a cell-penetrating peptide-botulinum toxin recombinant protein of the present invention can be transdermally delivered, it can have the intrinsic effects of botulinum toxin and maximize ease of use, and thus can be used as more safe and preferable therapeutic alternative. Therefore, the cell-penetrating peptide-botulinum toxin recombinant protein of the present invention can be effectively used as a topical agonist for the treatment of various diseases, and aesthetic and/or cosmetological purposes.

The invention claimed is:

1. A cell-penetrating botulinum toxin recombinant protein in which a cell-penetrating peptide consisting of the amino acid sequence as set forth in SEQ. ID. NO: 1 is conjugated with one or both termini of the light chain of botulinum toxin.

2. The cell-penetrating botulinum toxin recombinant protein of claim 1, wherein the botulinum toxin recombinant protein consists of an amino acid sequence selected from the group consisting of SEQ. ID. NO: 31 to SEQ. ID. NO: 58.

3. The cell-penetrating botulinum toxin recombinant protein of claim 1, wherein the light chain of botulinum toxin consists of an amino acid sequence selected from the group consisting of SEQ. ID. NO: 3 to SEQ. ID. NO: 9.

4. The cell-penetrating botulinum toxin recombinant protein of claim 1, wherein the light chain of botulinum toxin further comprises a hexahistidine tag at one terminus.

5. The cell-penetrating botulinum toxin recombinant protein of claim 1, wherein the light chain of botulinum toxin is selected from the group consisting of botulinum toxin serotypes A, B, C, D, E, F and G.

6. The cell-penetrating botulinum toxin recombinant protein of claim 1, wherein the conjugation is conjugation of the cell-penetrating peptide to a carboxyl terminus or an amino terminus of the light chain of botulinum toxin, or both thereof.

7. The cell-penetrating botulinum toxin recombinant protein of claim 1, wherein the conjugation is created by a peptide bond or a covalent bond.

8. A method for treating a disease selected from the group consisting of facial spasms, eyelid spasms, torticollis, blepharospasm, cervical dystonia, oropharynx dystonia, spasmodic dysphonia, migraines, pruritis ani and hyperhidrosis in a subject in need thereof, the method comprising:

transdermally administering the cell-penetrating botulinum toxin recombinant protein of claim 1 into a subject.

* * * * *